(12) United States Patent
Flynn et al.

(10) Patent No.: US 8,278,331 B2
(45) Date of Patent: Oct. 2, 2012

(54) N-ACYL UREAS EXHIBITING ANTI-CANCER AND ANTI-PROLIFERATIVE ACTIVITIES

(75) Inventors: Daniel L. Flynn, Lawrence, KS (US); Peter A. Petillo, Lawrence, KS (US); Michael D. Kaufman, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 273 days.

(21) Appl. No.: 12/608,578

(22) Filed: Oct. 29, 2009

(65) Prior Publication Data
US 2010/0120806 A1    May 13, 2010

Related U.S. Application Data

(60) Provisional application No. 61/109,309, filed on Oct. 29, 2008.

(51) Int. Cl.
*A61K 31/44* (2006.01)
(52) U.S. Cl. ..... 514/333; 514/269; 514/274; 546/268.1; 544/298
(58) Field of Classification Search ................... 544/298; 546/268.1
See application file for complete search history.

(56) References Cited

U.S. PATENT DOCUMENTS

| | | |
|---|---|---|
| 3,528,980 A | 9/1970 | Islip |
| 3,818,024 A | 6/1974 | Krenzer |
| 3,939,122 A | 2/1976 | Merten et al. |
| 3,949,002 A | 4/1976 | Feasey et al. |
| 4,093,624 A | 6/1978 | Revankar et al. |
| 4,296,237 A | 10/1981 | Cragoe, Jr. et al. |
| 4,366,189 A | 12/1982 | Burdeska et al. |
| 4,432,992 A | 2/1984 | Cragoe, Jr. et al. |
| 4,525,450 A | 6/1985 | Itoh et al. |
| 4,816,454 A | 3/1989 | Zoller et al. |
| 5,103,014 A | 4/1992 | Musser et al. |
| 5,162,360 A | 11/1992 | Creswell et al. |
| 5,319,099 A | 6/1994 | Kamata et al. |
| 5,494,925 A | 2/1996 | Court et al. |
| 5,621,010 A | 4/1997 | Sueda et al. |
| 5,721,231 A | 2/1998 | Moriwaki et al. |
| 5,811,456 A | 9/1998 | Seman et al. |
| 6,020,357 A | 2/2000 | Pinto et al. |
| 6,080,763 A | 6/2000 | Regan et al. |
| 6,197,599 B1 | 3/2001 | Chin et al. |
| 6,235,786 B1 | 5/2001 | Dai et al. |
| 6,294,573 B1 | 9/2001 | Curtin et al. |
| 6,319,921 B1 | 11/2001 | Cirillo et al. |
| 6,410,254 B1 | 6/2002 | Finer et al. |
| 6,500,628 B1 | 12/2002 | Robison |
| 6,525,046 B1 | 2/2003 | Cirillo et al. |
| 6,645,990 B2 | 11/2003 | Askew et al. |
| 6,916,924 B2 | 7/2005 | Tan et al. |
| 7,030,128 B2 | 4/2006 | Blackaby et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al |
| 7,342,037 B2 | 3/2008 | Flynn et al. |
| 7,531,566 B2 | 5/2009 | Flynn et al. |
| 2002/0058678 A1 | 5/2002 | Cirillo et al. |
| 2003/0060455 A1 | 3/2003 | Moss et al. |
| 2003/0207870 A1 | 11/2003 | Dumas et al. |
| 2003/0232865 A1 | 12/2003 | Cirillo et al. |
| 2004/0043388 A1 | 3/2004 | Come et al. |
| 2004/0157827 A1 | 8/2004 | Pevarello et al. |
| 2004/0171075 A1 | 9/2004 | Flynn et al. |
| 2004/0180906 A1 | 9/2004 | Flynn et al. |
| 2004/0229937 A1 | 11/2004 | Dumas et al. |
| 2005/0014753 A1 | 1/2005 | Ding et al. |
| 2005/0165024 A1 | 7/2005 | Milanov et al. |
| 2005/0165031 A1 | 7/2005 | Grotzfield et al. |
| 2005/0192314 A1 | 9/2005 | Mehta et al. |
| 2005/0197371 A1 | 9/2005 | Milanov et al. |
| 2005/0267182 A1 | 12/2005 | Milanov et al. |
| 2005/0288286 A1 | 12/2005 | Flynn et al. |
| 2007/0037794 A1 | 2/2007 | Ungashe et al. |
| 2007/0078121 A1 | 4/2007 | Flynn et al. |
| 2007/0155764 A1 | 7/2007 | Lang et al. |
| 2007/0191336 A1 | 8/2007 | Flynn et al. |
| 2007/0244116 A1* | 10/2007 | Bannen et al. ............. 514/234.8 |
| 2008/0045531 A1 | 2/2008 | Flynn et al. |

(Continued)

FOREIGN PATENT DOCUMENTS

DE    4343831    6/1995

(Continued)

OTHER PUBLICATIONS

Gavezzotti, Accounts of Chemical Research, 27, 309-314 (1994).*
S.R. Byrn et al, Solid-State Chemistry of Drugs, 516 (2nd ed., 1999).*
S.L. Morissette et al., Advanced Drug Delivery Reviews, 56, 275-300, 275 (2004).*
J. Aaltonen et al., European Journal of Pharmaceutics and Biopharmaceutics, 71, 23-37, 26 (2009).*

(Continued)

*Primary Examiner* — James O Wilson
*Assistant Examiner* — Alexander R Pagano

(57) ABSTRACT

Compounds of the present invention find utility in the treatment of mammalian cancers and especially human cancers including, but not limited to, malignant melanomas, solid tumors, glioblastomas, ovarian cancer, pancreatic cancer, prostate cancer, lung cancers, breast cancers, kidney cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, gastrointestinal stromal tumors, colonic cancers, ocular diseases characterized by hyperproliferation leading to blindness including various retinopathies, diabetic retinopathy, rheumatoid arthritis, asthma, chronic obstructive pulmonary disease, mastocytosis, mast cell leukemia, and diseases caused by PDGFR-α kinase, PDGFR-β kinase, c-KIT kinase, cFMS kinase, c-MET kinase, and oncogenic forms, aberrant fusion proteins and polymorphs of any of the foregoing kinases.

7 Claims, No Drawings

U.S. PATENT DOCUMENTS

| | | | |
|---|---|---|---|
| 2008/0045706 | A1 | 2/2008 | Flynn et al. |
| 2008/0090856 | A1* | 4/2008 | Flynn et al. .................. 514/275 |
| 2008/0113967 | A1 | 5/2008 | Flynn et al. |
| 2008/0132506 | A1 | 6/2008 | Flynn et al. |
| 2008/0187978 | A1 | 8/2008 | Flynn et al. |
| 2008/0220497 | A1 | 9/2008 | Flynn et al. |
| 2008/0248487 | A1 | 10/2008 | Flynn et al. |
| 2008/0248548 | A1 | 10/2008 | Flynn et al. |
| 2008/0261961 | A1* | 10/2008 | Flynn et al. ................ 514/227.8 |
| 2009/0069310 | A1 | 3/2009 | Flynn et al. |
| 2009/0075986 | A1 | 3/2009 | Flynn et al. |
| 2009/0105230 | A1 | 4/2009 | Flynn et al. |
| 2009/0137021 | A1 | 5/2009 | Flynn et al. |
| 2009/0312349 | A1 | 12/2009 | Flynn et al. |

FOREIGN PATENT DOCUMENTS

| | | |
|---|---|---|
| EP | 0021228 | 1/1981 |
| EP | 0025232 | 3/1981 |
| EP | 0661276 | 7/1995 |
| EP | 0692483 | 1/1996 |
| EP | 0739884 | 10/1996 |
| EP | 0867435 | 9/1998 |
| EP | 0927555 | 7/1999 |
| EP | 928790 | 7/1999 |
| EP | 0956855 | 11/1999 |
| EP | 1281399 | 2/2003 |
| FR | 2337554 | 8/1977 |
| FR | 2396549 | 2/1979 |
| GB | 971307 | 9/1964 |
| GB | 1127875 | 9/1968 |
| GB | 1410279 | 10/1975 |
| GB | 2220206 | 1/1990 |
| JP | 59-15247 | 1/1984 |
| JP | 59177557 | 10/1984 |
| JP | 9221476 | 8/1997 |
| JP | 2000275886 | 10/2000 |
| JP | 20012687 | 7/2002 |
| WO | WO 91/19708 | 12/1991 |
| WO | WO 92/08693 | 5/1992 |
| WO | WO 94/18176 | 8/1994 |
| WO | WO 94/21617 | 9/1994 |
| WO | WO 94/24095 | 10/1994 |
| WO | WO 95/15954 | 6/1995 |
| WO | WO 95/29902 | 11/1995 |
| WO | WO 95/34540 | 12/1995 |
| WO | WO 96/16046 | 5/1996 |
| WO | WO 96/19477 | 6/1996 |
| WO | WO 97/34900 | 9/1997 |
| WO | WO 97/40028 | 10/1997 |
| WO | WO 98/22103 | 5/1998 |
| WO | WO 98/52558 | 11/1998 |
| WO | WO 99/15164 | 4/1999 |
| WO | WO 99/23091 | 5/1999 |
| WO | WO 99/23093 | 5/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/37622 | 7/1999 |
| WO | WO 99/59959 | 11/1999 |
| WO | WO 00/06550 | 2/2000 |
| WO | WO 00/07980 | 2/2000 |
| WO | WO 00/18738 | 4/2000 |
| WO | WO 00/21927 | 4/2000 |
| WO | WO 00/41698 | 7/2000 |
| WO | WO 00/42012 | 7/2000 |
| WO | WO 00/43384 | 7/2000 |
| WO | WO 00/55139 | 9/2000 |
| WO | WO 00/59506 | 10/2000 |
| WO | WO 01/12621 | 2/2001 |
| WO | WO 01/14372 | 3/2001 |
| WO | WO 01/74771 | 10/2001 |
| WO | WO 01/96298 | 12/2001 |
| WO | WO 02/14291 | 2/2002 |
| WO | WO 02/14311 | 2/2002 |
| WO | WO 02/28835 | 4/2002 |
| WO | WO 02/34727 | 5/2002 |
| WO | WO 02/060869 | 8/2002 |
| WO | WO 02/060876 | 8/2002 |
| WO | WO 02/062763 | 8/2002 |
| WO | WO 02/070662 | 9/2002 |
| WO | WO 03/005999 | 1/2003 |
| WO | WO 03/053368 | 7/2003 |
| WO | WO 03/059373 | 7/2003 |
| WO | WO 03/068223 | 8/2003 |
| WO | WO 03/072577 | 9/2003 |
| WO | WO 03/084539 | 10/2003 |
| WO | WO 2004/004720 | 1/2004 |
| WO | WO 2004/056783 | 7/2004 |
| WO | WO 2004/060306 | 7/2004 |
| WO | WO 2004/061084 | 7/2004 |
| WO | WO 2004/078128 | 9/2004 |
| WO | WO 2004/113352 | 12/2004 |
| WO | WO 2005/002673 | 1/2005 |
| WO | WO 2005/110994 | 11/2005 |
| WO | WO 2006/014290 | 2/2006 |
| WO | WO 2006/071940 | 7/2006 |
| WO | WO 2006/081034 | 8/2006 |
| WO | WO 2007/008917 | 1/2007 |
| WO | WO 2007/076473 | 7/2007 |
| WO | WO 2008/046003 | 4/2008 |
| WO | WO 2008/131276 | 10/2008 |

OTHER PUBLICATIONS

U.S. Appl. No. 11/721,026, filed Nov. 2, 2008, Flynn et al.
U.S. Appl. No. 12/238,997, filed Nov. 11, 20008, Flynn et al.
"Additions and Corrections", Journal of Medicinal Chemistry, 32(12):2583 (1989).
Aklilu, et al., "Increased PTHRP Production by a Tyrosine Kinase Oncogene, Tpr-Met: Rose of the Ras Signaling Pathway", American Journal of Physiology—Endocrinology and Metabolism, 271(2) pp. E277-E283 (1996).
Albericio, et al., "Synthesis of a Sulfaydantion Library", J. Comb. Chem., 3:290-300 (2001).
Almerico, et al., "On the Preparation of 1-aryl-2-heteroaryl- and 2-aryl-1-heteroaryl-pyrroles as Useful Building Blocks for Biologically Interesting Heterocycles", ARKIVOC (vi), Rudy Abramovitch Issue, pp. 129-142 (2001).
Anzai, et al., "Alkyl- and Arylthiation of Uracil and Indole", J. Heterocyclic Chem., 16:567-569 (1979).
Askew, et al., "Molecular Recognition with Convergent Functional Groups: 6. Synthetic and Structural Studies with a Model Receptor for Nucleic Acid Components", J. Am. Chem., 111:1082-1090 (1989).
Bais, et al., "Inhibition of Endogenous Wxalate Production: Biochemical Consideration of the Roles of Glycollate Oxidase and Lactate Dehydrogenase", Clinical Science, 76:303-309 (1989).
Baker, et al., "Irreversible Enzyme Inhibitors. 188. Inhibition of Mammalian Thymidine Phosphorylase", Journal of Medicinal Chemistry, 14:812-816 (1971).
Barker, et al., "Characterization of pp60c-src Tyrosine Kinase Activities Using a Continuous Assay: Autoactivation of the Enzyme is an Intermolecular Autophosphorylation Process", Biochemistry, 35:14843-14851 (1995).
Bausch, et al., "Proton-Transfer Chemistry of Urazoles and Related Imides, and Diacyl Hydrazides", J. Org. Chem., 56:5643-5651 (1991).
Benvenuti, et al., "Crystallization of Soluble Proteins in Vapor Diffusion for X-Ray Crystallography", Nature Protocols, 2(7):1633-1651 (2007).
Bosca, et al., "Circular Dichroism Analysis of Ligand-Induced Conformational Changes in Protein Kinase C", Biochem J., 290:827-832 (1993).
Boschelli, et al., "4-Anilino-3-quinolinecarbonitriles: An Emerging Class of Kinase Inhibitors", Current Topics in Medicinal Chemistry, 2:1051-1063 (2002).
Bourdonnec, et al., "Synthesis and Pharmacological Evaluation of New Pyrazolidine-3,5-diones as AT1 Angiotensin II Receptor Antagonists", J. Med. Chem., 43:2685-2697 (2000).
Boyer, "Small Molecule Inhibitors of KDR (VEGFR-2) Kinase: An Overview of Structure Activity Relationships", Current Topics in Medicinal Chemisty, 2:973-1000 (2002).

Brady, et al., "Fast Prediction and Visualization of Protein Binding Pockets with PASS". Journal of Computer-Aided Molecular Design, 14:383-401 (2000).

Brasher, et al., "C-Abul has High Intrinsic Tyrosine Kinase Activity that is Stimulatad by Mutation of the Src Homology 3 Domain and by Autophosphorylation at Two Distinct Regulatory Tyrosines", Journal of Biological Chemistry, 275:35631-35637 (2000).

Bullock, et al., "Prospects for Kinase Activity Modulators in the Treatment of Diabetes and Diabetic Complications", Current Topics in Medicinal Chemistry, 2:915-938 (2002).

Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).

Cardillo, et al., "Sulle 1,2-difenil-3.5-dichetopirazolidine", Gazz. Chim., Ital., 9:973-985 (1966)—Italian Language—English Summary.

Charmm "NHLBI LBC Computational Biophysics Section", CHARMM Documentation Index, http://www.lobos.nih.gov/Charmm/chmdoc.html, printed Mar. 4, 2005 (1 page).

Chen, et al., "Biochemical Evidence for the Autophosphorylation and Transphosphorylation of Transforming Growth Factor b Receptor Kinases", Proc. Natl. Acad. Sci. USA, 92:1565-1569 (1995).

Cheng, et al., "Novel Solution Phase Strategy for the Synthesis of Chemical Libraries Containing Small Organic Molecules", J. Am. Chem. Soc., 118:2567-2573 (1996).

Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).

Chu, et al., "Using Affinity Capillary Electrophoresis to Determine Binding Stoichiometries of Protein-Ligand Interactions", Biochemistry, 33:10616-10621 (1994).

Cirillo, et al. "The Non-Diaryl Heterocycle Classes of p38 MAP Kinase Inhibitors", Current Topics in Medicinal Chemistry, 2:1021-1035 (2002).

Closier, et al., "Nitrofuryl Heterocyclics. 1", Journal of Medicinal Chemistry, 13(4):638-640 (1970).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recognition", Electrophoresis, 19:367-382 (1998).

Cortes, et al., "Results of Imatinib Mesylate Therapy in Patients with Refractory or Recurrent Acute Myeloid Leukemia, High-Risk Myelodysplastic Syndrime, and Myeloproliferative Disorders", Cancer, 97(11):2760-2766 (2003).

Cross, et al., "Inhibition of Glycogen Synthase Kinase-3 by Insulin Mediated by Protein Kinase B", Nature, 378:785-789 (1995).

Dajani, et al., "Crystal Structure of Glycogen Synthase Kinas 3b: Structural Basis for Phosphate-Primed Substrate Specificity and Autoinhibition", Cell, 105:721-732 (2001).

Dajani, et al., "Structural Basis for Recruitment of Glycogen Synthase Kinase 3b to the Axin-APC Scaffold Complex", EMBO J., 22(3):494-501 (2003).

Daley, et al., "Induction of Chronic Myelogenous Leukemia in Mice by the P210bcr/abl Gene of the Philadelphia Chromosome", Science, 247:824-830 (1990) (8 pgs).

Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).

de Boer, et al., "Synthesis and Characterization of Conjugated Mono- and Dithiol Oligomers and Characterization of Their Self-Assembled Monolayers", Langmuir, 19:4272-4284 (2003).

de Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).

Deng, et al., "Expression, Characterization, and Crystallization of the Pyrophosphate-Dependent Phosphofructo-1-Kinase of *Borrelia burgdorferi*", Archives of Biochemistry and Biophysics, 371(2):326-331 (1999).

Dess, et al., "A Useful 12-I-5 Triacetoxyperiodiane (the Dess-Martin Periodiane) for Selective Oxidation of Primary or Secondary Alcohols and a Variety of Related 12-I-5 Species", J. Am. Chem., Soc., 113:7277-7287 (1991).

Dumas, "Preface", Current Topics in Medicinal Chemistry 2(9):i (2002) (1 Page).

Dumas, "Protein Kinase Inhibitors: Emerging Pharmacophores", Exp. Opin. Ther. Patents, 11(3):405-429 (2001).

Dumas, et al., "Discovery of a New Class of p38 Kinase Inhibitors", Bioorganic & Medicinal Chemistry Letters, 10:2047-2050 (2000).

Dumas, et al., "Recent Developments in the Discovery of Protein Kinase Inhibitors from the Urea Class", Current Opinion in Drug Discovery & Development, 7(5):600-616 (2004).

Ettmayer, et al., "Lessons Learned from Marketed and Investigational Prodrugs", Journal of Medicinal Chemistry, 47(10):2393-2404 (2004).

Ewing, "Critical Evaluation of Search Algorithms for Automated Molecular Docking and Database Screening", Journal of Computational Chemistry, 18(9):1175-1189 (1997).

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).

Fathalla, "Synthesis of New Pyrazolo[1,5-a]pyrimidine Derivative Using 5-Aminouracil and Ketene Dithiacetal", Arch Pharm Res, 22(6):571-574 (1999).

Fathalla, et al., "Synthesis of New Uracil-5-Sulfonamide Derivatives and Immuno-Stimulatory Effect of a Chemically Modified Hemolymph of *Biomphalaria alexandrina* on *Schistosoma manosi* Infected Mice", Arch Pharm Res., 26(5):358-366 (2003).

Fathalla, et al., "Synthesis of New Uracil-5-Sulphonamide-p-Phenyl Derivatives and Their Effect on *Biomphalaria alexandrina* Snail's Nucleoproteins", Arch. Pharm. Res., 23(2):128-138 (2000).

Flatt, et al., "Synthesis of Thiol Substituted Oligoanilines for Molecular Device Candidates", Tetrahedron Letters, 44:6699-6702 (2003).

Fletcher, et al., "Diagnosis of Gastrointestinal Stromal Tumors: A Consensus Approach", Human Pathology 33(5):459-465 (2002).

Frame, et al., "A Common Phosphate Binding Site Explains the Unique Substrate Specificity of GSK3 and Its Inactivation by Phosphorylation", Molecular Cell, 7:1321-1327 (2001).

Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).

Garcia-Tellado, et al., "Molecular Recognition in the Solid Waste State: Controlled Assembly of Hydrogen-Bonded Molecular Sheets", J. Am. Chem. Soc., 113:9265-9269 (1991).

Gishizky, et al., "Efficient Transplantation of BCR-ABL-Induced Chronic Myelogenous Leukemia-Like Syndrome in Mice", Proceedings of the National Academy of Sciences of the United States of America, 90(8):3755-3759 (1993) (6 pages).

Greene, et al., "Chapter 7: Protection for the Amino Group", in Protective Groups in Organic Synthesis, Third Edition, John Wiley: New York, pp. 494-653 (1999).

Griffith, et al., "TPAP: Tetra-n-propylammonium Perruthenate, A Mild and Convenient Oxidant for Alcohols", Aldrichimica Acta, 23(1):13-19 (1990).

Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).

Haar, et al., "Structure of GSK3b Reveals a Primed Phosphorylation Mechanism", Nature Structural Biology, 8(7):593-596 (2001).

Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).

Heegaard, et al., "Affinity Capillary Electrophoresis: Important Application Areas and Some Recent Developments", Journal of Chromatography B, 715:29-54 (1998).

Honda, et al., "Determination of the Association Constant of Monovalent Mode Protein-Sugar Interaction by Capillary Zone Electrophoresis", Journal of Chromatography, 597:377-382 (1992).
Hu, et al., "Capillary Electrophoresis for the Analysis of Biopolymers", Anal., Chem., 74:2833-2850 (2002).
Huang, et al., "Inhibition of Nucleoside Transport by Protein Kinase Inhibitors", The Journal of Pharmacology and Experimental Therapeutics, 304(2):753-760 (2003).
Hubbard, "Crystal Structure of the Activated Insulin Receptor Tyrosine Kinase in Complex with Peptide Substrate and ATP Analog", EMBO J., 16(18):5573-5581 (1997).
Hubbard, et al., "Crystal Structure of the Tyrosine Kinase Domain of the Human Insulin Receptor", Nature, 372:746-754 (1994).
Hughes, et al., "Modulation of the Glycogen Synthase Kinase-3 Family by Tyrosine Phosphorylation", EMBO J., 12(2):803-808 (1993).
Huse, et al., "Crystal Structure of the Cytoplasmic Domain of the Type I TGFb Receptor in Complex with FKBP12", Cell, 96:425-436 (1999).
Huse, et al., "The Conformational Plasticity of Protein Kinases", Cell, 109:275-282 (2002).
Huse, et al., "The TGFb Receptor Activation Process: An Inhibitor- to Substrate-Binding Switch", Molecular Cell, 8:671-682 (2001).
Igarashi, et al., "Antimicrobial Activities of 2-arylthio-N-alkylmaleimides", Journal of Industrial Microbiology, 9:91-96 (1992).
International Human Genome Sequencing Consortium, "Initial Sequencing and Analysis of the Human Genome", Nature, 409:860-921 (2001).
Ishida, et al., "Molecular Arrangement and Electrical Conduction of Self-Assembled Monolayers Made from Terphenyl Thiols", Surface Sciences, 514:187-193 (2002).
Islip, et al., "Nitrofuryl Heterocyclics 3", Journal of Medicinal Chemistry, 16(11):1308-1310 (1973).
Jackson, et al., "N-Terminal Mutations Activate the Leukemogenic Potential of the Myristoylated form of c-abl", EMBO, 8(2):449-456 (1989).
Jackson, et al., "Pyridinylimidazole Based p38 MAP Kinase Inhibitors", Current Topics in Medicinal Chemistry, 2:1011-1020 (2002).
Jiang, et al., ""Soft Docking": Matching of Molecular Surface Cubes", J. Mol. Biol., 219:79-102 (1991).
Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit",J. Med. Chem. ,50:3870-82, (2007).
Johnson, "Circular Dichroism Spectroscopy and The Vacuum Ultraviolet Region", Ann. Rev. Phys. Chem., 29:93-114 (1978).
Johnson, "Protein Secondary Structure and Circular Dichroism: A Practical Guide", Proteins: Structure, Function, and Genetics, 7:205-214 (1990).
Johnson, et al., "An Evaluation of the Effect of Light Stabilisers on the Exterior Durability of Polyester Powder Coatings for the Architectural Market", Surface Coatings International, 3:134-141 (1999).
Johnson, et al., "The Stereochemistry of Oxidation at Sulfur Oxidation of 2-Thiabicyclo[2.2.1]Hpetane", Tetrahedron, 25:5649-5653 (1969).
Kallander, et al., "4-Aryl-1,2,3-triazole: A Novel Template for a Reversible Methionine Aminopeptidase 2 Inhibitor, Optimized to Inhibit Angiogenesis in Vivo", J Med Chem 48: 5644-5647 (2005).
Katritzky, et al., "Novel Chromophoric Heterocycles Based on Maleimide and Naphthoquinone", J. Heterocyclic Chem., 26:885-892 (1989).
Kern, et al., "Synthese von Makromolekeln einheitlicher Brobe. II Mitt: Syntheses neuer Diol-oligo-urethane nach dem Duplikationsverfahren", Makromolekulara Chemie, 16:89-107 (1955)—German—English Summary (20 pages).
Kim, et al., "Solid Phase Synthesis of Benzamidine and Butylamine-Derived Hydantoin Libraries", Molecular Diversity, 3:129-132 (1998).
Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).

Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982)—English Translation (10.
Kuhn, et al., "The Genesis of High-Throughput Structure-Based Drug Discovery using Protein Crystallography", Analytical Techniques, Current Opinion in Chemical Biology, 6:704-710 (2002).
Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61:525-536 (2004).
Kundu, et al., "Depropargylation Under Palladium-Copper Catalysis: Synthesis of Diaryl Sulfides", Tetrahedron, 57:5885-5895 (2001).
Kurogi, et al., "Discovery of Novel Mesangial Cell Proliferation Inhibitors Using a Three-Dimensional Database Searching Method", J. Med. Chem., 44:2304-2307 (2001).
Kwong, et al., "A General, Efficient, and Inexpensive Catalyst System for the Coupling Aryl Iodides and Thiols", Organic Letters, 4(20):3517-3520 (2002).
Laskowski, "SURFNET: A Program for Visualizing Molecular Surfaces, Cavities, and Intermolecular Interactions", Journal of Molecular Graphics, 13:323-330 (1995).
Leca, et al., "A New Practical One-Pot Access to Sulfonimidates", Organic Letters, 4(23):4093-4095 (2002).
Lefevre, et al., "Roles of Stem Cell Factor/c-Kit and Effects of Glivecâ/STI571 in Human Uveal Melanoma Cell Tumorigenesis", Journal of Biological Chemistry, 279(30):31769-31779 (2004).
Lesort, et al., "Insulin Transiently Increases Tau Phosphorylation: Involvement of Glycogen Synthase Kinase-3b and Fyn Tyrosine Kinase", Journal of Neurochemistry, 72(2):576-584 (1999).
Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).
Li, et al., "Targeting Serine/Threonine Protein Kinase B/Akt and Cell-cycle Checkpoint Kinases for Treating Cancer", Current Topics in Medicinal Chemistry, 2:939-971 (2002).
Li, et al., "The P190, P210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).
Link, et al., "Synthesis of 8-Substituted 5-Deazaflavins", J. Heterocyclic Chem, 22:841-848 (1985).
Lipinski, et al., "Experimental and Computational Approaches to Estimate Solubility and Permeability in Drug Discovery and Development Settings", Advanced Drug Delivery Reviews, 23:3-25 (1997).
Lohse, et al., The Palladium Catalyzed Suzuki Coupling of 2- and 4-Chloropyridines, Synlett 1: 45-48 (1999).
Loren, et al., "NH-1,2,3-Triazoles from Azidomethyl Pivalate and Carbamates: Base-Labile N-Protecting Groups", SYNLETT, 18:2847-2850 (2005).
Lorenzi, et al., "Amino Acid Ester Prodrugs of 2-Bromo-5,6-dichloro-1-(b-D-ribofuranosyl)benzimidazole Enhance Metabolic Stability in Vitro and in Vivo", Journal of Pharmacology and Experimental Therapeutics, 314(2):883-890 (2005).
Lowinger, et al., "Design and Discovery of Small Molecules Targeting Raf-1 Kinase", Current Pharmaceutical Design, 8:2269-2278 (2002) (11 pages).
Ma, et al., "c-MET Mutational Analysis in Small Cell Lung Cancer: Novel Juxtamembrane Domain Mutations Regulating Cytoskeletal Functions", Cancer Research, 63:6272-6281 (2003).
Ma, et al., "c-Met: Structure, Functions and Potential for Therapeutic Inhibition", Cancer and Metastasis Reviews, 22:309-325 (2003).
Mallkpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).

Mamaev, et al., "Synthesis of 2,5'-Bipyrimidines from Substituted 5-Cyanopyrimidines", Khimiya Geterotsiklicheskikh Soedinenni, 24(3):371-375—(1988)—English Translation.

Smith, et al. March's Advanced Organic Chemistry: Reactions, Mechanisms, and Structure, Fifth Edition, Smith and March Editors, Wiley-Interscience Publication (2001) (4 pages).

Smith, et al., "Tautomerism", from March's Advanced Organic Chemistry, Fifth Edition, Smith and March Editors, Wiley-Interscience Publication (2001) pp. 69-74.

Martinez, et al., "First Non-ATP Competitive Glycogen Synthase Kinase 3b (GSK-3b) Inhibitors: Thiadizolidinones (TDZD) as Potential Drugs for the Treatment of Alzheimers Disease", J. Med. Chem., 45(2002)1292-1299 (2002).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, 64: 4170-4177 (2000).

McPherson, "Current Approaches to Macromolecular Crystallization", Eur. J. Biochem, 189:1-23 (1990).

Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).

Medebielle, et al., "A New Convenient Synthesis of 5-Aryl Uracils Using SRN1 Aromatic Nucleophilic Substitution", Tetrahedron Letters, 34(21):3409-3412 (1993).

Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979)—English Translation (12 pages).

Morris, et al., "Automated Docking of Flexible Ligands to Macromolecules", AutoDock Website, www.scripps.edu/mb/olson/doc/autodock/, printed Mar. 3, 2005 (3 pages).

Morris, et al., "Automated Docking Using a Lamarckian Genetic Algorithm and an Empirical Binding Free Energy Function", Journal of Computational Chemistry, 19(14):1639-1662 (1998).

Morstyn, et al., "Stem Cell Factor Is a Potent Synergistic Factor in Hematopoiesis", Oncology, 51:205-214 (1994).

Moss, et al., "Basic Terminology of Stereochemistry", Pure & Appl. Chem., 68(12):2193-2222 (1996).

Muller, "Glossary of Terms Used in Physical Organic Chemistry", Pure & Appl. Chem., 66(5):1077-1184 (1994).

Muller, et al., "A General Synthesis of 4-Substituted 1,1-Dioxo-1,2,5-thiadiazolidin-3-ones Derived from a-Amino Acids", J. Org. Chem., 54:4471-473 (1989).

Murayama, et al., "JNK (c-Jun NH2 Terminal Kinase) and p38 During Ischemia Reperfusion Injury in the Small Intestine" Transplantation, 81(9):1325-1330 (2006).

Mutlib, et al., "Disposition of 1-[3-(Aminomethyl)phenyl]-N-[3-fluoro-2'-(methylsulfonyl)-[1,1'-biphenyl]-4-yl]-3(trifluoromethyl)-1H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).

Mutlib, et al., "P450-Mediated Metabolism of 1-[3-(Aminomethyl)phenyl]-N-[3-fluoro-2'-(methylsulfonyl)-[1,1'-biphenyl]-4-yl]-3(trifluoromethyl)-1H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).

Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. Nov. 1973.

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nagar, et al., "Structural Basis for the Autoinhibition of c-Abl Tyrosine Kinase", Cell, 112:859-871 (2003).

Nakopoulou, et al., "c-Met Tyrosine Kinase Receptor Expression is Associated with Abnormal b-catenin Expression and Favourable Prognostic Factors in Invasive Breast Carcinoma", Histopathology, 36:313-325 (2000).

Nantaka-Namirski, et al., "Condensation Reaction of Ethyl (4-Uracil)-Acetate with Ethyl Orthoformate", ACTA Polon. Pharm XXVII(5):455-463 (1971).

National Academy of Sciences, "Abstracts of Papers Presented at the Autumn Meeting, Nov. 14-16, 1960", Science, 132:1488-1501 (1960) (15 pages).

Nicolaou, et al.,"Molecular Design and Chemical Synthesis of a Highly Potent Epothilone", ChemMedChem, 1:41-44 (2006).

Nikolaev, et al., "Solubility Polytherm in the System HNO3-H2O-(C4H9O)PO(C4H9)2", Doklady Akademii Nauk SSSR, 160(4):841-844 (1965)—English Translation.

Nofal, et al., "Synthesis of Novel Uracil-5-Sulphonamide Derivatives of Possible Biological Activity", Egypt J. Chem., 33(4):375-380 (1990).

O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).

O'Neill, "Targeting Signal Transduction as a Strategy to Treat Inflammatory Diseases", Nature Review Drug Discovery, Published Online Jun. 9, 2006, www.nature.com/reviews/drugdisc (15 pages).

Okano, et al., "o-Bromophenylzinc Compound: A Readily Available and Efficient Synthetic Equivalent of o-Phenylene 1-Anion 2-Cation", Tetrahedron Letters 39:3001-3004 (1998).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Parang, et al., "Mechanism-based Design of a Protein Kinase Inhibitor", Nature Structural Biology, 8(1):37-41 (2001).

Pargellis, et al., "Inhibition of p38 MAP Kinase by Utilizing a Novel Allosteric Binding Site", Nature Structural Biology, 9(4):268-272 (2002).

Park, et al., "Mechanism of met Oncogene Activation", Cell, 45:895-904 (1986).

Pearlman, et al., "Assisted Model with Energy Refinement", Amber Home Page, amber.scripts.edu (9 pages), (Mar. 4, 2005).

Pedersen, "The Preparation of Some N-Methyl-1,2,3-Triazoles", Acta Chimica Scandinavica, 13(5):888-892 (1959).

Peng, et al., "Identification of Novel Inhibitors of BCR-ABL Tyrosine Kinase via Virtual Screening", Bioorganic & Medicinal Chemistry Letters, 13:3693-3699 (2003).

Pereira, et al., "The Role of c-kit and Imatinib Mesylate in Uveal Melonoma", Journal of Carcinogenesis, 4:19 (2005) (8 pages).

Picard, et al., "Inhibitors of Acyl-CoA: Cholesterol O-Acyltrasferase. 17. Structure-Activity Relationships of Several Series of Compounds Derived from N-Chlorosulfonyl Isocyanate", J. Med. Chem., 39:1243-1252 (1996).

Pluk, et al., "Autoinhibition of c-Abl", Cell, 108:247-259 (2002).

Ponzetto, et al., "A Novel Recognition Motif for Phosphatidylinositol 3-Kinase Binding Mediates Its Association with the Hepatocyte Growth Factor/Scatter Factor Receptor", Molecular and Cellular Biology, 13(8):4600-4608 (1993).

Raimbault, et al., "Effects of pH and KCl on the Conformations of Creatine Kinase from Rabbit Muscle", Eur. J. Biochem., 234:570-578 (1995).

Rebek, et al. "Convergent Functional Groups: Synthetic and Structural Studies", J. Am. Chem. Soc., 107:7476-7481 (1985).

Rebek, et al., "Convergent Functional Groups. 2. Structure and Selectivity in Olefin Epoxidation with Peracids", J. Org. Chem., 51:1649-1653 (1986).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Pyrazole Urea-Based Inhibitors of p38 MAP Kinase: From Lead Compound to Clinical Candidate", J. Med. Chem., 45:2994-3008 (2002).

Regan, et al., "Structure-Activity Relationships of the p38a MAP Kinase Inhibitor 1-(5-tert-Butyl-2-p-tolyl-2H-pyrazol-3-yl)-3-[4-(2-morpholin-4-yl-ethoxy)naph-thalen-1-yl]urea (BIRB 796)", J. Med. Chem., 46:4676-4686 (2003).

Rooney, et al., "Inhibitors of Gylcolic Acid Oxidase. 4-Substituted 3-Hydroxy-1H-pyrrole-2,5-dione Derivatives", J. Med. Chem., 26(5):700-714 (1983).

Roux, et al., "ERK and p38 MAPK-Activated Protein Kinases: a Family of Protein Kinases with Diverse Biological Functions", Microbiology and Molecular Biology Reviews, 68(2):320-344 (2004).

Rowley, "A New Consistent Chromosomal Abnormality in Chronic Myelogenous Leukaemia Identified by Quinacrine Fluorescence and Giemsa Staining", Nature, 243:290-293 (1973).

Russell, et al., "3-[3-(Piperdin-1-yl)propyl]indoles as Highly Selective h5-HT1D Receptor", J. Med. Chem., 42:4981-5001 (1999).

Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41:4629-4632 (2000).

Sakamoto, et al., "Condensed Heteroaromatic Ring Systems. XIX. Synthesis and Reactions of 5-(Tributylstannyl)Isoxazoles", Tetrahedron, 47(28):5111-5118 (1991).

Sakuma, et al., "c-kit Gene Mutations in Intracranial Germinomas", Cancer Sci, 95(9):716-720 (2004).

Satsangi, et al., "1-(4-Substituted-thiazol-2-yl)hydatoins as Anti-inflammatory and CNS-Active Agents", Pharmazie, 38:341-342 (1983).

Schiering, et al, "Crystal Structure of the Tyrosine Kinase Domain of the Hepatocyte Growth Factor Receptor c-Met and its Complex with the Microbial Alkaloid K-252b", Proc. Nat'l Acad. Sci 100(22): 12654-12659 (2003).

Schindler, et al., "Structural Mechanism for STI-571 Inhibition of Abelson Tyrosine Kinase", Science, 289:1938-1942 (2000).

Schmidt, et al., "Germline and Somatic Mutations in the Tyrosine Kinase Domain of the MET proto-oncogene in Papillary Renal Carcinomas", Nature Genetics, 16:68-73 (1997).

Schmidt, et al., "Novel Mutations of the MET Proto-oncogene in Papillary Renal Carcinomas", Oncogene, 18:2343-2350 (1999).

Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).

Seminario, et al., "Theoretical Study of a Molecular Resonant Tunneling Diode", J. Am. Chem. Soc., 122:3015-3020 (2000).

Shah, et al., "Circular Dichroic Studies of Protein Kinase C and its Interactions with Calcium and Lipid Vesicles", Biochimica et Biophysica Acta, 1119:19-26 (1992).

Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).

Shinkai, et al., "Coenzyme Models, Part 45. Synthesis of Atropisomeric Flavins and their Novel Redox-induced Racemisation", J. Chem. Soc. Perkin Trans., pp. 313-319 (1988).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).

Tanis, et al., "Two Distinct Phosphorylation Pathways Have Additive Effects on Abl Family Kinase Activation", Molecular and Cellular Biology, 23(11):3884-3896 (2003).

Teague, "Implications of Protein Flexibility for Drug Discovery", Nature Reviews Drug Discovery, 2:527-541 (2003).

Tominaga, et al., "General model for Estimation of the Inhibition of Protein Kinases Using Monte Carlo Simulations", J. Med. Chem., 47:2534-2549 (2004).

Tremblay, et al., "Efficient Solid-Phase Synthesis of Sulfahydantoins", J. Comb. Chem., 4:429-435 (2002).

"Trilateral Project WM4—Comparative Studies in New Technologies: Report on Comparative Study on Protein 3-Dimensional Structure Related Claims—Annex 3: Comments of the USPTO", Vienna, Austria, Nov. 4-8, pp. 58-79 (2002).

Tsuzuki, et al., "Synthesis and Structure-Activity Relationships of Novel 7-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).

Van Etten, "Cycling, Stressed-Out and Nervous: Cellular Functions of c-Abl", Trends in Cell Biology, 9:179-186 (1999).

Venter, et al., "The Sequence of the Human Genome", Science, 291:1304-1351, Feb. 16, 2001; Erratum, Jun. 8, 2001 (49 pages).

Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).

Wan, et al., "Mechanism of Activation of the RAF-ERK Signaling Pathway by Oncogenic Mutations of B-RAF", Cell, 116:855-867 (2004).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wentland, et al., "3-Quinolinecarboxamides. A Series of Novel Orally-Active Antiherpetic Agents", J. Med. Chem., 36:1580-1596 (1993).

Wilson, et al., "The Structural Basis for the Specificity of Pyridinylimidazole Inhibitors of p38 Map Kinase", Chemistry & Biology, 4(6):423-431 (1997).

Wilson, et al., "Laser-Jet Delayed Trapping: Electron-Transfer Trapping of the Photoenol from 2-Methylbenzophenone", J. Am. Chem. Soc., 109:4743-4745 (1987).

Wolter, et al., "Copper-Catalyzed Coupling of Aryl Iodides with Aliphatic Alcohols", Organic Letters, 4(6):973-976 (2002).

Wrana, et al., "Mechanism of Activation of the TGF-b Receptor", Nature, 370:341-347 (1994).

Wu, et al., "Discovery of a Novel Family of CDK Inhibitors with the Program LIDAEUS: Structual Basis for Ligand-Induced Disordering of the Acivation Loop", Structure, 11:399-410 (2003).

Yang, et al., "Molecular Mechanism for the Regulation of Protein Kinase B/Akt by Hydrophobic Motif Phosphorylation", Molecular Cell, 9:1227-1240 (2002).

Yang, et al., "Palladium-Catalyzed Amination of Arly Halides and Sulfonates", Journal of Organometallic Chemistry, 576:125-146 (1999).

Yarden, et al., "Human Proto-oncogene c-kit: a New Cell Surface Receptor Tyrosine Kinase for an Unidentified Ligand", The EMBO Journal, 6(11):3341-3351 (1987).

Yoneda, et al., "A New Synthesis of Purines", J.C.S. Chem. Comm., p. 551 (1974).

Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).

Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase", Journal of Medicinal Chemistry, 19(1):71-98 (1976).

Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).

Yu, et al., "Frequency of TPR-MET Rearrangement in Patients with Gastric Carcinoma and in First-Degree Relatives", Cancer, 88(8):1801-1806 (2000).

Zaidi, et al., "New Anti-Mycobacterial Hydantoins", Pharmazie, 35:755-756 (1980).

Zhen, et al., "Structural and Functional Domains Critical for Constitutive Activation of the HGF-Receptor (Met)", Oncogene, 9(6):1691-1697 (1994).

Zvilichovsky, et al., "Aminolysis and Polymerization of 3-(p-Toluenesulfonoxy) Hydantoin", Israel Journal of Chemistry, 7:547-554 (1969).

International Preliminary Search Report on Patentability for PCT/US2009/62575, mailed Dec. 24, 2009 (6 pages).

* cited by examiner

N-ACYL UREAS EXHIBITING ANTI-CANCER AND ANTI-PROLIFERATIVE ACTIVITIES

CROSS-REFERENCE TO RELATED APPLICATIONS

This application claims the benefit of U.S. Provisional Application No. 61/109,309 filed Oct. 29, 2008. This provisional application is incorporated by reference herein in its entirety.

SEQUENCE LISTING

The instant application contains a Sequence Listing which has been submitted via EFS-Web and is hereby incorporated by reference in its entirety. Said ASCII copy, created on Dec. 14, 2009, is named 22035111.txt, and is 13,485 bytes in size.

FIELD OF THE INVENTION

The present invention relates to novel kinase inhibitors and modulator compounds useful for the treatment of various diseases. More particularly, the invention is concerned with such compounds, methods of treating diseases, and methods of synthesis of the compounds. Preferably, the compounds are useful for the modulation of kinase activity of VEGFR-2 (KDR), c-MET, FLT-3c-KIT, PDGFRα, PDGFRβ, c-FMS kinase, and disease causing polymorphs and fusion proteins thereof.

BACKGROUND OF THE INVENTION

Several members of the protein kinase family have been clearly implicated in the pathogenesis of various proliferative and myeloproliferative diseases and thus represent important targets for treatment of these diseases. Some of the proliferative diseases relevant to this invention include cancer, rheumatoid arthritis, atherosclerosis, and retinopathies. Important examples of kinases which have been shown to cause or contribute to the pathogenesis of these diseases include c-ABL kinase and the oncogenic fusion protein BCR-ABL kinase, c-KIT kinase, c-MET, FGFR kinase family, PDGF receptor kinase, VEGF receptor kinases, FLT kinase family, the HER family and the cFMS kinase family. When such kinases are implicated in human disease, a kinase may present as an amplified kinase (i.e. overexpression of HER1 or HER2), a mutated kinase (i.e. c-KIT D816V) or an aberrant fusion protein (i.e. BCR-ABL).

c-KIT (KIT, CD117, stem cell factor receptor) is a 145 kDa transmembrane tyrosine kinase protein that acts as a type-III receptor (Pereira et al. J Carcin. (2005), 4: 19). The c-KIT proto-oncogene, located on chromosome 4q11-21, encodes the c-KIT receptor, whose ligand is the stem cell factor (SCF, steel factor, kit ligand, mast cell growth factor, Morstyn G, et al. *Oncology* (1994) 51(2):205; Yarden Y, et al. *Embo J* (1987) 6(11):3341). The receptor has tyrosine-protein kinase activity and binding of the ligands leads to the autophosphorylation of KIT and its association with substrates such as phosphatidylinositol 3-kinase (PI3K). Tyrosine phosphorylation by protein tyrosine kinases is of particular importance in cellular signalling and can mediate signals for major cellular processes, such as proliferation, survival, differentiation, apoptosis, attachment, invasiveness and migration. Defects in KIT are a cause of piebaldism, an autosomal dominant genetic developmental abnormality of pigmentation characterized by congenital patches of white skin and hair that lack melanocytes. Gain-of-function mutations of the c-KIT gene and the expression of phosphorylated KIT are found in most gastrointestinal stromal tumors and mastocytosis. Further, almost all gonadal seminomas/dysgerminomas exhibit KIT membranous staining, and several reports have clarified that some (10-25%) have a c-KIT gene mutation (Sakuma, Y. et al. *Cancer Sci* (2004) 95(9): 716). KIT defects have also been associated with testicular tumors including germ cell tumors (GCT) and testicular germ cell tumors (TGCT).

The role of c-KIT expression has been studied in hematologic and solid tumours, such as acute leukemias (Cortes J. et al. *Cancer* (2003) 97(11): 2760) and gastrointestinal stromal tumors (GIST, Fletcher J. et al. *Hum Pathol* (2002) 33(5): 459). The clinical importance of c-KIT expression in malignant tumors relies on studies with Gleevec® (imatinib mesylate, STI571, Novartis Pharma AG Basel, Switzerland) that specifically inhibits tyrosine kinase receptors (Lefevre G. et al. *J Biol Chem* (2004) 279(30): 31769). Moreover, a clinically relevant breakthrough has been the finding of anti-tumor effects of this compound in GIST, a group of tumors regarded as being generally resistant to conventional chemotherapy (de Silva C M, Reid R *Pathol Oncol Res* (2003) 9(1): 13-19). GIST most often become Gleevec resistant and molecularly targeted small therapies that target c-KIT secondary mutations remain elusive.

c-MET is a unique receptor tyrosine kinase (RTK) located on chromosome 7p and activated via its natural ligand hepatocyte growth factor. c-MET is found mutated in a variety of solid tumors (Ma P. C. et al. *Cancer Metastasis* (2003) 22: 309). Mutations in the tyrosine kinase domain are associated with hereditary papillary renal cell carcinomas (Schmidt L et al. *Nat. Genet.* (1997) 16: 68; Schmidt L, et al. *Oncogene* (1999) 18: 2343), whereas mutations in the sema and juxtamembrane domains are often found in small cell lung cancers (Ma P. C. et al. *Cancer Res* (2003) 63: 6272). Many activating mutations are also found in breast cancers (Nakopoulou et al. *Histopath* (2000) 36(4): 313). The panoply of tumor types for which c-MET mediated growth has been implicated suggests this is a target ideally suited for modulation by specific c-MET small molecule inhibitors.

The TPR-MET oncogene is a transforming variant of the c-MET RTK and was initially identified after treatment of a human osteogenic sarcoma cell line transformed by the chemical carcinogen N-methyl-N'-nitro-N-nitrosoguanidine (Park M. et al. *Cell* (1986) 45: 895). The TPR-MET fusion oncoprotein is the result of a chromosomal translocation, placing the TPR3 locus on chromosome 1 upstream of a portion of the c-MET gene on chromosome 7 encoding only for the cytoplasmic region. Studies suggest that TPR-MET is detectable in experimental cancers (e.g. Yu J. et al. *Cancer* (2000) 88: 1801). Dimerization of the $M_r$65,000 TPR-MET oncoprotein through a leucine zipper motif encoded by TPR leads to constitutive activation of the c-MET kinase (Zhen Z. et al. *Oncogene* (1994) 9: 1691). TPR-MET activates wild-type c-MET RTK and can activate crucial cellular growth pathways, including the Ras pathway (Aklilu F. et al. *Am J Physiol* (1996) 271: E277) and the phosphatidylinositol 3-kinase (PI3K)/AKT pathway (Ponzetto C. et al. *Mol Cell Biol* (1993) 13: 4600). Conversely, in contrast to c-MET RTK, TPR-MET is ligand independent, lacks the CBL-like SH2 domain binding site in the juxtamembrane region in c-MET, and is mainly cytoplasmic. c-MET immunohistochemical expression seems to be associated with abnormal β-catenin expression, a hallmark feature of epithelial to mesynchemal transition (EMT) and provides good prognostic and predictive factors in breast cancer patients.

The majority of small molecule kinase inhibitors that have been reported have been shown to bind in one of three ways.

Most of the reported inhibitors interact with the ATP binding domain of the active site and exert their effects by competing with ATP for occupancy. Other inhibitors have been shown to bind to a separate hydrophobic region of the protein known as the "DFG-in-conformation" pocket wherein such a binding mode by the inhibitor causes the kinase to adopt the "DFG-out" conformation, and still others have been shown to bind to both the ATP domain and the "DFG-in-conformation" pocket again causing the kinase to adopt the "DGF-out" conformation. Examples that induce the kinase to adopt the "DGF-out" conformation can be found in Lowinger et al, *Current Pharmaceutical Design* (2002) 8: 2269; Dumas, J. et al., *Current Opinion in Drug Discovery & Development* (2004) 7: 600; Dumas, J. et al, WO 2003068223 A1 (2003); Dumas, J., et al, WO 9932455 A1 (1999), and Wan, P. T. C., et al, *Cell* (2004) 116: 855.

Physiologically, kinases are regulated by a common activation/deactivation mechanism wherein a specific activation loop sequence of the kinase protein binds into a specific pocket on the same protein which is referred to as the switch control pocket. Such binding occurs when specific amino acid residues of the activation loop are modified for example by phosphorylation, oxidation, or nitrosylation. The binding of the activation loop into the switch pocket results in a conformational change of the protein into its active form (Huse, M. and Kuriyan, J. *Cell* (2002) 109: 275).

SUMMARY OF THE INVENTION

Compounds of the present invention find utility in the treatment of mammalian cancers and especially human cancers including, but not limited to, solid tumors, melanomas, glioblastomas, ovarian cancer, pancreatic cancer, prostate cancer, lung cancers, breast cancers, kidney cancers, cervical carcinomas, metastasis of primary tumor sites, myeloproliferative diseases, leukemias, papillary thyroid carcinoma, non small cell lung cancer, mesothelioma, hypereosinophilic syndrome, gastrointestinal stromal tumors, colonic cancers, ocular diseases characterized by hyperproliferation leading to blindness including various retinopathies, rheumatoid arthritis, asthma, chronic obstructive pulmonary disorder, mastocytosis, mast cell leukemia, and diseases caused by PDGFR-α kinase, PDGFR-β kinase, c-KIT kinase, cFMS kinase, c-MET kinase, and oncogenic forms, aberrant fusion proteins and polymorphs of any of the foregoing kinases.

In a first aspect, compounds the formula Ia are described herein:

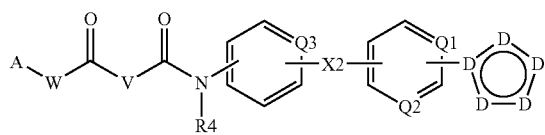

Ia and pharmaceutically acceptable salts, hydrates, solvates, prodrugs, and tautomers thereof;
wherein Q1, Q2, and Q3, are each individually and independently selected from the group consisting of N and CH and wherein at least one of Q1 and Q2 are N;
and wherein the ring containing Q1 and Q2 may be optionally substituted with (R20)$_x$ moieties;
each D is individually taken from the group consisting of C, CH, C—R20, N—Z3, N, and O, such that the resultant ring is taken from the group consisting of pyrazolyl, isoxazolyl, triazolyl and imidazolyl;
and wherein the ring containing Q3 may be optionally substituted with one to three R16 moieties;
V is NR4, or

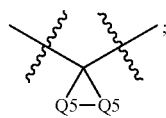

each Q5 is C(Z2B)$_2$;
W is a direct bond, —[C(R13)R14]$_m$—, —[C(R13)R14]$_m$NR4-, or NR4;
A is selected from the group consisting of indanyl, tetrahydronapthyl, thienyl, phenyl, naphthyl, pyrazinyl, pyridazinyl, triazinyl, pyridinyl, and pyrimidinyl;
X2 is —O—;
when A has one or more substitutable sp2-hybridized carbon atoms, each respective sp2 hybridized carbon atom may be optionally substituted with a Z1B substituent;
when A has one or more substitutable sp3-hybridized carbon atoms, each respective sp3 hybridized carbon atom may be optionally substituted with a Z2B substituent;
each Z1B is independently and individually selected from the group consisting of hydrogen, C1-6alkyl, branched C3-C7alkyl, halogen, fluoroC1-C6alkyl wherein the alkyl moiety can be partially or fully fluorinated, C1-C6alkoxy, fluoroC1-C6alkoxy wherein the alkyl moiety can be partially or fully fluorinated, and —(CH$_2$)$_n$CN;
each Z2B is independently and individually selected from the group consisting of hydrogen, C1-C6alkyl, and branched C3-C7alkyl;
each Z3 is independently and individually selected from the group consisting of hydrogen, C1-C6alkyl, branched C3-C7alkyl, C3-C8cycloalkyl, fluoroC1-C6alkyl wherein the alkyl moiety can be partially or fully fluorinated, hydroxyC2-C6alkyl-, R5C(O)(CH$_2$)$_n$—, (R4)$_2$NC(O)C1-C6alkyl-, R8C(O)N(R4)(CH$_2$)$_q$—, —(CH$_2$)$_q$CN, —(CH$_2$)$_q$—R5, and —(CH$_2$)$_q$N(R4)$_2$;
each R2 is selected from the group consisting of hydrogen, R17-substituted aryl-, C1-C6alkyl, branched C3-C8alkyl, R19 substituted C3-C8cycloalkyl-, and fluoroC1-C6alkyl- wherein the alkyl is fully or partially fluorinated;
each R3 is independently and individually selected from the group consisting of hydrogen, C1-C6alkyl, branched C3-C7alkyl, and C3-C8cycloalkyl;
each R4 is independently and individually selected from the group consisting of hydrogen, C1-C6alkyl, hydroxyC1-C6alkyl-, dihydroxyC1-C6alkyl-, C1-C6alkoxyC1-C6alkyl-, branched C3-C7alkyl, hydroxyl substituted branched C3-C6alkyl-, C1-C6alkoxy branched C3-C6alkyl-, dihydroxy substituted branched C3-C6alkyl-, —(CH$_2$)$_p$N(R7)$_2$, —(CH$_2$)$_p$R5, —(CH$_2$)$_p$C(O)N(R7)$_2$, —(CH$_2$)C(O)R5, —(CH$_2$)$_n$C(O)OR3, and R19 substituted C3-C8 cycloalkyl-;
each R5 is independently and individually selected from the group consisting of

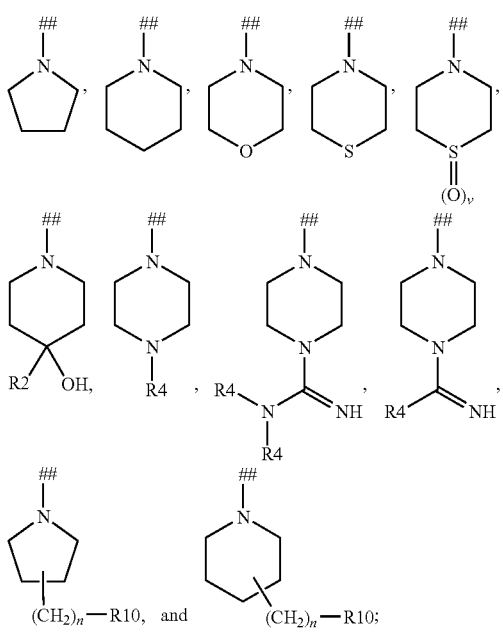

and wherein the symbol (##) is the point of attachment to respective R4, R7, R8, R20 or Z3 moieties containing a R5 moiety;

each R7 is independently and individually selected from the group consisting of hydrogen, C1-C6alkyl, hydroxyC2-C6alkyl-, dihydroxyC2-C6alkyl-, C1-C6alkoxyC2-C6alkyl-, branched C3-C7alkyl, hydroxy substituted branched C3-C6alkyl-, C1-C6alkoxy branched C3-C6alkyl-, dihydroxy substituted branched C3-C6alkyl-, —(CH$_2$)$_q$R5, —(CH$_2$)$_n$C(O)R5, —(CH$_2$)$_n$C(O)OR3, R19 substituted C3-C8cycloalkyl- and —(CH$_2$)$_n$R17;

each R8 is independently and individually selected from the group consisting of C1-C6alkyl, branched C3-C7alkyl, fluoroC1-C6alkyl- wherein the alkyl moiety is partially or fully fluorinated, R19 substituted C3-C8cycloalkyl-, phenyl, phenylC1-C6alkyl-, OH, C1-C6alkoxy, —N(R3)$_2$, —N(R4)$_2$, and R5;

each R10 is independently and individually selected from the group consisting of —CO$_2$H, —CO$_2$C1-C6alkyl, —C(O)N(R4)$_2$, OH, C1-C6alkoxy, and —N(R4)$_2$;

R13 and R14 are each individually and independently selected from the group consisting of hydrogen, C1-C6alkyl, branched C3-C8alkyl, fluoroC1-C6alkyl- wherein the alkyl is fully or partially fluorinated, hydroxyl substituted C1-C6alkyl-, C1-C6alkoxy substituted C1-C6alkyl-, hydroxyl substituted branched C3-C8alkyl-, and alkoxy substituted branched C3-C8alkyl;

each R16 is independently and individually selected from the group consisting of hydrogen, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, R3 substituted C2-C3alkynyl- and nitro;

each R17 is independently and individually selected from the group consisting of hydrogen, C1-C6alkyl, branched C3-C7alkyl, hydroxyC2-C6alkyl-, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, and nitro;

each R19 is independently and individually selected from the group consisting of hydrogen, OH and C1-C6alkyl;

each R20 is independently and individually selected from the group consisting of hydrogen, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, hydroxyC1-C6alkyl-, C1-C6alkoxyC1-C6alkyl-, C1-C6alkoxy, fluoroC1-C6alkoxy- wherein the alkyl moiety can be partially or fully fluorinated, —N(R3)$_2$, —N(R4)$_2$, —(CH$_2$)$_n$R5, —(CH$_2$)$_n$N(R3)C(O)R3, —(CH$_2$)$_n$C(O)N(R3)$_2$ and nitro;

each m is independently and individually 1-3, each n is independently and individually 0-6; each p is independently and individually 1-4; each q is independently and individually 2-6; each v is independently and individually 1 or 2; each x is independently and individually 0-2;

stereoisomers, regioisomers and tautomers of such compounds.

In some embodiments,

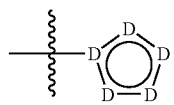

is selected from the group consisting of

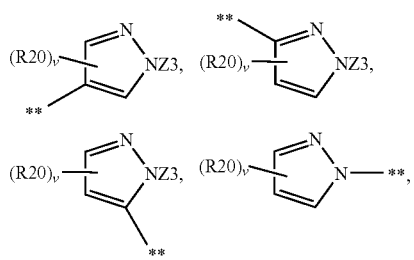

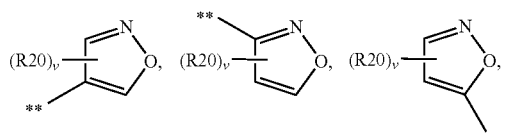

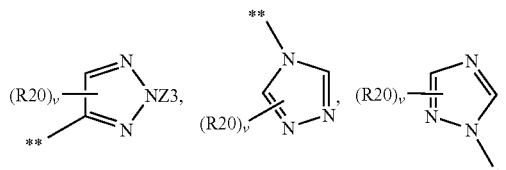

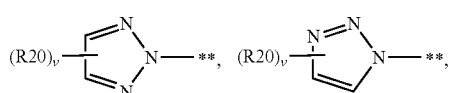

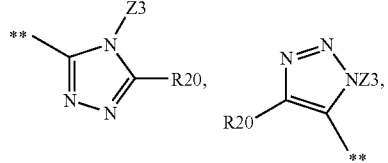

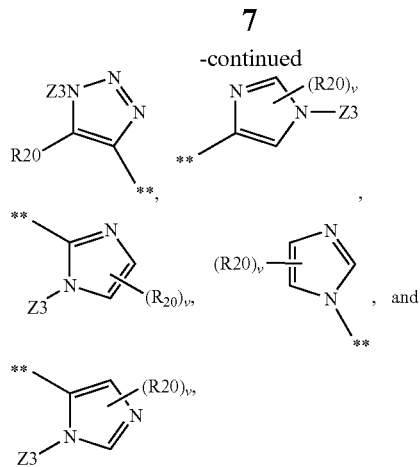

wherein the symbol (**) indicates the point of attachment to the heteroaryl Q1, Q2 containing ring.

In another embodiment, the compounds have formula Ib

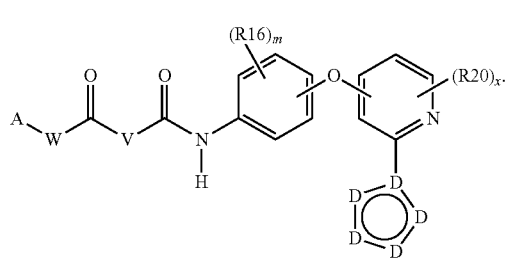

In another embodiment, the compounds have formula Ic

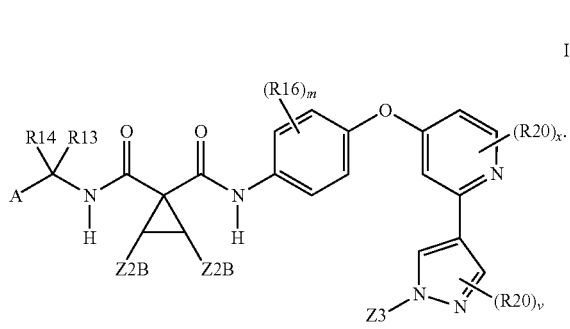

In another embodiment, the compounds have formula Id

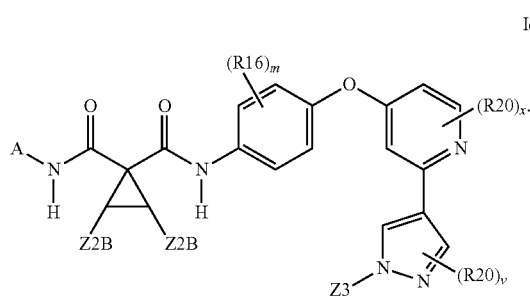

In another embodiment, the compounds have formula Ie

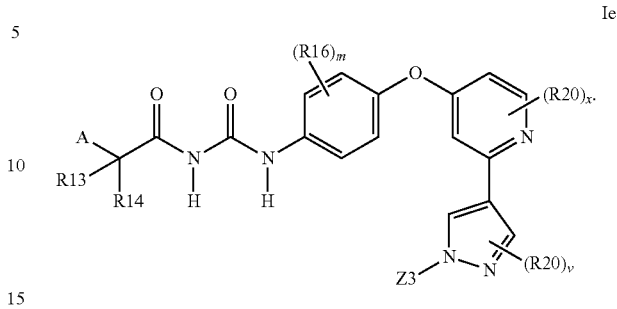

In another embodiment, the compounds have formula If

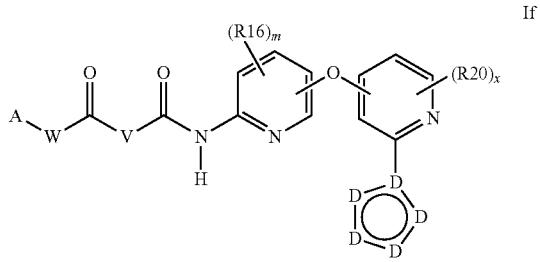

In another embodiment, the compounds have formula Ig

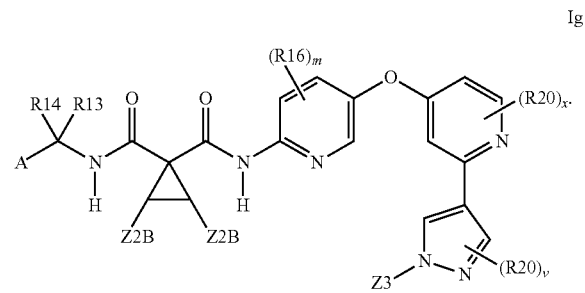

In another embodiment, the compounds have formula Ih

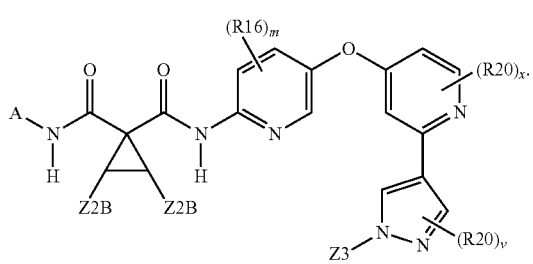

In another embodiment, the compounds have formula Ii

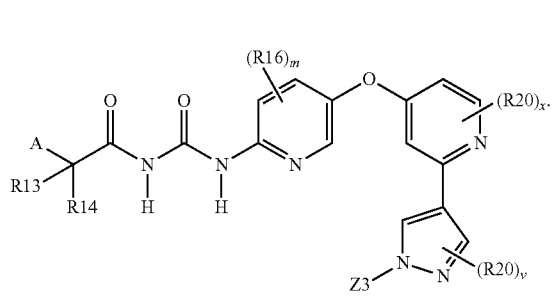

Ii

In another embodiment, the compounds have formula Ij

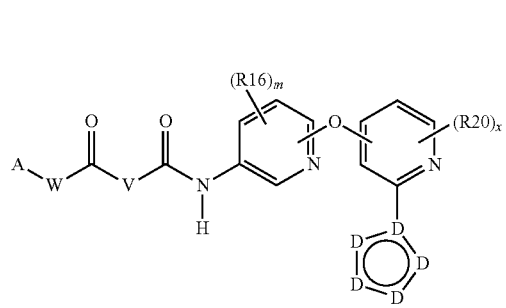

Ij

In another embodiment, the compounds have formula Ik

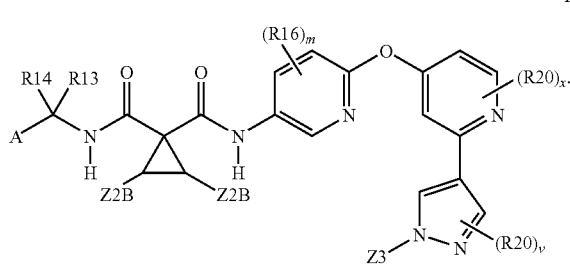

Ik

In another embodiment, the compounds have formula Il

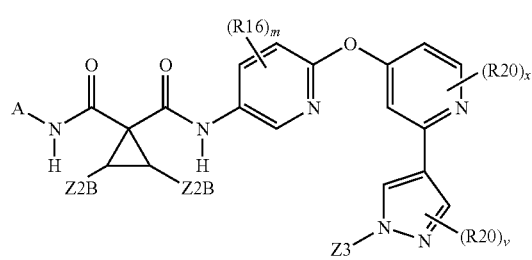

Il

In another embodiment, the compounds have formula Im

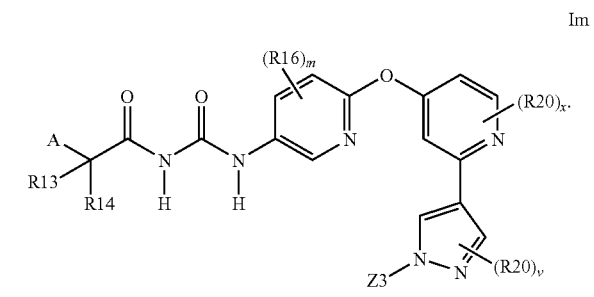

Im

In another embodiment, the compounds have formula In

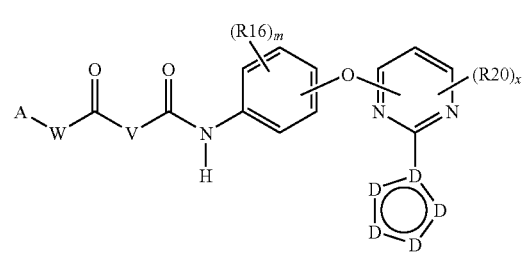

In

In another embodiment, the compounds have formula Io

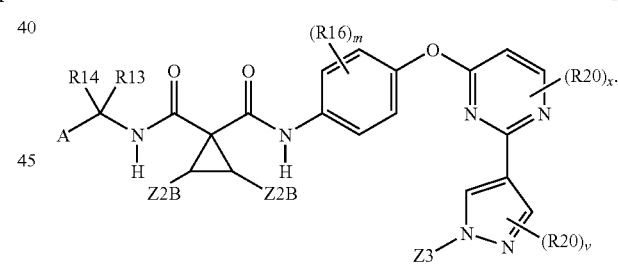

Io

In another embodiment, the compounds have formula Ip

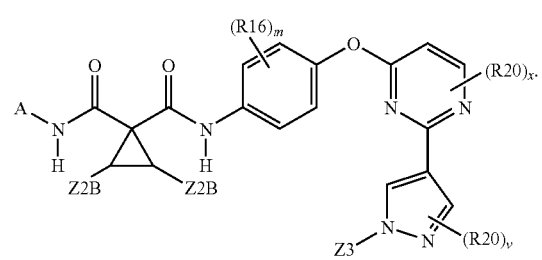

Ip

In another embodiment, the compounds have formula Iq

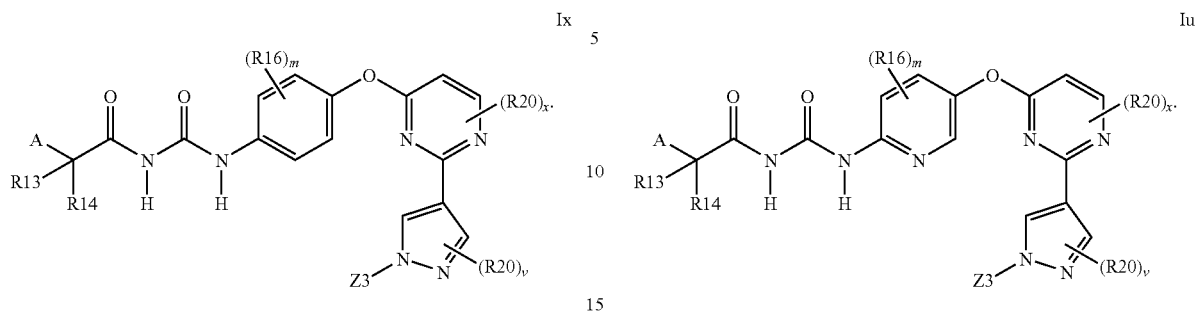

In another embodiment, the compounds have formula Ir

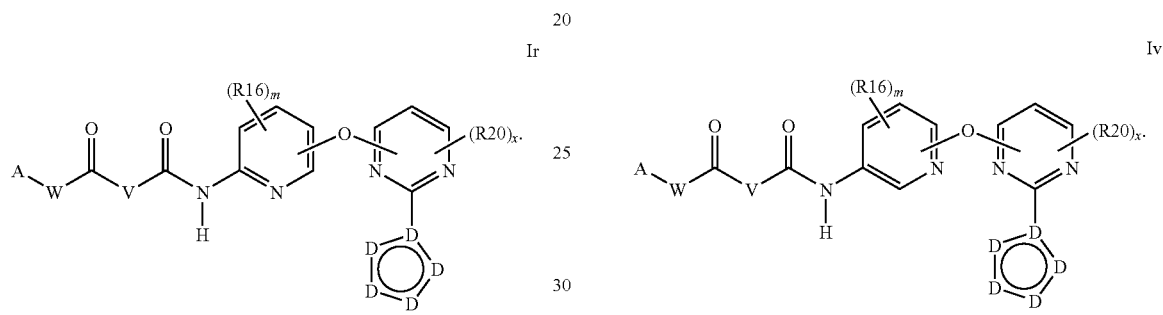

In another embodiment, the compounds have formula Is

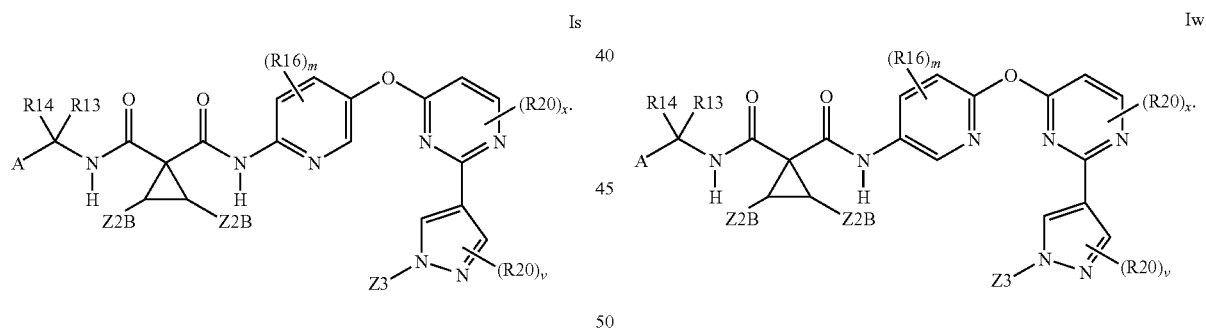

In another embodiment, the compounds have formula It

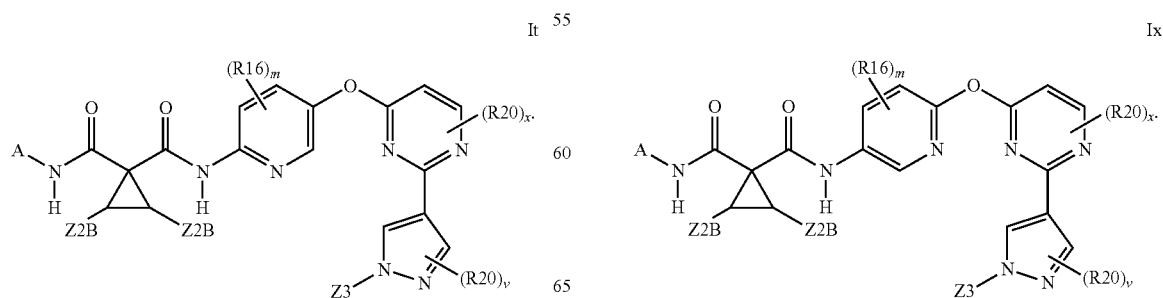

In another embodiment, the compounds have formula Iu

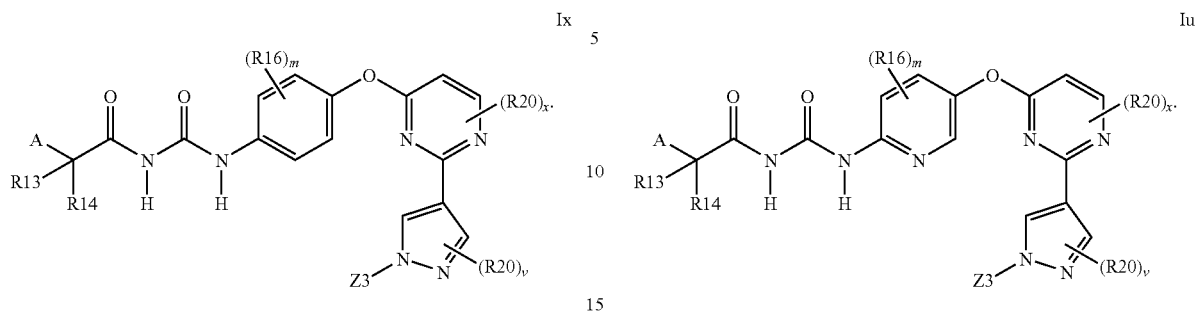

In another embodiment, the compounds have formula Iv

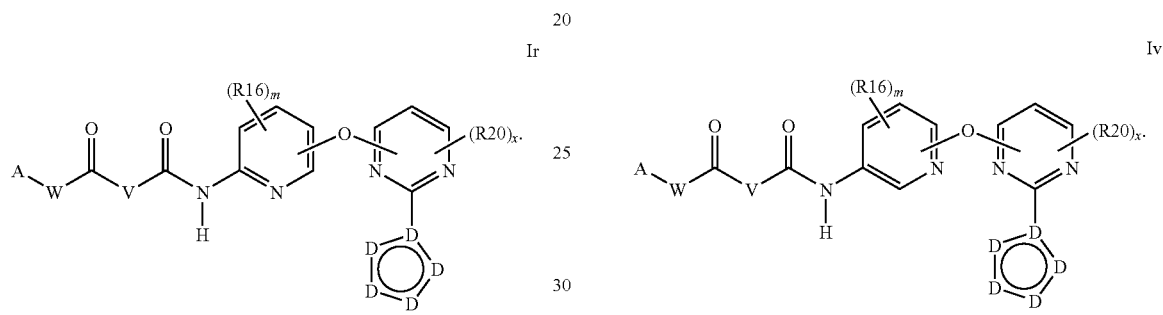

In another embodiment, the compounds have formula Iw

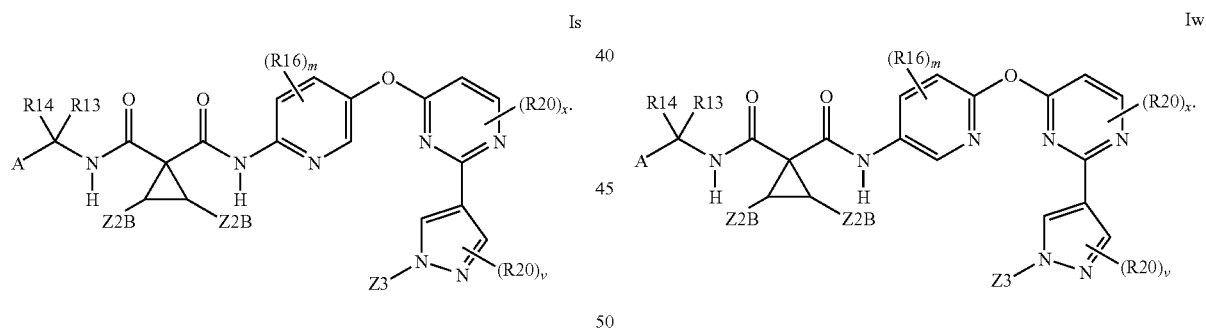

In another embodiment, the compounds have formula Ix

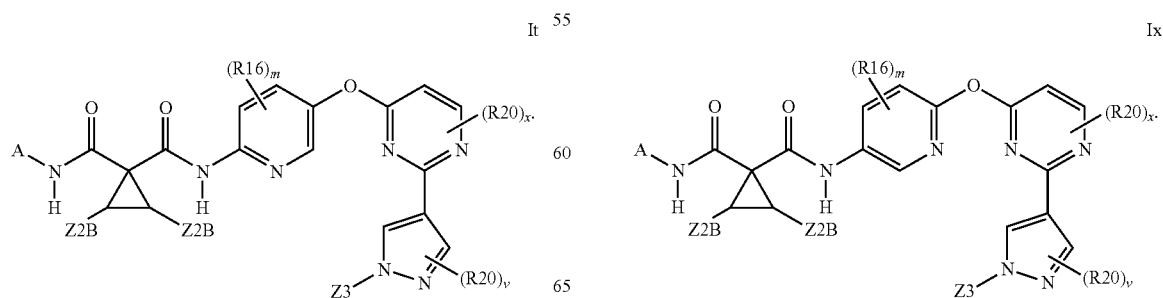

In another embodiment, the compounds have formula Iy

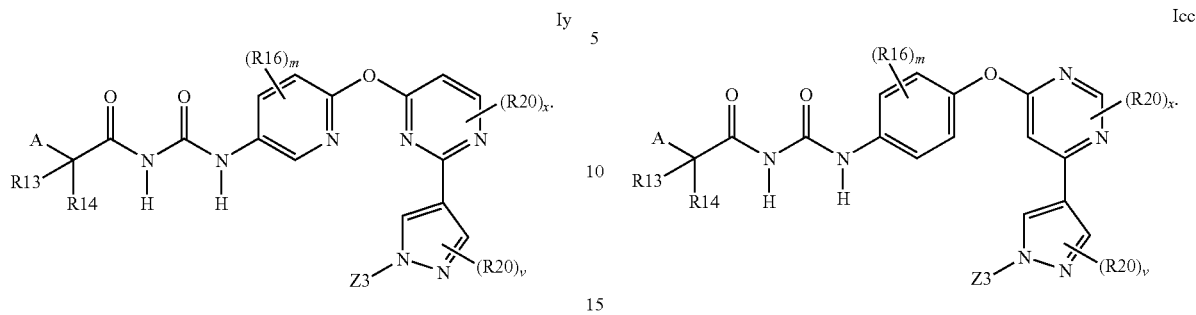

In another embdiment, the compounds have formula Iz

In another embodiment, the compounds have formula Iaa

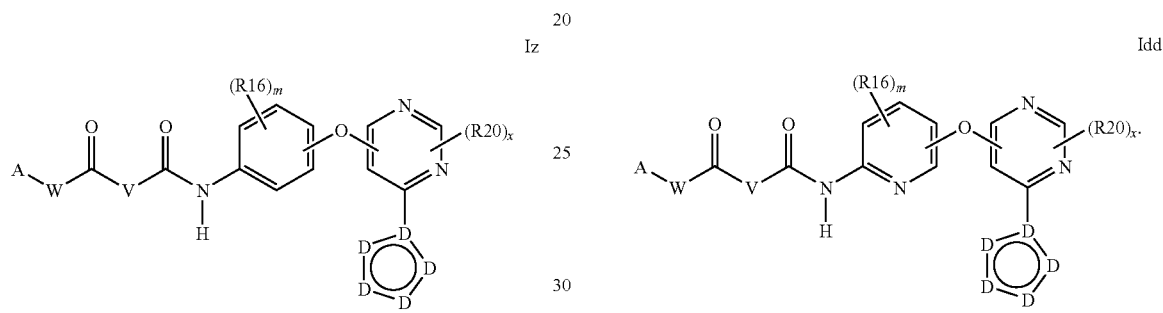

In another embodiment, the compounds have formula Ibb

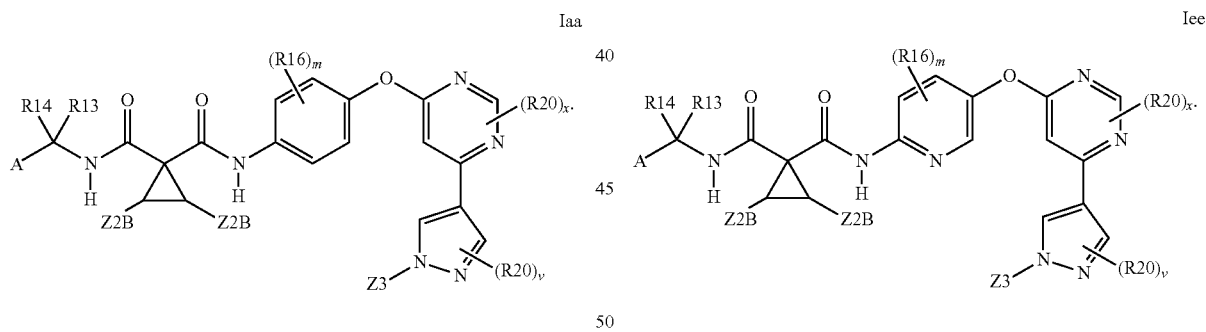

In another embodiment, the compounds have formula Icc

In another embodiment, the compounds have formula Idd

In another embodiment, the compounds have formula Iee

In another embodiment, the compounds have formula Iff

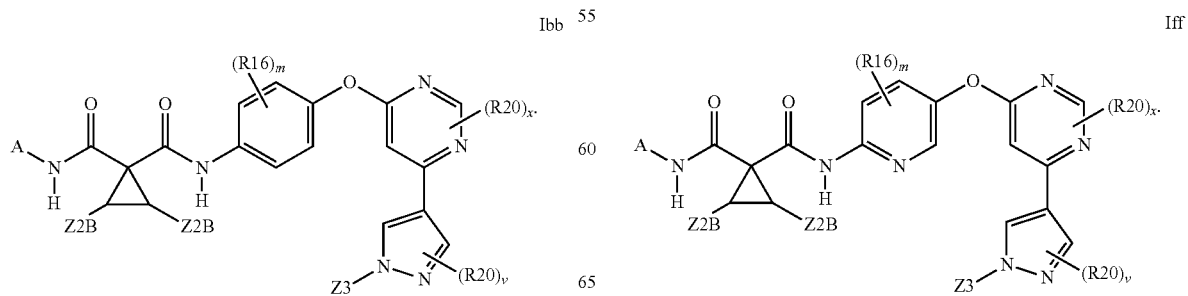

In another embodiment, the compounds have formula Igg

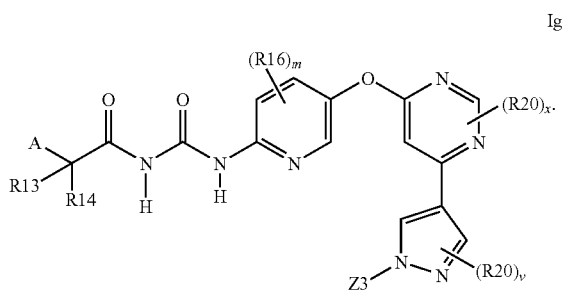

In another embodiment, the compounds have formula Ihh

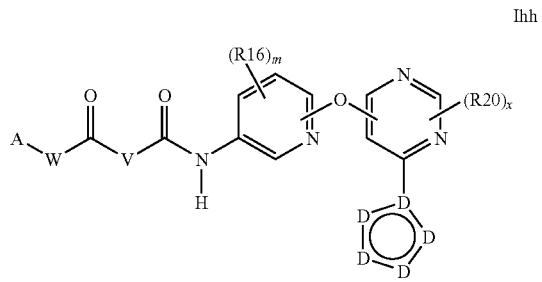

In another embodiment, the compounds have formula Iii

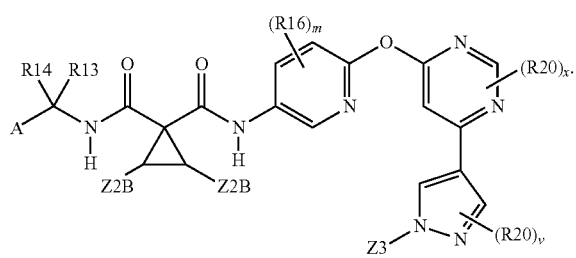

In another embodiment, the compounds have formula Ijj

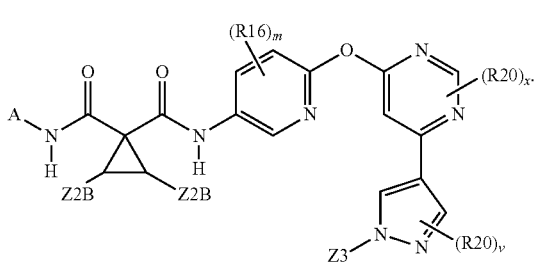

In another embodiment, the compounds have formula Ikk

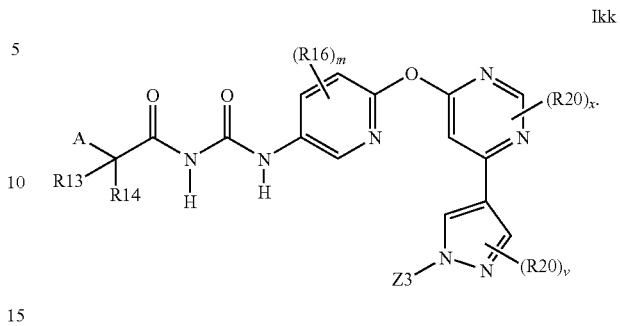

In another aspect, pharmaceutical compositions are described which comprise a compound of the invention, together with a pharmaceutically acceptable carrier, optionally containing an additive selected from the group consisting of adjuvants, excipients, diluents, and stabilizers.

Compounds of the present invention find utility in the treatment of mammalian cancers, hyperproliferative diseases, metabolic diseases, neurodegenerative diseases, or diseases characterized by angiogenesis including, but not limited to, solid tumors, melanomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, gastrointestinal stromal tumors, colonic cancers, ocular diseases characterized by hyperproliferation leading to blindness including retinopathies, diabetic retinopathy, age-related macular degeneration and hypereosinophilic syndrome, rheumatoid arthritis, asthma, chronic obstructive pulmonary, mastocytosis, mast cell leukemia, and diseases caused by PDGFR-α kinase, PDGFR-β kinase, c-KIT kinase, cFMS kinase, c-MET kinase, and oncogenic forms, aberrant fusion proteins and polymorphs of any of the foregoing kinases.

In some embodiments, the kinase is c-MET protein kinase, and any fusion protein, mutation and polymorphs thereof.

In some embodiments, the compound is administered by a method selected from the group consisting of oral, parenteral, inhalation, and subcutaneous.

SECTION 1—DETAILED DESCRIPTION OF THE INVENTION

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, pharmaceutically acceptable salts, and solvates thereof. Thus, the terms "compound" and "compounds" as used in this disclosure refer to the compounds of this disclosure and any and all possible isomers, stereoisomers, enantiomers, diastereomers, tautomers, pharmaceutically acceptable salts, and solvates thereof.

The following descriptions refer to various compounds and moieties thereof.

The term "cycloalkyl" refers to monocyclic saturated carbon rings taken from cyclopropyl, cyclobutyl, cyclopentyl, cyclohexyl, cycloheptanyl and cyclooctanyl.

The term "alkyl" refers to straight or branched chain C1-C6alkyls.

The term "halogen" refers to fluorine, chlorine, bromine, and iodine.

The term "alkoxy" refers to —O-(alkyl) wherein alkyl is defined as above.

The term "alkoxylalkyl" refers to -(alkyl)-O-(alkyl) wherein alkyl is defined as above.

The term "alkoxylcarbonyl" refers to —C(O)O-(alkyl) wherein alkyl is defined as above.

The term "carboxylC1-C6alkyl" refers to —(C1-C6alkyl) $CO_2H$ wherein alkyl is defined as above.

The term "substituted" in connection with a moiety refers to the fact that a further substituent may be attached to the moiety to any acceptable location on the moiety.

The term "salts" embraces pharmaceutically acceptable salts commonly used to form alkali metal salts of free acids and to form addition salts of free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, and heterocyclyl containing carboxylic acids and sulfonic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically-acceptable salts of free acid-containing compounds of Formula I include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from primary amines, secondary amines, tertiary amines and quaternary ammonium salts, including in part, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer", "administering", or "administration" as used in this disclosure refer to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used in this disclosure refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" is employed in this disclosure to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "prodrug" refers to derivatives of active compounds which revert in vivo into the active form. For example, a carboxylic acid form of an active drug may be esterified to create a prodrug, and the ester is subsequently converted in vivo to revert to the carboxylic acid form. See Ettmayer et. al, *J. Med. Chem* (2004) 47: 2393 and Lorenzi et. al, *J. Pharm. Exp. Therpeutics* (2005) 883 for reviews.

As used in this disclosure, the term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "treating" with regard to a subject, refers to improving at least one symptom of the subject's disorder. Treating can be curing, improving, or at least partially ameliorating the disorder.

The term "hydrate" refers to a compound as described herein which is associated with water in the molecular form, i.e., in which the H—OH bond is not split, and may be represented, for example, by the formula $R.H_2O$, where R is a compound as described herein. A given compound may form more than one hydrate including, for example, monohydrates ($R.H_2O$), dihydrates ($R.2H_2O$), trihydrates ($R.3H_2O$), and the like.

The term "solvate" refers to a compound of the present invention which is associated with solvent in the molecular form, i.e. in which the solvent is coordinatively bound, and may be represented, for example, by the formula R·(solvent), where R is a compound of the invention. A given compound may form more than one solvate including, for example, monosolvates (R·(solvent)) or polysolvates (R·n(solvent)) wherein n is an integer>1) including, for example, disolvates (R·2(solvent)), trisolvates (R·3(solvent)), and the like, or hemisolvates, such as, for example, R·n/2(solvent), R·n/3 (solvent), R·n/4(solvent) and the like wherein n is an integer. Solvents herein include mixed solvents, for example, methanol/water, and as such, the solvates may incorporate one or more solvents within the solvate.

The term "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

Structural, chemical and stereochemical definitions are broadly taken from IUPAC recommendations, and more specifically from Glossary of Terms used in Physical Organic Chemistry (IUPAC Recommendations 1994) as summarized by P. Müller, Pure Appl. Chem., (1994) 66: 1077-1184 and Basic Terminology of Stereochemistry (IUPAC Recommendations 1996) as summarized by G. P. Moss Pure and Applied Chemistry, (1996) 68: 2193-2222. Specific definitions are as follows:

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used in this disclosure refers to compounds produced by the phenomenon wherein a proton of one atom of a molecule shifts to another atom. (March, *Advanced Organic Chemistry: Reactions, Mechanisms and Structures*, 4th Ed., John Wiley & Sons, pp. 69-74 (1992)).

Tautomerism is defined as isomerism of the general form

where the isomers (called tautomers) are readily interconvertible; the atoms connecting the groups X, Y, Z are typically any of C, H, O, or S, and G is a group which becomes an electrofuge or nucleofuge during isomerization. The most common case, when the electrofuge is H+, is also known as "prototropy".

Tautomers are defined as isomers that arise from tautomerism, independent of whether the isomers are insoluble.

ChemDraw version 8.0 or 10. (CambridgeSoft Corporation, Cambridge, Mass.) was used to name structures.

1.1 First Aspect of the Invention—Compounds, Methods, and Preparations

Compounds of the formula Ia

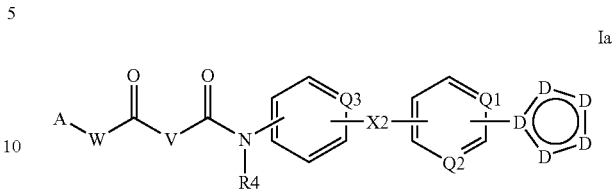

and pharmaceutically acceptable salts, hydrates, solvates, prodrugs, and tautomers thereof;

wherein Q1, Q2, and Q3, are each individually and independently selected from the group consisting of N and CH and wherein at least one of Q1 and Q2 are N;

and wherein the ring containing Q1 and Q2 may be optionally substituted with $(R20)_x$ moieties;

each D is individually taken from the group consisting of C, CH, C—R20, N—Z3, N, and O, such that the resultant ring is taken from the group consisting of pyrazolyl, isoxazolyl, triazolyl and imidazolyl;

and wherein the ring containing Q3 may be optionally substituted with one to three R16 moieties;

V is NR4, or

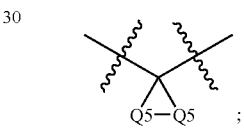

each Q5 is $C(Z2B)_2$;

W is a direct bond, $—[C(R13)R14]_m—$, $—[C(R13)R14]_m NR4-$, or NR4;

A is selected from the group consisting of indanyl, tetrahydronapthyl, thienyl, phenyl, naphthyl, pyrazinyl, pyridazinyl, triazinyl, pyridinyl, and pyrimidinyl;

X2 is —O—;

when A has one or more substitutable sp2-hybridized carbon atoms, each respective sp2 hybridized carbon atom may be optionally substituted with a Z1B substituent;

when A has one or more substitutable sp3-hybridized carbon atoms, each respective sp3 hybridized carbon atom may be optionally substituted with a Z2B substituent;

each Z1B is independently and individually selected from the group consisting of hydrogen, C1-6alkyl, branched C3-C7alkyl, halogen, fluoroC1-C6alkyl wherein the alkyl moiety can be partially or fully fluorinated, C1-C6alkoxy, fluoroC1-C6alkoxy wherein the alkyl moiety can be partially or fully fluorinated, and $—(CH_2)_nCN$;

each Z2B is independently and individually selected from the group consisting of hydrogen, C1-C6alkyl, and branched C3-C7alkyl;

each Z3 is independently and individually selected from the group consisting of hydrogen, C1-C6alkyl, branched C3-C7alkyl, C3-C8cycloalkyl, fluoroC1-C6alkyl wherein the alkyl moiety can be partially or fully fluorinated, hydroxyC2-C6alkyl-, $R5C(O)(CH_2)_n—$, $(R4)_2NC(O)C1-C6alkyl-$, $R8C(O)N(R4)(CH_2)_q—$, $—(CH_2)_qCN$, $—(CH_2)_q R5$, and $—(CH_2)_qN(R4)_2$;

each R2 is selected from the group consisting of hydrogen, R17-substituted aryl-, C1-C6alkyl, branched C3-C8alkyl, R19 substituted C3-C8cycloalkyl-, and fluoroC1-C6alkyl- wherein the alkyl is fully or partially fluorinated;

wherein each R3 is independently and individually selected from the group consisting of hydrogen, C1-C6alkyl, branched C3-C7alkyl, and C3-C8cycloalkyl;

each R4 is independently and individually selected from the group consisting of hydrogen, C1-C6alkyl, hydroxyC1-C6alkyl-, dihydroxyC1-C6alkyl-, C1-C6alkoxyC1-C6alkyl-, branched C3-C7alkyl, hydroxyl substituted branched C3-C6alkyl-, C1-C6alkoxy branched C3-C6alkyl-, dihydroxy substituted branched C3-C6alkyl-, —(CH$_2$)$_p$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, and R19 substituted C3-C8cycloalkyl-;

each R5 is independently and individually selected from the group consisting of

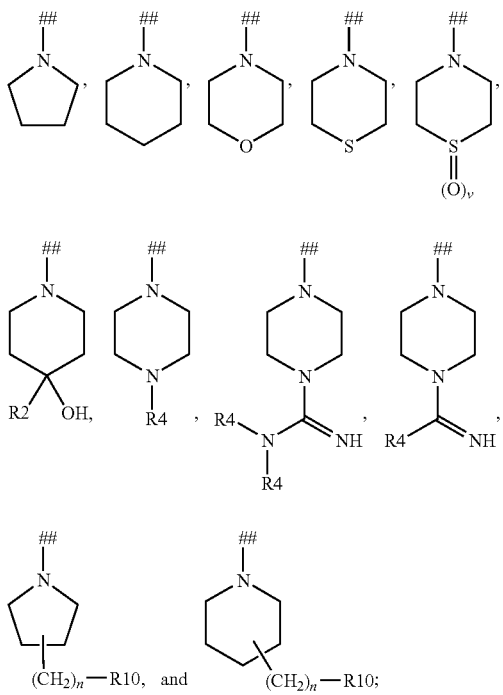

and wherein the symbol (##) is the point of attachment to respective R4, R7, R8, R20 or Z3 moieties containing a R5 moiety;

each R7 is independently and individually selected from the group consisting of hydrogen, C1-C6alkyl, hydroxyC2-C6alkyl-, dihydroxyC2-C6alkyl-, C1-C6alkoxyC2-C6alkyl-, branched C3-C7alkyl, hydroxy substituted branched C3-C6alkyl-, C1-C6alkoxy branched C3-C6alkyl-, dihydroxy substituted branched C3-C6alkyl-, —(CH$_2$)$_q$R5, —(CH$_2$)$_n$C(O)R5, —(CH$_2$)$_n$C(O)OR3, R19 substituted C3-C8cycloalkyl- and —(CH$_2$)$_n$R17;

each R8 is independently and individually selected from the group consisting of C1-C6alkyl, branched C3-C7alkyl, fluoroC1-C6alkyl- wherein the alkyl moiety is partially or fully fluorinated, R19 substituted C3-C8cycloalkyl-, phenyl, phenylC1-C6alkyl-, OH, C1-C6alkoxy, —N(R3)$_2$, —N(R4)$_2$, and R5;

each R10 is independently and individually selected from the group consisting of —CO$_2$H, —CO$_2$C1-C6alkyl, —C(O)N(R4)$_2$, OH, C1-C6alkoxy, and —N(R4)$_2$;

R13 and R14 are each individually and independently selected from the group consisting of hydrogen, C1-C6alkyl, branched C3-C8alkyl, fluoroC1-C6alkyl- wherein the alkyl is fully or partially fluorinated, hydroxyl substituted C1-C6alkyl-, C1-C6alkoxy substituted C1-C6alkyl-, hydroxyl substituted branched C3-C8alkyl-, and alkoxy substituted branched C3-C8alkyl;

each R16 is independently and individually selected from the group consisting of hydrogen, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, R3 substituted C2-C3alkynyl- and nitro;

each R17 is independently and individually selected from the group consisting of hydrogen, C1-C6alkyl, branched C3-C7alkyl, hydroxyC2-C6alkyl-, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, and nitro;

each R19 is independently and individually selected from the group consisting of hydrogen, OH and C1-C6alkyl;

each R20 is independently and individually selected from the group consisting of hydrogen, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, hydroxyC1-C6alkyl-, C1-C6alkoxyC1-C6alkyl-, C1-C6alkoxy, fluoroC1-C6alkoxy- wherein the alkyl moiety can be partially or fully fluorinated, —N(R3)$_2$, —N(R4)$_2$, —(CH$_2$)$_n$R5, —(CH$_2$)$_n$N(R3)C(O)R3, —(CH$_2$)$_n$C(O)N(R3)$_2$ and nitro;

each m is independently and individually 1-3; each n is independently and individually 0-6; each p is independently and individually 1-4; each q is independently and individually 2-6; each v is independently and individually 1 or 2; each x is independently and individually 0-2;

stereoisomers, regioisomers and tautomers of such compounds.

In the aforementioned compounds of formula Ia, subscript letters are frequently used to define variations in moiety and substituent structure. For instance, in the case where R4 on the amide nitrogen is —(CH$_2$)$_n$C(O)R5, and the R20 on the Q1/Q2 ring is —(CH$_2$)$_n$R5, each "n" subscript can be individually and independently varied from zero to six. For example, the situation wherein the R4 "n" subscript is 2 and the R20 "n" subscript is 6 results in a R4 substituent of —CH$_2$CH$_2$C(O)R5 and a R20 substituent of —CH$_2$CH$_2$CH$_2$CH$_2$CH$_2$CH$_2$R5 (see molecule 3 below). By extension, a subscript definition may be variably used to define different moieties residing within the same compound of formula Ia.

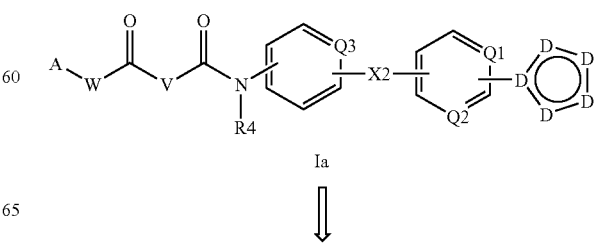

Ia

⇓

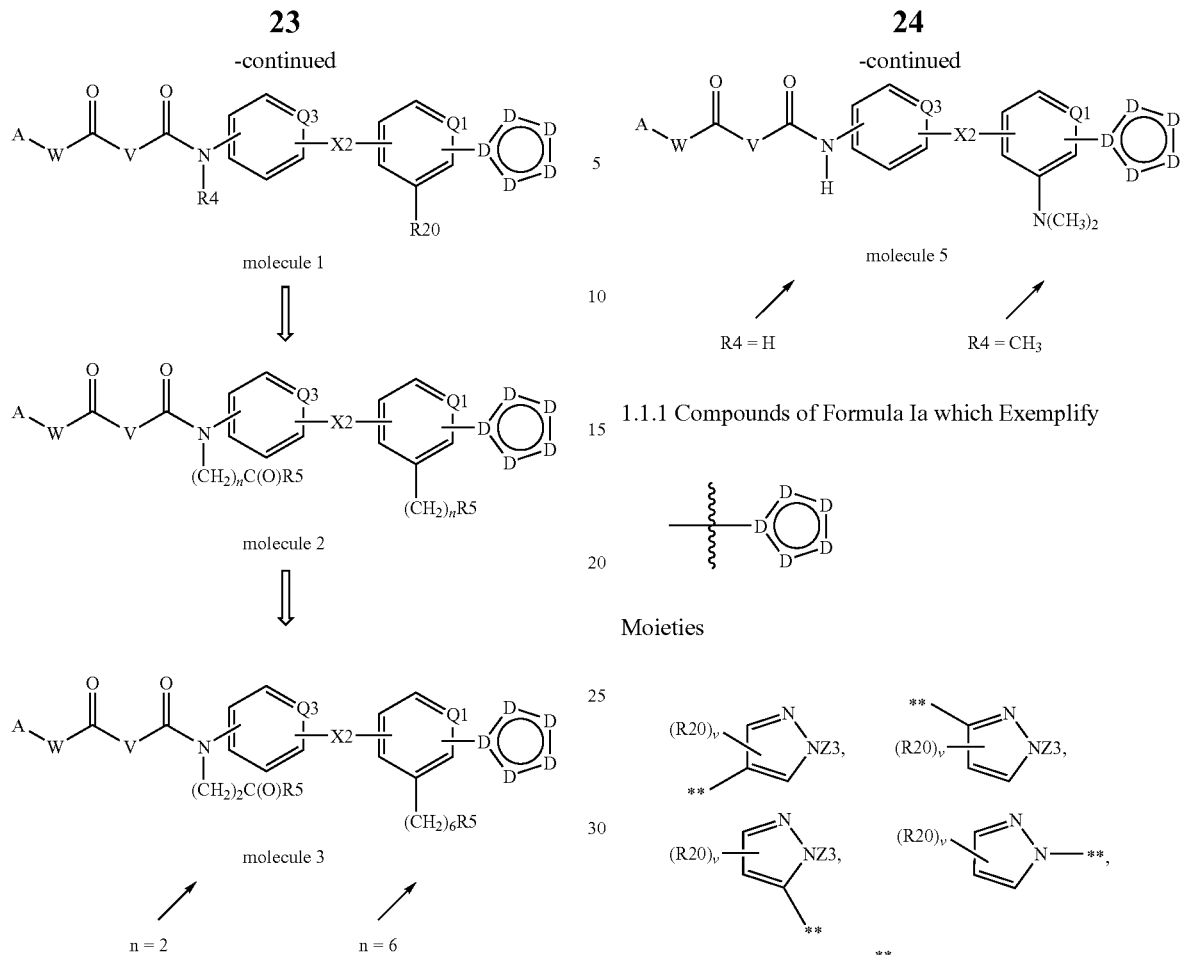

In the case where a specific moiety (e.g. R4) is used in more than one place within a molecule, each instance of R4 is individually and independently varied according to the definition of R4. As shown below, generic molecule Ia can be elaborated to "molecule "4" which has two instances of R4, each of which can be different (R4=H & R4=CH$_3$) as shown is "molecule 5".

1.1.1 Compounds of Formula Ia which Exemplify

Moieties

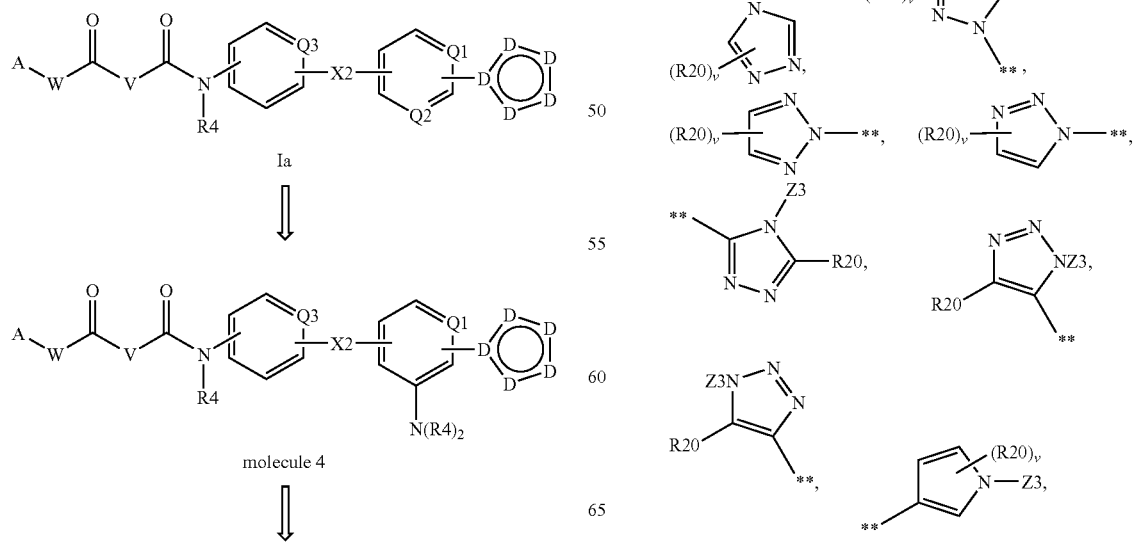

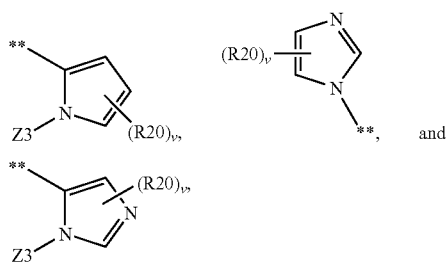
wherein the symbol (**) indicates the point of attachment to the heteroaryl Q1, Q2 containing ring.
1.1.2 Compounds of 1.1.1 which Exemplify Q1-Q3 Moieties
Ib
1.1.3 Compounds of 1.1.2 Having Formula Ic
Ic
1.1.4 Compounds of 1.1.2 Having Formula Id
Id
1.1.5 Compounds of 1.1.2 Having Formula Ie
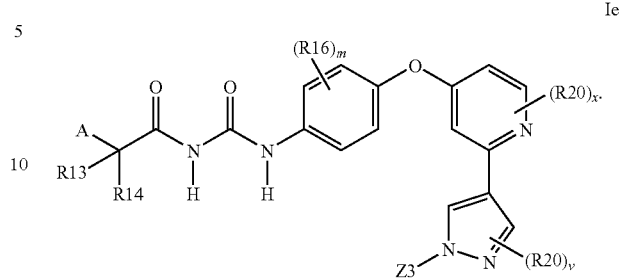
1.2 Compounds of 1.1.1 which Exemplify Q1-Q3 Moieties
If
1.2.1 Compounds of 1.2 Having Formula Ig
Ig
1.2.2 Compounds of 1.2 Having Formula Ih
Ih 1.2.3 Compounds of 1.2 Having Formula Ii
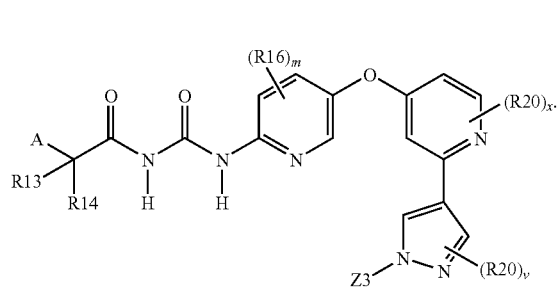
Ii
1.3.3 Compounds of 1.3 Having Formula Im
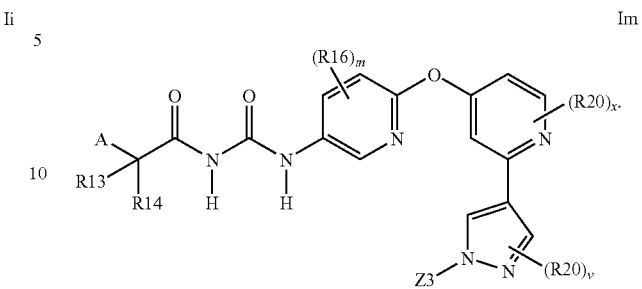
Im
1.3 Compounds of 1.1.1 which Exemplify Q1-Q3 Moieties
1.4 Compounds of 1.1.1 which Exemplify Q1-Q3 Moieties
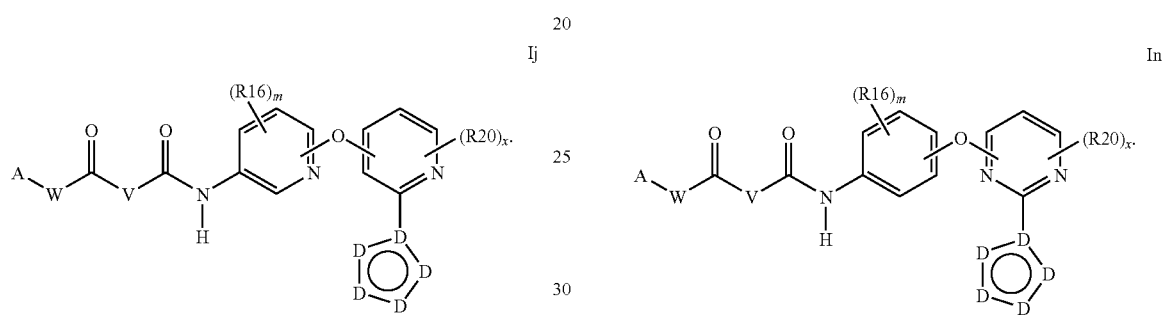
Ij
In
1.3.1 Compounds of 1.3 Having Formula Ik
1.4.1 Compounds of 1.4 Having Formula Io
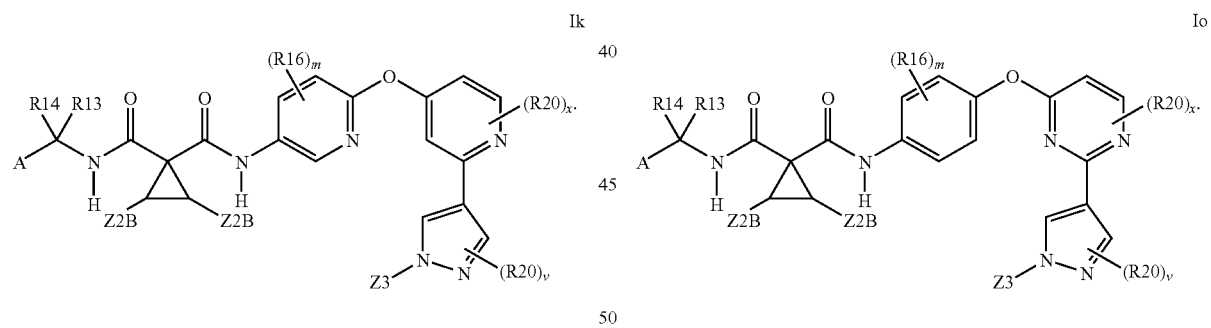
Ik
Io
1.3.2 Compounds of 1.3 Having Formula Il
1.4.2 Compounds of 1.4 Having Formula Ip
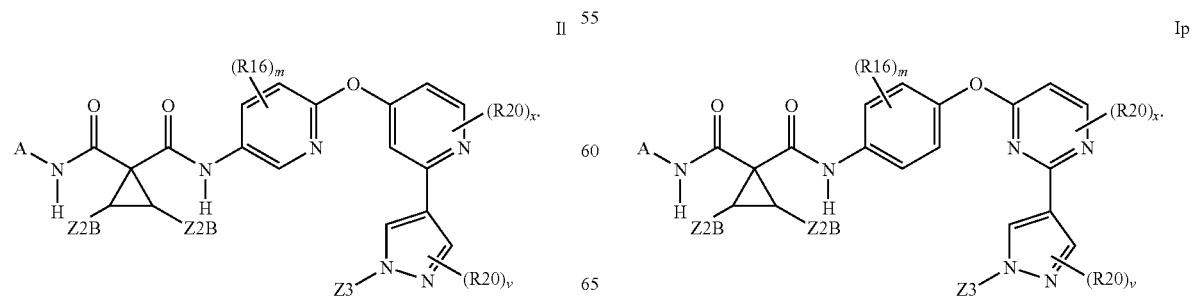
Il
Ip

1.4.3 Compounds of 1.4 Having Formula Iq
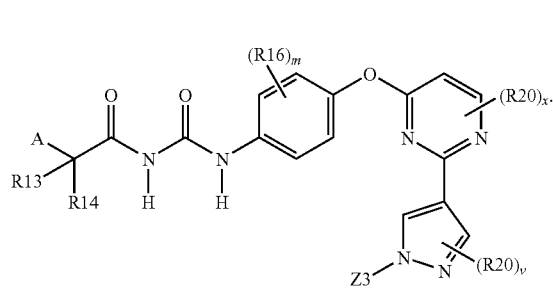
Iq
1.5 Compounds of 1.1.1 which Exemplify Q1-Q3 Moieties
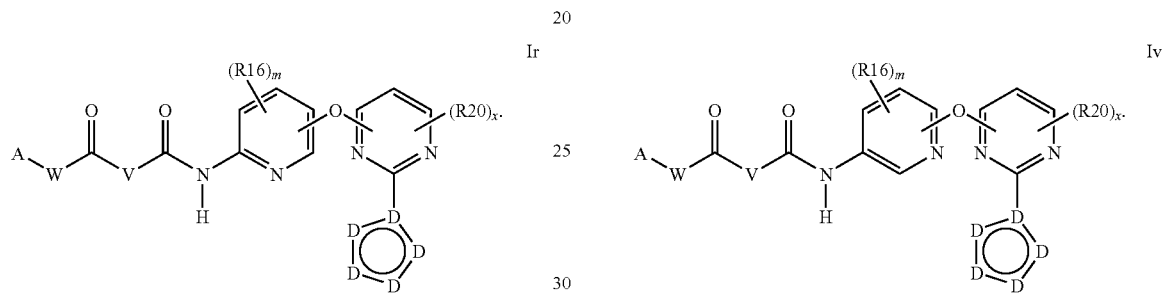
Ir
1.5.1 Compounds of 1.5 Having Formula Is
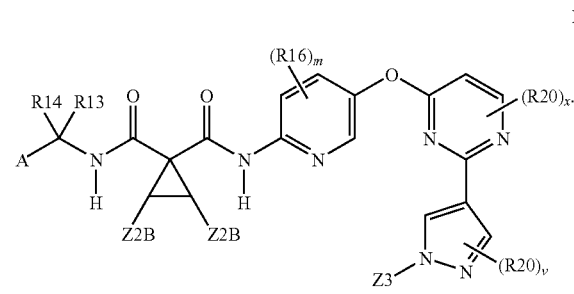
Is
1.5.2 Compounds of 1.5 Having Formula It
It
1.5.3 Compounds of 1.5 Having Formula Iu
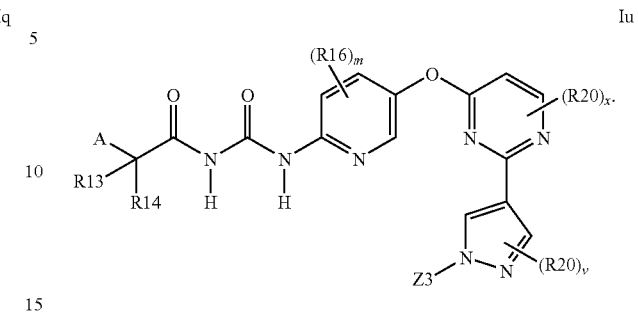
Iu
1.6 Compounds of 1.1.1 whch Exemplify Q1-Q3 Moieties
Iv
1.6.1 Compounds of 1.6 Having Formula Iw
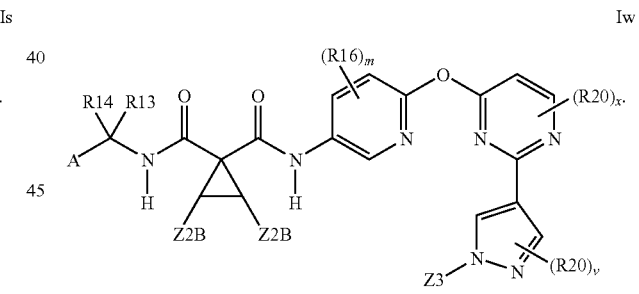
Iw
1.6.2 Compounds of 1.6 Having Formula Ix
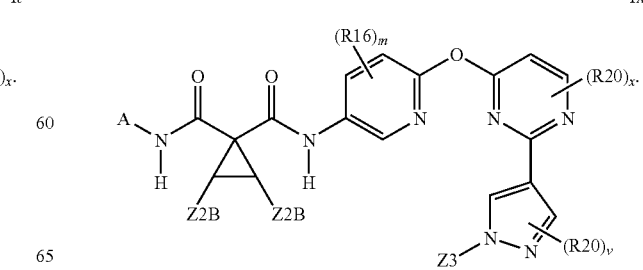
Ix 1.6.3 Compounds of 1.6 Having Formula Iy
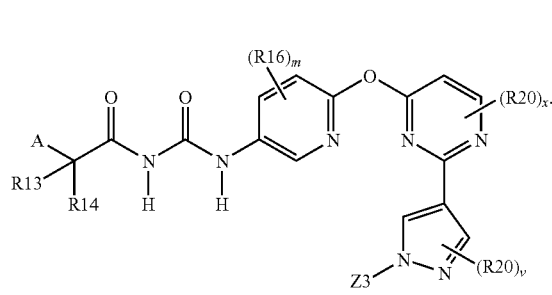
Iy
1.7 Compounds of 1.1.1 which Exemplify Q1-Q3 Moieties
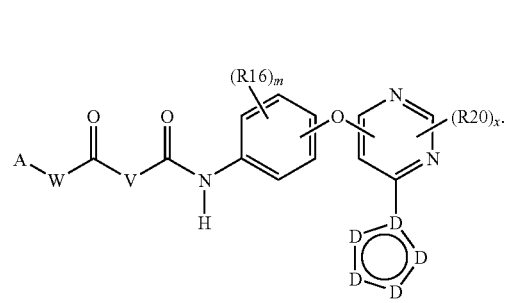
Iz
1.7.1 Compounds of 1.7 Having Formula Iaa
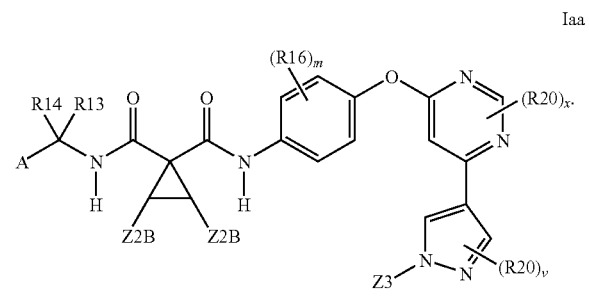
Iaa
1.7.2 Compounds of 1.7 Having Formula Ibb
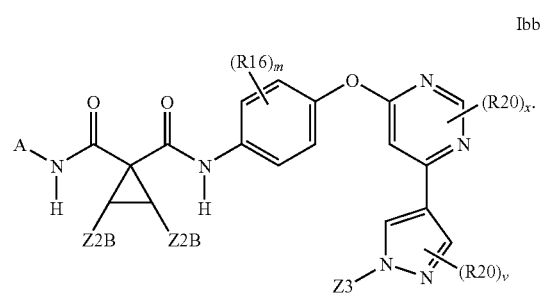
Ibb
1.7.3 Compounds of 7 Having Formula Icc
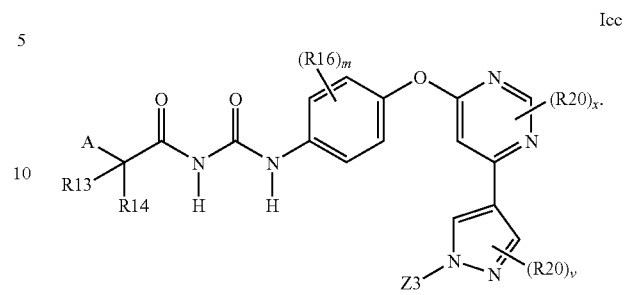
Icc
1.8 Compounds of 1.1.1 which Exemplify Q1-Q3 Moieties
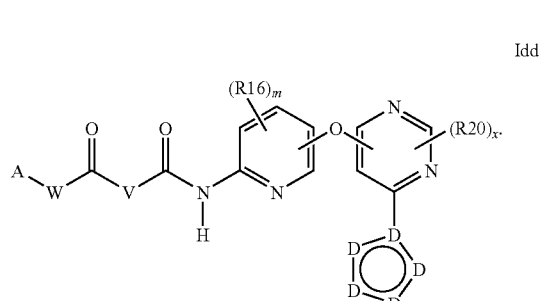
Idd
1.8.1 Compounds of 1.8 Having Formula Iee
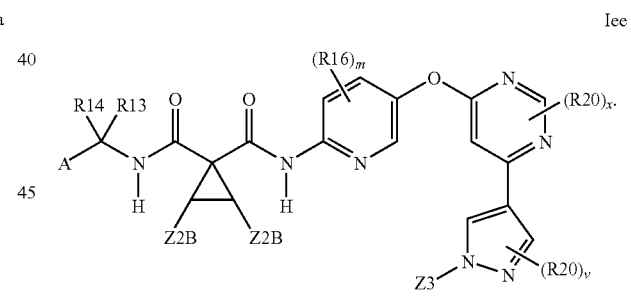
Iee
1.8.2 Compounds of 1.8 Having Formula Iff
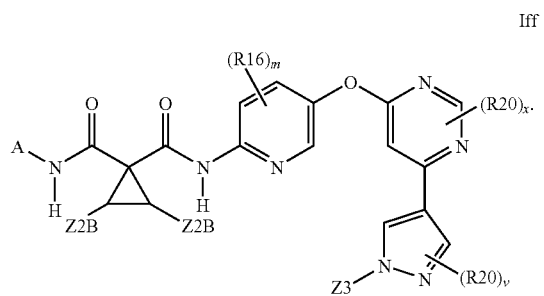
Iff

1.8.3 Compounds of 1.8 Having Formula Igg

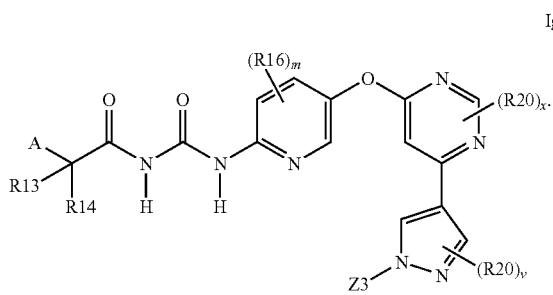

Igg

1.9 Compounds of 1.1.1 which Exemplify Q1-Q3 Moieties

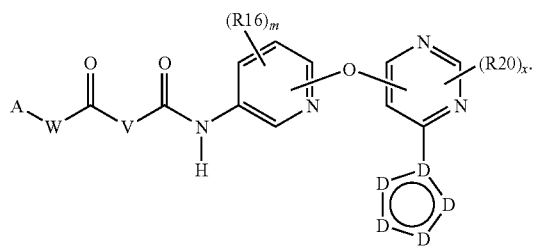

Ihh

1.9.1 Compounds of 1.9 Having Formula Iii

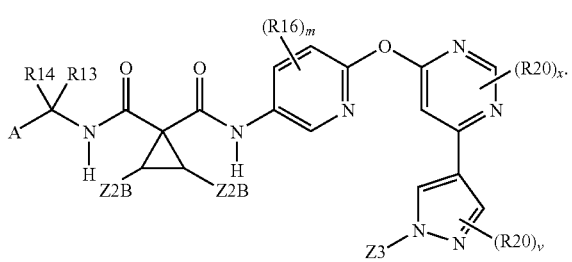

Iii

1.9.2 Compounds of 1.9 Having Formula Ijj

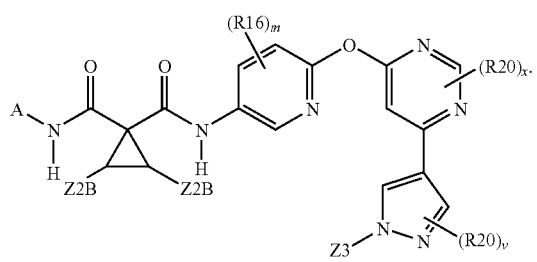

Ijj

1.9.3 Compounds of 1.9 Having Formula Ikk

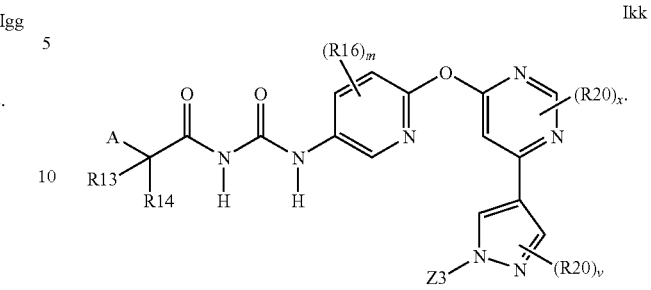

Ikk

1.10 Illustrative Compounds of Formula Ia

Illustrative compounds of formula Ia include, but are not limited to, N-(2,3-difluoro-4-(2-(1-methyl-1H-pyrazol-4-yl)pyridin-4-yloxy)phenyl)-N'-(4-fluorophenyl)cyclopropane-1,1-dicarboxamide, N-(3-fluoro-4-(2-(1-methyl-1H-pyrazol-4-yl)pyridin-4-yloxy)phenyl)-N'-(4-fluorophenyl) cyclopropane-1,1-dicarboxamide, N-benzyl-N'-(2,3-difluoro-4-(2-(1-methyl-1H-pyrazol-4-yl)pyridin-4-yloxy) phenyl)cyclopropane-1,1-dicarboxamide, N-benzyl-N'-(3-fluoro-4-(2-(1-methyl-1H-pyrazol-4-yl)pyridin-4-yloxy) phenyl)cyclopropane-1,1-dicarboxamide, N-(3-fluoro-4-(2-(1-methyl-1H-pyrazol-4-yl)pyridin-4-yloxy)phenyl)-N'-phenylcyclopropane-1,1-dicarboxamide, N-(3-fluoro-4-(2-(1-methyl-1H-pyrazol-4-yl)pyridin-4-yloxy)phenyl)-N'-(3-(trifluoromethyl)phenyl)cyclopropane-1,1-dicarboxamide, N-(2-fluoro-4-(2-(1-methyl-1H-pyrazol-4-yl)pyridin-4-yloxy)phenyl)-N'-(4-fluorophenyl)cyclopropane-1,1-dicarboxamide, N-(3-fluoro-4-(2-(1-methyl-1H-pyrazol-4-yl)pyridin-4-yloxy)phenyl)-N'-(4-methoxyphenyl)cyclopropane-1,1-dicarboxamide, N-(3-fluoro-4-(2-(1-methyl-1H-pyrazol-4-yl)pyridin-4-yloxy)phenyl)-N'-(3-methoxyphenyl)cyclopropane-1,1-dicarboxamide, N-(3-fluoro-4-(2-(1-methyl-1H-pyrazol-4-yl)pyridin-4-yloxy)phenyl)-N'-(3-fluorophenyl)cyclopropane-1,1-dicarboxamide, N-(4-fluorophenyl)-N'-(3-methyl-4-(2-(1-methyl-1H-pyrazol-4-yl)pyridin-4-yloxy)phenyl) cyclopropane-1,1-dicarboxamide, 1-(3-fluoro-4-(2-(1-methyl-1H-pyrazol-4-yl)pyridin-4-yloxy)phenyl)-3-(2-(4-fluorophenyl)acetyl)urea, N-(3-fluoro-4-(2-(1-methyl-1H-pyrazol-4-yl)pyridin-4-yloxy)phenyl)-N'-(pyridin-4-yl) cyclopropane-1,1-dicarboxamide, N-(3-fluoro-4-(2-(1-methyl-1H-pyrazol-4-yl)pyridin-4-yloxy)phenyl)-N'-(pyridin-3-yl)cyclopropane-1,1-dicarboxamide, N-(3-chlorobenzyl)-N'-(3-fluoro-4-(2-(1-methyl-1H-pyrazol-4-yl)pyridin-4-yloxy)phenyl)cyclopropane-1,1-dicarboxamide, N-(3-fluoro-4-(2-(1-methyl-1H-pyrazol-4-yl)pyridin-4-yloxy)phenyl)-N'-((S)-1-phenylethyl)cyclopropane-1,1-dicarboxamide, N-(3-fluoro-4-(2-(1-methyl-1H-pyrazol-4-yl)pyridin-4-yloxy)phenyl)-N'-((R)-1-phenylethyl)cyclopropane-1,1-dicarboxamide, N-(4-fluorobenzyl)-N'-(3-fluoro-4-(2-(1-methyl-1H-pyrazol-4-yl)pyridin-4-yloxy)phenyl)cyclopropane-1,1-dicarboxamide, N-(4-(2-(1-ethyl-1H-pyrazol-4-yl)pyridin-4-yloxy)-3-fluorophenyl)-N'-(4-fluorophenyl) cyclopropane-1,1-dicarboxamide, N-(3-fluoro-4-(2-(1-propyl-1H-pyrazol-4-yl)pyridin-4-yloxy)phenyl)-N'-(4-fluorophenyl)cyclopropane-1,1-dicarboxamide, N-(3-fluoro-4-(2-(1-(2-hydroxyethyl)-1H-pyrazol-4-yl)pyridin-4-yloxy)phenyl)-N'-(4-fluorophenyl)cyclopropane-1,1-dicarboxamide, N-(4-chlorophenyl)-N'-(2-fluoro-4-(2-(1-methyl-1H-pyrazol-4-yl)pyridin-4-yloxy)phenyl) cyclopropane-1,1-dicarboxamide, N-(2-fluoro-4-(2-(1-methyl-1H-pyrazol-4-yl)pyridin-4-yloxy)phenyl)-N'-p- tolylcyclopropane-1,1-dicarboxamide, N-(3,4-difluorophenyl)-N'-(2-fluoro-4-(2-(1-methyl-1H-pyrazol-4-yl)pyridin-4-yloxy)phenyl)cyclopropane-1,1-dicarboxamide, N-(2-fluoro-4-(2-(1-methyl-1H-pyrazol-4-yl)pyridin-4-yloxy)phenyl)-N'-(4-(trifluoromethyl)phenyl)cyclopropane-1,1-dicarboxamide, N-(3-cyano-4-fluorophenyl)-N'-(2-fluoro-4-(2-(1-methyl-1H-pyrazol-4-yl)pyridin-4-yloxy)phenyl)cyclopropane-1,1-dicarboxamide, N-(2,4-difluorophenyl)-N'-(2-fluoro-4-(2-(1-methyl-1H-pyrazol-4-yl)pyridin-4-yloxy)phenyl)cyclopropane-1,1-dicarboxamide, N-(4-cyanophenyl)-N'-(2-fluoro-4-(2-(1-methyl-1H-pyrazol-4-yl)pyridin-4-yloxy)phenyl)cyclopropane-1,1-dicarboxamide, N-(2-chloro-4-fluorophenyl)-N'-(2-fluoro-4-(2-(1-methyl-1-pyrazol-4-yl)pyridin-4-yloxy)phenyl)cyclopropane-1,1-dicarboxamide, N-(3-chloro-4-(2-(1-methyl-1H-pyrazol-4-yl)pyridin-4-yloxy)phenyl)-N'-(4-fluorophenyl)cyclopropane-1,1-dicarboxamide, N-(4-(2-(1H-pyrazol-4-yl)pyridin-4-yloxy)-3-fluorophenyl)-N'-(4-fluorophenyl)cyclopropane-1,1-dicarboxamide, N-(2-fluoro-3-methyl-4-(2-(1-methyl-1H-pyrazol-4-yl)pyridin-4-yloxy)phenyl)-N'-(4-fluorophenyl)cyclopropane-1,1-dicarboxamide, N-(3-fluoro-4-(2-(1-methyl-1H-pyrazol-4-yl)pyridin-4-yloxy)phenyl)-N'-((S)-1-(4-fluorophenyl)ethyl)cyclopropane-1,1-dicarboxamide hydrochloride, N-(3-fluoro-4-(2-(1-methyl-1H-pyrazol-4-yl)pyridin-4-yloxy)phenyl)-N'-((S)-1-(4-fluorophenyl)propyl)cyclopropane-1,1-dicarboxamide hydrochloride, N-(2-fluoro-4-(2-(1-methyl-1H-pyrazol-4-yl)pyridin-4-yloxy)phenyl)-N'-(thiophen-2-yl)cyclopropane-1,1-dicarboxamide, N-(3-fluoro-4-(2-(1-methyl-1H-pyrazol-4-yl)pyridin-4-yloxy)phenyl)-N'-((R)-1-(4-fluorophenyl)-2-methoxyethyl)cyclopropane-1,1-dicarboxamide, N-(4-fluorophenyl)-N-(4-(2-(4-(trifluoromethyl)-1H-imidazol-2-yl)pyridin-4-yloxy)phenyl)cyclopropane-1,1-dicarboxamide, N-(4-fluorophenyl)-N'-(6-(2-(1-methyl-1H-pyrazol-4-yl)pyridin-4-yloxy)pyridin-3-yl)cyclopropane-1,1-dicarboxamide, 2-(4-fluorophenyl)-N-(4-(2-(4-(trifluoromethyl)-1H-imidazol-2-yl)pyridin-4-yloxy)phenylcarbamoyl)acetamide, N-(2,5-difluoro-4-(2-(1-methyl-1H-pyrazol-4-yl)pyridin-4-yloxy)phenyl)-N'-(4-fluorophenyl)cyclopropane-1,1-dicarboxamide, N-(4-fluorophenyl)-N'-(5-(2-(1-methyl-1H-pyrazol-4-yl)pyridin-4-yloxy)pyridin-2-yl)cyclopropane-1,1-dicarboxamide, N-(2,5-difluoro-4-(2-(1-methyl-1H-pyrazol-4-yl)pyridin-4-yloxy)phenylcarbamoyl)-2-(4-fluorophenyl)acetamide, N-(2,3-difluoro-4-(2-(1-methyl-1H-pyrazol-4-yl)pyridin-4-yloxy)phenylcarbamoyl)-2-(4-fluorophenyl)acetamide, 2-(4-fluorophenyl)-N-(5-(2-(1-methyl-1H-pyrazol-4-yl)pyridin-4-yloxy)pyridin-2-ylcarbamoyl)acetamide, N-(2,5-difluoro-4-(2-(1-methyl-1H-pyrazol-4-yl)pyridin-4-yloxy)phenyl)-N-phenylcyclopropane-1,1-dicarboxamide, N-(5-chloro-2-fluoro-4-(2-(1-methyl-1H-pyrazol-4-yl)pyridin-4-yloxy)phenylcarbamoyl)-2-(4-fluorophenyl)acetamide, N-(5-chloro-2-fluoro-4-(2-(1-methyl-1H-pyrazol-4-yl)pyridin-4-yloxy)phenyl)-N-(4-fluorophenyl)cyclopropane-1,1-dicarboxamide, N-(3,5-difluoro-4-(2-(1-methyl-1H-pyrazol-4-yl)pyridin-4-yloxy)phenylcarbamoyl)-2-(4-fluorophenyl)acetamide, N-(4-(2-(1,3-dimethyl-1H-pyrazol-4-yl)pyridin-4-yloxy)-2,5-difluorophenyl)-N-(4-fluorophenyl)cyclopropane-1,1-dicarboxamide, N-(4-fluorophenyl)-N-(4-(2-(4-(trifluoromethyl)-1H-imidazol-2-yl)pyridin-4-yloxy)phenyl)cyclopropane-1,1-dicarboxamide, N-(2-fluoro-5-methyl-4-(2-(1-methyl-1H-pyrazol-4-yl)pyridin-4-yloxy)phenyl)-N'-(4-fluorophenyl)cyclopropane-1,1-dicarboxamide, N-(2-fluoro-4-methyl-5-(4-(1-methyl-1H-pyrazol-4-yl)pyrimidin-2-yloxy)phenyl)-N'-(4-fluorophenyl)cyclopropane-1,1-dicarboxamide, N-(2-fluoro-5-(4-(1-methyl-1H-pyrazol-4-yl)pyrimidin-2-yloxy)phenyl)-N'-(4-fluorophenyl)cyclopropane-1,1-dicarboxamide, N-(5-(4-(1H-pyrazol-4-yl)pyrimidin-2-yloxy)-2-fluoro-4-methylphenyl)-N-(4-fluorophenyl)cyclopropane-1,1-dicarboxamide, N-(5-(4-(1H-pyrazol-4-yl)pyrimidin-2-yloxy)-2-fluorophenyl)-N'-(4-fluorophenyl)cyclopropane-1,1-dicarboxamide, 2-(4-fluorophenyl)-N-(4-methyl-5-(2-(1-methyl-1H-pyrazol-4-yloxy)pyridin-2-ylcarbamoyl)acetamide, N-(2,5-difluoro-4-(3-(1-methyl-1H-pyrazol-4-yl)pyridin-4-yloxy)phenyl)-N'-(4-fluorophenyl)cyclopropane-1,1-dicarboxamide, N-(3-fluoro-4-(2-(1-methyl-1H-pyrazol-4-yl)pyridin-4-yloxy)phenyl)-N-(4-fluorophenyl)-N-methylcyclopropane-1,1-dicarboxamide, N-(2-fluoro-4-(2-(3-methylisoxazol-5-yl)pyridin-4-yloxy)phenyl)-N'-(4-fluorophenyl)cyclopropane-1,1-dicarboxamide, and N-(4-(2-(1H-1,2,3-triazol-4-yl)pyridin-4-yloxy)-2-fluorophenyl)-N'-(4-fluorophenyl)cyclopropane-1,1-dicarboxamide.

1.11 Methods 1.11a Methods of Protein Modulation

The invention includes methods of modulating kinase activity of a variety of kinases, e.g. VEGFR-2 (KDR) kinase, c-MET kinase, FLT-3 kinase, c-KIT kinase, PDGFR-α kinase, PDGFR-β kinase, and c-FMS kinase. The kinases may be wildtype kinases, oncogenic forms thereof, aberrant fusion proteins thereof or polymorphs of any of the foregoing. The method comprises the step of contacting the kinase species with compounds of the invention and especially those set forth in section 1. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, inhibition of phosphorylation, oxidation or nitrosylation of said kinase by another enzyme, enhancement of dephosphorylation, reduction or denitrosylation of said kinase by another enzyme, kinase cellular localization, and recruitment of other proteins into signaling complexes through modulation of kinase conformation.

1.11b Treatment Methods

The methods of the invention also include treating individuals suffering from a condition selected from the group consisting of cancer, hyperproliferative diseases, metabolic diseases, neurodegenerative diseases or diseases characterized by angiogenesis. These methods comprise administering to such individuals compounds of the invention, and especially those of section 1, said diseases including, but not limited to, solid tumors, malignant melanomas, glioblastomas, ovarian cancer, pancreatic cancer, prostate cancer, lung cancers, breast cancers, kidney cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, gastrointestinal stromal tumors, colonic cancers, ocular diseases characterized by hyperproliferation leading to blindness including various retinopathies, diabetic retinopathy and age-related macular degeneration and hypereosinophilic syndrome, rheumatoid arthritis, asthma, chronic obstructive pulmonary disorder, mastocytosis, mast cell leukemia, a disease caused by PDGFR-α kinase, a disease caused by PDGFR-β kinase, a disease caused by c-KIT kinase, a disease caused by cFMS kinase, a disease caused by c-MET kinase and oncogenic forms, aberrant fusion proteins and polymorphs thereof. The administration method is not critical, and may be from the group consisting of oral, parenteral, inhalation, and subcutaneous.

1.12 Pharmaceutical Preparations

The compounds of the invention, especially those of Section 1 may form a part of a pharmaceutical composition by combining one or more such compounds with a pharmaceutically acceptable carrier. Additionally, the compositions may include an additive selected from the group consisting of adjuvants, excipients, diluents, and stabilizers.

an activated acid halide, anhydride, mixed anhydride or an activated ester (such as a pentafluorophenyl ester or a p-nitrophenyl ester). Such activated intermediates (not shown) may or may not be isolated prior to reaction with amines 3 or 4. Those skilled in the art will further recognize that the carboxylic acid moieties of 2 may enter the reaction Scheme 1 masked as esters and the reaction sequences in Scheme 1 allow for additional de-protection steps, if necessary, to convert an ester derivative of 5, or 6 into acids 5 or 6 to facilitate the formation of the second amide bond.

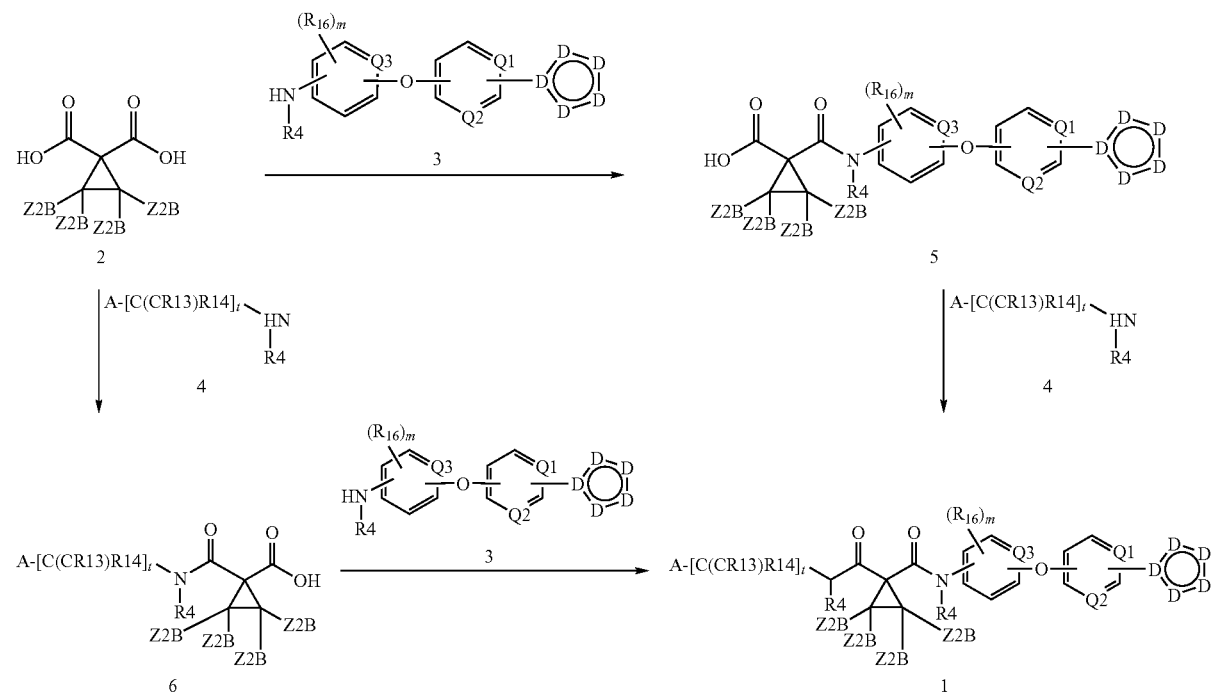

Scheme 1

SECTION 2. SYNTHESIS OF COMPOUNDS OF THE PRESENT INVENTION

The compounds of the invention are available by the general synthetic methods illustrated in the Schemes below and the accompanying examples.

In one aspect of the invention, compounds of general formula Ia contain an aminergic "W" group and a cyclopropyl "V" group, and are represented by general formula 1. Compounds of general formula 1 can be readily prepared by the union of amines of general formula 3, amines of general formula 4 (t=0-3), and a cyclopropane dicarboxylic acid of formula 2. As indicated below in Scheme 1, compounds of formula 1 can arise from the sequence 2→5→1 or alternately from the sequence 2→6→1. It will be recognized by those skilled in the art that the reaction arrows in Scheme 1 represent either a single reaction or a multi-step reaction sequence. Bis-acid 2 can be coupled in a step-wise manner with amines 3 and 4 through the use of standard peptide coupling agents known to those skilled in the art. Alternately, it will be understood in Scheme 1 that acid 2 may be joined with amines 3 or 4 by pre-activation of one or both carboxylic acid moieties as Non-limiting examples of Scheme 1 are shown in Schemes 2-4. Scheme 2 illustrates the preparation of compound II, an example of general formula 1 (wherein A is 4-fluorophenyl, t is 0, Z2B is H, Q3 is CH, the Q3 ring is substituted with fluorine, and the D-containing ring is pyrazole) by the general sequence of 2→5→1 (Scheme 1). Thus, as indicated below, the union of 1,1-cyclopropane bis-carboxylic acid (7, an example of general intermediate 2, vide supra), with amine 8 (an example of general amine 3) provides the amide/acid 9, an example of general intermediate 5. Conditions for the transformation include the in situ activation of bis-acid 7 by treatment with thionyl chloride in the presence of a tertiary base, such as triethylamine, followed by reaction with amine 8. Further reaction of 9 with amine 10 (an example of general intermediate 4) in the presence of a peptide coupling agent provides bis-amide 11. Coupling agents for the later transformation include TBTU (O-(benzotriazol-1-yl)-N,N,N',N'-tetramethyluronium tetrafluoroborate), PyBOP (benzotriazol-1-yloxy)tripyrrolidinophosphonium hexafluorophosphate), EDC (1-ethyl-3-(3-dimethylaminopropyl)carbodiimide hydrochloride) and BOP—Cl (bis(2-oxo-3-oxazolidinyl) phosphonic chloride).

Scheme 2

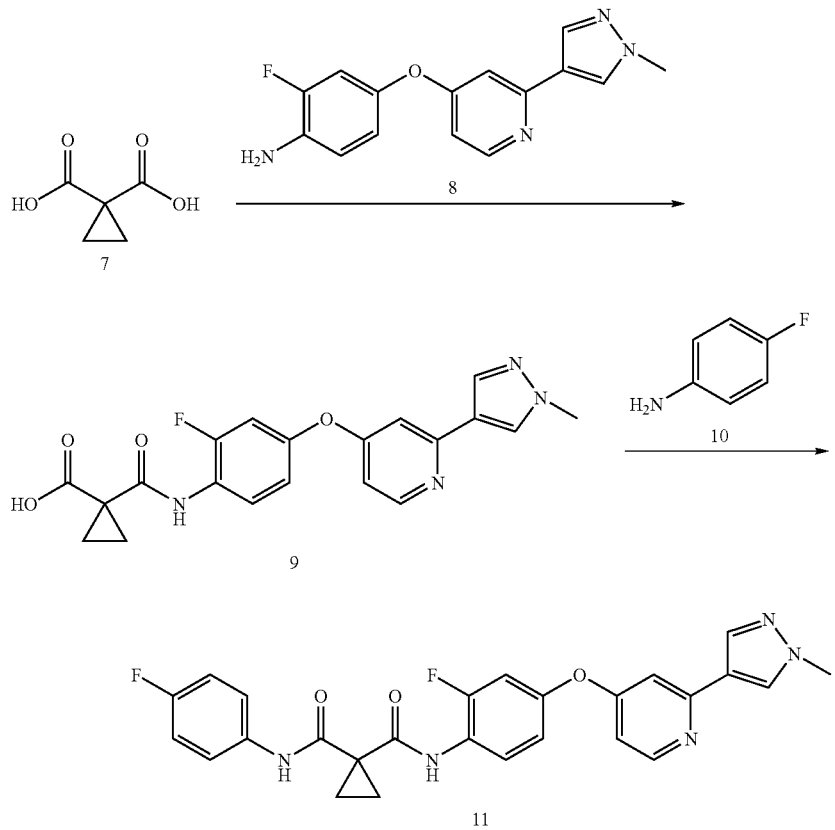

Similarly, Scheme 3 illustrates an additional example of the general sequence of 2→5→1 (Scheme 1) commencing with the mono-ester 12. Thus, acid/ester 12 is combined amine 13 to provide ester/amide 14. Saponification of the ester of 14 with lithium hydroxide provides the lithium carboxylate 15. Treatment of 15 with 10 and a peptide coupling reagent, for example TBTU, provides bis-amide 16, a further example of general formula 1

Scheme 3

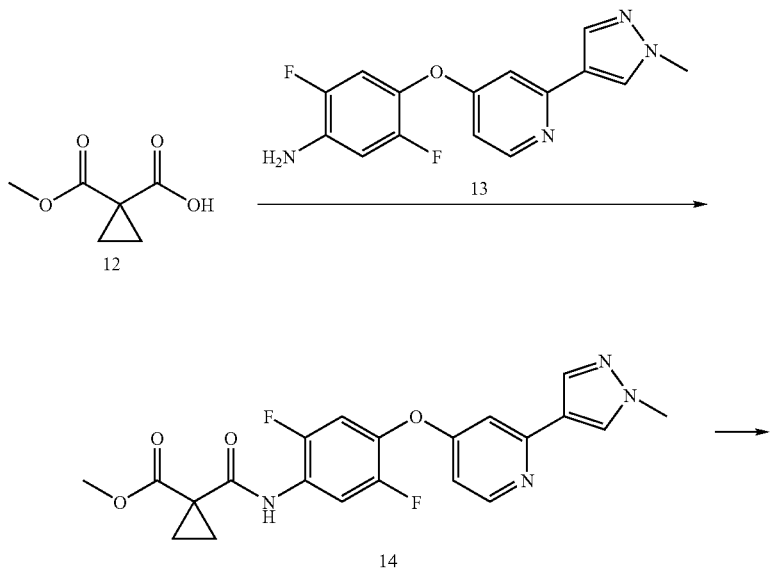

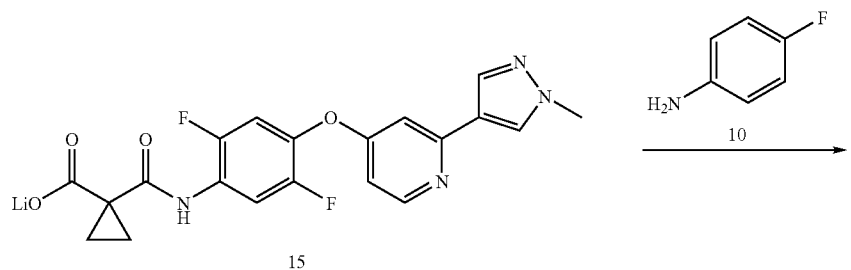
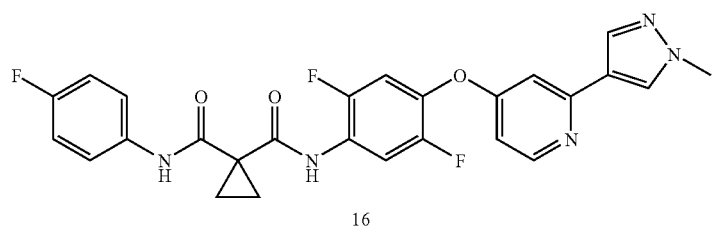
Scheme 4 illustrates the preparation of 19 as a non-limiting example of the general sequence 2→6→1 of Scheme 1. Thus, bis-acid 7 is first coupled with amine 10 to provide the amide/acid 17, which is in turn coupled with amine 18 to provide 19.
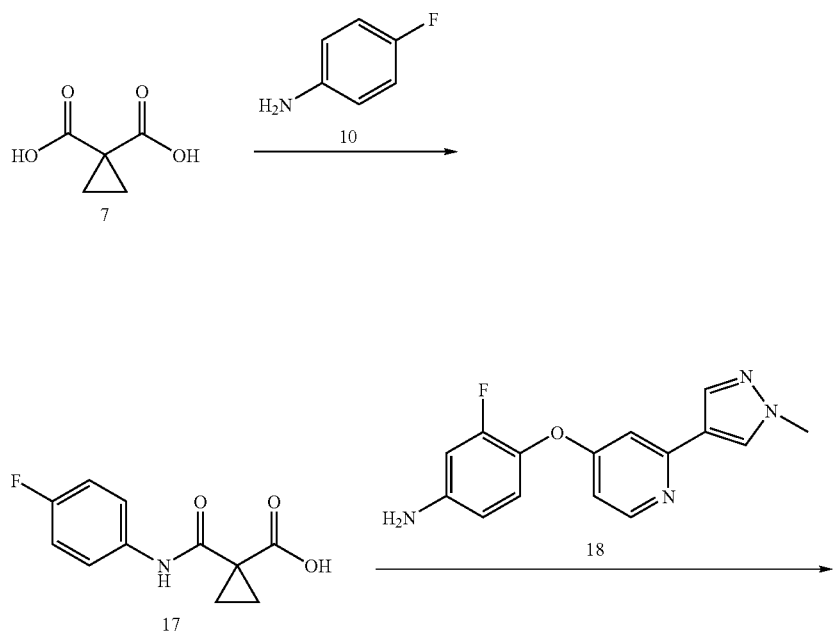

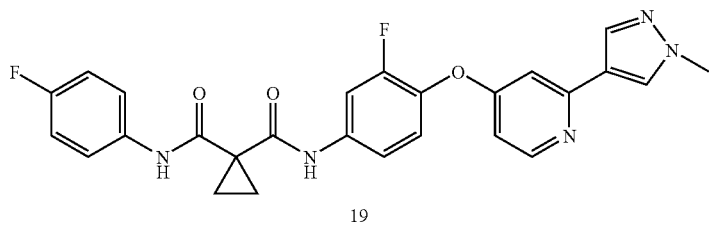

19

In another aspect of the invention, the "V" moiety of formula Ia is NR4. In these instances, compounds of formula 20 can be prepared as indicated in Scheme 5 by the reaction of general amine 3 with general intermediate 21, or, in the instance when R4 is H, with isocyanate 22.

Scheme 5

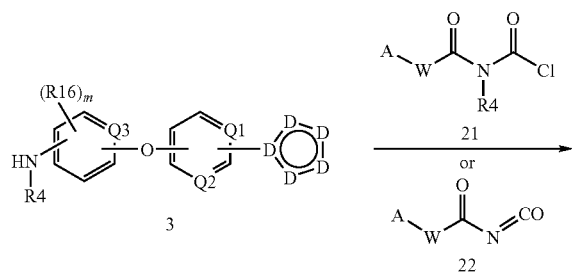

-continued

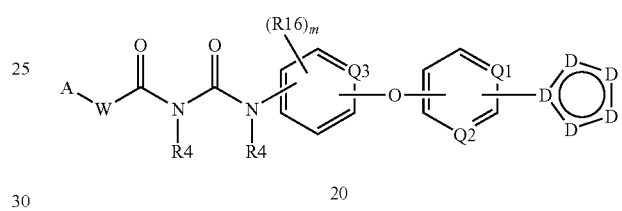

20

General intermediate 21 is available from 23 by reaction with phosgene or a phosgene surrogate such as diphosgene or triphosgene, as indicated in Scheme 6. Non-commercially-available isocyanates 22 can be prepared by the treatment of general acid chloride 24 with silver isocyanate. Acid chlorides 24 in turn are prepared from the corresponding acids by conditions familiar to those skilled in the art. Alternately, 22 can be prepared from amide 25 by treatment with oxalyl chloride or phosgene, optionally with heating.

Scheme 6

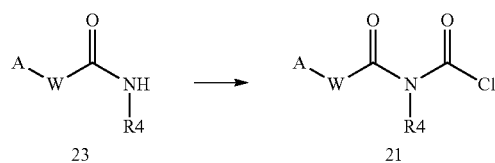

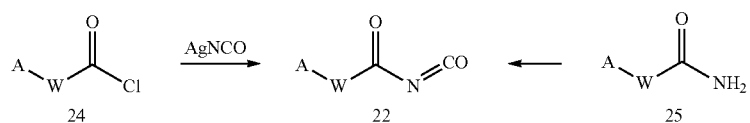

A non-limiting example of Schemes 5 and 6 is illustrated by the preparation of 29 in Scheme 7. Thus, acid 26 (see: Jiang, Y., et al., *J. Med. Chem.* (2007) 50(16): 3870) is converted to acid chloride 27 upon treatment with oxalyl chloride in toluene containing a catalytic amount of dimethylformamide. Further treatment of 27 with silver isocyanate provides isocyanate 28, an example of general intermediate 22 (Scheme 6). Finally, reaction of 28 with amine 18 provides N-acyl urea 29, an example of general formula 20 (wherein A is 4-fluorophenyl, W is —CH(CH$_3$)—, R4 is H, Q3 is CH, the Q3 ring is substituted with fluorine, Q2 is CH, Q1 is N, and the D-containing ring is pyrazole).

An additional example illustrating the general methods of Schemes 5 and 6 is the synthesis of 33 shown in Scheme 8. Thus, 4-fluorophenylacetamide 30, readily prepared from 4-fluorophenylacetic acid and ammonia, is first treated with oxalyl chloride with heating to provide 2-(4-fluorophenyl) acetyl isocyanate 31. Further treatment of isocyanate 31 with amine 32 provides the N-acyl urea 33, an example of general intermediate 20 (wherein A is 4-fluorophenyl, W is —CH$_2$—, R4 is H, Q3 is N, Q2 is CH, Q1 is N, and the D-containing ring is pyrazole).

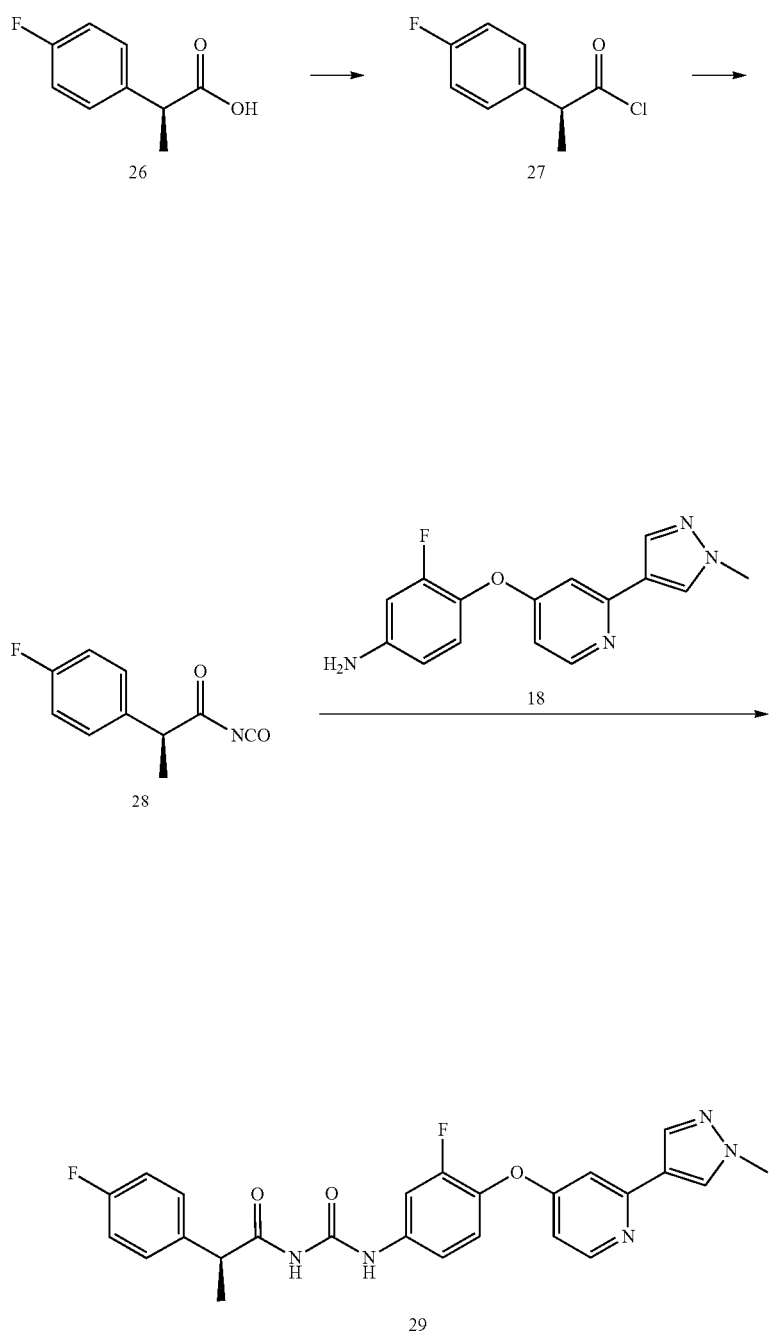

Scheme 8

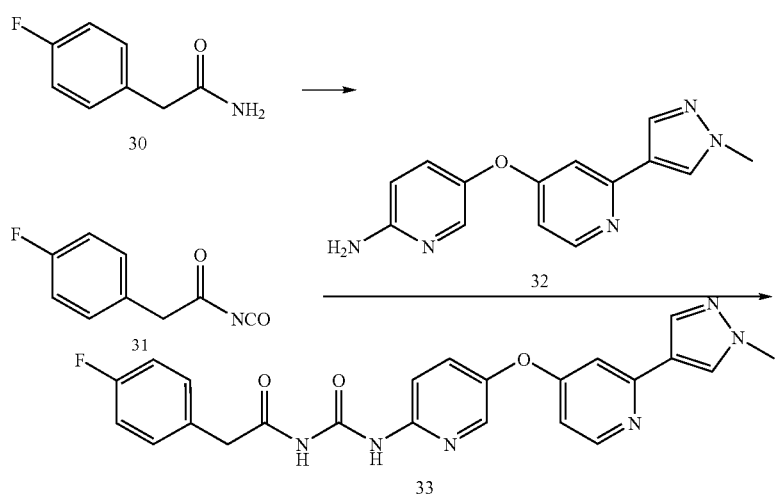

Amines 3 useful for the invention can be synthesized according to methods commonly known to those skilled in the art. One general preparation of amines of formula 3 involves the stepwise union of three monocyclic subunits by formation of a C—O bond between the Q1/Q2 and Q3 rings and the formation of a bond between the Q1/Q2 ring and the 5-membered D-ring. Variations of this method are shown in the following schemes.

Scheme 9 illustrates one general mode of assembly of 3 in which the ether oxygen atom of 3 is derived from a hydroxyl moiety on the Q3-containing subunit 34. The union of fragment 34 with the Q1/Q2-containing ring 35 is accomplished by treatment of 34 with a base, for example potassium tert-butoxide, and fragment 35 with optional heating to form the ether 36. In Scheme 9, the "LG" of monocycle 35 represents a moiety that can be directly displaced in a nucleophilic substitution reaction (with or without additional activation), for example a halide, sulfonate, sulfone or sulfoxide. The "X" group of monocycle 35 or bicycle 36 represents a moiety that allows the attachment of a 5-membered heterocyclic moiety. In one aspect, the "X" group represents a halogen atom that will participate in a transition-metal-mediated coupling with a pre-formed heterocyclic (D-ring) reagent (for example a boronic acid or ester, or heteroaryl stannane) to give rise to amine 3. In another aspect, the "X" group represents a leaving group to be displaced by a nitrogen atom of a pyrazole, imidazole or triazole to install the D-ring. In another aspect, the X group represents a moiety through which to construct the 5-membered D-ring (pyrazole, isoxazole, triazole, imidazole), for example a carboxylic acid or ester, alkyne, or aldehyde that can be transformed into a 5-membered ring.

Some non-limiting examples of general Scheme 9 are illustrated in the Schemes below. Scheme 10 illustrates the preparation of pyrazole 8, an example of general amine 3 (wherein R4 is H, Q3 is CH, the Q3 ring is substituted with fluorine, Q2 is CH, Q1 is N, and the D-containing ring is pyrazole). In Scheme 10, commercially available 3-fluoro-4-aminophenol (37) is reacted with potassium tert-butoxide and 2,4-dichloropyridine 38 (an example of 35 wherein LG and X are both chloro) to provide chloropyridine 39, an example of general intermediate 36. Possible conditions for this transformation are dimethylacetamide at a temperature between 80 and 100° C. The subsequent reaction of chloropyridine 39 with the commercially available pyrazole-4-boronic acid pinacol ester 40 in the presence of a palladium catalyst, for example tetrakis(triphenylphosphine) palladium(0), provides pyrazole amine 8.

Scheme 9

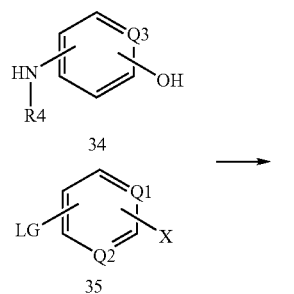

Scheme 10

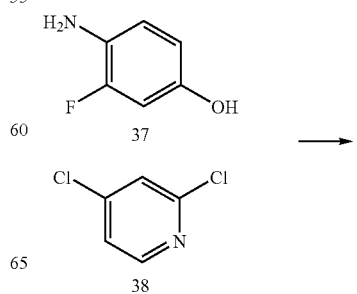

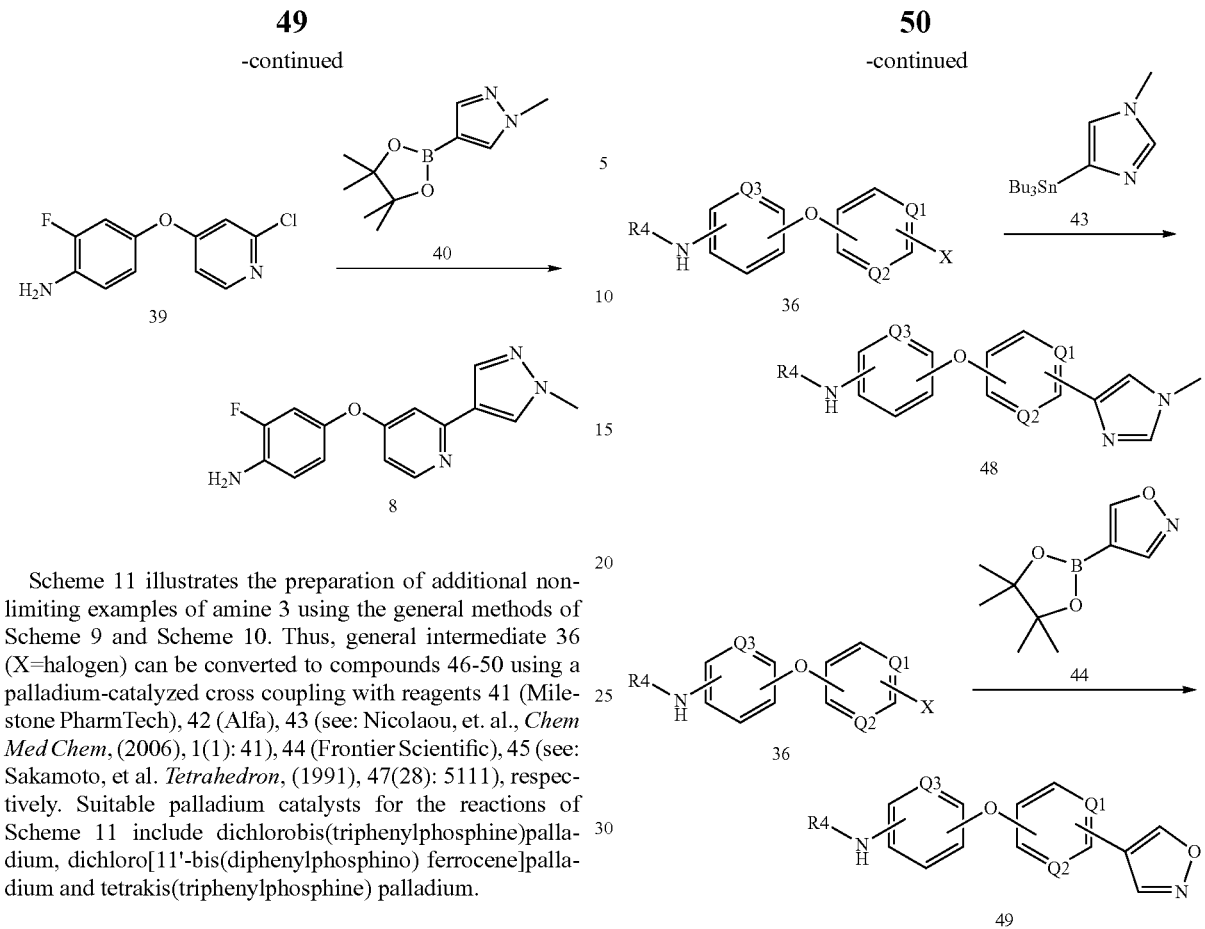

Scheme 11 illustrates the preparation of additional non-limiting examples of amine 3 using the general methods of Scheme 9 and Scheme 10. Thus, general intermediate 36 (X=halogen) can be converted to compounds 46-50 using a palladium-catalyzed cross coupling with reagents 41 (Milestone PharmTech), 42 (Alfa), 43 (see: Nicolaou, et. al., *Chem Med Chem*, (2006), 1(1): 41), 44 (Frontier Scientific), 45 (see: Sakamoto, et al. *Tetrahedron*, (1991), 47(28): 5111), respectively. Suitable palladium catalysts for the reactions of Scheme 11 include dichlorobis(triphenylphosphine)palladium, dichloro[11'-bis(diphenylphosphino) ferrocene]palladium and tetrakis(triphenylphosphine) palladium.

Scheme 11

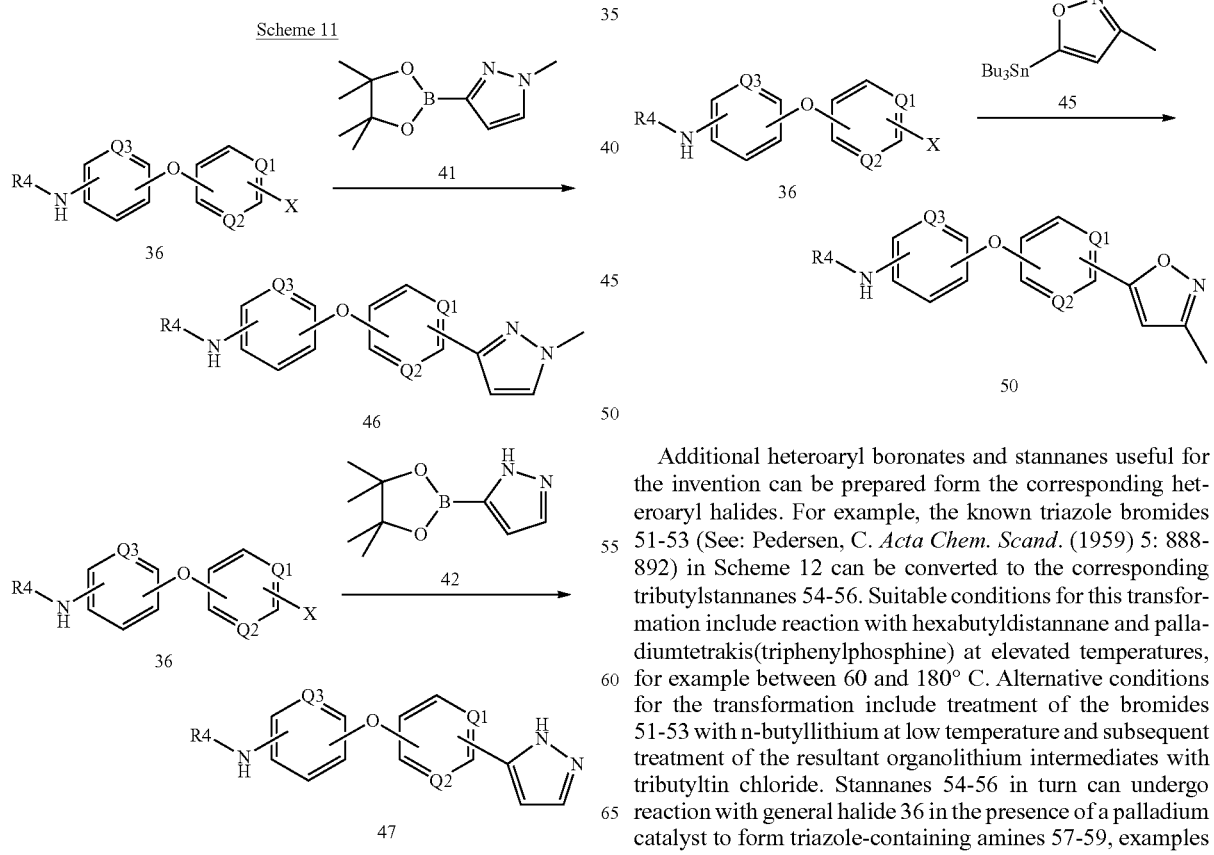

Additional heteroaryl boronates and stannanes useful for the invention can be prepared form the corresponding heteroaryl halides. For example, the known triazole bromides 51-53 (See: Pedersen, C. *Acta Chem. Scand.* (1959) 5: 888-892) in Scheme 12 can be converted to the corresponding tributylstannanes 54-56. Suitable conditions for this transformation include reaction with hexabutyldistannane and palladiumtetrakis(triphenylphosphine) at elevated temperatures, for example between 60 and 180° C. Alternative conditions for the transformation include treatment of the bromides 51-53 with n-butyllithium at low temperature and subsequent treatment of the resultant organolithium intermediates with tributyltin chloride. Stannanes 54-56 in turn can undergo reaction with general halide 36 in the presence of a palladium catalyst to form triazole-containing amines 57-59, examples of general amine 3.

Scheme 12

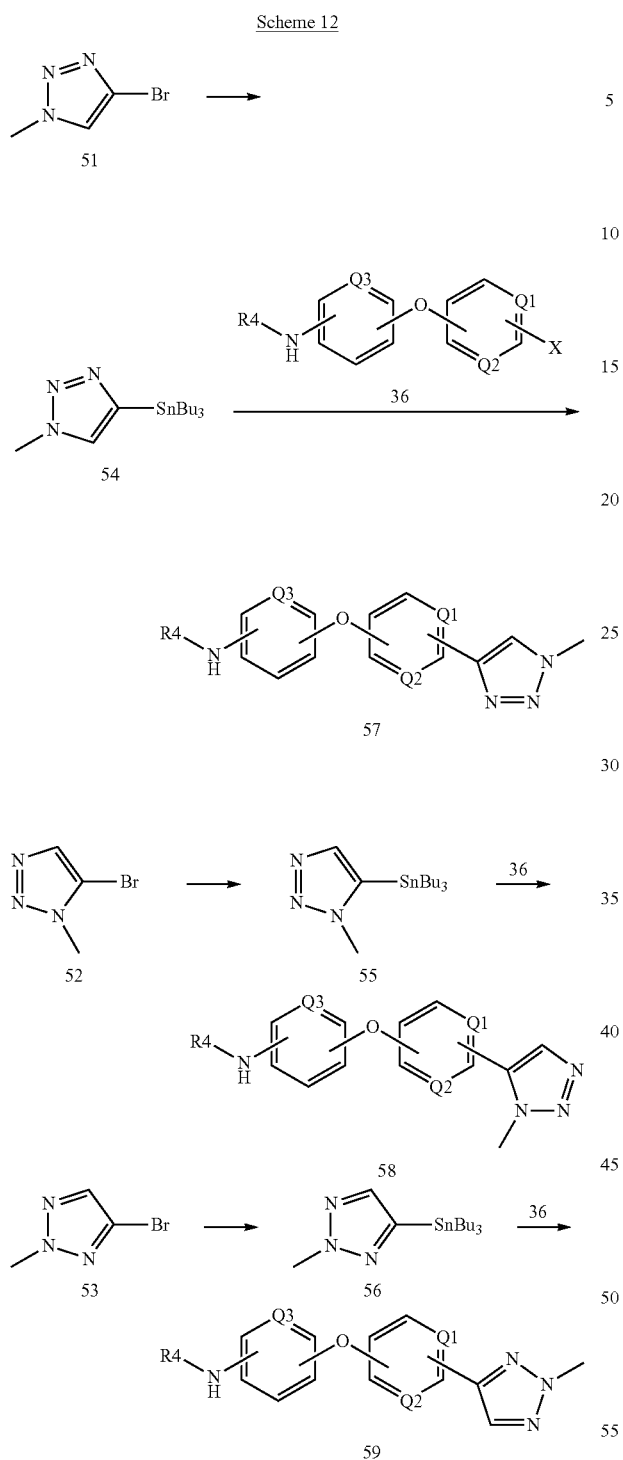

philic bases such as potassium carbonate, sodium hydride, 1,8-diazabicyclo[5.4.0]undec-7-ene (DBU), and the like. Possible temperatures are from ambient temperature up to about 250° C. and may optionally include the use of microwave irradiation or sonication.

Scheme 13 illustrates the reaction of general intermediate 36 with pyrazole 60 (example commercially available pyrazoles include those with R20=H, $CH_3$, CN, and $CF_3$), or pyrazole 61 (example commercially available pyrazoles include those with R20=$CH_3$, and $CF_3$) to provide pyrazoles 62, 63 or 64, non-limiting examples of general amine 3 wherein the D-ring is pyrazole.

Scheme 13

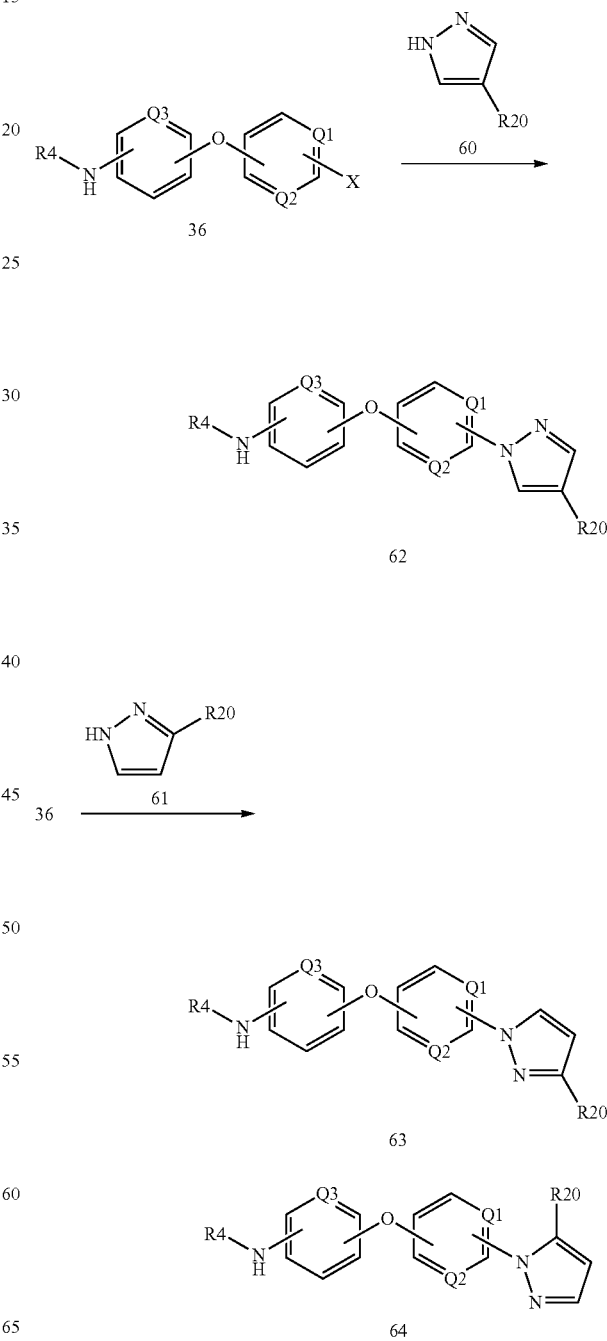

Schemes 13-16 illustrate the preparation of non-limiting examples general amine 3 wherein the D-ring is a pyrazole, imidazole or triazole ring linked to the Q1/Q2 ring through a nitrogen atom. Schemes 13-16 are examples of general Scheme 9 wherein the "X" group of 36 is a leaving group for nucleophilic aromatic substitution. Suitable X groups for Schemes 13-16 include halogen, including chlorine. Suitable conditions for Schemes 13-16 include the use of polar aprotic solvents such as 1-methyl-2-pyrrolidinone, dimethylacetamide, or dimethylsulfoxide in the presence of non-nucleo- Similarly, Scheme 14 illustrates the reaction of general intermediate 36 with imidazole 65 (example commercially available imidazoles include those with R20=H, CH₃, CN, CF₃, and 2-hydroxyethyl) to provide 66 and 67, non-limiting examples of general amine 3 wherein the D-ring is imidazole.

Scheme 14

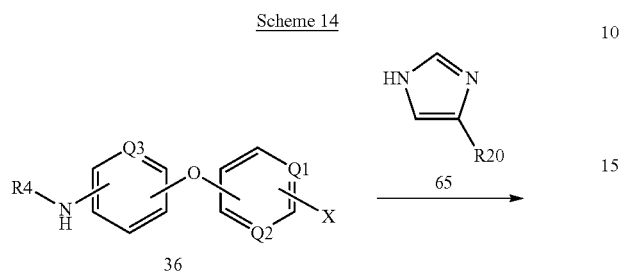

-continued

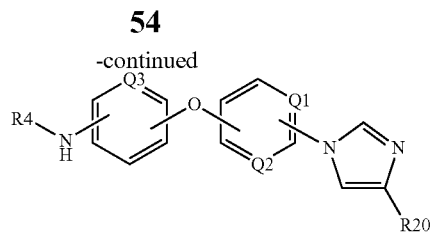

Scheme 15 illustrates the reaction of general intermediate 36 with triazole 68 (example commercially available triazoles include those with R20=H, CH₃, and CN) to provide 69, 70, and 71, non-limiting examples of general amine 3 wherein the D-ring is a 1,2,4-triazole.

Scheme 15

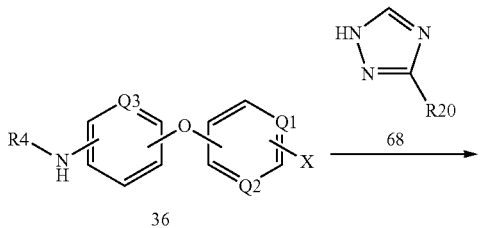

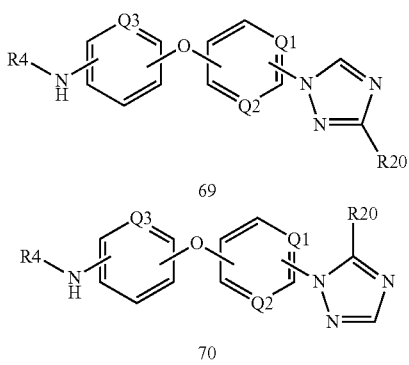

Scheme 16 illustrates the reaction of general intermediate 36 with triazole 72 (example commercially available triazoles include those with R20=H, hydroxymethyl) to provide 73, 74, and 75, non-limiting examples of general amine 3 wherein the D-ring is a 1,2,3-triazole.

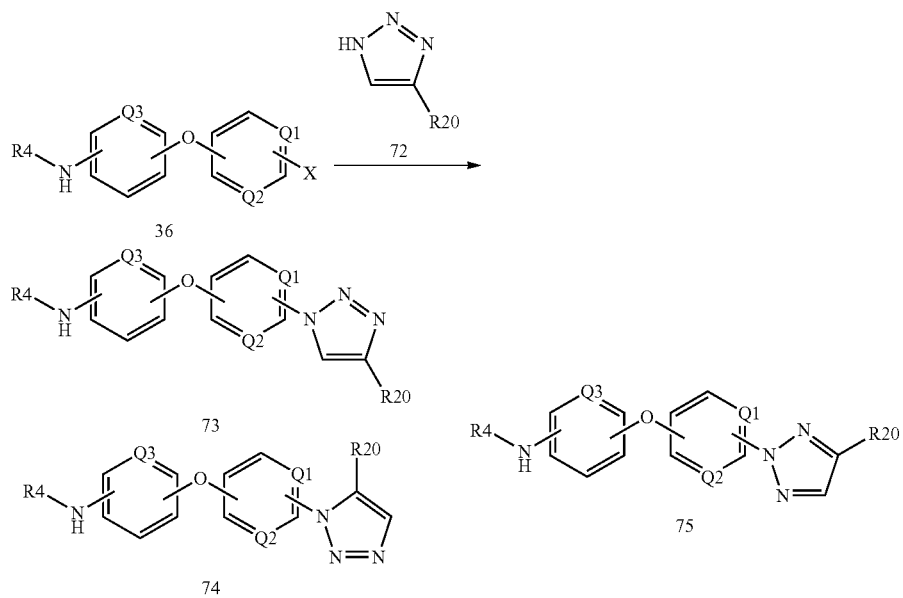

Scheme 17 illustrates the preparation of amines 78 and 79, non-limiting examples of general amines 3, as an example of Scheme 9 wherein an annulation sequence is employed to construct a triazole ring (D-ring). Thus, conversion of chloropyridine 39 into alkyne 76 is accomplished by Sonogashira cross-coupling with trimethylsilylacetylene, followed by removal of the trimethylsilyl group by conditions familiar to those skilled in the art, for example $K_2CO_3$ in methanol. Further reaction of alkyne 76 with azidomethyl pivalate (77) in the presence of copper sulfate and sodium ascorbate provides the N-pivaloylymethyl triazole amine 78 (see Loren, et. al. *Synlett*, (2005), 18: 2847). The pivalate 78 is a masked equivalent of NH-triazole 79. Removal of the pivalate moiety with NaOH provides 79. Alternately, 78 can be used directly in general Schemes 1 or 5 to provide compound of Formula 1 or 20 wherein the D-ring triazole is masked with the pivaloylymethyl group. Further treatment of such product with NaOH provides NH-triazoles of Formula 1 or 20.

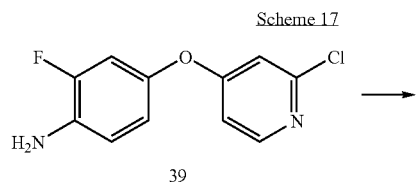

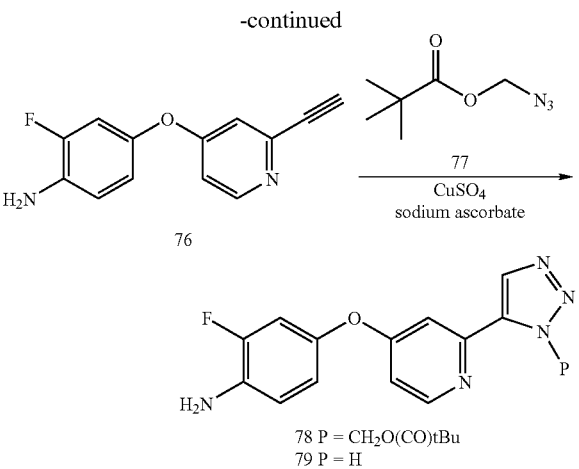

As an extension of Scheme 17, Z3-substituted triazoles of formula 81 and R20-substituted isoxazole of formula 83 can also be prepared by analogous 1,3-dipolar cycloadditions as shown in Scheme 18. Thus, combination of Z3-substituted azides 80, readily prepared from commercial alkyl halides and sodium azide, with alkyne 76, sodium ascorbate, and $Cu(SO_4)$ pentahydrate (See: Rostotsev, et. al. *Angew. Chem. Int. Ed*, (2002) 41 (14): 2596-2599) gives rise to Z3-substituted triazoles 81. In a similar sequence, the combination of R20-substituted oximes 82, readily prepared from aldehydes and hydroxylamine, with N-chlorosuccinimide in the presence of alkyne 76 with heating, or optional microwave irradiation, provides isoxazoles of formula 83, additional examples of general amine 3.

Scheme 18

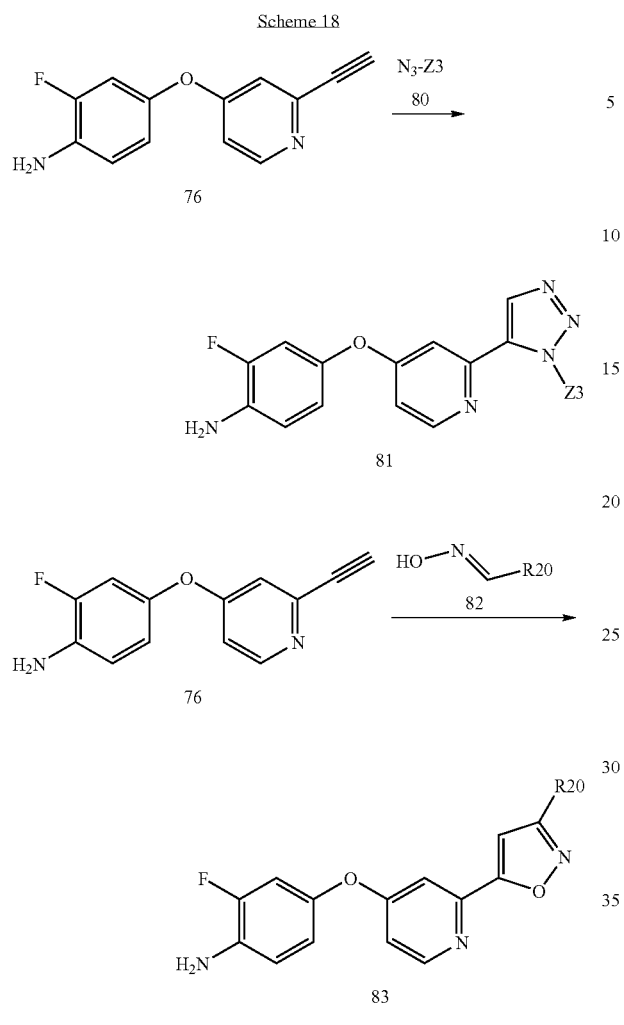

Scheme 19

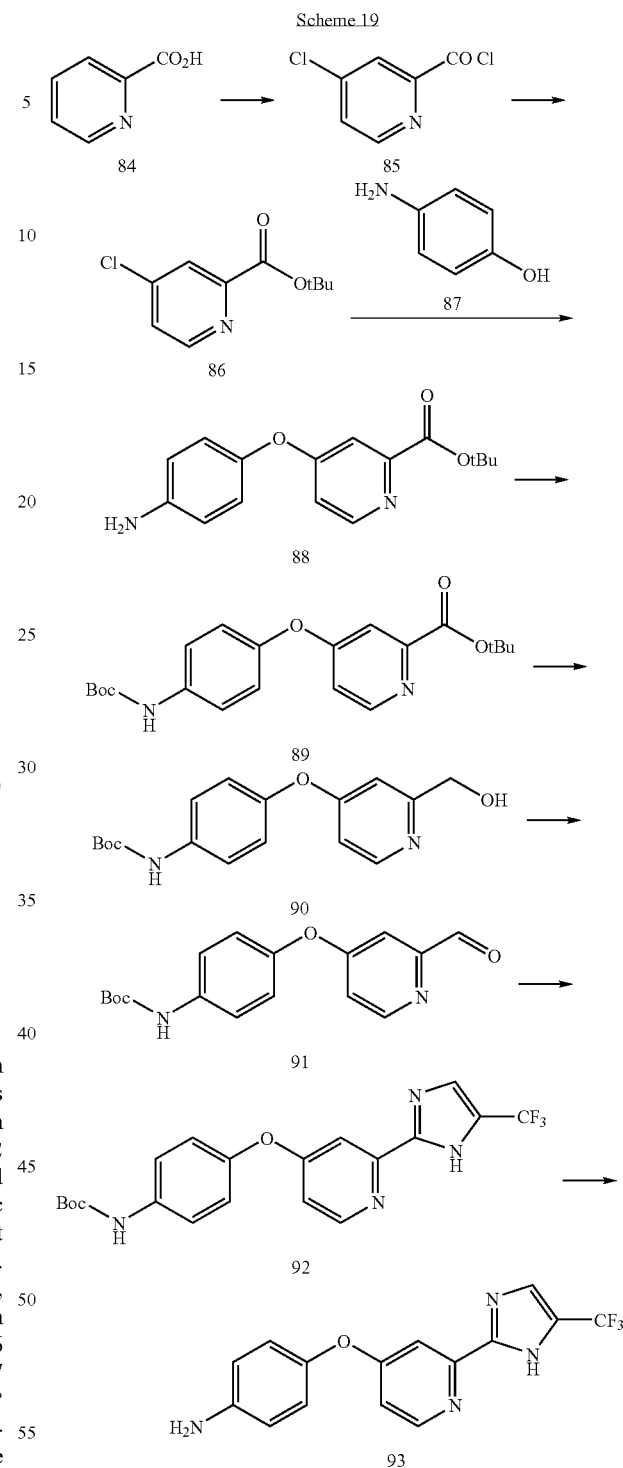

An additional example of Scheme 9 wherein an annulation sequence is employed to construct an imidazole D-ring is shown in Scheme 19 for the synthesis of imidazole 93, an example of general amine 3 (wherein R4 is H, Q3 is CH, Q2 is CH, Q1 is N, and the D-containing ring is substituted imidazole (R20=CF$_3$)). Conversion of pyridine-2-carboxylic acid (84) to chloro-pyridine 85 is accomplished by treatment with thionyl chloride and sodium bromide with heating. Reaction of 85 with tert-butanol provides the chloro-ester 86, an example of general intermediate 35 (Scheme 9, wherein LG is chloro and X is tert-butoxycarbonyl). Treatment of 86 with the sodium salt of 4-aminophenol 87, prepared from 87 with sodium hydride, and heating the resultant mixture to 80° C. provides ether-ester 88, an example of general intermediate 36 (Scheme 9, wherein X is tert-butoxycarbonyl). The further conversion of 88 to 93 illustrates the potential multi-step nature of the second reaction arrow of general Scheme 9. Thus, treatment of 88 with di-tert-butyl dicarbonate provides the Boc-protected intermediate 89. Reduction of the ester moiety of 89 with LiAlH$_4$ provides the alcohol 90, which in turn is oxidized with MnO$_2$ to provide aldehyde 91, a further example of general intermediate 36 (wherein X is formyl). Further reaction of 91 with 3,3-dibromo-1,1,1-trifluoro-propan-2-one, sodium acetate, and ammonium hydroxide provides the imidazole 92. Removal of the Boc group of 92 using aqueous HCl provides 93, an example of general amine 3.

Scheme 20 illustrates the general preparation of additional pyrazole and isoxazole isomers by an annulation sequence. Thus, aldehyde 91, a representative example of general intermediate 36 (wherein R4 is a Boc protecting group, Q3 is H, Q2 is H, Q1 is N and X is formyl), is converted to ketone 94 by sequential treatment with methyl magnesium bromide followed by oxidation using standard conditions familiar to those skilled in the art. Subsequent treatment of 94 with the dimethylacetal of dimethylformamide affords 95. Further treatment of 95 with Z3-substituted hydrazine 96 provides a mixture of 97 and 99 containing an N-Boc protecting group. Removal of the Boc protecting group under standard acidic conditions provides 98 and 100, examples of general amine 3 wherein the D-ring is Z3-substituted pyrazole. In a similar fashion, treatment of intermediate 95 with hydroxylamine provides isoxazoles 101 and 103 containing an N-Boc protecting group. Removal of the Boc protecting group under standard acidic conditions provides 102 and 104, examples of general amine 3 wherein the D-ring is isoxazole.

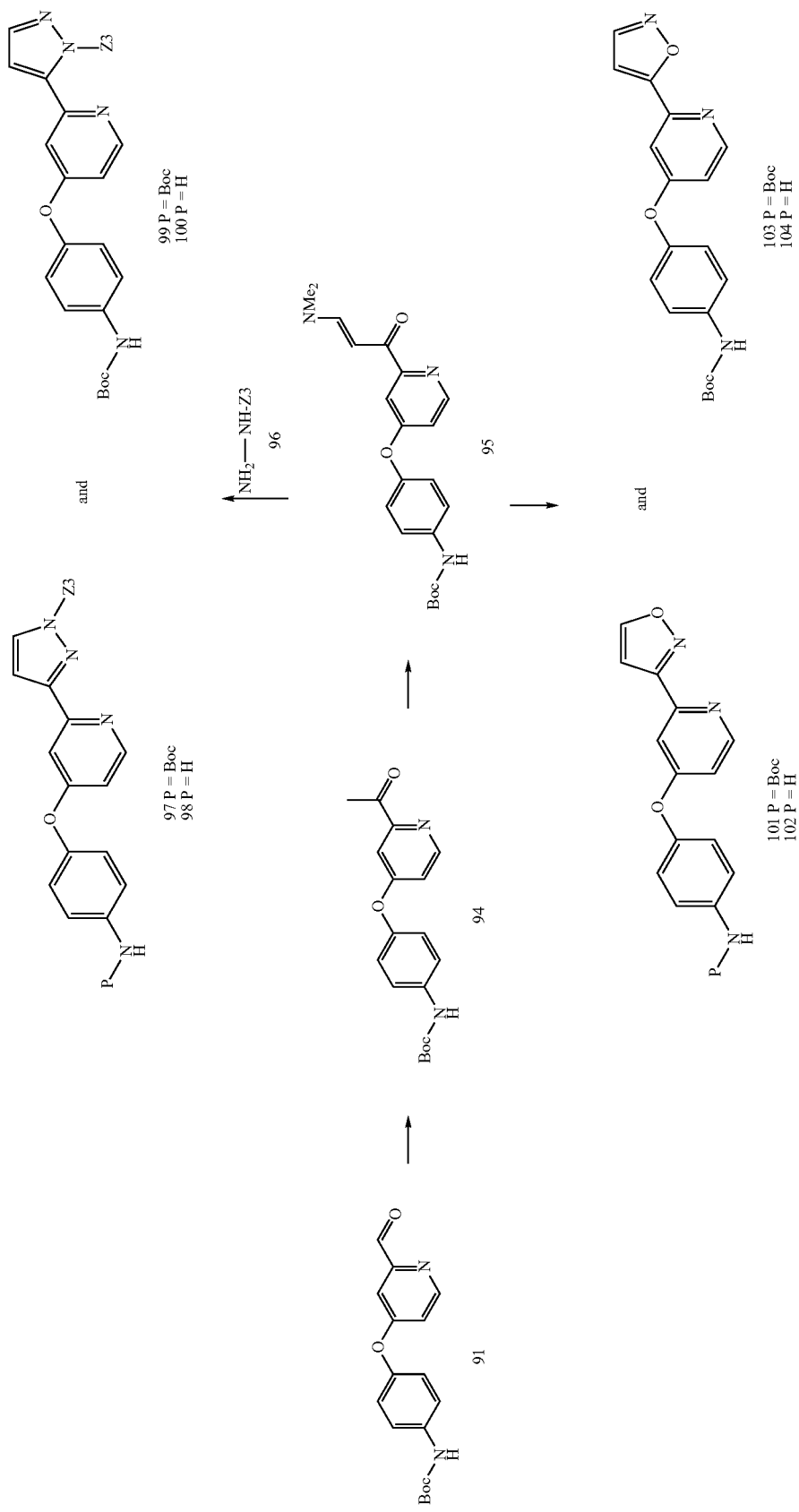

In a similar manner, Scheme 21 illustrates the preparation of R20-substituted pyrazole and isoxazole rings. Thus, ketone 94, a representative example of general intermediate 36 (wherein R4 is a Boc protecting group, Q3 is H, Q2 is H, Q1 is N and X is acetyl), is converted to di-ketone 105 by sequential treatment with a strong base and an R20-substituted acylation reagent, for example an acid halide or ester. Further treatment of 105 with Z3-substituted hydrazine 96 provides a mixture of 106 and 107 containing an N-Boc protecting group. Removal of the Boc protecting group under standard acidic conditions provides 108 and 109, examples of general amine 3 wherein the D-ring is an R20- and Z3-substituted pyrazole. In a similar fashion, treatment of intermediate 105 with hydroxylamine provides isoxazoles 110 and 111 containing an N-Boc protecting group. Removal of the Boc protecting group under standard acidic conditions provides 112 and 113, examples of general amine 3 wherein the D-ring is an R20-substituted isoxazole.

(with or without additional activation), for example a halide, sulfonate, sulfone, sulfoxide or nitro. The "X" group of monocycle 115 or bicycle 116 represents a moiety that allows the attachment of a 5-membered heterocyclic moiety. In one aspect, the "X" group represents a halogen atom that will participate in a transition-metal-mediated coupling with a pre-formed heterocyclic (D-ring) reagent (for example a boronic acid or ester, or heteroaryl stannane) to give rise to amine 118. In another aspect, the "X" group represents a leaving group to be displaced by a nitrogen atom of a pyrazole, imidazole or triazole to install the D-ring. In another aspect, the X group represents a moiety through which to construct the 5-membered D-ring (pyrazole, isoxazole, triazole, imidazole), for example a carboxylic acid or ester, alkyne, or aldehyde, that can be transformed into a 5-membered ring-containing intermediate 118. Subsequent to the formation of nitro ether 116, the nitro moiety is converted to an amino moiety by subjecting 116 to reducing conditions

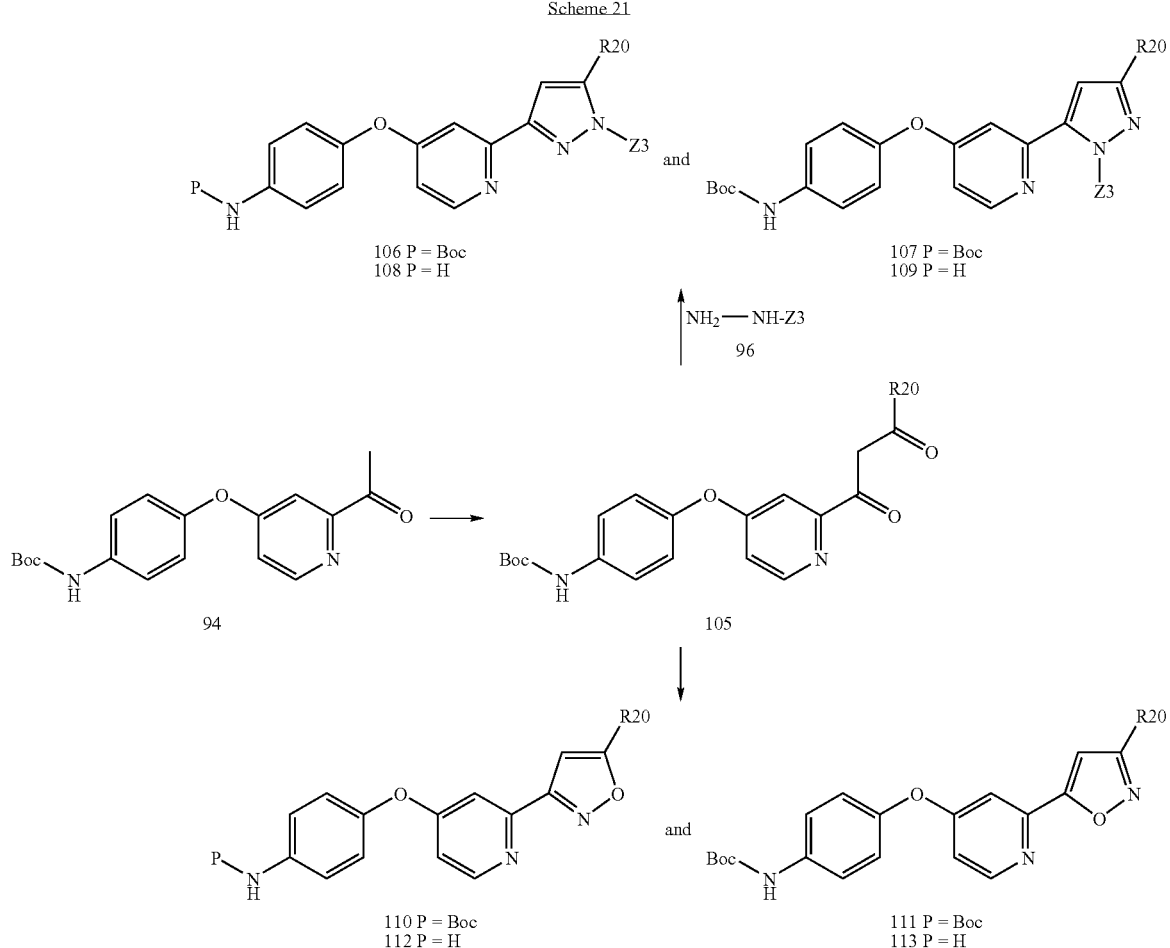

Scheme 22 illustrates another general mode of assembly of 3 in which the ether oxygen atom of 3 is derived from a hydroxyl moiety on the Q1/Q2-containing subunit 115. The union of intermediate 114 with the Q1/Q2-containing ring 115 is accomplished by treatment of 115 with a base, for example potassium tert-butoxide, and fragment 114 with optional heating to form the ether 116. In Scheme 22, the "LG" of monocycle 114 represents a moiety that can be directly displaced in a nucleophilic substitution reaction known to those skilled in the art, for example iron powder, zinc powder, indium powder, stannous chloride, or hydrogenation in the presence of a metallic catalyst, for example a nickel or palladium catalyst which affords amine 117. Conversion of the "X" group-containing intermediate 117 to the 5-membered D-ring-containing intermediate 118 is thus accomplished by the methods described in the schemes above to provide 118, an example of general amine 3 wherein R4 is H. If desired, amine 118 can be alkylated with an R4 moiety by standard conditions to provide general amine 3.

Scheme 22

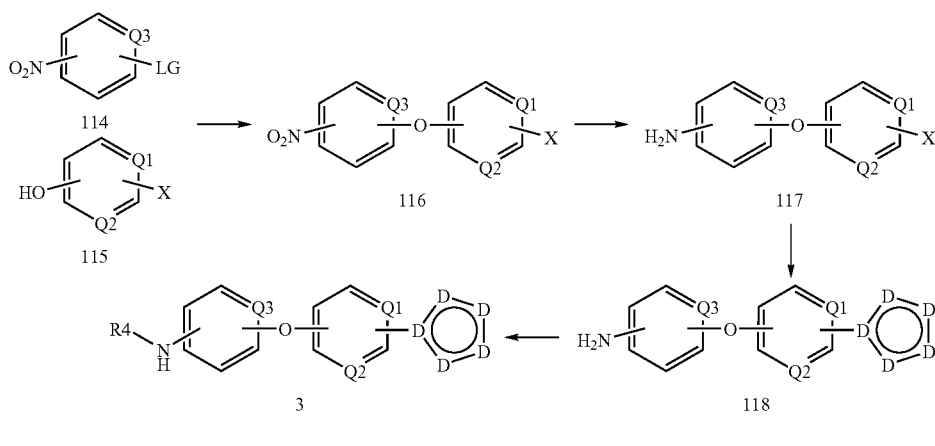

A non-limiting example of Scheme 22 is shown below for the preparation of 32 (Scheme 23), an example of general amine 118 (wherein Q3 is N, Q2 is CH, Q1 is N, and the D-containing ring is pyrazole). In Scheme 23, commercially available 5-bromo-2-nitropyridine (119) is reacted with 2-chloro-4-hydroxypyridine (120) and a base, for example cesium carbonate, at elevated temp, for example 80° C., to afford nitropyridine 121, an example of general intermediate 116. Possible conditions for this transformation are dimethylformamide at a temperature between 80 and 100° C. Further reaction of nitropyridine 121 with zinc dust in the presence of ammonium chloride provides aminopyridine 122. Further reaction of 122 with pyrazole-4-boronic acid pinacol ester 40 by the conditions described previously provide the pyrazole amine 32, an example of general amine 118.

Scheme 23

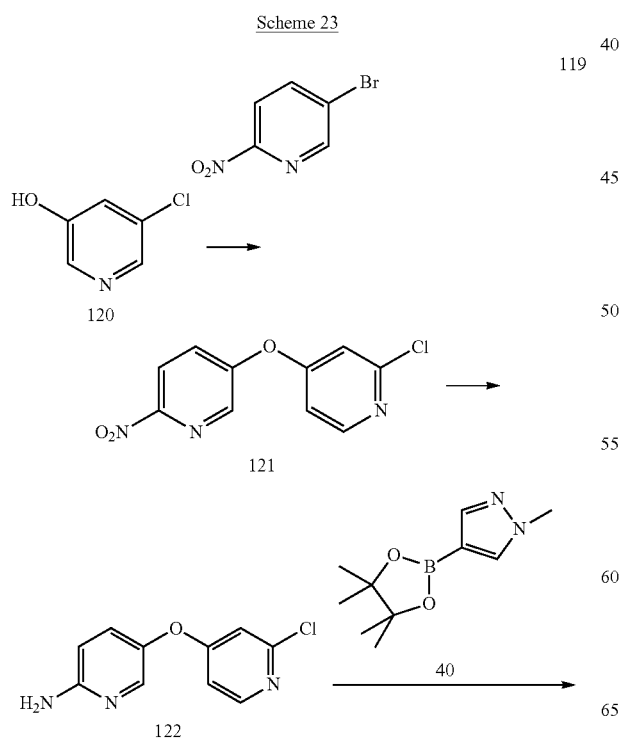

-continued

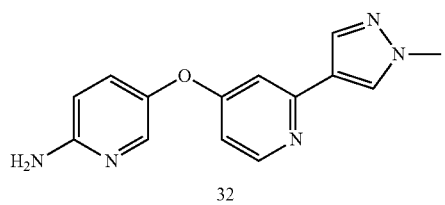

Scheme 24 illustrates another general method of preparing amines 3 by first attaching the 5-membered heterocycle to the Q1/Q2 ring (35). As described for Scheme 9, the "LG" of monocycle 35 represents a moiety that can be directly displaced in a nucleophilic substitution reaction (with or without additional activation). The "X" group of monocycle 35 represents a moiety that allows the attachment of a 5-membered heterocycle. In one aspect, the "X" group represents a halogen atom that will participate in a transition-metal-mediated coupling with a pre-formed heterocyclic reagent (for example, a boronic acid or ester, or heteroaryl stannane) to give rise to amine 3. In another aspect, the "X" group of 35 represents a functional group that can be converted to a five-membered heterocycle by an annulation reaction. Additionally, the "X" group of 35 may represent a leaving group (halogen, sulfoxide, sulfone, sulfonate) that can be displaced by a nucleophilic nitrogen atom of a pyrazole, triazole or imidazole ring. After conversion of 35 to 123, the "LG" moiety can be displaced by a hydroxyl group on the Q3-containing ring to provide the tricylic ether-amine 3. Those skilled in the art will recognize that each reaction arrow in Scheme 24 may represent a single transformation or a series of transformations.

Scheme 24

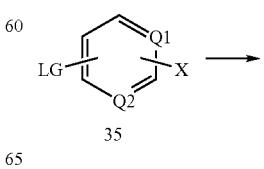

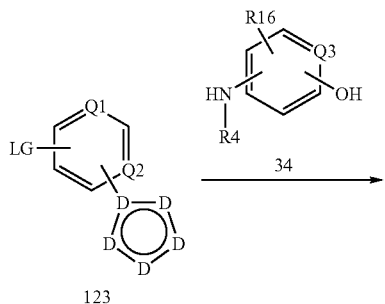

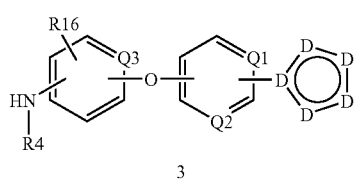

A specific, non-limiting example of Scheme 24 is illustrated in Scheme 25 by the preparation of amine 128, an example of general amine 3 (wherein Q3 is CH and the Q3 ring is substituted with fluoro, Q2 is N, Q1 is N, and the D-containing ring is pyrazole). Thus, commercially available pyrimidine 124, an example of general intermediate 35, undergoes a palladium-catalyzed coupling with the commercially available pyrazole boronate 40 to provide the bicycle 125, an example of general intermediate 123 (Scheme 24). Oxidation of the sulfide moiety of 125 (The "LG" group of general intermediate 123) with m-chloroperbenzoic acid further activates this moiety toward nucleophilic displacement and gives rise to intermediate 126. Treatment of sulfone 126 with phenol 127 in the presence of a base provides tricylic amine 128, an example of general amine 3. Possible bases for the later transformation include potassium carbonate and potassium tert-butoxide in polar aprotic solvents such as dimethylformamide or dimethylacetamide.

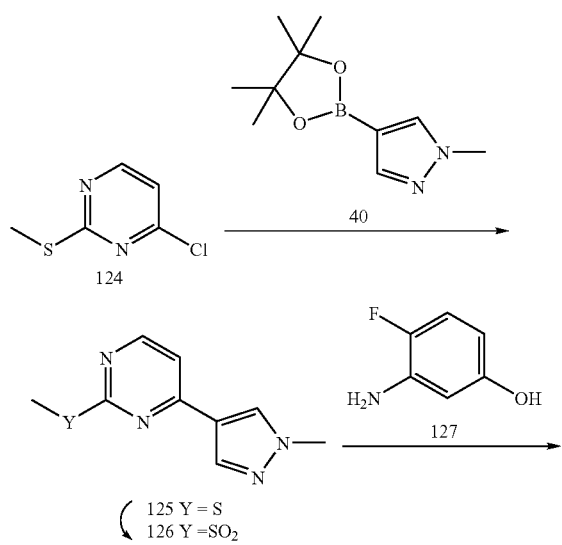

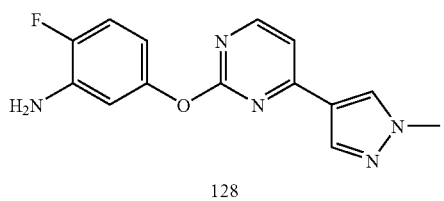

An additional non-limiting example of general Scheme 24 is illustrated in Scheme 26 by the preparation of 131, an additional example of general amine 3 (wherein Q3 is CH and the Q3 ring is substituted with fluoro, Q2 is N, Q1 is N, and the D-containing ring is pyrazole). Thus, commercially available dichloropyrimidine 129, an example of general intermediate 35 wherein both "LG" and "X" are chloro, undergoes a palladium-catalyzed coupling with the commercially available pyrazole boronate 40 to provide the bicycle 130, an example of general intermediate 123 (Scheme 24). Addition of phenol 37 in the presence of a base at elevated temperature then provides amine 131.

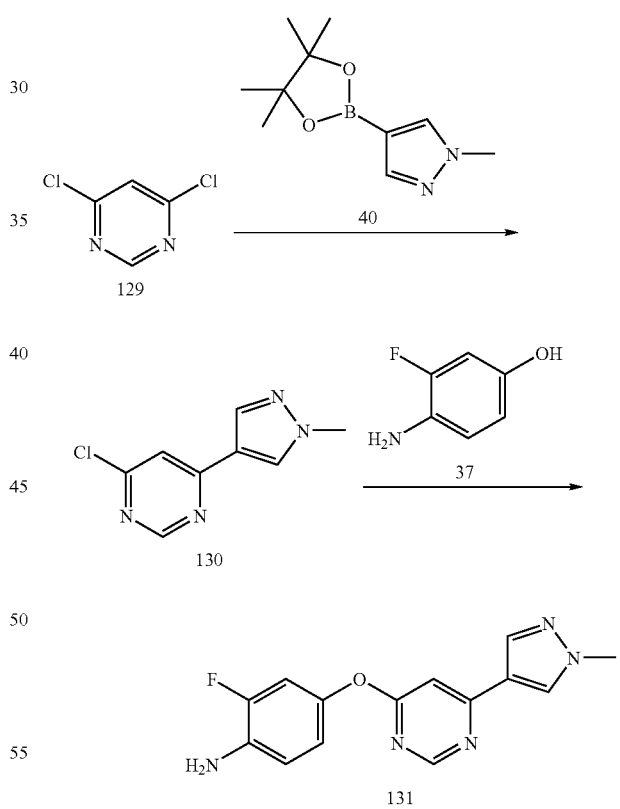

Scheme 27 illustrates the preparation amine 134 as an additional non-limiting example of general Scheme 9. Thus, by direct analogy to Scheme 10, 2,4-dichloropyrimidine (132) can be reacted with phenol 37 in the presence of a base to provide 133, an example of general intermediate 36 (Scheme 9). Further reaction of chloropyrimidine 133 with pyrazole boronate 40 in the presence of palladium catalyst provides amine 134, an example of general amine 3.

Scheme 27

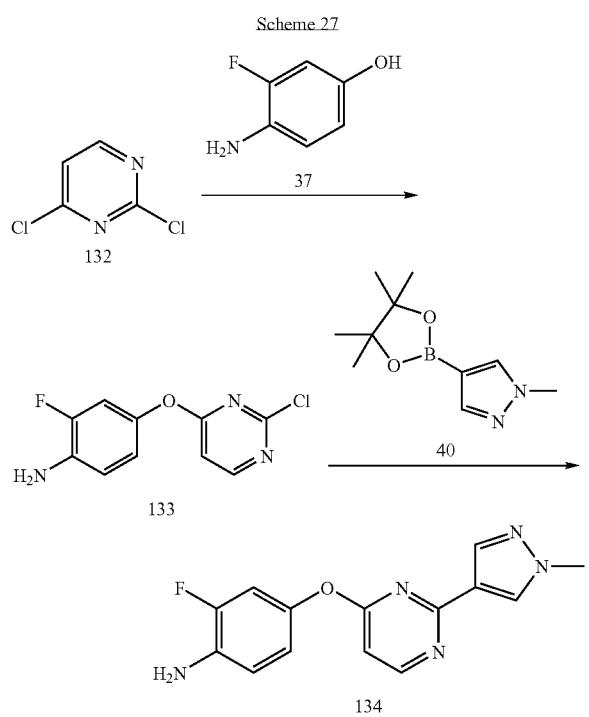

Additional preferred synthetic methods for the preparation of compounds of formula 1 are found in the following examples.

SECTION 3. EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example A1

A suspension of 3-fluoro-4-aminophenol (8.0 g, 63.0 mmol) in dimethylacetamide (80 mL) was de-gassed in vacuo and treated with potassium tert-butoxide (7.3 g, 65 mmol). The resultant mixture was stirred at RT for 30 min. 2,4-Dichloropyridine (8 g, 54 mmol) was added and the mixture was heated to 80° C. for 12 h. The solvent was removed under reduced pressure to give a residue which was partitioned between water and EtOAc (3×100 mL). The organic layers were washed with saturated brine, dried (MgSO$_4$), concentrated in vacuo and purified by silica gel column chromatography to give 4-(2-chloropyridin-4-yloxy)-2-fluorobenzenamine (11 g, 86% yield). $^1$H NMR (300 MHz, DMSO-d6): δ 8.24 (d, J=5.7 Hz, 1H), 7.00 (dd, J=9.0, 2.7 Hz, 1H), 6.89-6.73 (m, 4H), 5.21 (br s, 2H); MS (ESI) m/z: 239.2 (M+H$^+$).

A solution of 4-(2-chloropyridin-4-yloxy)-2-fluorobenzenamine (3 g, 12.6 mmol), 1-methyl-3-(4,4,5,5-tetramethyl-[1,3,2]dioxaborolan-2-yl)-1H-pyrazole (5.2 g, 25.2 mmol), and Na$_2$CO$_3$ (2.7 g, 25.2 mmol) in DME (18 mL)/water (6 mL) was sparged with nitrogen for 20 min. Pd(PPh$_3$)$_4$ (729 mg, 0.63 mmol) was added and the resulting mixture was heated to 100° C. for 16 h. The solvent was removed under reduced pressure and the crude product was suspended in water and extracted with EtOAc. The organic layer was washed with brine, dried (Na$_2$SO$_4$), concentrated in vacuo. and purified via silica gel chromatography to give 2-fluoro-4-(2-(1-methyl-1H-pyrazol-4-yl)pyridin-4-yloxy)benzenamine (2 g, 56% yield). $^1$H NMR (300 MHz, DMSO-d$_6$): δ 8.31 (d, J=5.7 Hz, 1H), 8.21 (s, 1H), 7.92 (s, 1H), 7.12 (d, J=2.4 Hz, 1H), 6.96 (m, 1H), 6.85-6.72 (m, 2H), 6.56 (m, 1H), 5.15 (s, 2H), 3.84 (s, 3H); MS (ESI) m/z: 285.0 (M+H$^+$).

Example A2

Using a procedure analogous to Example A1, 2-fluoro-4-aminophenol (2.6 g, 24 mmol) and 2,4-dichloropyridine (2.88 g, 20 mol) were combined to provide 4-(2-chloropyridin-4-yloxy)-3-fluoroaniline (3.2 g, 67% yield). $^1$H NMR (400 MHz, DMSO-d$_6$): δ 8.25 (d, J=5.6 Hz, 1H), 6.99 (m, 1H), 6.90 (m, 2H), 6.50 (d, J=1.6 Hz, 1H), 6.41 (d, J=10.4 Hz, 1H), 5.51 (s, 2H); MS (ESI) m/z: 239.1 (M+H$^+$).

Using a procedure analogous to Example A1, 4-(2-chloropyridin-4-yloxy)-3-fluoroaniline (3 g, 11.6 mmol), 1-methyl-4-(4,4,5,5-tetramethyl-1,3,2-dioxaborolan-2-yl)-1H-pyrazole (3.4 g, 16.4 mmol), Na$_2$CO$_3$ (2.7 g, 25.2 mmol) and Pd(Ph$_3$)$_4$ (1.5 g, 0.1 eq) were combined to give 3-fluoro-4-(2-(1-methyl-1H-pyrazol-4-yl)pyridin-4-yloxy)aniline (1.1 g, 34% yield). $^1$H NMR (400 MHz, DMSO-d$_6$): δ (8.31 (d, J=5.6 Hz, 1H), 8.22 (s, 1H), 7.93 (s, 1H), 7.14 (s, 1H), 6.98 (m, 1H), 6.55-6.49 (m, 2H), 6.42 (d, J=7.2 Hz, 1H), 5.44 (s, 2H), 3.86 (s, 3H); MS (ESI) m/z: (M+H$^+$): 285.2.

Example A3

1,2,3-Trifluoro-4-nitrobenzene (30 g, 0.17 mol), benzyl alcohol (18.4 g, 0.17 mol) and K$_2$CO$_3$ (35 g, 0.25 mol) were combined in DMF (300 mL) and were stirred at RT for 8 h. Water (300 mL) was added, and the mixture was extracted with EtOAc (3×500 mL). The combined organic layers were washed with brine, dried (MgSO$_4$), concentrated in vacuo and purified by column chromatography on silica gel to give 1-benzyloxy-2,3-difluoro-4-nitrobenzene (16 g, 36% yield). $^1$H NMR (400 MHz, DMSO-d$_6$): δ 8.06 (m, 1H), 7.49-7.30 (m, 6H), 5.37 (s, 2H).

A solution of 1-benzyloxy-2,3-difluoro-4-nitrobenzene (14 g, 52.8 mmol) in MeOH (200 mL) was stirred with Pd/C (10%, 1.4 g, 1.3 mmol) under a hydrogen atmosphere (30 psi) for 2 h. The catalyst was removed by filtration, and the filtrate was concentrated in vacuo to afford 4-amino-2,3-difluorophenol (7 g, 92% yield). $^1$H NMR (400 MHz, DMSO-d$_6$): δ 9.05 (s, 1H), 6.45 (t, J=8.8 Hz, 1H), 6.34 (t, J=9.2 Hz, 1H), 4.67 (s, 2H); MS (ESI) m/z: 146.1 [M+H]$^+$.

4-amino-2,3-difluorophenol (6 g, 41.4 mmol) and potassium tert-butoxide (4.9 g, 43.5 mmol) were suspended in DMAc (200 mL) and stirred at RT for 30 min under Ar atmosphere. 2,4-Dichloropyridine (6.1 g, 41.4 mmol) was added, and the resulting mixture was heated to 70° C. for 8 h. The reaction mixture was filtered, concentrated in vacuo and purified by silica gel chromatography to afford 4-(2-chloropyridin-4-yloxy)-2,3-difluoro-phenylamine (7 g, 66% yield). $^1$H NMR (400 MHz, DMSO-d$_6$): δ 8.27 (d, J=6.0 Hz, 1H), 7.05 (s, 1H), 6.95 (m, 1H), 6.92 (m, 1H), 6.62 (m, 1H), 5.60 (s, 2H); MS (ESI) m/z: 257.1 [M+H]$^+$.

Nitrogen was bubbled though a solution of 4-(2-chloropyridin-4-yloxy)-2,3-difluoro-phenylamine (2 g, 7.8 mmol), 1-methyl-4-(4,4,5,5-tetramethyl-[1,3,2]dioxaborolan-2-yl)-

1H-pyrazole (1.6 g, 7.8 mmol) and Na$_2$CO$_3$ (1.65 g, 15.6 mmol) in DME (12 mL)/H$_2$O (4 mL) for 20 min. Pd(PPh$_3$)$_4$ (450 mg, 0.4 mmol), was added and then resulting mixture was degassed in vacuo, blanketed with nitrogen and heated to 70° C. for 16 h. The reaction was concentrated to dryness under reduced pressure. The crude product was suspended in water and extracted with EtOAc (3×10 mL). The organic layer was washed with brine, dried (Na$_2$SO$_4$), concentrated in vacuo and purified by silica gel chromatography to give 2,3-difluoro-4-[2-(1-methyl-1H-pyrazol-4-yl)-pyridin-4-yloxy]-phenylamine (1.3 g, 55% yield). $^1$H NMR (400 MHz, DMSO-d$_6$): δ 8.40 (d, J=6.0 Hz, 1H), 8.32 (s, 1H), 8.02 (s, 1H), 7.26 (s, 1H), 6.96 (t, J=8.8 Hz, 1H), 6.71-6.68 (m, 2H), 5.62 (s, 2H), 3.92 (s, 3H); MS (ESI) m/z: 303.2 [M+H]$^+$.

Example A4

A solution of 4-amino-2-methyl-phenol (4.25 g, 34.5 mmol) in dimethylacetamide (50 mL) was degassed in vacuo and blanketed with argon. Potassium tert-butoxide (5.0 g, 44.6 mmol) was added and the reaction mixture was de-gassed a second time and stirred at RT under argon for 30 min. 2,4-Dichloro-pyridine (4.6 g, 31.3 mmol) was added and the mixture was heated to 100° C. overnight. The solvent was removed under reduced pressure and the residue was purified by silica gel chromatography to give 4-(2-chloropyridin-4-yloxy)-3-methylbenzenamine (4.5 g, 56% yield). $^1$H NMR (400 MHz, DMSO-d$_6$): δ 8.21 (d, J=5.2 Hz, 1H), 6.75-6.80 (m, 3H), 6.45-6.50 (m, 2H), 5.15 (s, 2H), 1.92 (s, 3H); MS (ESI) m/z: 235.1 (M+H$^+$).

A solution of 4-(2-chloropyridin-4-yloxy)-3-methylbenzenamine (595 mg, 2.54 mmol), 1-methyl-4-(4,4,5,5-tetramethyl)-[1,3,2]dioxaborolan-2-yl)-4H-pyrazole (790 mg, 3.80 mmol) and Cs$_2$CO$_3$ (2.53 g, 7.77 mmol) in 10 mL of DMF (10 mL)/water (3 mL) was de-gassed under vacuum and blanketed with nitrogen. Pd(PPh$_3$)$_4$ (295 mg, 0.26 mmol) was added and the reaction mixture was heated to 90° C. overnight. The reaction mixture was diluted with EtOAc (30 mL) and washed with water (2×10 mL) and brine (2×10 mL). The aqueous portion was extracted with EtOAc (2×15 mL) and the combined organics were washed with brine (10 mL), concentrated in vacuo and purified on silica gel to provide 3-methyl-4-(2-(1-methyl-1H-pyrazol-4-yl)pyridin-4-yloxy)benzenamine as a pale yellow foam (627 mg, 88% yield). $^1$H NMR (400 MHz, DMSO-d$_6$): δ 8.27 (d, J=6.0 Hz, 1H), 8.18 (s, 1H), 7.90 (d, J=0.7 Hz, 1H), 7.07 (d, J=2.2 Hz, 1H), 6.74 (d, J=8.6 Hz, 1H), 6.49 (d, J=2.5 Hz, 1H), 6.46-6.40 (m, 2H), 5.02 (s, 2H), 3.84 (s, 3H), 1.94 (s, 3H); MS (ESI) m/z: 281.2 (M+H$^+$).

Example A5

KOtBu (1.016 g, 9.05 mmol) was added to a solution of 4-amino-2-chlorophenol (1.00 g, 6.97 mmol) in DMF (35 ml) at RT and the resultant mixture was stirred 45 min. 2,4-Dichloropyridine (1.340 g, 9.05 mmol) was then added and the reaction was stirred with heating at 90° C. overnight. The reaction was cooled to RT and diluted generously with H$_2$O and EtOAc. The layers were separated. The aqueous was extracted with EtOAc (3×). The combined organics were washed with H$_2$O (1×) and brine (2×), dried (MgSO$_4$), concentrated in vacuo and purified by silica gel chromatography (EtOAc/hexanes) to afford 3-chloro-4-(2-chloropyridin-4-yloxy)benzenamine (0.89 g, 50% yield) as a waxy yellow solid. $^1$H NMR (400 MHz, DMSO-d$_6$): δ 8.24 (d, J=5.7 Hz, 1H), 7.02 (d, J=8.7 Hz, 1H), 6.87-6.82 (m, 2H), 6.73-6.72 (m, 1H), 6.58-6.56 (m, 1H), 5.50 (br s, 2H); MS (ESI) m/z: 254.9 (M+H$^+$); 256.9 (M+2+H$^+$).

3-Chloro-4-(2-chloropyridin-4-yloxy)benzenamine (0.89 g, 3.49 mmol), 1-methyl-4-(4,4,5,5-tetramethyl-1,3,2-dioxaborolan-2-yl)-pyrazole (0.871 g, 4.19 mmol) and K$_2$CO$_3$ (1.302 g, 9.42 mmol) were combined in DME (6 ml)/H$_2$O (7.5 ml) and the headspace was flushed with Ar for 10 min. Pd(Ph$_3$P)$_4$ (0.202 g, 0.174 mmol) was then added and the biphasic reaction was stirred with heating at 90° C. overnight. The reaction was cooled to RT and filtered to remove insoluble material. The filtrate was diluted with THF and washed with brine (3×). The combined aqueous phases were extracted with THF (2×). The combined organics were washed with brine (1×), dried (MgSO$_4$), concentrated in vacuo and purified by silica gel chromatography (MeOH/CHCl$_3$) to afford 3-chloro-4-(2-(1-methyl-1H-pyrazol-4-yl)pyridin-4-yloxy)benzenamine (1.10 g, 83% yield). $^1$H NMR (400 MHz, DMSO-d$_6$): δ 8.30-8.29 (m, 1H), 8.22 (s, 1H), 7.92 (s, 1H), 7.12 (m, 1H), 7.00-6.98 (m, 1H), 6.72 (br s, 1H), 6.58-6.54 (m, 1H), 6.47-6.44 (m, 1H), 5.44 (s, 2H), 3.84 (s, 3H); MS (ESI) m/z: 301.1 (M+H$^+$): 303.0 (M+2+H$^+$).

Example A6

To a solution of 4-(2-chloropyridin-4-yloxy)-3-fluoroaniline (3.0 g, 12.6 mmol, from Example A2) in a solvent comprised of toluene/ethanol/water (4:4:1, 50 mL) was added 4-(4,4,5,5-tetramethyl-[1,3,2]dioxaborolan-2-yl)-1H-pyrazole (3.17 g, 16.4 mmol), sodium carbonate (4.01 g, 37.8 mmol) and tetrakis(triphenylphosphine)palladium (0.73 g, 0.63 mmol). The headspace was evacuated and back-filled with nitrogen (3×) and then the reaction mixture was heated to 100° C. overnight. The reaction was concentrated under reduced pressure, and the residue was purified by silica gel column chromatography (ethyl acetate/petroleum ether) to give 4-(2-(1H-pyrazol-4-yl)pyridin-4-yloxy)-3-fluoroaniline (2.66 g, 78% yield). $^1$H NMR (400 MHz, DMSO-d$_6$): δ 13.03 (brs, 1H), 8.28-8.31 (m, 2H), 7.99 (s, 1H), 7.24 (s, 1H), 6.95-7.00 (m, 1H), 6.39-6.50 (m, 3H), 5.43 (brs, 2H); MS (ESI): m/z 271.1 [M+H]$^+$.

Example A7

A solution of 1,3-difluoro-2-methyl-benzene (15 g, 0.12 mol) in H$_2$SO$_4$ (100 mL) was treated dropwise with 65% HNO$_3$ (11.4 g, 0.12 mol) at −10° C. and the resultant mixture was stirred for about 30 min. The mixture was poured into ice-water and extracted with ethyl acetate (3×200 mL). The combined organic layers were washed with brine, dried (Na$_2$SO$_4$) and concentrated in vacuo to give 1,3-difluoro-2-methyl-4-nitro-benzene (16 g, 78% yield). $^1$H NMR (400 MHz, CDCl$_3$): δ 7.80 (m, 1H), 6.95 (m, 1H), 2.30 (s, 3H).

1,3-Difluoro-2-methyl-4-nitro-benzene (16 g, 0.092 mol), benzyl alcohol (10 g, 0.092 mol) and K$_2$CO$_3$ (25.3 g, 0.18 mol), were combined in DMF (300 mL) and heated to 100° C. overnight. The mixture was poured into water and extracted with ethyl acetate (3×200 mL). The combined organic layers were washed with brine, dried (Na$_2$SO$_4$), concentrated in vacuo and purified by silica gel chromatography to give 1-benzyloxy-3-fluoro-2-methyl-4-nitro-benzene (8 g, 33% yield). $^1$H NMR (400 MHz, DMSO-d$_6$): δ 8.04 (t, J=8.8 Hz, 1H), 7.30-7.46 (m, 5H), 7.08 (d, J=9.2 Hz, 1H), 5.28 (s, 2H), 2.13 (s, 3H).

Using a procedure analogous to Example A3, 1-benzyloxy-3-fluoro-2-methyl-4-nitro-benzene (8 g, 0.031 mol) was hydrogenated to give 4-amino-3-fluoro-2-methyl-phenol (4.2 g, 96% yield). $^1$H NMR (300 MHz, DMSO-d$_6$): δ 8.61 (s, 1H), 6.36 (m, 2H), 4.28 (s, 2H), 1.96 (s, 3H); MS (ESI) m/z: 142.1 [M+H]$^+$.

Potassium tert-butoxide (3.5 g, 31 mmol) was added to a solution of 4-amino-3-fluoro-2-methyl-phenol (4.2 g, 30 mmol) in dimethylacetamide. The mixture was stirred at RT for 30 min. A solution of 2,4-dichloropyridine (4.38 g, 30 mmol) in dimethylacetamide was added and the mixture was heated at 100° C. overnight. The reaction mixture was concentrated in vacuo and the residue was dissolved in ethyl acetate (200 mL) and filtered through silica gel. The filter cake was washed with ethyl acetate, the combined filtrates were concentrated in vacuo and purified by silica gel chromatography to give 4-(2-chloro-pyridin-4-yloxy)-2-fluoro-3-methyl-phenylamine (3.2 g, 42% yield). $^1$H NMR (400 MHz, DMSO-d$_6$): δ 8.21 (d, J=6.4 Hz, 1H), 6.84 (d, J=2.0 Hz, 1H), 6.81 (dd, J=5.6, 2.4 Hz, 1H), 6.67-6.65 (m, 2H), 5.13 (s, 2H), 1.91 (s, 3H); MS (ESI): m/z 253.2 [M+H]$^+$.

Using a procedure analogous to Example A1, 4-(2-chloro-pyridin-4-yloxy)-2-fluoro-3-methyl-phenylamine (1.0 g, 3.3 mmol), 1-methyl-4-(4,4,5,5-tetramethyl-[1,3,2]dioxaborolan-2-yl)-1H-pyrazole (1 g, 4.8 mmol), Na$_2$CO$_3$ (0.84 g, 6.6 mmol) and Pd(PPh$_3$)$_4$ (0.25 g, 0.2 mmol) were combined to give 2-fluoro-3-methyl-4-[2-(1-methyl-1H-pyrazol-4-yl)-pyridin-4-yloxy]-phenylamine (0.74 g, 75% yield). $^1$H NMR (400 MHz, DMSO-d$_6$): δ 8.27 (d, J=6.4 Hz, 1H), 8.18 (s, 1H), 7.90 (s, 1H), 7.07 (s, 1H), 6.68-6.61 (m, 2H), 6.45 (dd, J=5.6, 2.4 Hz, 1H), 5.06 (s, 2H), 3.82 (s, 3H), 1.95 (s, 3H); MS (ESI) m/z: 299.2 [M+H]$^+$.

Example A8

To a stirred solution of NaBr (4.2 g, 0.04 mol) in SOCl$_2$ (300 ml, 4.0 mol) was added pyridine-2-carboxylic acid (101 g, 0.81 mol) portion-wise, and the resultant mixture was heated to reflux overnight. The reaction mixture was concentrated to remove the solvent to give a crude 4-chloro-pyridine-2-carbonyl chloride (101 g) which was used in the next step reaction without further purification.

A solution of 4-chloro-pyridine-2-carbonyl chloride (150 g, 0.857 mol) in DCM (750 ml) was slowly added to a solution of 2-methyl-propan-2-ol (158.8 g, 2.14 mol) and DMAP (21 g, 0.171 mol) in DCM (750 mL) and pyridine (750 mL). The resultant mixture was stirred at 30° C. overnight. The reaction mixture was concentrated in vacuo and the residue was purified by chromatography to give 4-chloro-pyridine-2-carboxylic acid t-butyl ester (90 g, 49% yield) as a yellow solid. $^1$H NMR (CDCl$_3$): δ 8.63 (d, J=8.0 Hz, 1H), 8.03 (s, 1H), 7.44 (d, J=8.0 Hz 1H), 1.63 (s, 9H); MS (ESI) m/z: 214 (M+H$^+$).

A mixture of 4-aminophenol (2.6 g, 24 mmol) and NaH (1.1 g, 28 mmol) in dry DMF (50 ml) was stirred at RT for 30 min. 4-Chloro-pyridine-2-carboxylic acid t-butyl ester (5.0 g, 24 mmol) was added and the resulting mixture was stirred in a sealed tube at 80° C. for 12 h. The reaction mixture was concentrated in vacuo and was purified on silica gel to give 5-(4-amino-phenoxy)-pyridine-2-carboxylic acid t-butyl ester as a yellow solid (2.4 g, 35% yield). $^1$H NMR (300 MHz, DMSO-d$_6$): δ 8.48 (d, J=5.7 Hz, 1H), 7.33 (d, J=1.8 Hz, 1H), 7.03 (m, 1H), 6.84 (d, J=8.4 Hz, 1H), 6.62 (d, J=8.4 Hz, 1H), 5.18 (s, 2H), 1.50 (s, 9H); MS (ESI) m/z: 287.2 (M+H$^+$).

To a solution of 5-(4-amino-phenoxy)-pyridine-2-carboxylic acid t-butyl ester (1.0 g, 3.5 mmol) in THF (10 ml) was added aqueous NaOH (1 M, 7 ml, 7 mol) followed by (Boc)$_2$O (0.76 g, 3.5 mmol). The resulting mixture was heated to reflux for 2 h. The reaction mixture was concentrated, the residue diluted with water (20 mL) and extracted with dichloromethane (3×100 mL). The combined organic layers were washed with brine, dried (Na$_2$SO$_4$), concentrated and purified via chromatography to provide 5-(4-t-butoxycarbonylamino-phenoxy)-pyridine-2-carboxylic acid t-butyl ester (1.2 g, 89% yield). MS (ESI) m/z: (M+H$^+$) 387.3.

A solution of 5-(4-t-butoxycarbonylamino-phenoxy)-pyridine-2-carboxylic acid t-butyl ester (0.5 g, 1.3 mmol) in THF (2.0 ml) was added dropwise to a 0° C. suspension of LiAlH$_4$ (0.1 g, 2.6 mmol) in dry THF (5.0 ml). The reaction was stirred at 0° C. for 2 h and was quenched with 10% aqueous NaOH (1.0 mL). The mixture was filtered and the filtrate was concentrated in vacuo to give [4-(6-hydroxymethyl-pyridin-3-yloxy)-phenyl]-carbamic acid t-butyl ester (0.38 g, 92% yield). MS (ESI) m/z: (M+H$^+$) 317.2.

A solution of [4-(6-hydroxymethyl-pyridin-3-yloxy)-phenyl]-carbamic acid t-butyl ester (0.25 g, 0.8 mmol) in DCM (3.0 ml) was treated with activated MnO$_2$ (0.42 g, 4.8 mmol) and the suspension was stirred at RT for 2 h. The reaction suspension was filtered and the filtrate was concentrated in vacuo to provide [4-(6-formyl-pyridin-3-yloxy)-phenyl]-carbamic acid t-butyl ester (0.24 g, 95% yield). MS (ESI) m/z: 315.0 (M+H$^+$).

A solution of NaOAc (0.6 g, 7.4 mmol) in water (1.5 mL) was treated with 3,3-dibromo-1,1,1-trifluoro-propan-2-one (2.2 g, 8.3 mmol) and the resulting mixture was heated to reflux for 30 min. After cooling, the solution was added to [4-(6-formyl-pyridin-3-yloxy)-phenyl]-carbamicacid t-butyl ester (2.3 g, 7.4 mmol) in ammonium hydroxide (30%, 23 mL). The reaction mixture was stirred at RT for 5 h, concentrated in vacuo and purified via chromatography to give {4-[3-(4-trifluoromethyl-1H-imidazol-2-yl)-phenoxy]-phenyl}-carbamic acid t-butyl ester (2.1 g, 67% yield). MS (ESI) m/z: (M+H$^+$) 421.1.

A mixture of {4-[3-(4-trifluoromethyl-1H-imidazol-2-yl)-phenoxy]-phenyl}-carbamic acid t-butyl ester (2.1 g, 2.2 mmol) and aqueous HCl (1M, 30 mL) in isopropanol (20 ml) was stirred at 90° C. for 2 h. After cooling to RT, the reaction mixture was concentrated, and the residue was partitioned with water and dichloromethane. The organic layer was washed with brine, dried (Na$_2$SO$_4$), and concentrated to yield an HCl salt which was further neutralized to give 4-(2-(4-(trifluoromethyl)-1H-imidazol-2-yl)pyridin-4-yloxy)benzenamine (600 mg, 85% yield). $^1$H NMR (400 MHz, CDCl$_3$): δ 13.48 (br s, 1H), 8.46 (d, J=5.6 Hz, 1H), 7.81 (s, 1H), 7.34 (m, 1H), 6.97 (m, 1H), 6.86 (d, J=8.8 Hz, 2H), 6.66 (d, J=8.8 Hz, 2H), 5.15 (s, 2H); MS (ESI) m/z: 320 (M+H$^+$). MS (ESI) m/z: (M+H$^+$) 321.2.

Example A9

To 60% NaH in mineral oil (0.119 g, 2.97 mmol), under an atmosphere of argon, was added anhydrous DMF (3 mL) and the slurry was cooled in an ice bath. To this suspension was added, in portions, a solution of 2-chloropyridin-4-ol (0.35 g, 2.70 mmol) in DMF (2 mL). The reaction mixture was stirred cold for 5 minutes and then allowed to warm to RT and stirred for 20 minutes. 1,5-difluoro-2-methyl-4-nitrobenzene (0.514 g, 2.97 mmol) was added and the reaction mixture heated at 90° C. for 3 hours, cooled to RT, quenched with water and the mixture was extracted with EtOAc (3×). The combined organic phases were washed with brine, dried (Na$_2$SO$_4$), concentrated in vacuo and purified by silica gel column chromatography (EtOAc/hexanes) to obtain 2-chloro-4-(5-fluoro-2-methyl-4-nitrophenoxy)pyridine (0.48 g, 63% yield) MS (ESI) m/z: 283.0 (M+H$^+$).

To a solution of 2-chloro-4-(5-fluoro-2-methyl-4-nitrophenoxy)pyridine (0.48 g, 1.698 mmol) in ethanol (20 mL) was added Raney Ni (0.4 g). The mixture was stirred under a hydrogen atmosphere (1 atm) overnight at RT. The reaction mixture was filtered through a pad of Celite® and the filtrate was concentrated to obtain the crude 4-(2-chloropyridin-4-yloxy)-2-fluoro-5-methylbenzenamine (assuming a 100% yield).

To a solution of 4-(2-chloropyridin-4-yloxy)-2-fluoro-5-methylbenzenamine (0.43 g, 1.702 mmol) and 1-methyl-4-(4,4,5,5-tetramethyl-1,3,2-dioxaborolan-2-yl)-1H-pyrazole (0.389 g, 1.872 mmol) in DMF (20 ml) was added tetrakis(triphenylphosphine)palladium (0.197 g, 0.170 mmol) and an aqueous solution of potassium phosphate (1.084 g, 5.11 mmol). The reaction mixture was flushed with $N_2$ and then heated overnight at 90° C. Water was added and the solution was extracted with EtOAc (3×). The combined organic phases were washed with brine, dried ($Na_2SO_4$), concentrated in vacuo and purified by silica gel column chromatography (EtOAc/hexanes) to obtain 5-fluoro-2-methyl-4-(2-(1-methyl-1H-pyrazol-4-yl)pyridin-4-yloxy)benzenamine (0.13 g, 25.6% yield). $^1$H NMR (400 MHz, DMSO-$d_6$): δ 8.29 (m, 1H), 8.21 (s, 1H), 7.92 (s, 2H), 7.09 (m, 1H), 6.87 (m, 1H), 6.69 (m, 1H), 6.46 (m, 1H), 5.10 (s, 2H), 3.84 (s, 3H), 1.93 (s, 3H); MS (ESI) m/z: 299.1 (M+H$^+$).

Example A10

Potassium carbonate (7.8 g, 56.4 mmol) was added to a solution of 1,2,3-trifluoro-5-nitrobenzene (5 g, 28.2 mmol) and benzyl alcohol (3.2 g, 29.6 mmol) in N,N-dimethylformamide (70 mL). The resultant mixture was stirred at RT overnight. The reaction mixture was concentrated under reduced pressure and the residue was partitioned between ethyl acetate and water. The organic layer was separated and washed with brine, dried ($Na_2SO_4$), concentrated under reduced pressure and purified by column chromatography to give 2-(benzyloxy)-1,3-difluoro-5-nitrobenzene (5.3 g, 71% yield). $^1$H NMR (400 MHz, DMSO-$d_6$): δ 8.15 (d, J=8.4 Hz, 2H), 7.46-7.37 (m, 5H), 5.39 (s, 2H).

To a solution of 2-(benzyloxy)-1,3-difluoro-5-nitrobenzene (5.3 g, 20 mol) in ethanol (100 mL) was added 10% palladium on activated carbon (1.5 g). The mixture was hydrogenated (1 atm) at RT overnight. The reaction mixture was filtered and the filtrate was concentrated under reduced pressure to give 4-amino-2,6-difluorophenol (2.9 g, 95% yield). $^1$H NMR (400 MHz, DMSO-$d_6$): δ 8.68 (brs, 1H), 6.19 (d, J=10.8 Hz, 2H), 5.01 (s, 2H).

Potassium tert-butoxide (2.4 g, 22 mmol) was added to a solution of 4-amino-2,6-difluorophenol (2.9 g, 20 mmol) in N,N-dimethyl-acetamide (50 mL) and the mixture was stirred at RT under nitrogen for 0.5 h. A solution of 2,4-dichloropyridine (2.9 g, 20 mmol) in N,N-dimethyl-acetamide was added, and the reaction was heated to 100° C. under nitrogen for 10 h. After cooling to RT, the reaction was poured into water (100 mL) and the aqueous solution was extracted with ethyl acetate (3×70 mL). The combined organics were washed with brine, dried ($Na_2SO_4$), concentrated in vacuo and purified by silica gel chromatography to give 4-(2-chloropyridin-4-yloxy)-3,5-difluoroaniline (3.0 g, 59% yield). $^1$H NMR (300 MHz, DMSO-$d_6$): δ 8.31 (d, J=5.7 Hz, 1H), 7.10 (d, J=2.1 Hz, 1H), 7.01 (dd, J=5.7 Hz, 2.1 Hz, 1H), 6.38 (d, J=10.8 Hz, 2H), 5.86 (s, 2H).

To a solution of 4-(2-chloropyridin-4-yloxy)-3,5-difluoroaniline (3.0 g, 11.7 mmol) in a mixture of N,N-dimethylformamide and water (v/v=3:1, 80 mL) was added 1-methyl-4-(4,4,5,5-tetramethyl-[1,3,2]dioxaborolan-2-yl)-1H-pyrazole (3.6 g, 17.5 mmol), potassium phosphate (4.9 g, 23.4 mmol) and tetrakis(triphenylphosphine) palladium (0.7 g, 0.6 mmol). The mixture was degassed thoroughly, heated to 100° C. and stirred under nitrogen overnight. The solvent was removed under reduced pressure and the residue was purified by silica gel chromatography to give 3,5-difluoro-4-(2-(1-methyl-1H-pyrazol-4-yl)pyridin-4-yloxy)aniline (2.6 g, 74% yield). $^1$H NMR (400 MHz, DMSO-$d_6$): δ 8.36 (d, J=5.6 Hz, 1H), 8.28 (s, 1H), 7.98 (s, 1H), 7.24 (d, J=2.4 Hz, 1H), 6.64 (dd, J=5.6 Hz, J=2.4 Hz, 1H), 6.37 (d, J=10.8 Hz, 2H), 5.81 (s, 2H), 3.87 (s, 3H); MS (ESI): m/z 303.1 [M+H]$^+$.

Example A11

4-Fluoro-2-methyl-phenol (25 g, 0.2 mol) was added to a solution of sodium hydroxide (9.7 g, 0.24 mol) in water (160 mL) and the resultant solution was cooled to 0° C. Methyl chloroformate (24.2 g, 0.26 mol) was added dropwise at 0° C. At the completion of the reaction, the pH was adjusted to pH 8 with saturated aqueous $Na_2CO_3$ and then the mixture was extracted with ethyl acetate (3×300 mL). The combined organic extracts were washed with water and brine, dried ($MgSO_4$) and concentrated under reduced pressure to provide carbonic acid 4-fluoro-2-methyl-phenyl ester methyl ester (30 g, 82% yield). $^1$H NMR (300 MHz, DMSO-$d_6$): δ 7.22-7.13 (m, 2H), 7.05 (m, 1H), 3.81 (s, 3H), 2.12 (s, 3H).

To a solution of carbonic acid 4-fluoro-2-methyl-phenyl ester methyl ester (15 g, 81.5 mmol) in conc. sulfuric acid (100 mL) at 0° C. was added powdered $KNO_3$ (8.3 g, 82.2 mmol) in several portions. The reaction mixture was stirred for 1 hour at 0° C. and was then poured into ice water and extracted with ethyl acetate (3×100 mL). The extracts were washed with water and brine, dried ($MgSO_4$), concentrated in vacuo and purified by silica gel chromatography to provide carbonic acid 4-fluoro-2-methyl-5-nitrophenyl ester methyl ester (2.0 g, 11% yield). $^1$H NMR (300 MHz, DMSO-$d_6$): δ 8.14 (d, J=6.9, 1H), 7.60 (d, J=12.0 Hz, 1H), 3.86 (s, 3H), 2.25 (s, 3H).

To a solution of aqueous sodium hydroxide (1.2 N, 20 mL, 24 mmol) was added 4-fluoro-2-methyl-5-nitro-phenyl ester methyl ester (2.0 g, 8.7 mmol), and the resultant mixture was refluxed for 2 hours. The reaction was cooled to RT and partitioned between EtOAc and water. The organic layer was washed with water and brine, dried ($MgSO_4$), and concentrated in vacuo to provide 4-fluoro-2-methyl-5-nitro-phenol (1.4 g, 93% yield). $^1$H NMR (300 MHz, DMSO-$d_6$) δ 10.33 (s, 1H), 7.45 (d, J=6.6, 1H), 7.32 (d, J=12.3 Hz, 1H), 2.19 (s, 3H).

A mixture of 4-fluoro-2-methyl-5-nitro-phenol (1.4 g, 8.2 mmol) and 10% Pd/C (0.3 g, 20%/w) in MeOH (80 mL) was stirred under $H_2$ (30 psi) for 2 h. The Pd/C was removed by filtration and the filtrate was concentrated to give 5-amino-4-fluoro-2-methyl-phenol (0.68 g, 62% yield). $^1$H NMR (300 MHz, DMSO-$d_6$) δ 8.75 (s, 1H), 6.62 (d, J=12.0 Hz, 1H), 6.21 (d, J=8.1 Hz, 1H), 4.69 (s, 2H), 1.93 (s, 3H).

A mixture of 2-methanesulfonyl-4-(1-methyl-1H-pyrazol-4-yl)-pyrimidine and 2-methanesulfinyl-4-(1-methyl-1H-pyrazol-4-yl)-pyrimidine from Example A16 (1 g, 4.2 mmol), 5-amino-4-fluoro-2-methylphenol (1.2 g, 8.5 mmol) and $K_2CO_3$ (1.2 g, 8.6 mmol) were combined in DMF (10 mL) using a procedure analogous to Example A10 to provide 2-fluoro-4-methyl-5-(4-(1-methyl-1H-pyrazol-4-yl)pyrimidin-2-yloxy)benzenamine (420 mg). $^1$H NMR (400 MHz, DMSO-$d_6$): δ 8.42 (d, J=5.2 Hz, 1H), 8.39 (s, 1H), 8.07 (s, 1H), 7.40 (d, J=5.2 Hz, 1H), 6.90 (d, J=9.6 Hz, 1H), 6.47 (d, J=8.4 Hz, 1H), 5.02 (br s, 2H), 3.88 (s, 3H), 1.88 (s, 3H); MS (ESI) m/z: 300.2 (M+H$^+$).

Example A12

Anhydrous N,N-dimethylformamide (150 mL) was added to 60% NaH in mineral oil (2.72 g, 67.9 mmol) under an atmosphere of argon. The mixture was cooled in an ice bath and stirred. To this suspension was added, portion-wise, a solution of 2-chloropyridin-4-ol (8 g, 61.8 mmol) in DMF (30.0 mL). The reaction mixture was stirred cold for 5 minutes and the cooling bath was removed. The reaction mixture was warmed to RT and stirred for 20 minutes. 1,2,4-trifluoro-5-nitrobenzene (13.12 g, 74.1 mmol) was added and the reaction mixture heated at 90° C. for 3 hours. The reaction mixture was cooled to RT. The mixture was concentrated to dryness. EtOH (50 mL) and MeOH (20 mL) were added and the sample was stirred with gentle warming and then cooled to RT. The yellow solid was collected by filtration, and rinsed with EtOH (50 mL) and hexanes (20 mL). The solid was dried under vacuum overnight to provide 2-chloro-4-(2,5-difluoro-4-nitrophenoxy)pyridine as a yellow solid (11.68 g, 63% yield). $^1$H NMR (400 MHz, DMSO-d$_6$): δ 8.48 (dd, J=10.2, 7.0 Hz, 1H), 8.41 (d, J=5.6 Hz, 1H), 7.90 (dd, J=11.6, 6.7 Hz, 1H), 7.41 (d, J=2.1 Hz, 1H), 7.26 (dd, J=5.6, 2.4 Hz, 1H); MS (ESI): m/z 287.0 [M+H]$^+$ In a Parr Shaker flask was combined 2-chloro-4-(2,5-difluoro-4-nitrophenoxy)pyridine (11.68 g, 40.8 mmol) and MeOH (200 ml) under argon. Raney Ni (50% wet, 0.955 g, 8.15 mmol) was added. The argon atmosphere was removed and replaced with hydrogen (10-20 psi) and the reaction mixture shaken under hydrogen for 4 hours. The completed reaction mixture was filtered through a pad of Celite® and the filtrate was concentrated to dryness to provide 4-(2-chloropyridin-4-yloxy)-2,5-difluoroaniline (8.2 g, 72% yield). $^1$H NMR (400 MHz, DMSO-d$_6$): δ 8.28 (d, J=5.9 Hz, 1H), 7.25 (dd, J=11.2, 7.5 Hz, 1H), 7.02 (dd, J=2.2 Hz, 1H), 6.95 (dd, J=5.8, 2.0 Hz, 1H), 6.74 (dd, J=12.3, 8.3 Hz, 1H), 5.57 (s, 2H); MS (ESI): m/z 257.0 [M+H]$^+$ To a solution of 4-(2-chloropyridin-4-yloxy)-2,5-difluoroaniline (450 mg, 1.76 mmol) and 1-methyl-4-(4,4,5,5-tetramethyl-1,3,2-dioxaborolan-2-yl)-1H-pyrazole (400 mg, 1.9 mmol) in N,N-dimethylformamide (30 mL) was added tetrakis(triphenylphosphine)palladium (105 mg, 0.09 mmol) and an aqueous solution of potassium phosphate (2 M, 1.8 mL). The mixture was flushed with nitrogen for 10 min, and then stirred with heating at 90° C. under nitrogen overnight. After cooling to RT, the reaction mixture was partitioned between water and ethyl acetate. The aqueous layer was extracted with ethyl acetate (50 mL×3). The combined organic layers were washed with brine, dried (Na$_2$SO$_4$), concentrated under reduced pressure and purified by column chromatography on silica gel to give 2,5-difluoro-4-(2-(1-methyl-1H-pyrazol-4-yl)pyridin-4-yloxy)aniline (335 mg, 63% yield). $^1$H NMR (300 MHz, DMSO-d$_6$): δ 8.35 (d, J=5.7 Hz, 1H), 8.27 (s, 1H), 7.98 (s, 1H), 7.24-7.18 (m, 2H), 6.75 (dd, J=12.3, 8.1 Hz, 1H), 6.62 (dd, J=5.4, 2.1 Hz, 1H), 5.53 (br s, 2H), 3.87 (s, 3H); MS (ESI): m/z 303.1 [M+1]$^+$.

Example A13

5-Bromo-2-nitropyridine (1 g, 4.93 mmol) was dissolved in DMF (32 ml) and cooled to 0° C. Cesium carbonate (2.408 g, 7.39 mmol) was added, followed by 2-chloro-4-hydroxypyridine (0.702 g, 5.42 mmol). The mixture was stirred in an 80° C. oil bath for 24 hours. The reaction mixture was then cooled to RT, diluted with ethyl acetate (150 mL), washed with water (2×100 mL) and brine (50 mL), dried (MgSO$_4$), evaporated under reduced pressure and purified via silica gel chromatography (ethyl acetate-hexanes) to yield 2-chloro-4-(6-nitropyridin-3-yloxy)pyridine as a clear oil (0.540 g, 44% yield). $^1$H NMR (400 MHz, DMSO-d$_6$): δ 8.62 (d, 1H), 8.41 (m, 2H), 8.06 (d, 1H), 7.37 (d, 1H), 7.23 (dd, 1H); MS (ESI) m/z: 252.0 (M+H$^+$).

2-Chloro-4-(6-nitropyridin-3-yloxy)pyridine (0.540 g, 2.146 mmol) was dissolved in THF (54 ml) and MeOH (54 ml). Ammonium chloride (1.148 g, 21.46 mmol) was then added, followed by zinc dust (1.403 g, 21.46 mmol). The reaction was stirred at RT for 45 minutes, filtered over Celite® and concentrated under reduced pressure to yield 5-(2-chloropyridin-4-yloxy)pyridin-2-amine as a brown solid (0.49 g, 99%). It was used as is in the next reaction. $^1$H NMR (400 MHz, DMSO-d$_6$): δ 8.46 (d, 1H), 7.81 (d, 1H), 7.30 (dd, 1H), 6.90 (m, 2H), 6.50 (d, 1H), 6.08 (s, 2H); MS (ESI) m/z: 222.0 (M+H$^+$).

5-(2-Chloropyridin-4-yloxy)pyridin-2-amine (0.47 g, 2.121 mmol) was dissolved in DMF (11 ml). Water (3.67 ml) was added to the mixture, followed by 1-methyl-4(4,4,5,5-tetramethyl-1,3,2-dioxaborolan-2-yl)1H-pyrazole (0.662 g, 3.18 mmol), and cesium carbonate (2.63 g, 8.06 mmol). Argon was bubbled through the mixture for several minutes, and then palladium tetrakistriphenylphosphine (0.245 g, 0.212 mmol) was added. The flask was fitted with a condenser and argon was flushed through the system. The reaction mixture was then placed in a 90° C. oil bath under a balloon of argon and heated for 23 hours. The solution was then cooled to RT and diluted with THF (75 mL) and washed with brine (2×50 mL). The combined aqueous layers were then back extracted with THF (40 mL). The combined organic layers were dried (MgSO$_4$), concentrated under reduced pressure and purified via silica gel chromatography (THF-ethyl acetate) to yield 5-(2-(1-methyl-1H-pyrazol-4-yl)pyridin-4-yloxy)pyridin-2-amine as an off-white solid (0.357 g, 63% yield). $^1$H NMR (400 MHz, DMSO-d$_6$): δ 8.31 (d, 1H), 8.22 (s, 1H), 7.92 (s, 1H), 7.80 (d, 1H), 7.27 (dd, 1H), 7.14 (d, 1H), 6.85 (s, 1H), 6.57 (dd, 1H), 6.01 (s, 2H), 3.84 (s, 3H); MS (ESI) m/z: 268.1 (M+H$^+$).

Example A14

Sodium hydride (60% in mineral oil) (0.620 g, 15.5 mmol) was placed in a 100 mL round bottom flask under argon. Dry DMF (30 mL) was added, followed by portion wise addition of 2-chloro-4-hydroxypyridine (1.339 g, 10.33 mmol) at 0° C. The mixture was stirred at 0° C. for 30 minutes, and then slowly warmed to RT. A solution of 5-chloro-2,4-difluoronitrobenzene (2 g, 10.33 mmol) in DMF (4.4 mL) was added to the suspension, and the mixture was placed in a 90° C. oil bath to heat for 15 hours under argon. The reaction mixture was then cooled to RT and diluted with ethyl acetate (100 mL), washed with 10% aqueous LiCl (3×100 mL) and brine (2×100 mL), dried (MgSO$_4$) and purified via silica gel chromatography (ethyl acetate/hexanes) to yield 2-chloro-4-(2-chloro-5-fluoro-4-nitrophenoxy)pyridine as a bright yellow oil (1.415 g, 45% yield). $^1$H NMR (400 MHz, DMSO-d$_6$): δ 8.56 (dd, 1H), 8.35 (dd, 1H), 7.88 (dd, 1H), 7.32 (dd, 1H), 7.18 (m, 1H); MS (ESI) m/z: 303.0 (M+H$^+$).

2-Chloro-4-(2-chloro-5-fluoro-4-nitrophenoxy)pyridine (1.306 g, 4.31 mmol) was dissolved in THF (108 ml) and MeOH (108 ml). Ammonium chloride (2.305 g, 43.1 mmol) was then added, followed by zinc dust (2.82 g, 43.1 mmol). The reaction mixture was stirred for 1 hour at RT. The solids were filtered over Celite® and the solution was concentrated under reduced pressure to yield 5-chloro-4-(2-chloropyridin-4-yloxy)-2-fluorobenzenamine as a brown solid which was used without purification assuming a 100% yield. MS (ESI) m/z: 273.0 (M+H$^+$).

5-Chloro-4-(2-chloropyridin-4-yloxy)-2-fluorobenzenamine (1.177 g, 4.31 mmol) and 1-methyl(4,4,5,5-tetramethyl-1,3,2-dioxaborolan-2-yl)-1H-pyrazole (1.166 g, 5.60 mmol) were dissolved in DMF (16.16 ml), cesium carbonate (4.21 g, 12.93 mmol) was added, followed by water (5.39 ml). Argon was bubbled through the mixture for 5 minutes, and then palladium tetrakistriphenylphosphine (0.249 g, 0.215 mmol) was added. The flask was fitted with a reflux condenser, flushed with argon, and heated in a 90° C. oil bath under a balloon of argon for 4 hours. The reaction mixture was then cooled to RT and diluted with a 4:1 mixture of ethyl acetate and THF. The solution was extracted with 10% aqueous LiCl (2×150 mL) and brine (100 mL), dried (MgSO$_4$), evaporated under reduced pressure and purified via silica gel chromatography (ethyl acetate/hexanes) to yield 5-chloro-2-fluoro-4-(2-(1-methyl-1H-pyrazol-4-yl)pyridin-4-yloxy) benzenamine as a tan solid (1.062 g, 77% yield). $^1$H NMR (400 MHz, DMSO-d$_6$): δ 8.31 (d, 1H), 8.24 (s, 1H), 7.95 (s, 1H), 7.20 (d, 1H), 7.13 (d, 1H), 6.92 (d, 1H), 6.52 (dd, 1H), 5.49 (s, 2H), 3.84 (s, 3H); MS (ESI) m/z: 319.1 (M+H$^+$).

Example A15

Sodium hydride (136 mg, 3.4 mmol, 60% in mineral) was added to a 0° C. solution of 2-chloropyridin-4-ol (2 g, 15.4 mmol) in DMF (38 mL) under Ar. The mixture was stirred at 0° C. for 1 h. A solution of 1,2,4-trifluoro-5-nitrobenzene (626 mg, 3.1 mmol) in DMF (7.6 ml) was added and the reaction was stirred under Ar at 90° C. for 3 h. The mixture was cooled to RT and stirred overnight. The solvent was removed under reduced pressure and the crude product was partitioned between water (50 ml) and EtOAc (50 ml). The mixture was extracted with EtOAc (3×50 ml). The combined organic extracts were washed with brine, dried (Na$_2$SO$_4$), concentrated under reduced pressure and purified by silica gel column chromatography (hexanes/EtOAc) to yield 2-chloro-4-(2,5-difluoro-4-nitrophenoxy)pyridine (3.57 g, 81% yield). $^1$H NMR (400 MHz, DMSO-d$_6$): δ 8.43-8.33 (m, 2H), 7.85-7.79 (m, 1H), 7.33 (d, 1H), 7.20-7.18 (m, 1H); MS (ESI) m/z: 287.0 (M+H$^+$).

A mixture of 2-chloro-4-(2,5-difluoro-4-nitrophenoxy)pyridine (3.57 g, 2.1 mmol), zinc dust (8.14 g, 125 mmol) and ammonium chloride (6.66 g, 125 mmol) in THF (160 mL) and MeOH (160 ml) was stirred at RT for 2 h. The reaction mixture was filtered and the filtrate was concentrated under reduced pressure. The crude product was partitioned between EtOAc (50 ml) and a mixture of water and saturated NaHCO$_3$ (aq) (1:1; 50 ml). The mixture was extracted with EtOAc (2×50 ml). The combined organic extracts were dried (Na$_2$SO$_4$) and evaporated to yield 4-(2-chloropyridin-4-yloxy)-2,5-difluoroaniline (3.18 g, 100% yield). $^1$H NMR (400 MHz, DMSO-d$_6$): δ 8.26 (d, 1H), 7.24-7.19 (m, 1H), 7.00 (s, 1H), 6.94-6.92 (m, 1H), 6.74-6.69 (m, 1H), 5.54 (brs, 2H); MS (ESI) m/z: 257.0 (M+H$^+$).

3-Methyl-4-(4,4,5,5-tetramethyl-[1,3,2]dioxaborolan-2-yl)-1H-pyrazole (0.3 g, 1.442 mmol) and potassium carbonate (0.996 g, 7.21 mmol) were suspended in acetonitrile (10 ml) and stirred overnight at RT. Additional iodomethane (0.5 ml) was added and the mixture was stirred overnight at RT. The mixture was diluted with EtOAc and the inorganic salts were removed by filtration. The filtrate was evaporated to yield an inseparable mixture (2:1) of 1,3-dimethyl-4-(4,4,5,5-tetramethyl-1,3,2-dioxaborolan-2-yl)-1H-pyrazole and 1,5-dimethyl-4-(4,4,5,5-tetramethyl-1,3,2-dioxaborolan-2-yl)-1H-pyrazole (0.267 g, 83% yield). MS (ESI) m/z: 223.1 (M+H$^+$).

In a sealed tube, 4-(2-chloropyridin-4-yloxy)-2,5-difluoroaniline (0.257 g, 1.00 mmol), a (2:1) mixture of 1,3-dimethyl-4-(4,4,5,5-tetramethyl-1,3,2-dioxaborolan-2-yl)-1H-pyrazole and 1,5-dimethyl-4-(4,4,5,5-tetramethyl-1,3,2-dioxaborolan-2-yl)-1H-pyrazole (0.267 g, 1.20 mmol), potassium carbonate (0.415 g, 3.01 mmol) and tetrakistriphenylphosphine palladium(0) (0.058 g, 0.050 mmol) were suspended in a mixture of dioxane (10 ml) and water (1.667 ml). The mixture was degassed with Ar and heated at 90° C. overnight. The reaction was diluted with saturated aq. NaHCO$_3$ (25 ml) and extracted with EtOAc (3×25 ml). The combined organic extracts were concentrated in vacuo and purified by silica gel chromatography (hexanes/EtOAc) to elute an inseparable (2:1) mixture of 4-(2-(1,3-dimethyl-1H-pyrazol-4-yl)pyridin-4-yloxy)-2,5-difluorobenzenamine and 4-(2-(1,5-dimethyl-1H-pyrazol-4-yl)pyridin-4-yloxy)-2,5-difluorobenzenamine (0.31 g, 98% yield). MS (ESI) m/z: 317.1 (M+H$^+$).

Example A16

Methyl chloroformate (77.3 g, 0.82 mol) was added dropwise to a −10° C. solution of 2-chloro-4-fluorophenol (100 g, 0.68 mol) and sodium hydroxide (32.8 g, 0.82 mol) in water (550 mL). After complete addition, the precipitated solid was collected by filtration and washed with water to give 2-chloro-4-fluorophenyl methyl carbonate (110 g, 79% yield). $^1$H NMR (300 MHz, DMSO-d$_6$): δ 7.62 (dd, J=8.1, 2.7 Hz, 1H), 7.50 (dd, J=9.0, 5.4 Hz, 1H), 7.30 (td, J=8.1, 3.0 Hz, 1H), 3.86 (s, 3H); MS (ESI) m/z: 205.2 (M+H$^+$).

To a suspension of 2-chloro-4-fluorophenyl methyl carbonate (110 g, 0.54 mol) in conc. H$_2$SO$_4$ (50 mL) was slowly added a mixture comprised of conc. H$_2$SO$_4$ (40 mL) and fuming HNO$_3$ (40.8 mL, 0.89 mol). The resultant mixture was stirred for 30 min at 0° C. The reaction mixture was poured into ice water and the precipitated solid was collected by filtration and washed with water to give 2-chloro-4-fluoro-5-nitrophenyl methyl carbonate (120 g, 90% yield). $^1$H NMR (400 MHz, DMSO-d$_6$): δ 8.45 (d, J=7.2 Hz, 1H), 8.12 (d, J=10.8 Hz, 1H), 3.89 (s, 3H); MS (ESI) m/z: 250.1 (M+H$^+$).

2-Chloro-4-fluoro-5-nitrophenyl methyl carbonate (120 g 0.48 mol) was combined with a solution of sodium hydroxide (22.7 g, 0.57 mol) in water (300 mL) and the resultant mixture was refluxed for 4 h. The insoluble solids were removed by filtration and the filtrate was acidified with dilute HCl. The precipitated solid was collected by filtration and washed with water to give 2-chloro-4-fluoro-5-nitrophenol (90 g, 98% yield). $^1$H NMR (400 MHz, DMSO-d$_6$): δ 11.18 (s, 1H), 8.10 (d, J=10.4 Hz, 1H), 7.62 (d, J=7.2 Hz, 1H); MS (ESI) m/z: 192.1 (M+H$^+$).

2-Chloro-4-fluoro-5-nitrophenol (85 g, 0.45 mol) and 10% Pd/C (25 g, 0.023 mol) were combined in EtOH and hydrogenated (50 psi) for 12 h. The reaction mixture was filtered. The filtrate was concentrated in vacuo and purified by silica gel chromatography to provide 3-amino-4-fluorophenol (40 g 70% yield). $^1$H NMR (400 MHz, DMSO-d$_6$): δ 8.87 (s, 1H), 6.70 (dd, J=11.2, 8.8 Hz, 1H), 6.14 (dd, J=7.8, 2.4 Hz, 1H), 5.84 (m, 1H), 4.92 (s, 2H); MS (ESI) m/z: 128.2 (M+H$^+$).

4-Chloro-2-methylsulfanyl-pyrimidine (1.4 g, 8.8 mmol), 1-methyl-4-(4,4,5,5-tetramethyl-[1,3,2]dioxaborolan-2-yl)-1H-pyrazole (2.0 g, 1.1 eq), Na$_2$CO$_3$ (2.8 g, 3 eq) and Pd(PPh$_3$)$_4$ (500 mg, 0.43 mmol) were combined in a solvent comprised of toluene/EtOH/H$_2$O (4/4/1, 20 mL). The reaction mixture was purged with argon and heated to 100° C. overnight. The reaction was filtered to remove insolubles and the filtrate was concentrated in vacuo. The residue was purified by silica gel chromatography to provide 4-(1-methyl-1H-pyrazol-4-yl)-2-(methylthio)pyrimidine contaminated with triphenylphosphine oxide (2.0 g, >100% yield). $^1$H NMR (300 MHz, DMSO-d$_6$): δ 8.49 (d, J=5.1 Hz, 1H), 8.46 (s, 1H), 8.12 (s, 1H), 7.38 (d, J=5.1 Hz, 1H), 3.89 (s, 3H), 2.52 (s, 3H).

A solution of 4-(1-methyl-1H-pyrazol-4-yl)-2-methylsulfanyl-pyrimidine (2.0 g crude, 8.8 mmol) in dichloromethane (20 mL) was treated with m-CPBA (3.0 g, 17.4 mmol) portionwise at RT. The reaction was stirred 2 h and was quenched with saturated aqueous $NaS_2SO_3$ (3 mL). The mixture was partitioned with saturated aq $Na_2CO_3$ and the organics were washed with brine, dried ($Na_2SO_4$), and concentrated to provide a mixture (2.0 g) of 2-methanesulfonyl-4-(1-methyl-1H-pyrazol-4-yl)-pyrimidine and 2-methanesulfinyl-4-(1-methyl-1H-pyrazol-4-yl)-pyrimidine with a molar ratio of 1:0.3. $^1$H NMR (400 MHz, DMSO-$d_6$): δ 8.83 (d, J=5.2 Hz, 1H), 8.82 (d, J=5.2 Hz, 0.24H), 8.57 (s, 1H), 8.57 (s, 0.24H), 8.21 (s, 1H), 8.21 (s, 0.23H), 7.80 (d, J=5.6 Hz, 1H), 7.80 (d, J=5.6 Hz, 0.25H), 3.48 (s, 3H), 2.88 (s, 0.7H).

The above mixture of 2-methanesulfonyl-4-(1-methyl-1H-pyrazol-4-yl)-pyrimidine and 2-methanesulfinyl-4-(1-methyl-1H-pyrazol-4-yl)-pyrimidine (1 g, 4.2 mmol), 4-amino-3-fluoro-phenol (1.1 g, 8.6 mmol) and $K_2CO_3$ (1.2 g, 8.6 mmol) in DMF (10 mL) was heated at 100° C. for 12 h. The reaction was partitioned between $H_2O$ and EtOAc (3×50 mL). The combined organics were dried ($Na_2SO_4$), concentrated in vacuo and chromatographed to provide 2-fluoro-5-(4-(1-methyl-1H-pyrazol-4-yl)pyrimidin-2-yloxy)benzenamine (402 mg). $^1$H NMR (400 MHz, DMSO-$d_6$): δ 8.44 (d, J=5.2 Hz, 1H), 8.39 (s, 1H), 8.07 (s, 1H), 7.41 (d, J=5.2 Hz, 1H), 6.98 (t, J=9.6 Hz, 1H), 6.53 (dd, J=5.6, 2.0 Hz, 1H), 6.28 (d, J=8.4 Hz, 1H), 5.25 (br s, 2H), 3.88 (s, 3H). MS (ESI) m/z: 286.2 (M+H$^+$).

Example A17

Sulfuric acid (10 mL) was cooled to 0° C. and hydrogen peroxide (4.92 ml, 48.1 mmol) was added slowly, maintaining an internal temperature of less than 20° C. A solution of 2-amino-5-bromo-4-methylpyridine (1.5 g, 8.02 mmol) in 10 mL of sulfuric acid was then added. The mixture was stirred in the ice bath for 45 minutes, and then warmed to RT. After 1 hour at RT the color of the reaction mixture gradually changed from grass green to bright yellow. The reaction mixture was poured over ice (100 mL) and the solid that formed was collected via suction filtration and washed with water. The light orange solid was dried overnight to yield 5-bromo-4-methyl-2-nitropyridine (1.08 g, 62% yield), which was used without further purification. $^1$H NMR (400 MHz, DMSO-$d_6$): δ 8.77 (s, 1H), 8.38 (s, 1H), 2.51 (s, 3H).

2-Chloro-4-hydroxypyridine (0.239 g, 1.843 mmol) was dissolved in DMF (18.43 ml) and potassium t-butoxide (0.290 g, 2.58 mmol) was added. The solution was degassed for several minutes, and then 5-bromo-4-methyl-2-nitropyridine (0.4 g, 1.843 mmol) was added. The mixture was heated at 65° C. for 70 hours under argon and then at 80° C. for 24 hours. The reaction mixture was cooled to RT, diluted with ethyl acetate (150 mL), washed with water (75 mL), 10% aqueous LiCl (2×75 mL), saturated aqueous bicarbonate (75 mL) and brine (75 mL), dried (MgSO$_4$), evaporated and purified via silica gel chromatography (ethyl acetate/hexanes) to yield 2-chloro-4-(4-methyl-6-nitropyridin-3-yloxy)pyridine as a yellow solid (0.087 g, 18% yield). $^1$H NMR (400 MHz, DMSO-$d_6$): δ 8.49 (s, 1H), 8.47 (s, 1H), 8.35 (d, 1H), 7.24 (d, 1H), 7.12 (dd, 1H), 2.31 (s, 3H); MS (ESI) m/z: 266.0 (M+H$^+$).

2-Chloro-4-(4-methyl-6-nitropyridin-3-yloxy)pyridine was dissolved in THF (11.95 ml)/methanol (11.95 ml) and ammonium chloride (0.256 g, 4.78 mmol) was added, followed by zinc dust (0.313 g, 4.78 mmol). The mixture stirred at RT for 1.5 hours before it was filtered through Celite®. The filtrate was evaporated under reduced pressure to yield a magenta film which was partitioned between ethyl acetate/THF (4:1) and water. The organic layer was washed with brine, dried (MgSO$_4$) and evaporated to yield 5-(2-chloropyridin-4-yloxy)-4-methylpyridin-2-amine as a brown oil (0.116 g, 103%), which was used in the next step without purification. MS (ESI) m/z: 236.1 (M+H$^+$).

5-(2-chloropyridin-4-yloxy)-4-methylpyridin-2-amine (0.116 g, 0.492 mmol) was dissolved in DMF (2 ml) and 1-methyl-1H-pyrazole-4-boronic acid pinacol ester (0.154 g, 0.738 mmol) was added, followed by cesium carbonate (0.481 g, 1.477 mmol) and water (0.667 ml). Argon was bubbled through the mixture for several minutes, and then palladium tetrakistriphenylphosphine (0.028 g, 0.025 mmol) was added. The flask was fitted with a reflux condenser, flushed with argon, and heated under a balloon of argon at 90° C. for 16 hours. The mixture was then cooled to RT, and the solution was diluted with a 4:1 mix of ethyl acetate and THF (70 mL). It was washed with 10% aqueous LiCl (2×50 mL) and brine (50 mL), dried (MgSO$_4$), evaporated in vacuo and purified via silica gel chromatography (DCM/MeOH) to yield 4-methyl-5-(2-(1-methyl-1H-pyrazol-4-yl)pyridin-4-yloxy)pyridin-2-amine as a clear oil (0.084 g, 61% yield). $^1$H NMR (400 MHz, DMSO-$d_6$): δ 8.30 (d, 1H), 8.22 (s, 1H), 7.93 (s, 1H), 7.69 (s, 1H), 7.11 (d, 1H), 6.50 (dd, 1H), 6.38 (s, 1H), 5.89 (s, 2H), 3.84 (s, 3H), 1.95 (s, 3H); MS (ESI) m/z: 282.1 (M+H$^+$).

Example A18

4-Chloro-2-methylsulfanyl-pyrimidine (1.4 g, 8.8 mmol), 4-(4,4,5,5-tetramethyl-[1,3,2]dioxaborolan-2-yl)-1H-pyrazole (2.0 g, 10.3 mmol), Na$_2$CO$_3$ (2.8 g, 26.4) and Pd(PPh$_3$)$_4$ (500 mg, 0.43 mmol) were combined in a solvent comprised of toluene/EtOH/H$_2$O (4/4/1, 20 mL). The mixture was degassed by applying a vacuum and backfilling the headspace with argon. The reaction mixture was heated overnight at 100° C. The insoluble portion was filtered and the filtrate was concentrated and purified by silica gel chromatography to provide 2-(methylthio)-4-(1H-pyrazol-4-yl)pyrimidine (1.2 g, 71% yield). $^1$H NMR (400 MHz, CDCl$_3$) δ 8.45 (d, J=6.4 Hz, 1H), 8.24 (s, 1H), 7.23 (s, 1H), 7.05 (d, J=6.4 Hz, 1H), 2.51 (s, 3H).

To a solution of 2-(methylthio)-4-(1H-pyrazol-4-yl)pyrimidine (200 mg, 1 mmol) in dichloromethane (3 mL) and H$_2$O (1 mL) was added 4-methoxybenzylchloride (200 mg, 1.28 mmol) at 0° C. The mixture was stirred at RT overnight. The organic layer was separated, washed with brine and concentrated in vacuo to give crude 4-(1-(4-methoxybenzyl)-1H-pyrazol-4-yl)-2-(methylthio)pyrimidine. $^1$H NMR (300 MHz, DMSO-$d_6$) δ 8.58 (s, 1H), 8.50, (d, J=5.4 Hz, 1H), 8.16 (s, 1H), 7.40 (d, J=5.4 Hz, 1H), 7.27 (d, J=8.4 Hz, 2H), 7.22 (d, J=8.4 Hz, 2H), 5.30 (s, 2H), 3.72 (s, 3H), 2.51 (s, 3H); MS (ESI) m/z: 313 (M+H$^+$).

To a solution of 4-(1-(4-methoxybenzyl)-1H-pyrazol-4-yl)-2-(methylthio)pyrimidine (200 mg, 0.64 mmol) in dichloromethane was added m-CPBA (220 mg, 1.28 mmol). The reaction was stirred for 2 hour at RT. Water was added, the organic layer was separated and the aqueous layer was extracted with dichloromethane. The combined organics were washed with brine and concentrated in vacuo. The residue was combined with 3-amino-4-fluorophenol (165 mg, 1.28 mmol) and K$_2$CO$_3$ (176 mg, 1.28 mmol) in DMF (5 mL) and the resultant mixture was heated at 90° C. overnight. After filtration and concentration, the residue was purified by silica gel column chromatography to give 5-(4-(1-(4-methoxybenzyl)-1H-pyrazol-4-yl)pyrimidin-2-yloxy)-2-fluorobenzenamine (210 mg, 84% yield). $^1$H NMR (300 MHz, DMSO-d$_6$) δ 8.50 (s, 1H), 8.44, (d, J=5.4 Hz, 1H), 8.10 (s, 1H), 7.42 (d, J=5.4 Hz, 1H), 7.25 (d, J=8.4 Hz, 2H), 6.98 (t, J=9.6 Hz, 1H), 6.91 (d, J=8.4 Hz, 2H), 6.52 (dd, J=2.7, 8.7 Hz, 1H), 6.28 (m, 1H), 5.30 (br s, 2H), 5.26 (s, 2H), 3.72 (s, 3H); MS (ESI) m/z: 392.2 (M+H$^+$).

To a solution of 5-(4-(1-(4-methoxybenzyl)-1H-pyrazol-4-yl)pyrimidin-2-yloxy)-2-fluorobenzenamine (50 mg, 0.13 mmol) in dichloromethane (3 mL) was added TFA (0.3 mL) at 0° C. and the reaction stirred at RT for 12 h. The solvent was removed in vacuo, the residue was washed with ether and treated with saturated ammonia solution. The solid was collected via filtration and dried under vacuum to give 5-(4-(1H-pyrazol-4-yl)pyrimidin-2-yloxy)-2-fluorobenzenamine (15 mg, 43% yield). $^1$H NMR (300 MHz, MeOD) δ 8.44 (d, J=5.1 Hz, 1H), 8.23 (br s, 2H), 7.40 (d, J=5.4, 1H), 7.02 (dd, J=10.8, 8.7 Hz, 1H), 6.73 (dd, J=2.7, 7.2 Hz, 1H), 6.50 (m, 1H); MS (ESI) m/z: 272.2 (M+H$^+$).

Example A19

2,5-Difluoro-4-nitro-phenol (1.739 g, 9.93 mmol) and 3-bromo-4-chloro-pyridine (0.637 g, 3.31 mmol) were dissolved in chlorobenzene (6 ml) and heated at 145° C. overnight. The solvent was removed under reduced pressure and the residue partitioned between EtOAc and 10% K$_2$CO$_3$ $_{(aq)}$. The mixture was extracted with EtOAc (2×). The combined organic extracts were washed with 10% K$_2$CO3$_{(aq)}$ and brine, dried, evaporated and purified by silica gel chromatography (hexanes/EtOAc) to yield 3-bromo-4-(2,5-difluoro-4-nitrophenoxy)pyridine (414 mg, 38% yield). $^1$H NMR (400 MHz, DMSO-d$_6$): δ 8.84 (s, 1H), 8.51-8.45 (m, 2H), 7.82-7.78 (m, 1H), 7.22 (d, 1H); MS (ESI) m/z: 331.0 (M+H$^+$).

3-Bromo-4-(2,5-difluoro-4-nitrophenoxy)pyridine (0.414 g, 1.25 mmol) was dissolved in EtOH (30 ml). Tin (II) chloride dihydrate (1.129 g, 5.00 mmol) was added and the mixture was heated at 80° C. for 4 h. The solvent was removed under reduced pressure and the residue quenched with sat. NaHCO$_3$ $_{(aq)}$. The mixture was diluted with EtOAc and filtered through Celite®. The Celite bed was washed with water (2×) and EtOAc (2×). The filtrate was extracted with EtOAc (2×). The combined organic extracts were dried and evaporated to yield 4-(3-bromopyridin-4-yloxy)-2,5-difluorobenzenamine (0.42 g, 112% yield). $^1$H NMR (400 MHz, DMSO-d$_6$): δ 8.68 (s, 1H), 8.33 (d, 1H), 7.28-7.23 (m, 1H), 6.76-6.71 (m, 2H), 5.56 (br s, 2H); MS (ESI) m/z: 301.0 (M+H$^+$).

In a sealed tube, 4-(3-bromopyridin-4-yloxy)-2,5-difluorobenzenamine (0.42 g, 1.395 mmol), 1-methyl-4-(4,4,5,5-tetramethyl-1,3,2-dioxaborolan-2-yl)-1H-pyrazole (0.363 g, 1.744 mmol), potassium carbonate (0.578 g, 4.18 mmol), and tetrakistriphenylphosphine palladium (0) (0.081 g, 0.070 mmol) were suspended in dioxane (8 ml) and water (1.333 ml). The mixture was degassed with Ar and heated at 90° C. overnight. The reaction mixture was cooled and partitioned between EtOAc and sat. NaHCO$_3$ $_{(aq)}$. The mixture was extracted with EtOAc (3×). The combined organic extracts were dried, evaporated and purified by silica gel chromatography (hexanes/EtOAc) to yield 2,5-difluoro-4-(3-(1-methyl-1H-pyrazol-4-yl)pyridin-4-yloxy)benzenamine (272 mg, 65% yield). $^1$H NMR (400 MHz, DMSO-d$_6$): δ 8.80 (s, 1H) 8.22-8.20 (m, 2H), 8.00 (s, 1H), 7.24-7.19 (m, 1H), 6.76-6.71 (m, 1H), 6.62 (d, 1H), 5.50 (br s, 2H), 3.78 (s, 3H); MS (ESI) m/z: 301.0 (M+H$^+$).

Example A20

To a solution of 4-(1-(4-methoxybenzyl)-1H-pyrazol-4-yl)-2-(methylthio)pyrimidine from Example A18 (200 mg, 0.64 mmol) in dichloromethane was added m-CPBA (220 mg, 1.28 mmol). The reaction was stirred for 2 hour at RT. Water was added, the organic layer was separated and the aqueous layer was extracted with dichloromethane. The combined organics were washed with brine and concentrated in vacuo. The residue was combined with 5-amino-4-fluoro-2-methylphenol (180 mg, 1.28 mmol) and K$_2$CO$_3$ (176 mg, 1.28 mmol) in DMF (5 mL) and the resultant mixture was heated at 90° C. overnight. After filtration and concentration, the residue was purified by silica gel column chromatography to give 5-(4-(1-(4-methoxybenzyl)-1H-pyrazol-4-yl)pyrimidin-2-yloxy)-2-fluoro-4-methylbenzenamine (210 mg, 84% yield). MS (ESI) m/z: 406.2 (M+H$^+$).

A solution of 5-(4-(1-(4-methoxybenzyl)-1H-pyrazol-4-yl)pyrimidin-2-yloxy)-2-fluoro-4-methylbenzenamine (0.5 g, 1.2 mmol) in dichloromethane (20 mL) was treated with TFA (5 mL) at 0° C. The mixture was then stirred at RT for 12 h. The solvent was removed in vacuo, the residue was washed with ether and treated with saturated ammonia solution. The solid was collected via filtration and dried under vacuum to give 5-(4-(1H-pyrazol-4-yl)pyrimidin-2-yloxy)-2-fluoro-4-methylbenzenamine (240 mg, 68%, yield). $^1$H NMR (400 MHz, MeOD): δ 8.41 (d, J=5.2 Hz, 1H), 8.21 (br s, 2H), 7.40 (d, J=5.2, 1H), 6.90 (d, J=11.6 Hz, 1H), 6.62 (d, J=8.0 Hz, 1H), 1.99 (s, 3H). MS (ESI) m/z: 286.1 (M+H$^+$).

Example A21

To a degassed solution of 4-(2-chloropyridin-4-yloxy)-2-fluoroaniline from Example A1 (0.801 g, 3.36 mmol) in DMF (2 mL) and TEA (2 mL) was added ethynyltrimethylsilane (0.929 ml, 6.71 mmol), trans-dichloro-bis(triphenyl phosphine) palladium(0) (0.236 g, 0.336 mmol) and copper (I) iodide (0.064 g, 0.336 mmol) and the mixture was stirred at 90° C. for 16 h. Water (60 ml) was added to the mixture, product was extracted with EtOAc (2×45 ml) and the combined organics were washed with brine, dried (Na$_2$SO$_4$) and concentrated to afford crude product. The product was dissolved in methanol (10 ml), K$_2$CO$_3$ (0.5 g) was added and the mixture was stirred at RT for 2 h. Solvent was removed, water (60 mL) and EtOAc (40 ml) were added, the layers were separated and the aqueous layer was extracted with EtOAc (1×30 mL). The combined organic layer was washed with brine, dried (Na$_2$SO$_4$), concentrated and purified by column chromatography (ethylacetate/hexanes) to afford 4-(2-ethynylpyridin-4-yloxy)-2-fluorobenzenamine as a thick residue (0.56 g, 73% yield). $^1$H NMR (400 MHz, DMSO-d$_6$): δ 8.37 (d, J=6.0 Hz, 1H), 6.98 (dd, J=8.0 Hz, 2.4 Hz, 1H), 6.95 (d, J=6.0 Hz, 1H), 6.87 (dd, J=6.0 Hz, 2.4 Hz, 1H), 6.81-6.73 (m, 2H), 5.20 (brs, 2H), 4.03 (s, 1H); MS (ESI) m/z: 229.1 (M+H$^+$).

Acetaldoxime (0.078 g, 1.321 mmol) and triethylamine (0.246 ml, 1.761 mmol) were added to a solution of 4-(2-ethynylpyridin-4-yloxy)-2-fluorobenzenamine (0.201 g, 0.881 mmol) in THF (4 mL) in a microwave reaction vial. To this solution was added 1-chloropyrrolidine-2,5-dione (0.176 g, 1.32 mmol) and the mixture was stirred at 130° C. for 45 min under microwave irradiation. An additional 1.5 eq each of acetaldoxime and 1-chloropyrrolidine-2,5-dione were added and the reaction heated for an additional 45 min at 130° C. This process was repeated one more time. The mixture was poured into a biphasic solution of water (40 mL) and EtOAc (30 mL). The organic layer was separated and the aqueous layer was extracted with EtOAc (2×20 ml). The combined organics were washed with brine, dried (Na$_2$SO$_4$), concentrated in vacuo and purified by column chromatography (EtOAc-hexanes) to afford 2-fluoro-4-(2-(3-methylisoxazol- 5-yl)pyridin-4-yloxy)benzenamine (58 mg, 23% yield) as light red colored residue. MS (ESI) m/z: 286.1 (M+H$^+$).

Example A22

Using a procedure analogous to Example A1, 5-amino-2-hydroxypyridine (10.15 g, 92 mmol) and 2,4-dichloropyridine (13.64 g, 92 mmol) were combined to provide 6-(2-chloropyridin-4-yloxy)pyridin-3-amine (7.09 g, 35% yield). $^1$H NMR (400 MHz, DMSO-d$_6$): δ 8.12 (m, 1H), 7.61 (m, 1H), 7.26 (m, 1H), 7.0 (s, 1H), 6.97-6.94 (m, 2H), 5.4 (brs, 2H); MS (ESI) m/z: 222.0 (M+H$^+$).

Using a procedure analogous to Example A13, 6-(2-chloropyridin-4-yloxy)pyridin-3-amine (6.06 g, 27.3 mmol) and 1-methyl-4-(4,4,5,5-tetramethyl-1,3,2-dioxaborolan-2-yl)-1H-pyrazole (8.53 g, 41.0 mmol) were combined to provide 6-(2-(1-methyl-1H-pyrazol-4-yl)pyridin-4-yloxy)pyridin-3-amine (4.67 g, 64% yield). $^1$H NMR (400 MHz, DMSO-d$_6$): δ 8.3 (m, 1H), 8.2 (s, 1H), 7.98 (s, 1H), 7.65 (s, 1H), 7.3 (s, 1H), 7.25-7.2 (m, 1H), 6.85-6.81 (m, 1H), 6.6-6.55 (m, 1H), 5.3 (s, 2H), 3.8 (s, 3H); MS (ESI) m/z: 268.1 (M+H$^+$).

Example A23

Sodium azide (1.942 g, 29.9 mmol) was added to a suspension of chloromethyl pivalate (3.00 g, 19.92 mmol) in water (5 mL) and stirred vigorously at 90° C. for 16 h. The reaction mixture was diluted with water (20 mL) and EtOAc (20 ml). The organic layer was washed with brine, dried (Na$_2$SO$_4$) and concentrated to afford azidomethyl pivalate as a liquid (2 g, 64% yield). $^1$H NMR (400 MHz, Acetone-d$_6$): δ 5.23 (s, 2H), 1.22 (s, 9H).

To a suspension of azidomethyl pivalate (0.075 g, 0.477 mmol), 4-(2-ethynylpyridin-4-yloxy)-2-fluorobenzenamine from Example A21 (0.109 g, 0.477 mmol) in t-butanol (0.6 mL) and water (0.6 mL) was added sodium ascorbate (0.021 g, 0.095 mmol). Copper(II)sulfate in water (0.048 ml, 0.048 mmol) was added to the above suspension and the dark red mixture was stirred for 3 h at RT. It was diluted with water (30 mL) and EtOAc (20 mL), the layers were separated and the aqueous layer was extracted with EtOAc (2×15 mL). The combined organics were washed with brine, dried (Na$_2$SO$_4$) and concentrated to afford (4-(4-(4-amino-3-fluorophenoxy)pyridin-2-yl)-1H-1,2,3-triazol-1-yl)methyl pivalate as a red solid. (0.165 g, 90% yield). $^1$H NMR (400 MHz, DMSO-d$_6$): δ 8.54 (s, 1H), 8.46 (brs, 1H), 7.60 (s, 1H), 6.98 (d, J=8.8 Hz, 1H), 6.94 (d, J=3.6 Hz, 1H), 6.83-6.81 (m, 2H), 6.42 (s, 2H), 4.78 (s, 2H), 1.17 (s, 9H); MS (ESI) m/z: 386.1 (M+H$^+$).

Example B1

A solution of 1,1-cyclopropanedicarboxylic acid (3.07 g, 23.60 mmol) in THF (40 mL) was cooled to 0° C. and treated with Et$_3$N (3.30 mL, 23.7 mmol) and thionyl chloride (1.72 mL, 23.6 mmol). The resultant reaction mixture was stirred 30 min at 0° C. 4-Fluoroaniline (2.30 mL, 23.9 mmol) was added and the reaction mixture was allowed to slowly warm to RT overnight. The slurry was diluted with EtOAc (200 mL) and was extracted into 1 N aq NaOH (3×60 mL). The aqueous portion was washed with ether (50 mL) and acidified to pH 1-2 with 6 N aq HCl. The resulting precipitate was collected by filtration and washed with water. The remaining solids were dissolved in a mixture of acetonitrile-MeOH and the solution was concentrated in vacuo until precipitation began. Complete dissolution was affected by warming to 70° C. The resultant solution was allowed to cool to RT overnight to provide large crystals. The crystals were isolated by filtration, washed with acetonitrile and dried in vacuo to provide 1-((4-fluorophenyl)carbamoyl)cyclopropanecarboxylic acid (1.76 g). The mother liquors were concentrated to initiate a second crystallization, which provided an additional crop of 1-((4-fluorophenyl)carbamoyl)cyclopropanecarboxylic acid (1.39 g, 60% yield overall). $^1$H NMR (400 MHz, DMSO-d$_6$): δ 13.06 (s, 1H), 10.55 (s, 1H), 7.60 (m, 2H), 7.12 (m, 2H), 1.39 (s, 4H); MS (ESI) m/z: 224.1 (M+H$^+$).

Example B2

A solution of 1,1-cyclopropanecarboxylic acid (0.23 g, 1.74 mmol) in THF (5 mL) was cooled to 0° C. and treated with triethylamine (0.48 ml, 3.47 mmol) and thionyl chloride (0.13 ml, 1.74 mmol). The reaction mixture was stirred 30 min at 0° C. A solution of Example A3 (0.5 g, 1.65 mmol) in THF (5 mL) was added. The reaction mixture was stirred at 0° C. for 1 h and then stirred overnight at RT. The reaction mixture was treated with 1 M HCl, and then EtOAc was added. The resultant precipitate was collected by filtration, washed with EtOAc, and dried under vacuum to obtain 1-((2,3-difluoro-4-(2-(1-methyl-1H-pyrazol-4-yl)pyridin-4-yloxy)phenyl)carbamoyl)cyclopropanecarboxylic acid (60% purity, 0.6 g, 53% yield). MS (ESI) m/z: 415.1 (M+H$^+$). This material was used without further purification.

Example B3

To a stirring solution of 1,1-cyclopropanedicarboxylic acid (0.178 g, 1.367 mmol) in THF (4 ml) at 0° C. was added Et$_3$N (0.190 ml, 1.367 mmol) followed by thionyl chloride (0.099 ml, 1.367 mmol). The reaction was stirred at 0° C. for 30 min. Example A2 (0.370 g, 1.301 mmol), DMF (4.00 ml) and Et$_3$N (0.380 ml, 2.73 mmol) were added and the reaction was stirred overnight with warming to RT. The reaction was quenched with 1M HCl (4 ml) and stirred for 15 min. The pH was adjusted back to 7 with 50% NaOH and the mixture extracted with EtOAc (3×). The combined organics were washed with H$_2$O (1×) and brine (2×), dried (MgSO$_4$), and evaporated to afford a solid. The crude solid was triturated with CH$_2$Cl$_2$/hexanes. The remaining solids were collected by filtration, rinsed with hexanes and dried in vacuo to afford 1-((3-fluoro-4-(2-(1-methyl-1H-pyrazol-4-yl)pyridin-4-yloxy)phenyl)carbamoyl)cyclopropanecarboxylic acid (0.199 g, 39% yield) as cream-colored solid which was used without further purification. $^1$H NMR (400 MHz, DMSO-d$_6$): δ 10.76 (s, 1H), 8.3 (d, J=5.7 Hz, 1H), 8.26 (s, 1H), 7.96 (s, 1H), 7.84 (dd, J=2.4, 13 Hz, 1H), 7.44-7.43 (m, 1H), 7.42-7.41 (m, 1H), 7.33 (s, 1H), 6.66-6.64 (m, 1H), 3.84 (s, 3H), 1.39 (s, 4H); MS (ESI) m/z: 397.1 (M+H$^+$).

Example B4

Thionyl chloride (1.09 mL, 15.0 mmol) was added slowly over 2 min to a stirring solution of 1,1-cyclopropanedicarboxylic acid (1.95 g, 15.0 mmol) and Et$_3$N (4.29 g, 42.4 mmol) in THF (15 mL) at 0° C. After complete addition, the reaction was further diluted with THF (25 mL) and the reaction was stirred vigorously at 0° C. for 30 min. The hydrochloride salt of Example A1 (4.00 g, 12.5 mmol) was added in three portions and the resulting mixture was allowed to slowly warm to RT over 4 h. The reaction mixture was concentrated to dryness in vacuo and the residue was digested with aqueous MeOH. The remaining solids were collected by filtration. This solid was dissolved in 1 M aq NaOH (30 mL) and methanol. The methanol was removed in vacuo, the remaining aqueous phase was diluted with water to a volume of 150 mL and extracted with EtOAc (3×50 mL). The combined EtOAc extracts were washed with sat aq NaHCO$_3$. The combined aqueous was acidified to pH 6 with 0.5 M HCl. The resultant fine precipitate was collected by filtration, washed with acetonitrile (20 mL) and dried in vacuo to provide 1-((2-fluoro-4-(2-(1-methyl-1H-pyrazol-4-yl)pyridin-4-yloxy)phenyl)carbamoyl)cyclopropanecarboxylic acid (1.177 g). The remaining aqueous was concentrated in vacuo to about ⅓ volume and the pH was reduced to pH 5 with 1 M aq HCl. The additional precipitate that formed was collected by filtration, washed with acetonitrile and dried in vacuo to provide an additional crop (1.34 g) of 1-((2-fluoro-4-(2-(1-methyl-1H-pyrazol-4-yl)pyridin-4-yloxy)phenyl)carbamoyl)cyclopropanecarboxylic acid (2.517 g total, 51% yield). $^1$H NMR (400 MHz, DMSO-d$_6$): δ 13.51 (br s, 1H), 11.30 (s, 1H), 8.37 (d, J=5.7 Hz, 1H), 8.25 (s, 1H), 8.19 (t, J=9.0 Hz, 1H), 7.95 (s, 1H), 7.28 (dd, J=11.6, 2.7 Hz, 1H), 7.22 (d, J=1.6 Hz, 1H), 7.01 (m, 1H), 6.69 (dd, J=5.6, 2.3 Hz, 1H), 3.84 (s, 3H), 1.58-1.51 (m, 4H); MS (ESI) m/z: 397.1 (M+H$^+$).

Example B5

To a solution of Example A12 (9.66 g, 32.0 mmol) in DMF (100 mL) were added cyclopropane-1,1-dicarboxylic acid monomethyl ester (6.91 g, 47.9 mmol), TBTU (15.39 g, 47.9 mmol) and DIPEA (27.9 mL, 160 mmol). The sides of the flask were rinsed with DMF (10 mL) and the resultant reaction mixture was stirred at RT overnight. The solvent was removed under high vacuum and the residue was dissolved in EtOAc (600 mL). The organic phase was washed with water (100 mL), sat. aq. NaHCO$_3$ (200 mL) and brine (50 mL), dried (MgSO$_4$), and was concentrated in vacuo and purified by silica gel chromatography (CH$_2$Cl$_2$—MeOH) to provide methyl 1-((2,5-difluoro-4-(2-(1-methyl-1H-pyrazol-4-yl)pyridin-4-yloxy)phenyl)carbamoyl)cyclopropanecarboxylate (10.1 g, 69% yield). $^1$H NMR (400 MHz, DMSO-d$_6$): δ 10.94 (s, 1H), 8.39 (d, J=5.7 Hz, 1H), 8.29 (s, 1H), 8.19 (dd, J=12.2, 7.2 Hz, 1H), 7.99 (s, 1H), 7.59 (dd, J=11.0, 7.4 Hz, 1H), 7.26 (d, J=2.6 Hz, 1H), 6.73 (dd, J=5.6, 2.5 Hz, 1H), 3.86 (s, 3H), 3.70 (s, 3H), 1.61-1.54 (m, 4H); MS (ESI): m/z 429.1 [M+1]$^+$.

To a suspension of methyl 1-((2,5-difluoro-4-(2-(1-methyl-1H-pyrazol-4-yl)pyridin-4-yloxy)phenyl)carbamoyl)cyclopropanecarboxylate (5.8 g, 13.54 mmol) in THF (100 mL) were added water (50.0 mL) and lithium hydroxide monohydrate (2.84 g, 67.7 mmol). The reaction mixture was stirred at RT for 40 minutes. The layers were separated and the organic phase washed with brine (50 mL), dried (MgSO$_4$) and concentrated to dryness to afford lithium 1-((2,5-difluoro-4-(2-(1-methyl-1H-pyrazol-4-yl)pyridin-4-yloxy)phenyl)carbamoyl)cyclopropanecarboxylate (5.11 g, 86% yield) as an off-white foam. MS (ESI): m/z 415.1 [M+1]$^+$.

Example 1

Example B1 (0.060 g, 0.269 mmol), Example A3 (0.060 g, 0.198 mmol), TBTU (0.129 g, 0.403 mmol) and i-Pr$_2$NEt (0.089 ml, 0.538 mmol) were combined in DMF (2 mL). The resultant mixture was stirred overnight at RT. An additional portion of Example B1 (60 mg), TBTU (120 mg) and i-Pr$_2$NEt (0.080 mL) was added and the mixture was stirred an additional 24 h. The reaction mixture was partitioned between water and EtOAc. The organic layer was washed with 5% aq LiCl, dried (MgSO$_4$), concentrated in vacuo and purified by chromatography on silica gel and reverse-phase silica gel to provide N-(2,3-difluoro-4-(2-(1-methyl-1H-pyrazol-4-yl)pyridin-4-yloxy)phenyl)-N'-(4-fluorophenyl)cyclopropane-1,1-dicarboxamide (21 mg, 15% yield). $^1$H NMR (400 MHz, DMSO-d$_6$): δ 10.82 (s, 1H), 9.89 (s, 1H), 8.38 (d, J=5.5 Hz, 1H), 8.27 (s, 1H), 7.97 (s, 1H), 7.76 (m, 1H), 7.61-7.57 (m, 2H), 7.29 (d, J=2.5 Hz, 1H), 7.22-7.13 (m, 3H), 6.71 (m, 1H), 3.84 (s, 3H), 1.61 (m, 2H), 1.55 (m, 2H); MS (ESI) m/z: 508.1 (M+H$^+$).

Example 2

Example B1 (51 mg, 0.229 mmol), Example A2 (50 mg, 0.176 mmol), TBTU (85 mg, 0.264 mmol) and DIEA (35 μl, 0.212 mmol) were combined in DMF (1 mL) and stirred overnight at RT. The reaction mixture was diluted with EtOAc (20 mL) and washed with water, satd aq NaHCO$_3$, and brine. The organics were dried (MgSO$_4$), concentrated in vacuo and was purified via silica gel chromatography to provide N-(3-fluoro-4-(2-(1-methyl-1H-pyrazol-4-yl)pyridin-4-yloxy)phenyl)-N'-(4-fluorophenyl)cyclopropane-1,1-dicarboxamide (65 mg, 76% yield). $^1$H NMR (400 MHz, DMSO-d$_6$): δ 10.35 (s, 1H), 9.97 (s, 1H), 8.35 (d, J=5.7 Hz, 1H), 8.25 (s, 1H), 7.95 (s, 1H), 7.85 (dd, J=13.2, 2.2 Hz, 1H), 7.64-7.60 (m, 2H), 7.46 (m, 1H), 7.32 (t, J=9.0 Hz, 1H), 7.22 (d, J=2.5 Hz, 1H), 7.12 (m, 2H), 6.60 (dd, J=5.7, 2.4 Hz, 1H), 3.84 (s, 3H), 1.46 (m, 2H), 1.43 (m, 2H); MS (ESI) m/z: 490.1 (M+H$^+$).

Example 3

Example B2 (60% purity, 0.15 g, 0.22 mmol), benzylamine (0.036 ml, 0.326 mmol), EDC (0.062 g, 0.326 mmol), HOBT (0.050 g, 0.326 mmol) and Et$_3$N (0.091 ml, 0.652 mmol) were combined in DMF (2.5 ml) and stirred at RT. Additional benzyl amine (10 mg) was added and then the reaction was stirred overnight at RT. The completed reaction was poured into water and extracted with EtOAc (3×). The combined organic layers were washed with NaHCO$_3$, LiCl, brine, dried (Na$_2$SO$_4$) and purified by silica gel column chromatography (EtOAc/hexane→MeOH/CH$_2$Cl$_2$) to obtain N-benzyl-N'-(2,3-difluoro-4-(2-(1-methyl-1H-pyrazol-4-yl)pyridin-4-yloxy)phenyl)cyclopropane-1,1-dicarboxamide (22 mg, 20% yield) following lyophilzation. $^1$H NMR (400 MHz, DMSO-d$_6$): δ 11.9 (s, 1H), 8.45 (t, J=5.6 Hz, 1H), 8.38 (m, 1H), 8.26 (s, 1H), 7.96 (m, 2H), 7.1-7.4 (m, 7H), 6.73 (dd, J=5.2, 2.4 Hz, 1H), 4.32 (d, J=5.6 Hz, 2H), 3.84 (s, 3H), 1.55 (s, 4H); MS (ESI) m/z: 504.1 (M+H$^+$).

Example 4

Benzylamine (0.017 ml, 0.151 mmol), Example B3 (0.040 g, 0.101 mmol) and i-Pr$_2$NEt (0.025 ml, 0.151 mmol) were combined in DMF (0.4 mL). TBTU (0.049 g, 0.151 mmol) was added and the mixture was stirred at RT overnight. The completed reaction was diluted with EtOAc (30 mL), washed with H$_2$O (15 mL), 5% citric acid (15 mL) and saturated brine, dried (MgSO$_4$), concentrated in vacuo and purified by chromatography to afford N-benzyl-N'-(3-fluoro-4-(2-(1-methyl-1H-pyrazol-4-yl)pyridin-4-yloxy)phenyl)cyclopropane-1,1-dicarboxamide (0.028 g, 57% yield). It was converted to the corresponding HCl salt by reacting with HCl (4.0 M HCl in dioxane, 1.0 eq.). $^1$H NMR (DMSO-d$_6$): δ 10.97 (s, 1H), 8.55-8.44 (m, 3H), 8.23 (s, 1H), 7.90 (dd, J=13.6, 1.6 Hz, 1H), 7.59 (s, 1H), 7.50-7.38 (m, 2H), 7.31-7.19 (m, 5H), 6.98 (s, 1H), 4.31 (d, J=6.0 Hz, 2H), 3.89 (s, 3H), 1.40-1.39 (m, 4H); MS (ESI) m/z: 486.2 (M+H$^+$).

Example 5

Using a procedure analogous to Example 4, aniline (0.015 ml, 0.159 mmol) and Example B3 (0.042 g, 0.106 mmol)

were combined to provide N-(3-fluoro-4-(2-(1-methyl-1H-pyrazol-4-yl)pyridin-4-yloxy)phenyl)-N'-phenylcyclopropane-1,1-dicarboxamide (0.040 g, 79% yield) as a light yellow oil. It was converted to the corresponding HCl salt by reacting with HCl (4.0 M HCl in dioxane, 1.0 eq.). $^1$H NMR (DMSO-$d_6$): δ 10.43 (s, 1H), 9.96 (s, 1H), 8.52-8.49 (m, 2H), 8.21 (s, 1H), 7.92 (d, J=11.2 Hz, 1H), 7.64-7.52 (m, 4H), 7.42 (t, J=8.8 Hz, 1H), 7.34-7.30 (m, 2H), 7.08 (t, J=6.8 Hz, 1H), 6.95 (s, 1H), 3.91 (s, 3H), 1.50-1.44 (m, 4H); MS (ESI) m/z: 472.1 (M+H$^+$).

Example 6

Using a procedure analogous to Example 4, Example B3 (0.042 g, 0.106 mmol) and 3-aminobenzotrifluoride (0.020 ml, 0.159 mmol) were combined to provide N-(3-fluoro-4-(2-(1-methyl-1H-pyrazol-4-yl)pyridin-4-yloxy)phenyl)-N'-(3-(trifluoromethyl)phenyl)cyclopropane-1,1-dicarboxamide (0.018 g, 32% yield) as a light yellow oil. It was converted to the corresponding HCl salt by reacting with HCl (4.0 M HCl in dioxane, 1.0 eq.). $^1$H NMR (DMSO-$d_6$): δ 10.39 (s, 1H), 10.28 (s, 1H), 8.52-8.46 (m, 2H), 8.18 (s, 1H), 8.15 (s, 1H), 7.58-7.49 (m, 3H), 7.44-7.38 (m, 2H), 6.93 (s, 1H), 3.91 (s, 3H), 1.50-1.42 (m, 4H); MS (ESI) m/z: 540.1 (M+H$^+$).

Example 7

Example B4 (1.19 g, 3.00 mmol), 4-fluoroaniline (0.367 g, 3.30 mmol), and DIEA (0.54 ml, 3.27 mmol) were combined in DMF (10.5 mL). TBTU (1.25 g, 3.89 mmol) was added and the resultant solution was stirred at RT. After 36 h, the reaction mixture was diluted with EtOAc (150 mL) and washed with water (50 mL), brine (2×50 mL), satd sodium bicarbonate solution (2×50 mL) and brine (50 mL). The combined aqueous phases were back extracted with EtOAc (50 mL). The combined organics were dried (Na$_2$SO$_4$) and concentrated to a viscous oil. The residue was completely dissolved in acetonitrile (15 mL) and the solution was sonicated until precipitation occurred. The fine suspension was allowed to stand overnight, and collected by filtration, washed with acetonitrile (25 mL), and dried in vacuo to provide N-(2-fluoro-4-(2-(1-methyl-1H-pyrazol-4-yl)pyridin-4-yloxy)phenyl)-N'-(4-fluorophenyl)cyclopropane-1,1-dicarboxamide (1.258 g). The filtrate was concentrated to about a 3 mL volume to afford a second crop (0.106 g, 92% total yield). $^1$H NMR (400 MHz, DMSO-$d_6$): δ 10.62 (s, 1H), 9.91 (s, 1H), 8.38 (d, J=4.9 Hz, 1H), 8.25 (s, 1H), 7.96-7.90 (m, 2H), 7.60-7.56 (m, 2H), 7.26-7.23 (m, 2H), 7.15 (m, 2H), 7.01 (m, 1H), 6.67 (m, 1H), 3.84 (s, 3H), 1.60 (m, 2H), 1.54 (m, 2H); MS (ESI) m/z: 490.2 (M+H$^+$).

Example 8

4-Methoxyaniline (0.020 g, 0.159 mmol) and Example B3 (0.042 g, 0.106 mmol) were combined using a procedure analogous to Example 4 to provide N-(3-fluoro-4-(2-(1-methyl-1H-pyrazol-4-yl)pyridin-4-yloxy)phenyl)-N'-(4-methoxyphenyl)cyclopropane-1,1-dicarboxamide (0.019 g, 36% yield). $^1$H NMR (DMSO-$d_6$): δ 10.41 (s, 1H), 9.76 (s, 1H), 8.35 (dd, J=6.0, 1.2 Hz, 1H), 8.24 (s, 1H), 7.95 (s, 1H), 7.85 (d, J=13.2 Hz, 1H), 7.50-7.44 (m, 3H), 7.32 (t, J=8.8 Hz, 1H), 7.22 (s, 1H), 6.86 (dd, J=9.2, 1.6 Hz, 2H), 6.60 (m, 1H), 3.84 (s, 3H), 3.70 (s, 3H), 1.50-1.42 (m, 4H); MS (ESI) m/z: 502.1 (M+H$^+$).

Example 9 m-Anisidine (0.020 g, 0.159 mmol) and Example B3 (0.042 g, 0.106 mmol) were combined using a procedure analogous to Example 4 to provide N-(3-fluoro-4-(2-(1-methyl-1H-pyrazol-4-yl)pyridin-4-yloxy)phenyl)-N'-(3-methoxyphenyl)cyclopropane-1,1-dicarboxamide (0.031 g, 58% yield) as a colorless oil. It was converted to the corresponding HCl salt by reacting with HCl (4.0 M HCl in dioxane, 1.0 eq.). $^1$H NMR (DMSO-$d_6$): δ 10.42 (s, 1H), 9.92 (s, 1H), 8.68 (d, J=2.4 Hz, 1H), 8.60 (d, J=6.8 Hz, 1H), 8.34 (d, J=3.6 Hz, 1H), 7.93 (dd, J=12.8, 1.6 Hz, 1H), 7.80 (d, J=2.8 Hz, 1H), 7.55-7.52 (m, 1H), 7.44 (t, J=8.8 Hz, 1H), 7.31 (s, 1H), 7.20-7.16 (m, 3H), 6.63 (m, 1H), 3.92 (s, 3H), 3.70 (s, 3H), 1.50-1.41 (m, 4H); MS (ESI) m/z: 502.2 (M+H$^+$).

Example 10

3-Fluoroaniline (0.018 g, 0.159 mmol) and Example B3 (0.042 g, 0.106 mmol) were combined using a procedure analogous to Example 4 to provide N-(3-fluoro-4-(2-(1-methyl-1H-pyrazol-4-yl)pyridin-4-yloxy)phenyl)-N'-(3-fluorophenyl)cyclopropane-1,1-dicarboxamide (0.022 g, 42% yield). $^1$H NMR (DMSO-$d_6$): δ 10.27 (s, 1H), 10.17 (s, 1H), 8.35 (d, J=5.6 Hz, 1H), 8.25 (s, 1H), 7.95 (s, 1H), 7.84 (dd, J=13.2, 2.4 Hz, 1H), 7.62 (d, J=12.0 Hz, 1H), 7.46 (d, J=8.8, 1.6 Hz, 1H), 7.38-7.29 (m, 3H), 7.22 (d, J=2.0 Hz, 1H), 6.89 (t, J=8.0 Hz, 1H), 6.60 (dd, J=5.6, 2.0 Hz, 1H), 3.84 (s, 3H), 1.47-1.42 (m, 4H); MS (ESI) m/z: 490.1 (M+H$^+$).

Example 11

Example B1 (53 mg, 0.237 mmol), Example A4 (51 mg, 0.182 mmol), TBTU (88 mg, 0.273 mmol) and i-Pr$_2$NEt (0.045 mL, 0.272 mmol) were combined in DMF (1 mL) using a procedure analogous to Example 2 to afford N-(4-fluorophenyl)-N'-(3-methyl-4-(2-(1-methyl-1H-pyrazol-4-yl)pyridin-4-yloxy)phenyl)cyclopropane-1,1-dicarboxamide (70 mg, 80% yield). $^1$H NMR (400 MHz, DMSO-$d_6$): δ 10.12 (s, 1H), 10.00 (s, 1H), 8.31 (d, J=6.0 Hz, 1H), 8.22 (s, 1H), 7.92 (s, 1H), 7.64-7.60 (m, 3H), 7.54 (m, 1H), 7.16-7.11 (m, 3H), 7.04 (d, J=8.8 Hz, 1H), 6.46 (dd, J=5.6, 2.4 Hz, 1H), 3.84 (s, 3H), 2.08 (s, 3H), 1.45 (m, 4H); MS (ESI) m/z: 486.2 (M+H$^+$).

Example 12

A solution of 2-(4-fluorophenyl)acetyl chloride (0.173 g, 1.0 mmol) in dry ether (1.0 mL) was slowly added to a suspension of silver cyanate (0.180 g, 1.2 mmol) in ether (1.5 mL). The mixture was subsequently refluxed for 2 h under N$_2$. After filtration of the silver salts, solvent was removed under reduced pressure and the residue was dissolved in CH$_2$Cl$_2$ (4.0 mL).

A portion of the above solution (0.179 g, 1.0 mmol) and Example A2 (0.071 g, 0.25 mmol) were combined in CH$_2$Cl$_2$ (2.0 mL). After stirring at RT overnight, the reaction was concentrated in vacuo and purified by chromatography to afford 1-(3-fluoro-4-(2-(1-methyl-1H-pyrazol-4-yl)pyridin-4-yloxy)phenyl)-3-(2-(4-fluorophenyl)acetyl)urea (0.020 g, 17% yield) as a white solid. $^1$H NMR (DMSO-$d_6$): δ 11.03 (s, 1H), 10.57 (s, 1H), 8.35 (d, J=5.6 Hz, 1H), 8.24 (s, 1H), 7.95 (s, 1H), 7.76 (dd, J=12.8, 2.4 Hz, 1H), 7.37-7.32 (m, 4H), 7.20-7.13 (m, 3H), 6.61 (dd, J=5.6, 2.4 Hz, 1H), 3.84 (s, 3H), 3.73 (s, 2H); MS (ESI) m/z: 464.1 (M+H$^+$).

Example 13

To a solution of 4-aminopyridine (0.019 g, 0.202 mmol) in CH$_2$Cl$_2$ (5 ml) was added Example B3 (0.040 g, 0.101 mmol), TBTU (0.039 g, 0.151 mmol) and triethylamine (0.020 g, 0.202 mmol). The reaction mixture was stirred at RT for 13 hours, washed with water, the organic layer was concentrated and purified by chromatography (THF/acetonitrile) to provide N-(3-fluoro-4-(2-(1-methyl-1H-pyrazol-4-yl)pyridin-4-yloxy)phenyl)-N'-(pyridin-4-yl)cyclopropane-1,1-dicarboxamide (0.032 g, 67% yield) as a white solid. $^1$H NMR (400 MHz, DMSO-$d_6$): δ 10.45 (s, 1H), 10.25 (s, 1H), 8.42 (d, J=6 Hz, 2H), 8.35 (d, J=6 Hz, 1H), 8.25 (s, 1H), 7.95 (s, 1H), 7.82 (m, 1H), 7.65 (d, J=6 Hz, 2H), 7.44 (m, 1H), 7.32 (m, 1H), 7.20 (d, J=2.4 Hz, 1H), 6.60 (m, 1H), 3.85 (s, 3H), 1.47 (s, 4H); MS (ESI) m/z: 473.1 (M+H$^+$).

Example 14

Using a procedure analogous to Example 13, 3-aminopyridine (0.019 g, 0.202 mmol), Example B3 (0.040 g, 0.101 mmol), TBTU (0.039 g, 0.151 mmol) and triethylamine (0.020 g, 0.202 mmol) were combined in CH$_2$Cl$_2$ (5 ml) to provide N-(3-fluoro-4-(2-(1-methyl-1H-pyrazol-4-yl)pyridin-4-yloxy)phenyl)-N'-(pyridin-3-yl)cyclopropane-1,1-dicarboxamide (0.032 g, 67% yield) as a white solid. $^1$H NMR (400 MHz, DMSO-$d_6$): δ 10.36 (s, 1H), 10.16 (s, 1H), 8.78 (d, J=2.5 Hz, 1H), 8.35 (d, J=6 Hz, 1H), 8.25 (m, 2H), 8.00 (m, 1H), 7.94 (s, 1H), 7.84 (m, 1H), 7.44 (m, 1H), 7.33 (m, 2H), 7.22 (d, J=2.5 Hz, 1H), 6.60 (m, 1H), 3.85 (s, 3H), 1.47 (s, 4H); MS (ESI) m/z: 473.1 (M+H$^+$).

Example 15

To a solution of 3-chlorobenzylamine (0.029 g, 0.202 mmol) in CH$_2$Cl$_2$ (3 ml) was added Example B3 (0.040 g, 0.101 mmol), TBTU (0.039 g, 0.151 mmol) and triethylamine (0.020 g, 0.202 mmol). The reaction mixture was stirred at RT for 13 hours. The reaction mixture was washed with saturated NaHCO$_3$ and brine, dried and the solvent evaporated to provide N-(3-chlorobenzyl)-N'-(3-fluoro-4-(2-(1-methyl-1H-pyrazol-4-yl)pyridin-4-yloxy)phenyl)cyclopropane-1,1-dicarboxamide (0.036 g, 69% yield) as a white solid. $^1$H NMR (400 MHz, DMSO-$d_6$): δ 10.80 (s, 1H), 8.49 (m, 2H), 8.35 (d, J=6 Hz, 1H), 8.25 (s, 1H), 7.95 (s, 1H), 7.82 (m, 2H), 7.55-7.18 (m, 5H), 6.60 (m, 1H), 4.31 (d, J=6 Hz, 2H), 3.85 (s, 3H), 1.38 (s, 4H); MS (ESI) m/z: 520.2 (M+H$^+$).

Example 16

To a solution of (S)-(−)-alpha-methylbenzylamine (0.024 g, 0.202 mmol) in CH$_2$Cl$_2$ (3 ml) was added Example B3 (0.040 g, 0.101 mmol), TBTU (0.039 g, 0.151 mmol) and triethylamine (10.21 mg, 0.101 mmol). The reaction mixture was stirred at RT for 13 hours. The reaction mixture was washed with saturated NaHCO$_3$ and brine, dried, concentrated in vacuo and recrystalled (acetonitrile) to provide N-(3-fluoro-4-(2-(1-methyl-1H-pyrazol-4-yl)pyridin-4-yloxy)phenyl)-N'-((S)-1-phenylethyl)cyclopropane-1,1-dicarboxamide (0.04 g, 79% yield) as a white solid. $^1$H NMR (400 MHz, DMSO-$d_6$): δ 10.72 (s, 1H), 8.34 (d, J=5.5 Hz, 1H), 8.31 (d, J=8 Hz, 1H), 8.25 (s, 1H), 7.95 (s, 1H), 7.82 (m, 1H), 7.42 (m, 1H), 7.29 (m, 5H), 7.19 (m, 2H), 6.60 (m, 1H), 4.99 (m, 1H), 3.85 (s, 3H), 1.40 (m, 7H); MS (ESI) m/z: 500.2 (M+H$^+$).

Example 17

Using a procedure analogous to Example 16, (R)-(+)-alpha-methylbenzylamine (0.024 g, 0.202 mmol), Example B3 (0.040 g, 0.101 mmol), TBTU (0.039 g, 0.151 mmol) and triethylamine (0.020 g, 0.202 mmol) were combined in CH$_2$Cl$_2$ (3 ml) and the crude material was recrystallized (methanol) to provide N-(3-fluoro-4-(2-(1-methyl-1H-pyrazol-4-yl)pyridin-4-yloxy)phenyl)-N'-((R)-1-phenylethyl)cyclopropane-1,1-dicarboxamide (0.040 g, 79% yield) as a white solid. $^1$H NMR (400 MHz, DMSO-$d_6$): δ 10.72 (s, 1H), 8.34 (d, J=5.5 Hz, 1H), 8.31 (d, J=8 Hz, 1H), 8.25 (s, 1H), 7.95 (s, 1H), 7.82 (m, 1H), 7.42 (m, 1H), 7.29 (m, 5H), 7.19 (m, 2H), 6.60 (m, 1H), 4.99 (m, 1H), 3.85 (s, 3H), 1.40 (m, 7H); MS (ESI) m/z: 500.1 (M+H$^+$).

Example 18

To a solution of 4-fluorobenzylamine (0.019 g, 0.151 mmol) in CH$_2$Cl$_2$ was added Example B3 (0.030 g, 0.076 mmol), TBTU (0.039 g, 0.151 mmol) and triethylamine (0.015 g, 0.151 mmol). The reaction mixture was stirred at RT for 3 hours. The reaction mixture was washed with saturated sodium bicarbonate and brine, dried, concentrated in vacuo and the residue was recrystallized (methanol) to provide N-(4-fluorobenzyl)-N'-(3-fluoro-4-(2-(1-methyl-1H-pyrazol-4-yl)pyridin-4-yloxy)phenyl)cyclopropane-1,1-dicarboxamide (0.025 g, 66% yield) as a white solid. $^1$H NMR (400 MHz, DMSO-$d_6$): δ 10.83 (s, 1H), 8.40 (t, J=5.5 Hz, 1H), 8.34 (d, J=5.5 Hz, 1H), 8.25 (s, 1H), 7.95 (s, 1H), 7.82 (m, 1H), 7.43 (m, 1H), 7.30 (m, 3H), 7.20 (d, J=2.5 Hz, 1H), 7.12 (m, 2H), 6.59 (m, 1H), 4.32 (d, J=6 Hz, 2H), 3.85 (s, 3H), 1.40 (s, 4H); MS (ESI) m/z: 504.1 (M+H$^+$).

Example 19

Example 31 (0.061 g, 0.128 mmol), K$_2$CO$_3$ (0.053 g, 0.385 mmol) and iodoethane (0.060 g, 0.385 mmol) were combined in DMSO (1 mL) and the mixture was stirred at RT for 24 h. The reaction mixture was poured into EtOAc (20 mL) and water (30 mL). The layers were separated and the aqueous layer was extracted with EtOAc (15 mL). The combined organics were washed with brine, dried (Na$_2$SO$_4$), concentrated and purified by silica gel chromatography (EtOAc-hexanes) to afford N-(4-(2-(1-ethyl-1H-pyrazol-4-yl)pyridin-4-yloxy)-3-fluorophenyl)-N'-(4-fluorophenyl)cyclopropane-1,1-dicarboxamide (37 mg; 57% yield) as a white solid. $^1$H NMR (400 MHz, DMSO-$d_6$): δ 10.35 (s, 1H), 9.97 (s, 1H), 8.35 (d, J=6.0 Hz, 1H), 8.23 (s, 1H), 7.96 (s, 1H), 7.85 (dd, J=13.2 Hz, 2.0 Hz, 1H), 7.63-7.60 (m, 2H), 7.45 (dd, J=8.8 Hz, 1.6 Hz, 1H), 7.31 (t, J=8.8 Hz, 1H), 7.23 (d, J=2.0 Hz, 1H), 7.15-7.11 (m, 2H), 6.59 (dd, J=5.6 Hz, 2.4 Hz, 1H), 4.13 (q, J=7.2 Hz, 2H), 1.45-1.42 (m, 4H), 1.37 (t, J=7.2 Hz, 3H); MS (ESI) m/z: 504.1 (M+H$^+$).

Example 20

Using a procedure analogous to Example 19, Example 31 (0.061 g, 0.128 mmol), K$_2$CO$_3$ (0.053 g, 0.385 mmol) and 1-iodopropane (0.11 g, 0.64 mmol) were combined to afford N-(3-fluoro-4-(2-(1-propyl-1H-pyrazol-4-yl)pyridin-4-yloxy)phenyl)-N'-(4-fluorophenyl)cyclopropane-1,1-dicarboxamide as a white solid. (51 mg, 77% yield). $^1$H NMR (400 MHz, DMSO-$d_6$): δ 10.35 (s, 1H), 9.97 (s, 1H), 8.35 (d, J=5.6 Hz, 1H), 8.28 (s, 1H), 7.96 (s, 1H), 7.84 (dd, J=13.2 Hz, 2.0 Hz, 1H), 7.63-7.60 (m, 2H), 7.46 (dd, J=8.8 Hz, 1.2 Hz, 1H), 7.31 (t, J=8.8 Hz, 1H), 7.23 (d, J=2.0 Hz, 1H), 7.15-7.11 (m, 2H), 6.59 (dd, J=5.6 Hz, 2.4 Hz, 1H), 4.06 (t, J=6.8 Hz, 2H), 1.82-1.73 (m, 2H), 1.47-1.41 (m, 4H), 0.80 (t, J=7.2 Hz, 3H); MS (ESI) m/z: 518.2 (M+H$^+$).

Example 21

Using a procedure analogous to Example 19, Example 31 (0.091 g, 0.19 mmol), K$_2$CO$_3$ (0.08 g, 0.57 mmol) and ethyl 2-bromoacetate (0.16 g, 0.96 mmol) were combined to afford N-(3-fluoro-4-(2-(1-(1-ethoxy2-acetyl)-1H-pyrazol-4-yl)pyridin-4-yloxy)phenyl)-N'-(4-fluorophenyl)cyclopropane-1,1-dicarboxamide (97 mg, 90% yield) as a white solid. $^1$H NMR (400 MHz, DMSO-d$_6$): δ 10.35 (s, 1H), 9.97 (s, 1H), 8.37 (d, J=5.6 Hz, 1H), 8.29 (s, 1H), 8.02 (s, 1H), 7.85 (dd, J=13.2 Hz, 2.0 Hz, 1H), 7.63-7.60 (m, 2H), 7.47-7.45 (m, 1H), 7.32 (t, J=8.8 Hz, 1H), 7.23 (d, J=2.8 Hz, 1H), 7.15-7.11 (m, 2H), 6.64 (dd, J=6.0 Hz, 2.4 Hz, 1H), 5.07 (s, 2H), 4.14 (q, J=7.2 Hz, 2H), 1.45-1.42 (m, 4H), 1.19 (t, J=7.2 Hz, 3H); MS (ESI) m/z: 562.1 (M+H$^+$).

To a solution of N-(3-fluoro-4-(2-(1-(1-ethoxy2-acetyl)-1H-pyrazol-4-yl)pyridin-4-yloxy)phenyl)-N'-(4-fluorophenyl)cyclopropane-1,1-dicarboxamide (0.097 g, 0.173 mmol) in THF (4 mL) was added LiAlH$_4$ (2 M in THF, 0.173 ml, 0.345 mmol) at −78° C. The mixture was warmed to RT and stirred for 1 h. It was cooled to 0° C., methanol (0.2 ml) and sat. aq Na$_2$SO$_4$ solution (0.2 ml) were added and the mixture stirred for 4 h at RT. The mixture was filtered through a Celite® pad, and the pad was washed with THF (2×2 mL). The combined filtrate was concentrated to afford crude product which was purified by silica gel chromatography (CH$_2$Cl$_2$-MeOH) to afford N-(3-fluoro-4-(2-(1-(2-hydroxyethyl)-1H-pyrazol-4-yl)pyridin-4-yloxy)phenyl)-N'-(4-fluorophenyl)cyclopropane-1,1-dicarboxamide. (41 mg, 46% yield). $^1$H NMR (400 MHz, DMSO-d$_6$): δ 10.35 (s, 1H), 9.97 (s, 1H), 8.35 (d, J=4.8 Hz, 1H), 8.26 (s, 1H), 7.98 (s, 1H), 7.85 (dd, J=13.2 Hz, 2.4 Hz, 1H), 7.63-7.60 (m, 2H), 7.47-7.44 (m, 1H), 7.32 (t, J=9.2 Hz, 1H), 7.24 (d, J=1.6 Hz, 1H), 7.15-7.11 (m, 2H), 6.62-6.60 (m, 1H), 4.85 (brs, 1H), 4.14 (t, J=5.2 Hz, 2H), 3.72 (t, J=5.2 Hz, 2H), 1.47-1.41 (m, 4H); MS (ESI) m/z: 520.1 (M+H$^+$).

Example 22

Using a procedure analogous to Example 15, 4-chloroaniline (0.064 g, 0.505 mmol) in CH$_2$Cl$_2$ (5 mL), Example B4, (0.100 g, 0.252 mmol), TBTU (0.096 g, 0.378 mmol) and triethylamine (0.051 g, 0.505 mmol) were combined and purified by silica gel chromatography (EtOAc/CH$_2$Cl$_2$) to provide N-(4-chlorophenyl)-N'-(2-fluoro-4-(2-(1-methyl-1H-pyrazol-4-yl)pyridin-4-yloxy)phenyl)cyclopropane-1,1-dicarboxamide (0.138 mmol, 55% yield) as a white solid. $^1$H NMR (400 MHz, DMSO-d$_6$): δ 10.48 (s, 1H), 10.00 (s, 1H), 8.40 (d, J=5.5 Hz, 1H), 8.25 (s, 1H), 7.95 (s, 1H), 7.90 (m, 1H), 7.62 (d, J=9 Hz, 2H), 7.37 (d, J=9 Hz, 2H), 7.25 (m, 2H), 7.0 (m, 1H), 6.66 (m, 1H), 3.85 (s, 3H), 1.54 (m, 4H); MS (ESI) m/z: 506.2 (M+H$^+$).

Example 23

Using a procedure analogous to Example 15, Example B4 (0.100 g, 0.252 mmol), TBTU (0.071 g, 0.278 mmol), triethylamine (0.051 g, 0.505 mmol) and p-toluidine (0.054 g, 0.505 mmol) were combined and purified by silica gel chromatography to provide N-(2-fluoro-4-(2-(1-methyl-1H-pyrazol-4-yl)pyridin-4-yloxy)phenyl)-N'-p-tolylcyclopropane-1,1-dicarboxamide (0.070 g, 57% yield) as a white solid. $^1$H NMR (400 MHz, DMSO-d$_6$): δ 10.68 (s, 1H), 9.79 (s, 1H), 8.40 (d, J=5.5 Hz, 1H), 8.25 (s, 1H), 7.95 (m, 2H), 7.43 (d, J=8 Hz, 2H), 7.22 (m, 2H), 7.11 (d, J=8 Hz, 2H), 7.02 (m, 1H), 6.67 (m, 1H), 3.85 (s, 3H), 2.24 (s, 3H), 1.57 (m, 4H); MS (ESI) m/z: 486.2 (M+H$^+$).

Example 24

Using a procedure analogous to Example 15, 3,4-difluoroaniline (0.065 g, 0.505 mmol), Example B4 (0.100 g, 0.252 mmol), TBTU (0.071 g, 0.278 mmol) and triethylamine (0.051 g, 0.505 mmol) were combined and purified by silica gel chromatography to provide N-(3,4-difluorophenyl)-N'-(2-fluoro-4-(2-(1-methyl-1H-pyrazol-4-yl)pyridin-4-yloxy)phenyl)cyclopropane-1,1-dicarboxamide (0.06 g, 47% yield). $^1$H NMR (400 MHz, DMSO-d$_6$): δ 10.48 (s, 1H), 10.22 (s, 1H), 8.46 (d, J=5.5 Hz, 1H), 8.33 (s, 1H), 7.99 (s, 1H), 7.95 (m, 1H), 7.84 (m, 1H), 7.40 (m, 2H), 7.35 (m, 2H), 7.10 (m, 1H), 6.74 (m, 1H), 3.95 (s, 3H), 1.61 (m, 4H); MS (ESI) m/z: 508.2 (M+H$^+$).

Example 25

4-Trifluoroaniline (0.081 g, 0.505 mmol), Example B4 (0.100 g, 0.252 mmol), TBTU (0.071 g, 0.278 mmol) and triethylamine (0.051 g, 0.505 mmol) were combined using a procedure analogous to Example 15 to provide N-(2-fluoro-4-(2-(1-methyl-1H-pyrazol-4-yl)pyridin-4-yloxy)phenyl)-N'-(4-(trifluoromethyl)phenyl)cyclopropane-1,1-dicarboxamide (0.028 g, 21% yield). $^1$H NMR (400 MHz, DMSO-d$_6$): δ 10.33 (s, 1H), 10.31 (s, 1H), 8.40 (d, J=5.5 Hz, 1H), 8.25 (s, 1H), 7.95 (s, 1H), 7.82 (m, 3H), 7.67 (m, 2H), 7.25 (m, 2H), 7.02 (m, 1H), 6.66 (m, 1H), 3.85 (s, 3H), 1.53 (m, 4H); MS (ESI) m/z: 540.2 (M+H$^+$).

Example 26

Example B4 (0.050 g, 0.126 mmol), N,N-diisopropylethylamine (0.016 g, 0.126 mmol), 5-amino-2-fluorobenzonitrile (0.017 g, 0.126 mmol), and BOP-chloride (0.032 g, 0.126 mmol) were combined in CH$_2$Cl$_2$ (5 mL) using a procedure analogous to Example 28 to provide N-(3-cyano-4-fluorophenyl)-N'-(2-fluoro-4-(2-(1-methyl-1H-pyrazol-4-yl)pyridin-4-yloxy)phenyl)cyclopropane-1,1-dicarboxamide (0.030 g, 47% yield). $^1$H NMR (400 MHz, DMSO-d$_6$): δ 10.38 (s, 1H), 10.27 (s, 1H), 8.40 (d, J=5.5 Hz, 1H), 8.25 (s, 1H), 8.11 (m, 1H), 7.95 (s, 1H), 7.88 (m, 2H), 7.50 (m, 1H), 7.25 (m, 2H), 7.02 (d, J=10 Hz, 1H), 6.89 (m, 1H), 3.85 (s, 3H), 1.55 (m, 4H); MS (ESI) m/z: 515.2 (M+H$^+$).

Example 27

Example B4 (0.100 g, 0.252 mmol), N,N-diisopropylethylamine (0.033 g, 0.252 mmol), 2,4-difluoroaniline (0.065 g, 0.505 mmol), and BOP-chloride (0.064 g, 0.252 mmol) were combined in CH$_2$Cl$_2$ (5 mL) using a procedure analogous to Example 28 to provide N-(2,4-difluorophenyl)-N'-(2-fluoro-4-(2-(1-methyl-1H-pyrazol-4-yl)pyridin-4-yloxy)phenyl)cyclopropane-1,1-dicarboxamide (0.034 g, 27% yield). $^1$H NMR (400 MHz, DMSO-d$_6$): δ 10.59 (s, 1H), 10.23 (s, 1H), 8.40 (d, J=5.5 Hz, 1H), 8.25 (s, 1H), 7.95 (s, 1H), 7.89 (m, 1H), 7.71 (m, 1H), 7.35 (m, 1H), 7.26 (m, 2H), 7.02 (m, 2H), 6.68 (m, 1H), 3.85 (s, 3H), 1.66 (m, 4H); MS (ESI) m/z: 508.2 (M+H$^+$).

Example 28

To a solution of 4-aminobenzonitrile (0.089 g, 0.757 mmol) in CH$_2$Cl$_2$ (5 mL) was added Example B4 (0.150 g, 0.378 mmol), BOP-chloride (0.096 g, 0.378 mmol) and diisopropylethyl amine (0.098 g, 0.757 mmol). The reaction mixture was stirred at RT for 13 hours. The solvent from the reaction mixture was completely removed and the residue was purified by flash chromatography to provide N-(4-cyanophenyl)-N'-(2-fluoro-4-(2-(1-methyl-1H-pyrazol-4-yl)pyridin-4-yloxy)phenyl)cyclopropane-1,1-dicarboxamide (0.075 g, 40% yield). $^1$H NMR (400 MHz, DMSO-d$_6$): δ

10.38 (s, 1H), 10.15 (s, 1H), 8.33 (d, J=5.5 Hz, 1H), 8.20 (s, 1H), 7.90 (s, 1H), 7.75 (m, 4H), 7.20 (m, 3H), 6.96 (m, 1H), 6.62 (m, 1H), 3.85 (m 3H), 1.50 (m, 4H); MS (ESI) m/z: 497.2 (M+H$^+$).

Example 29

2-Chloro-4-fluoroaniline (0.073 g, 0.505 mmol), Example B4 (0.100 g, 0.252 mmol), BOP-chloride (0.064 g, 0.252 mmol) and diisopropylethylamine (0.065 g, 0.505 mmol) were combined in CH$_2$Cl$_2$ (5 mL) using a procedure analogous to Example 28 to provide N-(2-chloro-4-fluorophenyl)-N'-(2-fluoro-4-(2-(1-methyl-1H-pyrazol-4-yl)pyridin-4-yloxy)phenyl)cyclopropane-1,1-dicarboxamide (0.055 g, 42% yield). $^1$H NMR (400 MHz, DMSO-d$_6$): δ 10.53 (s, 1H), 10.48 (s, 1H), 8.40 (d, J=5.5 Hz, 1H), 8.25 (s, 1H), 7.95 (s, 1H), 7.82 (m, 2H), 7.50 (m, 1H), 7.25 (m, 3H), 7.02 (d, J=10 Hz, 1H), 6.89 (m, 1H), 3.85 (s, 3H), 1.70 (m, 4H); MS (ESI) m/z: 524.2 (M+H$^+$).

Example 30

Example B1 (80 mg, 0.36 mmol), Example A5 (108 mg, 0.36 mmol), i-Pr$_2$NEt (0.1 mL, 0.54 mmol) and TBTU (180 mg, 0.54 mmol) were combined in DMF (3 mL) and the mixture was stirred overnight at RT. Water was added and resultant precipitate was collected by filtration. The solid was dissolved in EtOAc and the organic layer was dried (Na$_2$SO$_4$), concentrated in vacuo and purified by silica gel chromatography (EtOAc-hexanes). The pure fractions were combined and concentrated in vacuo and the residue was precipitated from EtOAc-hexanes. The resultant solid was collected by filtration and dried under vacuum to obtain N-(3-chloro-4-(2-(1-methyl-1H-pyrazol-4-yl)pyridin-4-yloxy)phenyl)-N'-(4-fluorophenyl)cyclopropane-1,1-dicarboxamide (95 mg, 52% yield). $^1$H NMR (400 MHz, DMSO-d$_6$): δ 10.3 (s, 1H), 9.99 (s, 1H), 8.34 (d, J=5.6 Hz, 1H), 8.25 (s, 1H), 8.04 (d, J=2.4 Hz, 1H), 7.95 (s, 1H), 7.62 (m, 3H), 7.32 (d, J=8.8 Hz, 1H), 7.20 (d, J=2.8 Hz, 1H), 7.11 (m, 2H), 6.52 (dd, J=5.6, 2.4, Hz, 1H), 3.89 (s, 3H), 1.44 (m, 4H); MS (ESI) m/z: 506.1 (M+H$^+$).

Example 31

To a solution of Example A6 (0.242 g, 0.896 mmol) in DMF (3 ml) was added Example B1 (0.20 g, 0.896 mmol), EDC (0.258 g, 1.344 mmol), and HOBt (0.206 g, 1.344 mmol). The mixture was stirred at RT for 3 hours. Water was added and the solution was extracted with EtOAc (3×). The organic extracts were washed with brine, dried (Na$_2$SO$_4$), concentrated in vacuo and purified by silica gel column chromatography (EtOAc/hexane). Pure fractions containing product were combined and concentrated. The residue was treated with EtOAc/hexane and the resultant precipitate was collected by filtration and dried under vacuum to obtain N-(4-(2-(1H-pyrazol-4-yl)pyridin-4-yloxy)-3-fluorophenyl)-N'-(4-fluorophenyl)cyclopropane-1,1-dicarboxamide (0.205 g, 48% yield). $^1$H NMR (400 MHz, DMSO-d$_6$): δ 13.1 (br s, 1H), 10.4 (s, 1H), 9.98 (s, 1H), 8.35 (d, J=5.2 Hz, 1H), 8.32 (brs, 1H), 8.02 (br s, 1H), 7.85 (dd, J=13.2, 2.4 Hz, 1H), 7.61 (m, 2H), 7.46 (m, 1H), 7.32 (m, 2H), 7.13 (m, 2H), 6.58 (dd, J=6.6, 2.4 Hz, 1H), 1.44 (m, 4H); MS (ESI) m/z: 476.2 (M+H$^+$).

Example 32

To a solution of Example B1 (0.100 g, 0.448 mmol) in CH$_2$Cl$_2$ (5 mL) was added Example A7 (0.134 g, 0.448 mmol), BOP-chloride (0.228 g, 0.896 mmol) and diisopropylethylamine (0.116 g, 0.896 mmol). The reaction mixture was stirred at RT for 15 hours. The solvent from the reaction mixture was completely removed and the residue was recrystallized (acetonitrile) to provide N-(2-fluoro-3-methyl-4-(2-(1-methyl-1H-pyrazol-4-yl)pyridin-4-yloxy)phenyl)-N'-(4-fluorophenyl)cyclopropane-1,1-dicarboxamide (0.060 g, 27% yield). $^1$H NMR (400 MHz, DMSO-d$_6$): δ 10.74 (s, 1H), 9.80 (s, 1H), 8.40 (d, J=5.5 Hz, 1H), 8.25 (s, 1H), 7.95 (s, 1H), 7.82 (m, 1H), 7.60 (m, 2H), 7.20 (m, 3H), 6.95 (d, J=10 Hz, 1H), 6.56 (m, 1H), 3.83 (s, 3H), 2.00 (s, 3H), 1.65 (m, 4H); MS (ESI) m/z: 504.2 (M+H$^+$).

Example 33

Example B3 (65 mg, 0.164 mmol), TBTU (79 mg, 0.246 mmol), DIEA (0.114 ml, 0.656 mmol) and (S)-1-(4-fluorophenyl)ethylamine (27.4 mg, 0.197 mmol) were combined in DMF (2 ml) and stirred at RT overnight. The reaction was diluted with satd. NaHCO$_3$ and extracted with EtOAc (2×). The combined organics were washed with satd. LiCl (2×), dried (MgSO$_4$), concentrated in vacuo and purified by reverse phase C18 chromatography (MeCN (w/0.1% TFA)/H$_2$O (w/0.1% TFA)). Pure fractions were combined, treated with satd. NaHCO$_3$ (pH 8) and extracted with EtOAc (3×). The combined organics were washed with brine (1×), dried (MgSO$_4$), filtered and evaporated. The material was dissolved in MeCN/H$_2$O, treated with 0.1 N HCl (1.14 ml, 0.114 mmol), frozen and lyophilized to afford N-(3-fluoro-4-(2-(1-methyl-1H-pyrazol-4-yl)pyridin-4-yloxy)phenyl)-N'-((S)-1-(4-fluorophenyl)ethyl)cyclopropane-1,1-dicarboxamide hydrochloride (55 mg) as a white solid. $^1$H NMR (400 MHz, DMSO-d$_6$): δ 10.78 (s, 1H), 8.48-8.47 (m, 2H), 8.29 (d, J=7.95 Hz, 1H), 8.16 (br s, 1H), 7.90 (dd, J=2.0, 14 Hz, 1H), 7.54-7.32 (m, 5H), 7.14-7.1 (m, 2H), 6.92 (br s, 1H), 5.04-4.97 (m, 1H), 3.89 (s, 3H), 1.41-1.36 (m, 7H); MS (ESI) m/z: 518.2 (M+H$^+$).

Example 34

Using a procedure analogous to Example 33, Example B3 (65 mg, 0.164 mmol), TBTU (79 mg, 0.246 mmol), DIEA (0.114 ml, 0.656 mmol) and (1S)-1-(4-fluorophenyl)propylamine hydrochloride (37.3 mg, 0.197 mmol) were combined in DMF (2 ml) to provide N-(3-fluoro-4-(2-(1-methyl-1H-pyrazol-4-yl)pyridin-4-yloxy)phenyl)-N'-((S)-1-(4-fluorophenyl)propyl)cyclopropane-1,1-dicarboxamide. It was further reacted with 0.1 N HCl (0.94 ml, 1.0 eq) to provide N-(3-fluoro-4-(2-(1-methyl-1H-pyrazol-4-yl)pyridin-4-yloxy)phenyl)-N'-((S)-1-(4-fluorophenyl)propyl)cyclopropane-1,1-dicarboxamide hydrochloride (49 mg) as an off-white solid. $^1$H NMR (400 MHz, DMSO-d$_6$): δ 10.8 (s, 1H), 8.49-8.47 (m, 2H), 8.26 (d, J=8.4 Hz, 1H), 8.2 (br s, 1H), 7.88 (dd, J=2.1, 13.2 Hz, 1H), 7.54-7.31 (m, 5H), 7.14-7.1 (m, 2H), 6.9 (brs, 1H), 4.73 (q, J=8.3 Hz. 1H), 3.89 (s, 3H), 1.78-1.63 (m, 2H), 1.44-1.32 (m, 4H), 0.83 (t, J=7.1 Hz, 3H); MS (ESI) m/z: 532.2 (M+H$^+$).

Example 35

To a solution of thiophenecarboxylic acid (0.5 g, 3.90 mmol) in tBuOH (10 ml) was added Et$_3$N (0.571 ml, 4.10 mmol) and DPPA (0.883 ml, 4.10 mmol). The solution was heated at 90° C. for 4 hours. The reaction mixture was cooled to RT and the solvent was removed in vacuo. The residue was treated with benzene and then the solution was washed with 5% citric acid, and sat'd NaHCO$_3$. Solid was filtered off and the filtrate was washed with brine. The organic layer was dried (MgSO$_4$), concentrated in vacuo and the residue was purified by silica gel column chromatography (EtOAc/hexanes) to obtain tert-butyl thiophen-2-ylcarbamate (0.39 g, 50% yield). $^1$H NMR (400 MHz, DMSO-d$_6$): δ 10.4 (brs, 1H), 6.84 (dd, J=1.6, and 5.2 Hz, 1H), 6.75 (dd, J=4.0, and 5.6 Hz, 1H), 6.48 (dd, J=1.6, and 4.0 Hz, 2H), 1.45 (s, 9H); MS (ESI) m/z: 222.0 (M+22+H$^+$).

Acetyl chloride (0.36 mL) was added dropwise to a solution of EtOAc (4 mL) and MeOH (0.203 mL) at 0° C. A solution of tert-butyl thiophen-2-ylcarbamate (0.10 g, 0.502 mmol) in EtOAc (1 mL) was added dropwise to the reaction mixture while maintaining the temperature under 0° C. The solution was stirred for 1 hour (the ice bath was allowed to melt during this time) and then concentrated to obtain thiophen-2-amine which was used for the next reaction without purification.

Example B4 (0.10 g, 0.252 mmol), thiophen-2-amine (0.050 g, 0.505 mmol), and DIEA (0.125 ml, 0.757 mmol) were combined in DMF (2 ml). TBTU (0.105 g, 0.328 mmol) was added and the resultant solution was stirred overnight at RT. The reaction was diluted with water and extracted with EtOAc (3×). The combined organic phases were washed with brine, dried (Na$_2$SO$_4$), concentrated in vacuo and purified by silica gel column chromatography (EtOAc/hexanes) to give a residue. The residue was treated with CH$_3$CN: H$_2$O (1:1, 4 mL) and lyophilized to obtain N-(2-fluoro-4-(2-(1-methyl-1H-pyrazol-4-yl)pyridin-4-yloxy)phenyl)-N'-(thiophen-2-yl)cyclopropane-1,1-dicarboxamide (0.025 g, 21% yield). $^1$H NMR (400 MHz, DMSO-d$_6$): δ 11.0 (s, 1H), 10.6 (s, 1H), 8.38 (d, J=5.6 Hz, 1H), 8.25 (s, 1H), 7.95 (m, 2H), 7.25 (m, 2H), 7.02 (m, 1H), 6.98 (dd, J=1.2, and 5.6 Hz, 1H), 6.83 (m, 2H), 6.68 (m, 1H), 3.84 (s, 3H), 1.57 (m, 4H); MS (ESI) m/z: 478.0 (M+H$^+$).

Example 36

To a stirring suspension of Example B3 (65 mg, 0.164 mmol), TBTU (79 mg, 0.246 mmol) and (R)-1-(4-fluorophenyl)-2-methoxyethanamine (40.5 mg, 0.197 mmol; prepared according to the published method: J. Med. Chem. (1999), 42(24), 4981) in DMF (2 ml) was added DIEA (0.171 ml, 0.984 mmol). The resulting clear solution was stirred at RT overnight. After stirring overnight, the reaction was diluted with satd. NaHCO$_3$ and extracted with EtOAc (2×). The combined organics were washed with satd. NaHCO$_3$ (1×), satd. LiCl (2×), and brine (1×), dried (MgSO$_4$), evaporated in vacuo and purified by reverse phase chromatography. Pure fractions were pooled, treated with satd. NaHCO$_3$ (pH 8) and extracted with EtOAc (3×). The combined organics were washed with satd. NaHCO$_3$ (1×), brine (1×), dried (MgSO$_4$), and evaporated to afford N-(3-fluoro-4-(2-(1-methyl-1H-pyrazol-4-yl)pyridin-4-yloxy)phenyl)-N'-((R)-1-(4-fluorophenyl)-2-methoxyethyl)cyclopropane-1,1-dicarboxamide as an oil. This was dissolved in 4:1 MeCN/H$_2$O, treated with certified 0.1N HCl (1.37 ml, 1.0 eq), frozen and lyophilized to afford 63 mg (66% yield) of the HCl salt as a solid. $^1$H NMR (400 MHz, DMSO-d$_6$): δ 10.64 (s, 1H), 8.49-8.48 (m, 2H), 8.44-8.42 (m, 1H), 8.18 (brs, 1H), 7.89-7.85 (m, 1H), 7.54 (brs, 1H), 7.48-7.35 (m, 4H), 7.16-7.11 (m, 2H), 6.92 (brs, 1H), 5.13-5.06 (m, 1H), 3.89 (s, 3H), 3.61-3.56 (m, 1H), 3.49-3.46 (m, 1H), 3.25 (s, 3H), 1.45-1.33 (m, 4H); MS (ESI) m/z: 516.1 (M+H$^+$).

Example 37

To a solution of Example B1 (0.070 g, 0.314 mmol) in DMF (1 ml) was added Example A8 (0.100 g, 0.314 mmol), Hunigs base (0.078 ml, 0.470 mmol) and TBTU (0.151 g, 0.470 mmol). The mixture was stirred overnight at RT and then diluted with EtOAc. The resultant solution was washed with water and NaHCO$_3$, dried (Na$_2$SO$_4$), concentrated in vacuo and purified by silica gel column chromatography (EtOAc/hexanes) to give a residue. The residue was treated with CH$_3$CN and kept overnight at RT. The solid was filtered and dried under vacuum to obtain N-(4-fluorophenyl)-N'-(4-(2-(4-(trifluoromethyl)-1H-imidazol-2-yl)pyridin-4-yloxy)phenyl)cyclopropane-1,1-dicarboxamide (0.105 g, 64% yield). $^1$H NMR (400 MHz, DMSO-d$_6$, major isomer): δ 13.5 (s, 1H), 10.2 (s, 1H), 10.1 (s, 1H), 8.52 (d, J=5.6 Hz, 1H), 7.84 (m, 1H), 7.75 (m, 2H), 7.62 (m, 2H), 7.35 (d, J=2.8 Hz, 1H), 7.14 (m, 2H), 7.12 (m, 3H), 7.06 (dd, J=2.4, and 5.6 Hz, 1H), 1.44 (m, 4H); MS (ESI) m/z: 526.1 (M+H$^+$).

Example 38

To a solution of Example B1 (0.100 g, 0.448 mmol) in dichloromethane (5 ml) was added Example A22 (0.120 g, 0.448 mmol) followed by Bop-chloride (0.228 g, 0.896 mmol) and diisopropylethylamine (0.116 g, 0.896 mmol). The reaction mixture was stirred at RT for 15 hours, concentrated in vacuo, stirred with water, filtered, washed and dried. The solid was purified by chromatography (ethyl acetate/hexanes) to provide N-(4-fluorophenyl)-N'-(6-(2-(1-methyl-1H-pyrazol-4-yl)pyridin-4-yloxy)pyridin-3-yl)cyclopropane-1,1-dicarboxamide (0.055 g, 26% yield) as an off-white solid. $^1$H NMR (400 MHz, DMSO-d$_6$ δ10.25 (s, 1H), 10.03 (s, 1H), 8.45 (s, 1H), 8.40 (m, 1H), 8.25 (s, 1H), 8.18 (m, 1H), 8.00 (s, 1H), 7.60 (m, 2H), 7.40 (s, 1H), 7.16 (m 3H), 6.85 (m, 1H), 3.80 (s, 3H), 1.40 (s, 4H); MS (ESI) m/z: 473.1 (M+H$^+$).

Example 39

To a solution of 4-fluorophenylacetyl chloride (0.500 g, 2.90 mmol) in toluene (8.0 ml) was added silver cyanate (0.456 g, 3.05 mmol) at RT. The reaction mixture was shielded from light and heated to reflux. After 2 hours, the mixture was cooled to RT and the solution was filtered using 0.45 μM Teflon syringe filter. The filtrate, 2-(4-fluorophenyl)acetyl isocyanate solution (0.4M: 0.52 g/7 mL) was used as is in the next reaction.

To a solution of 2-(4-fluorophenyl)acetyl isocyanate (4.68 ml, 1.873 mmol) in toluene (4.68 ml) was added Example A8 (0.10 g, 0.312 mmol) to form a heterogeneous mixture. THF (5 mL) was added and the reaction mixture was stirred overnight at RT. The solid was filtered and purified by silica gel column chromatography (EtOAc/hexanes) to obtain 1-(2-(4-fluorophenyl)acetyl)-3-(4-(2-(4-(trifluoromethyl)-1H-imidazol-2-yl)pyridin-4-yloxy)phenyl)urea (0.097 g, 62% yield). $^1$H NMR (400 MHz, DMSO-d$_6$, major isomer): δ 13.5 (s, 1H), 11.0 (s, 1H), 10.5 (s, 1H), 8.52 (d, J=5.6 Hz, 1H), 7.83 (m, 1H), 7.64 (m, 2H), 7.1-7.4 (m, 7H), 7.04 (dd, J=2.8, and 5.6 Hz, 1H), 3.71 (s, 2H); MS (ESI) m/z: 500.1 (M+H$^+$).

Example 40

To a solution of Example B5 (9.91 g, 23.58 mmol) in DMF (80 mL), under an atmosphere of argon, were added TBTU (11.36 g, 35.4 mmol), DIPEA (20.59 ml, 118 mmol) and 4-fluoroaniline (3.93 g, 35.4 mmol). The reaction mixture was stirred at RT overnight. An additional portion of TBTU (7.5 g, 17.8 mmol) was added and stirring was continued. After 2 h, an additional portion of TBTU (3.5 g, 8.33 mmol) was added and stirring was continued for 2 h. The solvent was removed under high vacuum and the residue was dissolved in EtOAc (700 mL) and washed with sat. aq. NaHCO$_3$ (2×200 mL) and brine (50 mL), dried (MgSO$_4$), concentrated to dryness and purified by silica gel chromatography (MeOH-DCM) to provide N-(2,5-difluoro-4-(2-(1-methyl-1H-pyrazol-4-yl)pyridin-4-yloxy)phenyl)-N'-(4-fluorophenyl)cyclopropane-1,1-dicarboxamide (7.2 g, 59% yield). $^1$H NMR (400 MHz, DMSO-d$_6$): δ 11.14 (s, 1H), 9.76 (s, 1H), 8.39 (d, J=5.6 Hz, 1H), 8.28 (s, 1H), 8.13 (dd, J=12.1, 7.1 Hz, 1H), 7.99 (s, 1H), 7.62-7.53 (m, 3H), 7.27 (d, J=2.6 Hz, 1H), 7.22-7.15 (m, 2H), 6.71 (dd, J=5.6, 2.4 Hz, 1H), 3.86 (s, 3H), 1.69-1.56 (m, 4H); MS (ESI): m/z 508.1 [M+1]$^+$.

Example 41

To a solution of Example B1 (0.100 g, 0.448 mmol) in dichloromethane (5 ml) was added Example A13 (0.120 g, 0.448 mmol), followed by Bop-chloride (0.228 g, 0.896 mmol) and diisopropylethylamine (0.116 g, 0.896 mmol). The reaction mixture was stirred at RT for 15 hours, concentrated in vacuo, stirred with water, filtered, washed, dried and crystallized (acetonitrile) to provide N-(4-fluorophenyl)-N'-(5-(2-(1-methyl-1H-pyrazol-4-yl)pyridin-4-yloxy)pyridin-2-yl)cyclopropane-1,1-dicarboxamide (0.005 g, 2.3% yield) as a solid. $^1$H NMR (400 MHz, DMSO-d$_6$ δ 9.70 (s, 1H), 8.40 (d, J=5 Hz, 1H), 8.26 (s, 1H), 8.15 (d, J=11 Hz, 1H), 7.98 (s, 1H), 7.65 (dd, J=9, 5 Hz, 1H), 7.60 (m, 2H), 7.20 (brs, 1H), 7.15 (m, 2H), 6.70 (m, 1H), 3.80 (s, 3H), 1.60 (m, 2H), 1.50 (m, 2H); MS (ESI) m/z: 473.2 (M+H$^+$).

Example 42

4-Fluorophenylacetic acid (1 g, 6.49 mmol) was dissolved in acetonitrile (40 ml) and cooled to 0° C. in an ice bath. 1-Ethyl-3-(3-dimethylaminopropyl)carbodiimide hydrochloride (1.492 g, 7.79 mmol) was added, followed by 1-hydroxybenzotriazole (1.19 g, 7.79 mmol). The mixture was stirred at 0° C. for 2.5 hours, and then concentrated ammonium hydroxide (0.865 ml, 13.0 mmol) was added slowly. The mixture then stirred at RT for an additional 2 hours. After this time the solids were filtered off, and the filtrate was diluted with ethyl acetate (50 mL). The solution was washed with saturated aqueous NaHCO$_3$ (2×50 mL) and brine (50 mL), dried (MgSO$_4$) and concentrated in vacuo to yield 2-(4-fluorophenyl)acetamide (0.87 g, 88% yield) as a white solid which was used as is in the next reaction. $^1$H NMR (400 MHz, DMSO-d$_6$): δ 7.45 (broad s, 1H), 7.26 (m, 2H), 7.09 (m, 2H), 6.87 (broad s, 1H), 3.34 (s, H).

2-(4-Fluorophenyl)acetamide (0.046 g, 0.298 mmol) was dissolved in dichloroethane (3 ml) and oxalyl chloride (0.026 ml, 0.298 mmol) was added. The mixture was heated in an 85° C. oil bath under a balloon of argon for 14 hours. The reaction mixture was then cooled to RT and concentrated to dryness under reduced pressure. It was dissolved in NMP (1.5 ml) and Example A12 (0.045 g, 0.149 mmol) was added. The mixture stirred for 1.5 hours at RT and was then diluted with ethyl acetate (50 mL), washed with water (3×50 mL) and brine (50 mL), dried (MgSO$_4$), concentrated in vacuo and purified via silica gel chromatography (THF-hexanes) to yield 1-(2,5-difluoro-4-(2-(1-methyl-1H-pyrazol-4-yl)pyridin-4-yloxy)phenyl)-3-(2-(4-fluorophenyl)acetyl)urea as an off-white solid (0.059 g, 82% yield). $^1$H NMR (400 MHz, DMSO-d$_6$): δ 11.26 (s, 1H), 10.89 (s, 1H), 8.36 (d, 1H), 8.26 (s, 1H), 8.18 (dd, 1H), 7.97 (s, 1H), 7.59 (dd, 1H), 7.34 (m, 2H), 7.22 (d, 1H), 7.16 (m, 2H), 6.70 (dd, 1H), 3.84 (s, 3H), 3.74 (s, 2H); MS (ESI) m/z: 482.1 (M+H$^+$).

Example 43

4-Fluorophenylacetyl chloride (0.5 g, 2.90 mmol) was added to a suspension of silver cyanate (1.30 g, 8.70 mmol) in toluene (8 ml) at RT. The reaction mixture was shielded from light and heated to reflux. After 2 h, the mixture was cooled to RT and filtered. The filtrate containing 2-(4-fluorophenyl)acetyl isocyanate (0.363 M) was used without further purification. An aliquot of the 2-(4-fluorophenyl)acetyl isocyanate solution (0.363 M in toluene, 3.5 mL, 1.271 mmol) was treated with Example A3 (0.192 g, 0.635 mmol) and the mixture was stirred at RT overnight. The resultant precipitate was collected by filtration and further purified by reverse-phase silica gel chromatography (acetonitrile/water (0.1% TFA)). Pure fractions were combined, concentrated, basified with NaHCO$_3$ and extracted with EtOAc (2×). The combined extracts were washed with brine, dried (MgSO$_4$) and concentrated in vacuo to provide 1-(2,3-difluoro-4-(2-(1-methyl-1H-pyrazol-4-yl)pyridin-4-yloxy)phenyl)-3-(2-(4-fluorophenyl)acetyl)urea (0.066 g, 22% yield) as a white solid. $^1$H NMR (400 MHz, DMSO-d$_6$): δ 11.25 (s, 1H), 10.84 (s, 1H), 8.39 (d, J=5.6 Hz, 1H), 8.28 (s, 1H), 8.01-7.97 (m, 2H), 7.39-7.35 (m, 2H), 7.27 (d, J=2.5 Hz, 1H), 7.26-7.21 (m, 1H), 7.21-7.15 (m, 2H), 6.75 (dd, J=5.6, 2.6 Hz, 1H), 3.86 (s, 3H), 3.76 (s, 2H); MS (ESI) m/z: 482.1 (M+H$^+$).

Example 44

2-(4-Fluorophenyl)acetamide from Example 42 (0.115 g, 0.748 mmol) was dissolved in dichloroethane (8 ml) and oxalyl chloride (0.082 ml, 0.935 mmol) was added. The mixture was stirred at 85° C. under a balloon of argon for 18 hours. The mixture was cooled to RT, evaporated to dryness, and added to a solution of Example A13 (0.357 g, 0.935 mmol) in NMP (5 ml). The mixture was stirred at RT for 45 minutes, diluted with ethyl acetate (50 mL), washed with water (2×50 mL) and brine (50 mL) dried (MgSO$_4$), concentrated under reduced pressure and purified via silica gel chromatography (THF-hexanes) to yield 1-(2-(4-fluorophenyl)acetyl)-3-(5-(2-(1-methyl-1H-pyrazol-4-yl)pyridin-4-yloxy)pyridin-2-yl)urea (0.185 g, 54% yield). $^1$H NMR (400 MHz, DMSO-d$_6$): δ 11.12 (s, 1H), 10.93 (s, 1H), 8.36 (d, 1H), 8.24 (m, 2H), 8.07 (d, 1H), 7.96 (s, 1H), 7.72 (dd, 1H), 7.35 (m, 2H), 7.18 (m, 3H), 6.69 (dd, 1H), 3.83 (s, 3H), 3.74 (s, 2H); MS (ESI) m/z: 447.2 (M+H$^+$).

Example 45

Using a procedure analogous to Example 2, Example B5 (0.11 g, 0.265 mmol), diisopropylethylamine (0.051 ml, 0.292 mmol), aniline (1.004 ml, 0.345 mmol) and TBTU (0.111 g, 0.345 mmol) were combined and purified via silica gel chromatography (methanol-methylene chloride) to yield N-(2,5-difluoro-4-(2-(1-methyl-1H-pyrazol-4-yl)pyridin-4-yloxy)phenyl)-N'-phenylcyclopropane-1,1-dicarboxamide as a clear film (0.030 g, 23% yield). MS (ESI) m/z: 490.2 (M+H$^+$).

N-(2,5-Difluoro-4-(2-(1-methyl-1H-pyrazol-4-yl)pyridin-4-yloxy)phenyl)-N'-phenylcyclopropane-1,1-dicarboxamide was dissolved in acetonitrile (5 ml) and 4M HCl in dioxane (0.068 ml, 0.274 mmol) was added slowly with stirring. The mixture was stirred for 1.5 hours at RT as a white solid slowly precipitated from the solution. The salt was collected via suction filtration and washed with diethyl ether. A suspension of the product in a 4:1 mix of acetonitrile and water was lyophilized overnight to obtain N-(2,5-difluoro-4-(2-(1-methyl-1H-pyrazol-4-yl)pyridin-4-yloxy)phenyl)-N'-phenylcyclopropane-1,1-dicarboxamide hydrochloride as a white powder (0.047 g, 65% yield). $^1$H NMR (400 MHz, DMSO-d$_6$): δ 11.18 (s, 1H), 9.64 (s, 1H), 8.43 (m, 2H), 8.13 (m, 2H), 7.60 (m, 1H), 7.51 (m, 3H), 7.28 (m, 2H), 7.05 (m, 1H), 6.97 (broad s, 1H), 3.84 (s, 3H), 1.63 (m, 2H), 1.53 (m, 2H); MS (ESI) m/z: 490.2 (M+H$^+$).

Example 46

4-Fluorophenylacetic acid (0.144 g, 0.941 mmol) was dissolved in dichloroethane (9.51 ml) and oxalyl chloride (0.082 ml, 0.941 mmol) was added. The mixture was heated in an 85° C. oil bath under argon for 14 hours, cooled to RT and concentrated under reduced pressure. The crude yellow oil was then re-dissolved in NMP (4.75 ml) and Example A14 (0.15 g, 0.471 mmol) was added. The mixture was stirred for 2.5 hours at RT, diluted with ethyl acetate (70 mL), washed with water (2×40 mL) and brine (40 mL), dried (MgSO$_4$), concentrated in vacuo and purified via silica gel chromatography (ethyl acetate/hexanes) to yield 1-(5-chloro-2-fluoro-4-(2-(1-methyl-1H-pyrazol-4-yl)pyridin-4-yloxy)phenyl)-3-(2-(4-fluorophenyl)acetyl)urea as a white solid. It was triturated in DCM (4 mL) and ethyl acetate (0.2 mL) and collected by suction filtration to give 1-(5-chloro-2-fluoro-4-(2-(1-methyl-1H-pyrazol-4-yl)pyridin-4-yloxy)phenyl)-3-(2-(4-fluorophenyl)acetyl)urea (0.1456 g, 62% yield). MS (ESI) m/z: 498.1 (M+H$^+$).

1-(5-Chloro-2-fluoro-4-(2-(1-methyl-1H-pyrazol-4-yl)pyridin-4-yloxy)phenyl)-3-(2-(4-fluorophenyl)acetyl)urea (0.146 g, 0.293 mmol) was fully dissolved in a mixture of THF (4 ml), acetonitrile (4 mL), and methanol (0.5 mL). Methanesulfonic acid (19 µl, 0.293 mmol) was added, and after stirring for several minutes a precipitate started to form. The mixture was stirred at RT for 5 hours. 1-(5-Chloro-2-fluoro-4-(2-(1-methyl-1H-pyrazol-4-yl)pyridin-4-yloxy)phenyl)-3-(2-(4-fluorophenyl)acetyl)urea mesylate salt was obtained by suction filtration and was washed with acetonitrile (0.148 g, 82% yield). $^1$H NMR (500 MHz, DMSO-d$_6$): δ 11.33 (s, 1H), 10.97 (s, 1H), 8.59 (m, 2H), 8.46 (d, 1H), 8.26 (s, 1H), 7.74 (d, 1H), 7.65 (s, 1H), 7.36 (m, 2H), 7.17 (m, 3H), 3.92 (s, 3H), 3.77 (s, 2H), 2.33 (s, 3H); MS (ESI) m/z: 498.1 (M+H$^+$).

Example 47

Example B1 (1.484 g, 6.65 mmol) was dissolved in thionyl chloride (14 ml, 192 mmol) at 60° C. The reaction mixture stirred for 30 minutes under argon, then the solution was cooled to RT and the mixture was azeotroped with toluene (4×10 mL) to give 1-((4-fluorophenyl)carbamoyl)cyclopropanecarbonyl chloride as an off-white solid, which was used in the next step without purification, assuming a 100% yield. MS (ESI) m/z (methanol quench): 238.1 (M+H$^+$).

Example A14 (1.696 g, 5.32 mmol) was dissolved in THF (15 ml) and added to 1-((4-fluorophenyl)carbamoyl)cyclopropanecarbonyl chloride (1.545 g, 6.39 mmol), followed by triethylamine (0.964 ml, 6.92 mmol). The mixture was stirred at RT for 5 minutes and then the mixture was filtered to remove triethylamine HCl. The filtrate was concentrated under reduced pressure and purified via silica gel chromatography (DCM/MeOH) to yield N-(5-chloro-2-fluoro-4-(2-(1-methyl-1H-pyrazol-4-yl)pyridin-4-yloxy)phenyl)-N'-(4-fluorophenyl)cyclopropane-1,1-dicarboxamide as a white foam (2.55 g, 91% yield). $^1$H NMR (400 MHz, DMSO-d$_6$): δ 11.03 (s, 1H), 9.77 (s, 1H), 8.37 (d, 1H), 8.27 (m, 2H), 7.97 (s, 1H), 7.57 (m, 3H), 7.22 (d, 1H), 7.16 (m, 2H), 6.61 (dd, 1H), 3.84 (s, 3H), 1.64 (m, 2H), 1.56 (m, 2H); MS (ESI) m/z: 524.2 (M+H$^+$).

Example 48

A suspension of silver cyanate (0.434 g, 2.90 mmol) in toluene (8.0 ml) was treated with 4-fluorophenylacetyl chloride (0.397 ml, 2.90 mmol), the mixture shielded from light and heated to reflux for 2 hours. The mixture was cooled to RT, filtered through a syringe filter, treated with Example A10 (0.438 g, 1.449 mmol) and stirred overnight at RT. The solid was filtered, rinsed with a small amount of toluene and dried in a vacuum oven at 70° C. for 2 days to afford 1-(3,5-difluoro-4-(2-(1-methyl-1H-pyrazol-4-yl)pyridin-4-yloxy) phenyl)-3-(2-(4-fluorophenyl)acetyl)urea (620 mg, 89% yield) as a white solid. $^1$H NMR (400 MHz, DMSO-d$_6$): 3.74 (s, 2H), 3.84 (s, 3H), 6.71 (dd, 1H), 7.15 (t, 2H), 7.27 (d, 1H), 7.34 (m, 2H), 7.62 (d, 2H), 7.98 (s, 1H), 8.27 (s, 1H), 8.37 (d, 1H), 10.65 (s, 1H), 11.10 (s, 1H); MS (ESI) m/z: 482.2 (M+H$^+$).

Example 49

Example B1 (0.241 g, 1.078 mmol) was dissolved in thionyl chloride (4 ml, 54.8 mmol) and heated at 60° C. for 3 h. The reaction was azeotroped with toluene (3×). The crude acid chloride was dissolved in THF (5 ml) and added dropwise to a 0° C. solution of Example A15 (0.31 g, 0.980 mmol) and N,N-diisopropylethylamine (0.171 ml, 0.980 mmol) in THF (5 ml). The mixture was stirred overnight at RT, saturated aq. NaHCO$_3$ (25 ml) was added and the mixture extracted with EtOAc (3×25 ml). The combined organic extracts were dried (Na$_2$SO$_4$), evaporated and purified by silica gel chromatography (hexanes/EtOAc) to elute two products. N-(4-(2-(1,3-Dimethyl-1H-pyrazol-4-yl)pyridin-4-yloxy)-2,5-difluorophenyl)-N-(4-fluorophenyl)cyclopropane-1,1-dicarboxamide (278 mg; 54.4%) (eluted first) and N-(4-(2-(1,5-dimethyl-1H-pyrazol-4-yl)pyridin-4-yloxy)-2,5-difluorophenyl)-N'-(4-fluorophenyl)cyclopropane-1,1-dicarboxamide (81 mg; 16%) (eluted second). N-(4-(2-(1,3-Dimethyl-1H-pyrazol-4-yl)pyridin-4-yloxy)-2,5-difluorophenyl)-N'-(4-fluorophenyl)cyclopropane-1,1-dicarboxamide: $^1$H NMR (400 MHz, DMSO-d$_6$): δ 11.07 (s, 1H), 9.75 (s, 1H), 8.42 (d, 1H), 8.12-8.07 (m, 1H), 7.85 (s, 1H), 7.83-7.15 (m, 4H), 7.20-7.12 (m, 2H), 6.68-6.6.66 (m, 1H), 3.75 (s, 3H), 2.54 (s, 3H), 1.67-1.64 (m, 2H), 1.58-1.55 (m, 2H); MS (ESI) m/z: 522.2 (M+H$^+$). N-(4-(2-(1,5-Dimethyl-1H-pyrazol-4-yl)pyridin-4-yloxy)-2,5-difluorophenyl)-N'-(4-fluorophenyl)cyclopropane-1,1-dicarboxamide: $^1$H NMR (400 MHz, DMSO-d$_6$): δ 11.10 (s, 1H), 9.74 (s, 1H), 8.41 (d, 1H), 8.14-8.08 (m, 2H), 7.59-7.53 (m, 4H), 7.19-7.14 (m, 1H), 7.07 (d, 1H), 6.72-6.70 (m, 1H), 3.75 (s, 3H), 2.36 (s, 3H), 1.67-1.64 (m, 2H), 1.58-1.55 (m, 2H); MS (ESI) m/z: 522.2 (M+H$^+$).

N-(4-(2-(1,3-Dimethyl-1H-pyrazol-4-yl)pyridin-4-yloxy)-2,5-difluorophenyl)-N'-(4-fluorophenyl)cyclopropane-1,1-dicarboxamide (0.278 g, 0.533 mmol) was dissolved in THF (5 ml) and warmed until reflux. Methanesulfonic acid (0.035 ml, 0.533 mmol) was added. A precipitate immediately formed. The mixture was sonicated for 10 min and allowed to cool to RT. The precipitate was filtered off and dried overnight in the drying pistol (80° C.) to yield N-(4-(2-(1,3-Dimethyl-1H-pyrazol-4-yl)pyridin-4-yloxy)-2,5-difluorophenyl)-N'-(4-fluorophenyl)cyclopropane-1,1-dicarboxamide mesylate (234 mg, 71.1% yie3ld). $^1$H NMR (400 MHz, DMSO-d$_6$): δ 11.20 (s, 1H), 9.71 (s, 1H), 8.57 (d, 1H), 8.19-8.14 (m, 1H), 7.90 (s, 1H), 7.66-7.62 (m, 1H), 7.58-7.55 (m, 2H), 7.38 (s, 1H), 7.19-7.14 (m, 2H), 7.05-7.02 (m, 1H), 3.79 (s, 3H), 2.34 (s, 3H), 2.29 (s, 3H), 1.68-1.65 (m, 2H), 1.58-1.56 (m, 2H); MS (ESI) m/z: 522.2 (M+H$^+$).

Example 50

N-(4-(2-(1,5-Dimethyl-1H-pyrazol-4-yl)pyridin-4-yloxy)-2,5-difluorophenyl)-N'-(4-fluorophenyl)cyclopropane-1,1-dicarboxamide from Example 49 (0.081 g, 0.155 mmol) was dissolved in THF (2.5 ml) and warmed until reflux. Methanesulfonic acid (10.09 µl, 0.155 mmol) was added and the mixture cooled to RT. The mixture was slowly diluted with Et$_2$O (5 ml). A precipitate immediately began to form upon addition. After the addition was complete, the mixture was sonicated for 20 min. The precipitate was filtered off to yield N-(4-(2-(1,5-dimethyl-1H-pyrazol-4-yl)pyridin-4-yloxy)-2,5-difluorophenyl)-N'-(4-fluorophenyl)cyclopropane-1,1-dicarboxamide mesylate (79 mg, 82% yield). $^1$H NMR (400 MHz, DMSO-d$_6$): δ 11.18 (s, 1H), 9.72 (s, 1H), 8.52 (d, 1H), 8.20-8.14 (m, 2H), 7.63-7.56 (m, 3H), 7.25 (s, 1H), 7.18-7.14 (m, 2H), 6.99-6.94 (m, 1H), 3.74 (s, 3H), 2.35 (s, 3H), 2.28 (s, 3H), 1.67-1.64 (m, 2H), 1.58-1.55 (m, 2H); MS (ESI) m/z: 522.2 (M+H$^+$).

Example 51

1-((4-fluorophenyl)carbamoyl)cyclopropanecarbonyl chloride prepared via the procedure in Example 47 (0.13 g, 0.538 mmol), Example A9 (0.123 g, 0.414 mmol), and triethylamine (0.065 ml, 0.621 mmol) were dissolved in THF (3 ml). The mixture was stirred at RT for 30 min, filtered to remove triethylamine HCl, concentrated under reduced pressure and purified by silica gel column chromatography (MeOH/DCM) to obtain N-(2-fluoro-5-methyl-4-(2-(1-methyl-1H-pyrazol-4-yl)pyridin-4-yloxy)phenyl)-N'-4-fluorophenyl)cyclopropane-1,1-dicarboxamide (0.067 g, 32% yield). MS (ESI) m/z: 504.2 (M+H$^+$).

N-(2-fluoro-5-methyl-4-(2-(1-methyl-1H-pyrazol-4-yl)pyridin-4-yloxy)phenyl)-N'-(4-fluorophenyl)cyclopropane-1,1-dicarboxamide (0.067 g, 0.133 mmol) was dissolved in CH$_2$Cl$_2$ (1 ml), 1.0 M methanesulfonic acid (0.133 ml, 0.133 mmol) was added and the reaction mixture was stirred at RT for 1 hour. The solid was filtered to obtain N-(2-fluoro-5-methyl-4-(2-(1-methyl-1H-pyrazol-4-yl)pyridin-4-yloxy)phenyl)-N'-(4-fluorophenyl)cyclopropane-1,1-dicarboxamide methanesulfonate salt (55 mg, 67% yield). $^1$H NMR (400 MHz, DMSO-d$_6$): δ 10.8 (brs, 1H), 9.81 (s, 1H), 8.53 (m, 2H), 8.18 (m, 1H), 8.01 (m, 1H), 7.57 (m, 3H), 7.32 (m, 1H), 7.16 (m, 2H), 6.94 (m, 1H), 3.90 (s, 3H), 2.29 (s, 3H), 2.09 (s, 3H), 1.5-1.7 (m, 4H).

Example 52

A solution of Example A11 (0.107 g, 0.359 mmol) and triethylamine (0.075 ml, 0.538 mmol) in THF (3.0 ml) was sparged with argon for several minutes, treated with 1-((4-fluorophenyl)carbamoyl)cyclopropanecarbonyl chloride from Example 51 (0.130 g, 0.538 mmol) and the mixture stirred at RT under an argon atmosphere for 30 minutes. The mixture was filtered, rinsed with THF and the filtrate concentrated to dryness. The resulting residue was triturated with diethyl ether, sonicated for several minutes and the resulting solid filtered, rinsed with Et$_2$O and dried in vacuo to afford N-(2-fluoro-4-methyl-5-(4-(1-methyl-1H-pyrazol-4-yl)pyrimidin-2-yloxy)phenyl)-N'-(4-fluorophenyl)cyclopropane-1,1-dicarboxamide (154 mg, 85% yield) as an off-white solid. $^1$H NMR (400 MHz, DMSO-d$_6$): 1.52 (m, 2H), 1.57 (m, 2H), 2.04 (s, 3H), 3.87 (s, 3H), 7.15 (t, 2H), 7.25 (d, 1H), 7.44 (d, 1H), 7.56 (m, 2H), 7.71 (d, 1H), 8.08 (s, 1H), 8.43 (m, 2H), 9.83 (brs, 1H), 10.71 (brs, 1H); MS (ESI) m/z: 505.2 (M+H$^+$).

Example 53

To a suspension of Example B1 (0.293 g, 1.315 mmol) and cyanuric chloride (0.097 g, 0.526 mmol) in acetonitrile (5 ml) was added N-methylpyrrolidine (0.112 g, 1.32 mmol) and the reaction was stirred at RT for 20 minutes. To this reaction mixture was added Example A16 (0.250 g, 0.876 mmol), and stirring continued at RT for 13 hours. The reaction mixture was concentrated in vacuo, the residue stirred in dichloromethane, filtered, washed and dried. The resultant solid was stirred in hot methanol, cooled to RT, filtered, washed and dried to provide N-(2-fluoro-5-(4-(1-methyl-1H-pyrazol-4-yl)pyrimidin-2-yloxy)phenyl)-N'-(4-fluorophenyl)cyclopropane-1,1-dicarboxamide (0.096 g, 22% yield) as white solid. $^1$H NMR (400 MHz, DMSO-d$_6$) δ 11.15 (s, 1H), 10.89 (s, 1H)), 9.79 (s, 1H), 8.47 (d, J=5 Hz, 1H), 8.42 (s, 1H), 8.08 (s, 1H), 7.86 (s, 1H), 7.57 (m, 1H), 7.45 (d, J=5.7 Hz, 1H), 7.32 (dd, J=9, 11.5 Hz, 1H), 7.15 (t, J=9 Hz, 2H), 7.00 (m, 1H), 3.87 (s, 3H), 1.60 (m, 2H), 1.53 (m, 2H); MS (ESI) m/z: 491.2 (M+H$^+$).

Example 54

1-((4-Fluorophenyl)carbamoyl)cyclopropanecarbonyl chloride from Example 51 (0.13 g, 0.538 mmol), Example A20 (0.102 g, 0.359 mmol), and triethylamine (0.075 ml, 0.717 mmol) were dissolved in THF (3 ml). The mixture was stirred at RT. After 1 hour, the reaction was filtered to remove triethylamine HCl, concentrated in vacuo, and purified by silica gel column chromatography (EtOAc/hexanes) to obtain a residue. The residue was treated with Et$_2$O. The solid formed was filtered and dried to obtain N-(5-(4-(1H-pyrazol-4-yl)pyrimidin-2-yloxy)-2-fluoro-4-methylphenyl)-N'-(4-fluorophenyl)cyclopropane-1,1-dicarboxamide (80 mg, 45% yield). $^1$H NMR (400 MHz, DMSO-d$_6$): δ 13.3 (s, 1H), 10.7 (s, 1H), 9.84 (s, 1H), 8.49 (s, 1H), 8.43 (d, J=5.2 Hz, 1H), 8.11 (d, J=1.6 Hz, 1H), 7.70 (d, J=7.2 Hz, 1H), 7.56 (m, 2H), 7.49 (d, J=5.2 Hz, 1H), 7.25 (d, J=11.6 Hz, 1H), 7.13 (m, 2H), 2.05 (s, 3H), 1.58 (m, 2H), 1.51 (m, 2H); MS (ESI) m/z: 491.2 (M+H$^+$).

Example 55

A solution of Example B1 (196 mg, 0.811 mmol) in THF (2 mL) was added to a stirred mixture of triethylamine (200 mg, 2.212 mmol) and Example A18 (200 mg, 0.737 mmol) in THF (4 mL). The mixture was then stirred at RT. The mixture was further treated with Example B1 (~75 mg) in THF (1 mL). The mixture was stirred at RT for 3 hrs, then diluted with ethyl acetate (30 mL) and washed with 10% potassium carbonate (30 mL), brine (30 mL), dried (Na$_2$SO$_4$), evaporated at reduced pressure and purified by reverse phase chromatography (CH$_3$CN/H$_2$O with 0.1% TFA) to give an aqueous residue was then treated with saturated sodium bicarbonate (4 mL) and allowed to precipitate. The solid was collected by filtration, washed with water (1 mL) and dried on a high vacuum line at 80° C. to give N-(5-(4-(1H-pyrazol-4-yl)pyrimidin-2-yloxy)-2-fluorophenyl)-N'-(4-fluorophenyl)cyclopropane-1,1-dicarboxamide (26 mg, 7% yield). $^1$H NMR (400 MHz, DMSO-d$_6$): δ 1.50-1.60 (m, 4H), 6.90-7.01 (m, 1H), 7.15 (t, 2H), 7.31 (t, 1H), 7.49-7.50 (m, 1H), 7.55-7.58 (m, 2H), 7.84-7.85 (m, 1H), 8.15 (br. s, 1H), 8.46 (d, 1H), 8.50 (br. s, 1H), 9.80 (s, 1H), 10.87 (s, 1H), 13.3 (s, 1H); MS (ES-API) m/z: 477.2 (M+H$^+$).

Example 56

2-(4-Fluorophenyl)acetamide from Example 42 (0.091 g, 0.597 mmol) was dissolved in dichloroethane (6 ml) and oxalyl chloride (0.052 ml, 0.597 mmol) was added. The mixture was heated at 85° C. under a balloon of argon for 15 hours. The reaction mixture was cooled to RT and the solvent was removed under reduced pressure. The residue that remained was dissolved in NMP (3.00 ml) and added to Example A17 (0.084 g, 0.299 mmol). The solution stirred at RT for 30 minutes under argon. The reaction mixture was diluted with a 4:1 mixture of ethyl acetate and THF (60 mL) and washed with 10% aqueous LiCl (2×50 mL) and brine (50 mL), dried (MgSO$_4$), evaporated in vacuo and purified via silica gel chromatography (ethyl acetate/hexanes) to yield 1-(2-(4-fluorophenyl)acetyl)-3-(4-methyl-5-(2-(1-methyl-1H-pyrazol-4-yl)pyridin-4-yloxy)pyridin-2-yl)urea as an off-white solid (0.097 g, 71% yield). $^1$H NMR (400 MHz, DMSO-d$_6$): δ 11.11 (s, 1H), 10.89 (s, 1H), 8.33 (d, 1H), 8.24 (s, 1H), 8.12 (s, 1H), 8.00 (s, 1H), 7.95 (s, 1H), 7.35 (m, 2H), 7.25 (m, 1H), 7.14 (m, 2H), 6.59 (dd, 1H), 3.83 (s, 3H), 3.74 (s, 2H), 2.15 (s, 3H); MS (ESI) m/z: 461.1 (M+H$^+$).

Example 57

Example B1 (0.092 g, 0.412 mmol) was dissolved in thionyl chloride (6 ml, 82 mmol) and heated at 80° C. for 1 h. The mixture was cooled and azeotroped with toluene (3×10 ml). The crude acid chloride was dissolved in THF (5 ml) and added dropwise to a 0° C. solution of Example A19 (0.113 g, 0.375 mmol) and N,N-diethylisopropylamine (0.131 ml, 0.749 mmol) in THF (5 ml). The mixture was stirred overnight at RT. The reaction was not complete. Additional acid chloride was generated from Example B1 (65 mg, 0.29 mmol) using the above method. The crude acid chloride was dissolved in THF (5 ml) and added to the reaction mixture. The solution was stirred at RT for 4 h, diluted with EtOAc and washed with sat. NaHCO$_3$ $_{(aq)}$. The organic extract was dried, evaporated and purified by silica gel chromatography (hexanes/EtOAc) and reverse phase chromatography (water (0.1% TFA)/acetonitrile (0.1% TFA)), treated with sat. NaHCO$_3$ $_{(aq)}$ until basic and the resulting solid removed by filtration. The solid was dried under vacuum at 80° C. to yield N-(2,5-difluoro-4-(3-(1-methyl-1H-pyrazol-4-yl)pyridin-4-yloxy)phenyl)-N'-(4-fluorophenyl)cyclopropane-1,1-dicarboxamide (57 mg, 30% yield). The mesylate salt was formed by taking N-(2,5-difluoro-4-(3-(1-methyl-1H-pyrazol-4-yl)pyridin-4-yloxy)phenyl)-N'-(4-fluorophenyl)cyclopropane-1,1-dicarboxamide (0.057 g, 0.112 mmol) and dissolving it in refluxing acetonitrile (5 ml). Methanesulfonic acid (7.29 μl, 0.112 mmol) was added and the mixture was cooled to RT, concentrated (~2 ml) and ether (5 ml) was added dropwise. A solid precipitated. The resulting mixture was sonicated for 30 min. The solid was filtered off and dried overnight in the drying pistol to yield N-(2,5-difluoro-4-(3-(1-methyl-1H-pyrazol-4-yl)pyridin-4-yloxy)phenyl)-N'-(4-fluorophenyl)cyclopropane-1,1-dicarboxamide mesylate (50 mg, 74% yield). $^1$H NMR (400 MHz, DMSO-d$_6$): δ 11.27 (s, 1H), 9.74 (s, 1H), 9.11 (s, 1H), 8.49 (d, 1H), 8.43 (s, 1H), 8.22-8.19 (m, 1H), 8.16 (d, 1H), 7.74-7.70 (m, 1H), 7.60-7.57 (m, 2H), 7.21-7.15 (m, 3H), 3.92 (s, 3H), 2.34 (s, 3H), 1.71-1.68 (m, 2H), 1.61-1.59 (m, 2H); MS (ESI) m/z: 508.2 (M+H$^+$).

Example 58

Using a procedure analogous to Example B1, 1,1-cyclopropanedicarboxylic acid (2 g, 15.37 mmol), Et$_3$N (2.14 mL, 15.4 mmol), thionyl chloride (1.12 mL, 15.4 mmol), and 4-fluoro-N-methylaniline (1.83 g, 14.6 mmol) were combined to provide 1-((4-fluorophenyl)(methyl)carbamoyl)cyclopropanecarboxylic acid (2.79 g, 72% yield). MS (ESI) m/z: 260.0 (M+Na$^+$).

Example A2 (136 mg, 0.479 mmol), 1-((4-fluorophenyl)(methyl)carbamoyl)cyclopropanecarboxylic acid (125 mg, 0.525 mmol), TBTU (0.169 g, 0.525 mmol) and i-Pr$_2$NEt (0.18 mL, 1.050 mmol) were combined in DMF (3 mL). The resultant mixture was stirred overnight at RT. Additional portions of TBTU (0.169 g, 0.525 mmol) and i-Pr$_2$NEt (0.18 mL, 1.05 mmol) were added and the mixture was stirred an additional 24 h. The reaction mixture was poured into water (30 mL) and extracted with EtOAc (3×30 mL). The organic extracts were washed with satd aq NaHCO$_3$ and brine, were dried (MgSO$_4$), and were concentrated in vacuo. The residue was dissolved in CH$_2$Cl$_2$ (20 mL) and the solution was shaken overnight with polymer-bound isocyanate resin (1.7 mmol/g; 0.5 g). The mixture was filtered and the filtrate was concentrated to dryness and purified by reverse phase chromatography (acetonitrile (with 0.1% TFA added)/water (with 0.1% TFA added)). The pure fractions were combined and concentrated to dryness. THF (10 mL) and polymer-bound carbonate resin (200 mg) were added to the residue and the mixture was shaken for 2 h. The mixture was filtered and the filtrate was treated with aq HCl (2 N, 2 mL, 4 mmol). The solution was concentrated in vacuo, dissolved in acetonitrile-water (1:1, 6 mL), frozen and lyophilized to provide N-(3-fluoro-4-(2-(1-methyl-1H-pyrazol-4-yl)pyridin-4-yloxy)phenyl)-N'-(4-fluorophenyl)-N'-methylcyclopropane-1,1-dicarboxamide HCl salt as a yellow powder (50 mg, 18% yield). $^1$H NMR (400 MHz, DMSO-d$_6$): δ 10.00 (br s, 1H), 8.70 (s, 1H), 8.54 (d, 1H), 8.38 (s, 1H), 7.73 (s, 1H), 7.51 (br s, 1H), 7.44-7.20 (m, 4H), 7.15-6.97 (m, 3H), 3.93 (s, 3H), 3.23 (s, 3H), 1.43 (s, 2H), 1.22 (s, 2H); MS (ESI) m/z: 504.1 (M+H$^+$).

Example 59

Thionyl chloride (1 ml, 13.70 mmol) was added to Example B1 (0.131 g, 0.589 mmol; DP-4180) and mixture was stirred at 60° C. under Ar atmosphere for 30 min. The mixture was concentrated in vacuo and azeotroped with toluene (2×8 mL) to furnish acid chloride as a white solid. To this solid added a solution of Example A21 (0.12 g, 0.421 mmol) and triethylamine (0.292 ml, 2.10 mmol) in THF (3 mL) and the reaction was stirred for 1 h at RT. The mixture was partitioned between EtOAc (30 mL) and NaHCO$_3$ solution (30 mL). The aqueous layer was extracted with EtOAc (1×20 mL) and combined organics were washed with brine, dried (Na$_2$SO$_4$), concentrated in vacuo and purified by chromatography (ethylacetate/hexanes) to afford N-(2-fluoro-4-(2-(3-methylisoxazol-5-yl)pyridin-4-yloxy)phenyl)-N'-(4-fluorophenyl)cyclopropane-1,1-dicarboxamide (87 mg, 42% yield) as a white solid. $^1$H NMR (400 MHz, DMSO-d$_6$): δ 10.06 (s, 1H), 9.92 (s, 1H), 8.57 (d, J=5.6 Hz, 1H), 7.97 (t, J=8.8 Hz, 1H), 7.61-7.57 (m, 2H), 7.37 (d, J=2.4 Hz 1H), 7.34 (dd, J=11.6 Hz, 2.4 Hz, 1H), 7.15 (t, J=9.2 Hz, 2H), 7.09 (dd, J=8.8 Hz, 1.6 Hz, 1H), 7.03 (dd, J=5.6 Hz, 2.4 Hz, 1H), 6.96 (s, 1H), 2.28 (s, 3H), 1.58-1.54 (m, 4H); MS (ESI) m/z: 491.2 (M+H$^+$).

Example 60

Using a procedure analogous to Example 59, Example B1 (0.113 g, 0.506 mmol) was converted to 1-(4-fluorophenylcarbamoyl)cyclopropanecarbonyl chloride. To the solid acid chloride was added a solution of Example A23 (0.13 g, 0.337 mmol) and triethylamine (0.187 ml, 1.349 mmol) in THF (4 mL). The mixture was stirred for 5 h at RT, concentrated in vacuo, dissolved in methanol (4 mL) and 2N aq. NaOH (0.093 mL, 0.186 mmol) was added. The mixture was stirred for 30 min at RT, concentrated in vacuo, diluted with 5% citric acid (25 mL) and extracted with EtOAc (2×35 mL). The combined organics were washed with brine, dried (Na₂SO₄), concentrated in vacuo and purified by reverse phase chromatography (acetonitrile/water (0.1% TFA)) to afford N-(4-(2-(1H-1,2,3-triazol-4-yl)pyridin-4-yloxy)-2-fluorophenyl)-N'-(4-fluorophenyl)cyclopropane-1,1-dicarboxamide (37 mg, 42% yield) as a white solid. ¹H NMR (400 MHz, DMSO-d₆): δ 10.49 (s, 1H), 9.91 (s, 1H), 8.45 (brs, 1H), 8.17 (s, 1H), 7.90 (t, J=8.8 Hz, 1H), 7.55 (dd, J=8.8 Hz, 5.2 Hz, 2H) 7.31 (brs, 1H), 7.29-7.26 (m, 1H), 7.10 (t, J=8.8 Hz, 2H), 7.03 (d, J=8.0 Hz, 1H), 6.91 (s, 1H), 1.55-1.50 (m, 4H); MS (ESI) m/z: 477.2 (M+H⁺).

SECTION 4. BIOLOGICAL DATA c-KIT Kinase Assay

Activity of c-KIT kinase (Seq. ID no. 1) was determined by following the production of ADP from the kinase reaction through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 µl) contained c-KIT (cKIT residues T544-V976, from ProQinase, 5.4 nM), polyE4Y (SEQ ID NO: 4) (1 mg/ml), MgCl₂ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with c-KIT (Seq. ID no. 1) and other reaction reagents at 22° C. for <2 min before ATP (200 µM) was added to start the reaction. The absorption at 340 nm was monitored continuously for 0.5 hours at 30° C. on Polarstar Optima plate reader (BMG). The reaction rate was calculated using the 0 to 0.5 h time frame. Percent inhibition was obtained by comparison of reaction rate with that of a control (i.e. with no test compound). IC₅₀ values were calculated from a series of percent inhibition values determined at a range of inhibitor concentrations using software routines as implemented in the GraphPad Prism software package.

c-KIT with N-terminal GST fusion
(Seq ID No. 1)
LGYWKIKGLVQPTRLLLEYLEEKYEEHLYERDEGDKWRNKKFELGLEFPN

LPYYIDGDVKLTQSMAIIRYIADKHNMLGGCPKERAEISMLEGAVDIRYG

VSRIAYSKDFETLKVDFLSKLPEMLKMFEDRLCHKTYLNGDHVTHPDFML

YDALDVVLYMDPMCLDAFPKLVCFKKRIEAIPQIDKYLKSSKYIWPLQGW

QATFGGGDHPPKSDLVPRHNQTSLYKKAGSAAAVLEENLYFQGTYKYLQK

PMYEVQWKVVEEINGNNYVYIDPTQLPYDHKWEFPRNRLSFGKTLGAGAF

GKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEA

ALYKNLLHSKESSCSDSTNEYMDMKPGVSYVVPTKADKRRSVRIGSYIER

DVTPAIMEDDELALDLEDLLSFSYQVAKGMAFLASKNCIHRDLAARNILL

THGRITKICDFGLARDIKNDSNYVVKGNARLPVKWMAPESIFNCVYTFES

DVWSYGIFLWELFSLGSSPYPGMPVDSKFYKMIKEGFRMLSPEHAPAEMY

DIMKTCWDADPLKRPTFKQIVQLIEKQISESTNHIYSNLANCSPNRQKPV

VDHSVRINSVGSTASSSQPLLVHDDV c-MET Kinase Assay

Activity of c-MET kinase (Seq. ID no. 2) was determined by following the production of ADP from the kinase reaction through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 µl) contained c-MET (c-MET residues: 956-1390, from Invitrogen, catalogue #PV3143, 6 nM), polyE4Y (SEQ ID NO: 4) (1 mg/ml), MgCl₂ (10 mM), pyruvate kinase (4 units), lactate dehydrogenase (0.7 units), phosphoenol pyruvate (1 mM), and NADH (0.28 mM) in 90 mM Tris buffer containing 0.25 mM DTT, 0.2% octyl-glucoside and 1% DMSO, pH 7.5. Test compounds were incubated with C-Met (Seq. ID no. 2) and other reaction reagents at 22° C. for 0.5 h before ATP(100 µM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). IC₅₀ values were calculated from a series of percent inhibition values determined at a range of inhibitor concentrations using software routines as implemented in the GraphPad Prism software package.

cMET Kinase
(Seq ID No. 2)
MSYYHHHHHHDYDIPTTENLYFQGAMLVPRGSPWIPFTMKKRKQIKDLGS

ELVRYDARVHTPHLDRLVSARSVSPTTEMVSNESVDYRATFPEDQFPNSS

QNGSCRQVQYPLTDMSPILTSGDSDISSPLLQNTVHIDLSALNPELVQAV

QHVVIGPSSLIVHFNEVIGRGHFGCVYHGTLLDNDGKKIHCAVKSLNRIT

DIGEVSQFLTEGIIMKDFSHPNVLSLLGICLRSEGSPLVVLPYMKHGDLR

NFIRNETHNPTVKDLIGFGLQVAKGMKYLASKKFVHRDLAARNCMLDEKF

TVKVADFGLARDMYDKEYYSVHNKTGAKLPVKWMALESLQTQKFTTKSDV

WSFGVLLWELMTRGAPPYPDVNTFDITVYLLQGRRLLQPEYCPDPLYEVM

LKCWHPKAEMRPSFSELVSRISAIFSTFIGEHYVHVNATYVNVKCVAPYP

SLLSSEDNADDEVDTRPASFWETS

KDR Kinase Assay

Assay K1

The activity of KDR kinase was determined by following the production of ADP from the kinase reaction through coupling with the pyruvate kinase/lactate dehydrogenase system (e.g., Schindler et al. Science (2000) 289: 1938-1942). In this assay, the oxidation of NADH (thus the decrease at A₃₄₀ ₙₘ) was continuously monitored spectrophotometrically. The reaction mixture (100 µl) contained KDR (Seq ID No. 3, 1.5 nM to 7.1 nM, nominal concentration), polyE₄Y (SEQ ID NO: 4) (1 mg/ml), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM MgCl₂, 6.8 mM DTT, and 3.5% DMSO at pH 7.5. The reaction was initiated by adding ATP (0.2 mM, final concentration). The absorption at 340 nm was continuously monitored for 3 h at 30° C. on a Polarstar Optima plate reader (BMG) or instrument of similar capacity. The reaction rate was calculated using the 1 h to 2 h time frame. Percent inhibition was obtained by comparison of reaction rate with that of a control (i.e. with no test compound). IC₅₀ values were calculated from a series of percent inhibition values determined at a range of inhibitor concentrations using software routines as implemented in the GraphPad Prism software package.

Assay K2

KDR kinase assay K2 is the same as for assay K1 except that (1) a nominal concentration of 2.1 nM of enzyme was employed (2) the reaction was pre-incubated at 30° C. for 2 h prior to initiation with ATP and (3) 1.0 mM ATP (final concentration) was used to initiate the reaction.

Assay K3

KDR kinase assay K3 is the same as for assay K1 except that (1) a nominal concentration of 1.1 nM of enzyme was employed, (2) the buffer components per 100 µl reaction mixture were as follows: 75 mM Tris buffer containing 0.066% octyl-glucoside, 17 mM $MgCl_2$, and 1% DMSO at pH 7.5, (3) the final concentration of DTT was 0.66 mM, (4) the reaction was pre-incubated at 30° C. for 1 h prior to initiation with ATP, and (5) 1.0 mM ATP (final concentration) was used to initiate the reaction.

```
KDR protein sequence used for screening
                                        (Seq. ID No. 3)
DPDELPLDEHCERLPYDASKWEFPRDRLKLGKPLGRGAFGQVIEADAFGI

DKTATCRTVAVKMLKEGATHSEHRALMSELKILIHIGHHLNVVNLLGACT

KPGGPLMVIVEFCKFGNLSTYLRSKRNEFVPYKVAPEDLYKDFLTLEHLI

CYSFQVAKGMEFLASRKCIHRDLAARNILLSEKNVVKICDFGLARDIYKD

PDYVRKGDARLPLKWMAPETIFDRVYTIQSDVWSFGVLLWEIFSLGASPY

PGVKIDEEFCRRLKEGTRMRAPDYTTPEMYQTMLDCWHGEPSQRPTFSEL

VEHLGNLLQANAQQD
```

HUVEC Cell Culture

HUVEC (Human umbilical vein endothelial cell) cells were obtained from Lonza (Lonza, Walkersville, Md.). Briefly, cells were grown in EGM-2 (Lonza, Walkersville, Md.) at 37 degrees Celsius, 5% $CO_2$, 95% humidity. Cells were allowed to expand until reaching 90-95% saturation at which point they were subcultured or harvested for assay use. For assay use, cells were harvested and grown in EGM-2 medium supplemented with 2% FBS (Lonza, Walkersville, Md.).

HUVEC VEGF/KDR ELISA

Twenty-five thousand cells were added per well in a 96-well black clear bottom plate (Corning, Corning, N.Y.). Cells were then incubated overnight at 37 degrees Celsius, 5% $CO_2$, 95% humidity. A serial dilution of test compound was dispensed into another 96-well black clear bottom plate (Corning, Corning, N.Y.) containing EBM-2 supplemented with 2% FBS. Compound was added to plates containing cells and incubated for 4 hours at 37 degrees Celsius, 5% $CO_2$, 95% humidity. Cells were stimulated with 100 ng/mL VEGF (R&D Systems, Minneapolis, Minn.) for 5 minutes, then lysed. Cell lysates were used to detect phospho-VEGF R2 using DuoSet IC HUVEC VEGF/KDR ELISA (R&D Systems, Minneapolis, Minn.). Data was analyzed using Prism software (Graphpad, San Diego, Calif.) to calculate $IC_{50}$'s.

EBC-1 Cell Culture

EBC-1 cells (catalog #JCRB0820) were obtained from the Japan Health Science Research Resources Bank, Osaka, Japan. Briefly, cells were grown in DMEM supplemented with 10% characterized fetal bovine serum (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

EBC-1 Cell Proliferation Assay

A serial dilution of test compound was dispensed into a 96-well black clear bottom plate (Corning, Corning, N.Y.). For each cell line, five thousand cells were added per well in 200 µL complete growth medium. Plates were incubated for 67 hours at 37 degrees Celsius, 5% $CO_2$, 95% humidity. At the end of the incubation period 40 µL of a 440 µM solution of resazurin (Sigma, St. Louis, Mo.) in PBS was added to each well and incubated for an additional 5 hours at 37 degrees Celsius, 5% $CO_2$, 95% humidity. Plates were read on a Synergy2 reader (Biotek, Winooski, Vt.) using an excitation of 540 nM and an emission of 600 nM. Data was analyzed using Prism software (Graphpad, San Diego, Calif.) to calculate $IC_{50}$ values.

M-NFS-60 Cell Culture

M-NFS-60 cells (catalog #CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37 degrees Celsius, 5% $CO_2$, and 95% humidity. Cells were allowed to expand until reaching saturation at which point they were subcultured or harvested for assay use.

M-NFS-60 Cell Proliferation Assay

A serial dilution of test compound was dispensed into a 384-well black clear bottom plate (Corning, Corning, N.Y.). Two thousand five hundred cells were added per well in 50 µL complete growth medium. Plates were incubated for 67 hours at 37 degrees Celsius, 5% $CO_2$, and 95% humidity. At the end of the incubation period 10 µL of a 440 µM solution of resazurin (Sigma, St. Louis, Mo.) in PBS was added to each well and incubated for an additional 5 hours at 37 degrees Celsius, 5% $CO_2$, and 95% humidity. Plates were read on a Synergy2 reader (Biotek, Winooski, Vt.) using an excitation of 540 nM and an emission of 600 nM. Data was analyzed using Prism software (Graphpad, San Diego, Calif.) to calculate $IC_{50}$ values.

FMS Kinase Assay

Activity of FMS kinase was determined by following the production of ADP from the kinase reaction through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 µl) contained FMS (purchased from Invitrogen or Millipore, 6 nM), polyE4Y (SEQ ID NO: 4) (1 mg/ml), $MgCl_2$ (10 mM), pyruvate kinase (4 units), lactate dehydrogenase (0.7 units), phosphoenol pyruvate (1 mM) and NADH (0.28 mM) and ATP (500 µM) in a 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on a Polarstar Optima or Synergy 2 plate reader. The reaction rate was calculated using the 2 to 3 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

PDGFRα Kinase Assay

Activity of PDGFRα kinase was determined by following the production of ADP from the kinase reaction through coupling with the pyruvate kinase/lactate dehydrogenase system. In this assay, the oxidation of NADH (thus the decrease at A340 nm) was continuously monitored spectrophometrically. The reaction mixture (100 μl) contained PDGFRα (Invitrogen, 10 nM), polyE4Y (SEQ ID NO: 4) (1 mg/ml), MgCl$_2$ (10 mM), pyruvate kinase (4 units), lactate dehydrogenase (0.7 units), phosphoenol pyruvate (1 mM) and NADH (0.28 mM) and ATP (500 μM) in a 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on a Polarstar Optima or Synergy 2 plate reader. The reaction rate was calculated using the 2 to 3 h time frame. Percent inhibition was obtained by comparison of reaction rate with that of a control (i.e. with no test compound). IC$_{50}$ values were calculated from a series of percent inhibition values determined at a range of inhibitor concentrations using software routines as implemented in the GraphPad Prism software package.

PDGFRβ Kinase Assay

This was done as described for PDGFRα except that PDGFRβ (Invitrogen, 11 nM) was used.

As shown in Tables 1 and 2, compounds of formula Ia exhibit inhibitory activity in one or more of the aforementioned assays when evaluated at concentrations ≦10 μM.

TABLE 1

Enzymatic Activity

| Example # | cMET Enzyme Assay | cKIT Enzyme Assay | KDR Enzyme Assay | FMS Enzyme Assay | PDGFRa Enzyme Assay | PDGFRb Enzyme Assay |
|---|---|---|---|---|---|---|
| 1 | +++ | ++ | ++ | NT | +++ | ++ |
| 3 | + | NT | ++ | NT | ++ | + |
| 4 | + | ++ | ++ | +++ | + | + |
| 5 | +++ | NT | NT | NT | NT | NT |
| 6 | ++ | + | +++ | ++ | ++ | + |
| 7 | +++ | + | ++ | +++ | ++ | + |
| 8 | + | NT | NT | NT | NT | NT |
| 10 | ++ | NT | NT | NT | NT | NT |
| 11 | ++ | NT | NT | NT | NT | NT |
| 12 | +++ | +++ | + | +++ | +++ | +++ |
| 13 | + | NT | NT | NT | NT | NT |
| 14 | ++ | NT | NT | NT | NT | NT |
| 15 | ++ | NT | NT | NT | NT | NT |
| 16 | ++ | +++ | + | +++ | ++ | + |
| 17 | + | ++ | + | +++ | + | + |
| 18 | ++ | NT | NT | NT | NT | NT |
| 19 | +++ | NT | NT | NT | NT | NT |
| 20 | ++ | NT | NT | NT | NT | NT |
| 21 | ++ | ++ | ++ | NT | ++ | + |
| 22 | ++ | ++ | ++ | +++ | ++ | ++ |
| 23 | ++ | + | + | ++ | + | + |
| 24 | ++ | NT | NT | NT | NT | NT |
| 25 | ++ | NT | NT | NT | NT | NT |
| 26 | + | NT | NT | NT | NT | NT |
| 27 | ++ | NT | NT | NT | NT | NT |
| 28 | + | NT | NT | NT | NT | NT |
| 29 | ++ | NT | NT | NT | NT | NT |
| 30 | +++ | +++ | NT | NT | ++ | + |
| 31 | +++ | NT | NT | NT | NT | NT |
| 32 | ++ | NT | + | ++ | NT | NT |
| 33 | ++ | NT | NT | NT | NT | NT |
| 34 | ++ | NT | NT | NT | NT | NT |
| 35 | ++ | NT | NT | NT | NT | NT |
| 36 | ++ | NT | NT | NT | NT | NT |
| 38 | ++ | NT | + | + | NT | NT |
| 39 | NT | NT | NT | NT | +++ | ++ |
| 40 | +++ | +++ | +++ | NT | ++ | + |
| 41 | ++ | ++ | ++ | +++ | ++ | + |
| 42 | +++ | +++ | + | NT | +++ | + |
| 43 | ++ | ++ | + | +++ | +++ | ++ |
| 44 | ++ | ++ | + | +++ | +++ | +++ |
| 45 | +++ | +++ | ++ | NT | + | + |
| 46 | +++ | +++ | ++ | NT | +++ | +++ |
| 47 | +++ | +++ | ++ | NT | +++ | + |
| 48 | + | ++ | ++ | + | + | + |
| 49 | +++ | +++ | ++ | ++ | + | + |
| 50 | +++ | +++ | +++ | NT | ++ | + |
| 51 | +++ | +++ | ++ | +++ | ++ | ++ |
| 52 | + | NT | + | + | NT | NT |
| 53 | + | NT | + | + | NT | NT |
| 54 | + | NT | + | + | NT | NT |
| 55 | + | + | + | + | + | + |
| 58 | + | + | + | NT | + | NT |
| 59 | +++ | NT | + | +++ | NT | NT |
| 60 | ++ | NT | NT | NT | NT | NT |

+ less than 10 μM activity
++ less than 2 μM activity
+++ less than 200 nM activity
NT not tested

TABLE 2

Cellular Acitivity

| Example # | EBC1 Cell Proliferation | M-NFS-60 Cell Proliferation | HUVEC pKDR | Mo-7e pKIT |
|---|---|---|---|---|
| 6 | + | NT | NT | NT |
| 7 | +++ | NT | ++ | NT |
| 12 | +++ | +++ | +++ | ++ |
| 16 | + | NT | NT | NT |
| 19 | ++ | NT | NT | NT |
| 20 | ++ | NT | NT | NT |
| 21 | ++ | NT | NT | NT |
| 22 | ++ | NT | NT | NT |
| 23 | ++ | NT | NT | NT |
| 30 | ++ | NT | NT | NT |
| 31 | ++ | NT | NT | NT |
| 40 | +++ | NT | ++ | NT |
| 41 | NT | + | NT | NT |
| 42 | +++ | NT | NT | ++ |
| 44 | NT | +++ | ++ | +++ |
| 45 | +++ | NT | NT | +++ |
| 46 | +++ | NT | NT | NT |
| 47 | +++ | NT | NT | NT |
| 49 | ++ | NT | NT | NT |
| 50 | +++ | NT | NT | NT |
| 51 | ++ | NT | NT | NT |

+ less than 10 μM activity
++ less than 2 μM activity
+++ less than 200 nM activity
NT not tested

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:
1. A compound of formula Ia

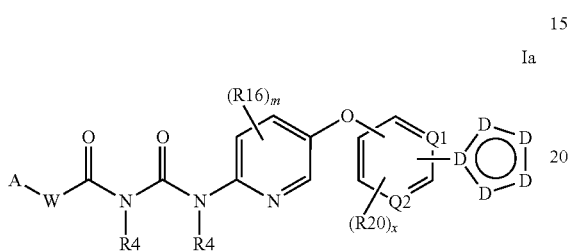

or a pharmaceutically acceptable salt or tautomer thereof;
wherein Q1 and Q2 are each individually and independently selected from the group consisting of N and CH and wherein at least one of Q1 and Q2 are N;
each D is individually taken from the group consisting of C, CH, C—R20, N—Z3, N, and O, such that the resultant ring is taken from the group consisting of pyrazolyl, isoxazolyl, triazolyl and imidazolyl;
W is a direct bond, or —[C(R13)R14]$_m$—;
A is selected from the group consisting of phenyl, pyridinyl, thienyl, indanyl, tetrahydronapthyl, naphthyl, pyrazinyl, pyridazinyl, triazinyl, and pyrimidinyl;
when A has one or more substitutable sp2-hybridized carbon atoms, each respective sp2 hybridized carbon atom may be optionally substituted with a Z1B substituent;
when A has one or more substitutable sp3-hybridized carbon atoms, each respective sp3 hybridized carbon atom may be optionally substituted with a Z2B substituent;
each Z1B is independently and individually selected from the group consisting of hydrogen, halogen, C1-6alkyl, branched C3-C7alkyl, fluoroC1-C6alkyl wherein the alkyl moiety can be partially or fully fluorinated, C1-C6alkoxy, fluoroC1-C6alkoxy wherein the alkyl moiety can be partially or fully fluorinated, and —(CH$_2$)$_n$CN;
each Z2B is independently and individually selected from the group consisting of hydrogen, C1-C6alkyl, and branched C3-C7alkyl;
each Z3 is independently and individually selected from the group consisting of C1-C6alkyl, hydrogen, branched C3-C7alkyl, C3-C8cycloalkyl, fluoroC1-C6alkyl wherein the alkyl moiety can be partially or fully fluorinated, hydroxyC2-C6alkyl-, R5C(O)(CH$_2$)$_n$—, (R4)$_2$NC(O)C1-C6alkyl-, R8C(O)N(R4)(CH$_2$)$_q$—, —(CH$_2$)$_q$CN, —(CH$_2$)$_q$R5, and —(CH$_2$)$_q$N(R4)$_2$;
each R2 is selected from the group consisting of hydrogen, R17-substituted aryl-, C1-C6alkyl, branched C3-C8alkyl, R19 substituted C3-C8cycloalkyl-, and fluoroC1-C6alkyl- wherein the alkyl is fully or partially fluorinated;
wherein each R3 is independently and individually selected from the group consisting of hydrogen, C1-C6alkyl, branched C3-C7alkyl, and C3-C8cycloalkyl;

each R4 is independently and individually selected from the group consisting of hydrogen, C1-C6alkyl, hydroxyC1-C6alkyl-, dihydroxyC1-C6alkyl-, C1-C6alkoxyC1-C6alkyl-, branched C3-C7alkyl, hydroxyl substituted branched C3-C6alkyl-, C1-C6alkoxy branched C3-C6alkyl-, dihydroxy substituted branched C3-C6alkyl-, —(CH$_2$)$_p$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, and R19 substituted C3-C8cycloalkyl-;
each R5 is independently and individually selected from the group consisting of

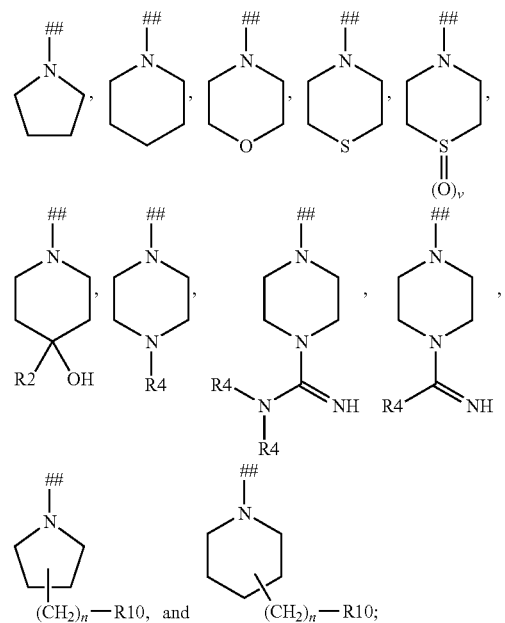

and wherein the symbol (##) is the point of attachment to respective R4, R7, R8, R20 or Z3 moieties containing a R5 moiety;
each R7 is independently and individually selected from the group consisting of hydrogen, C1-C6alkyl, hydroxyC2-C6alkyl-, dihydroxyC2-C6alkyl-, C1-C6alkoxyC2-C6alkyl-, branched C3-C7alkyl, hydroxy substituted branched C3-C6alkyl-, C1-C6alkoxy branched C3-C6alkyl-, dihydroxy substituted branched C3-C6alkyl-, —(CH$_2$)$_q$R5, —(CH$_2$)$_n$C(O)R5, —(CH$_2$)$_n$C(O)OR3, R19 substituted C3-C8cycloalkyl- and —(CH$_2$)$_n$R17;
each R8 is independently and individually selected from the group consisting of C1-C6alkyl, branched C3-C7alkyl, fluoroC1-C6alkyl- wherein the alkyl moiety is partially or fully fluorinated, R19 substituted C3-C8cycloalkyl-, phenyl, phenylC1-C6alkyl-, OH, C1-C6alkoxy, —N(R3)$_2$, —N(R4)$_2$, and R5;

each R10 is independently and individually selected from the group consisting of —CO$_2$H, —CO$_2$C1-C6alkyl, —C(O)N(R4)$_2$, OH, C1-C6alkoxy, and —N(R4)$_2$;

R13 and R14 are each individually and independently selected from the group consisting of hydrogen, C1-C6alkyl, branched C3-C8alkyl, fluoroC1-C6alkyl- wherein the alkyl is fully or partially fluorinated, hydroxyl substituted C1-C6alkyl-, C1-C6alkoxy substituted C1-C6alkyl-, hydroxyl substituted branched C3-C8alkyl-, and alkoxy substituted branched C3-C8alkyl;

each R16 is independently and individually selected from the group consisting of hydrogen, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, R3 substituted C2-C3alkynyl- and nitro;

each R17 is independently and individually selected from the group consisting of hydrogen, C1-C6alkyl, branched C3-C7alkyl, hydroxyC2-C6alkyl-, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, and nitro;

each R19 is independently and individually selected from the group consisting of hydrogen, OH and C1-C6alkyl;

each R20 is independently and individually selected from the group consisting of hydrogen, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, hydroxyC1-C6alkyl-, C1-C6alkoxyC1-C6alkyl-, C1-C6alkoxy, fluoroC1-C6alkoxy- wherein the alkyl moiety can be partially or fully fluorinated, —N(R3)$_2$, —N(R4)$_2$, —(CH$_2$)$_n$R5, —(CH$_2$)$_n$N(R3)C(O)R3, —(CH$_2$)$_n$C(O)N(R3)$_2$ and nitro;

each m is independently and individually 1-3, each n is independently and individually 0-6; each p is independently and individually 1-4; each q is independently and individually 2-6; each v is independently and individually 1 or 2; each x is independently and individually 0-2.

2. The compound of claim 1 wherein

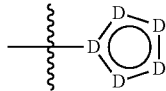

is selected from the group consisting of

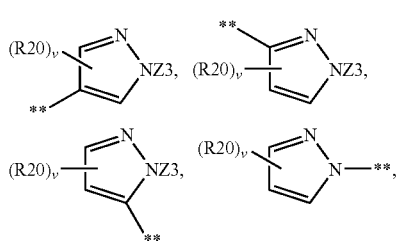

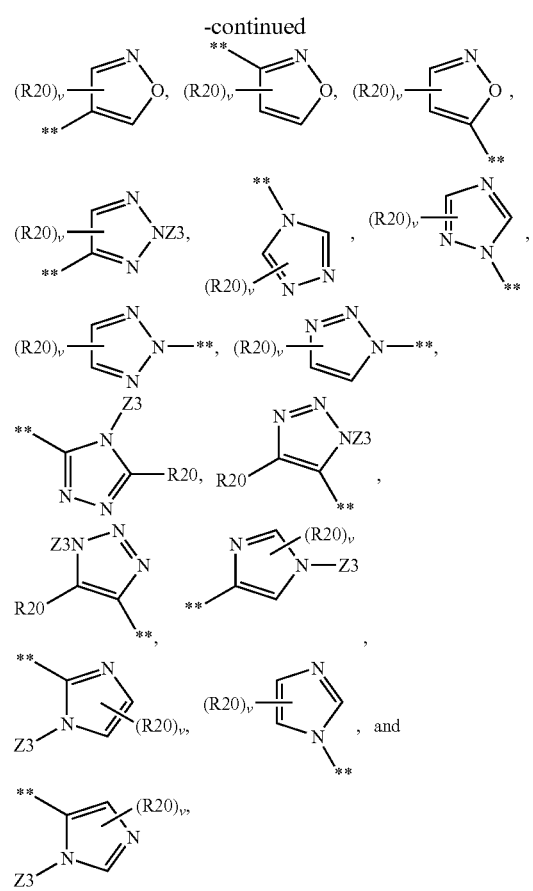

wherein the symbol (**) indicates the point of attachment to the heteroaryl Q1, Q2 containing ring.

3. The compound of claim 2 having formula Ii

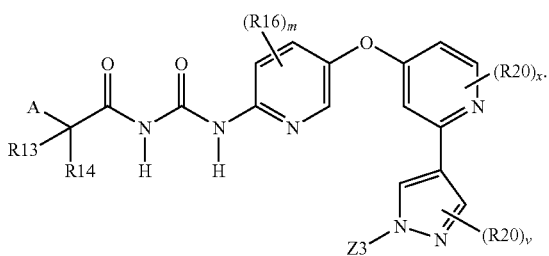

Ii

4. The compound of claim 2 having formula Iu

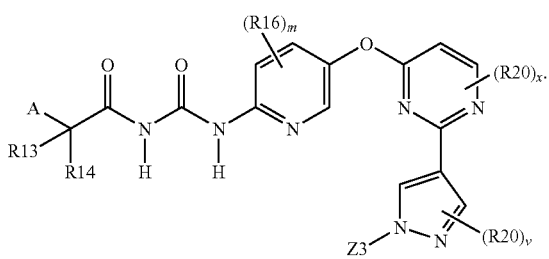

Iu

5. The compound of claim 2 having formula Igg

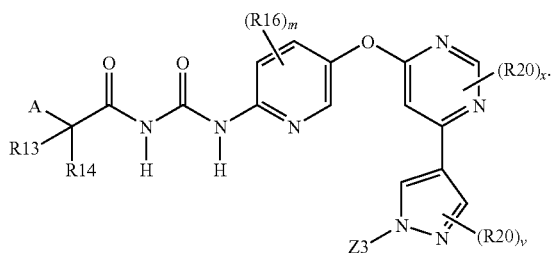

6. A compound selected from the group consisting of 2-(4-fluorophenyl)-N-(5-(2-(1-methyl-1H-pyrazol-4-yl)pyridin-4-yloxy)pyridin-2-ylcarbamoyl)acetamide, 2-(4-fluorophenyl)-N-(4-methyl-5-(2-(1-methyl-1H-pyrazol-4-yl)pyridin-4-yloxy)pyridin-2-ylcarbamoyl)acetamide and pharmaceutically acceptable salts and tautomers thereof.

7. A pharmaceutical composition comprising a compound of claim 1, together with a pharmaceutically acceptable carrier, optionally containing an additive selected from the group consisting of adjuvants, excipients, diluents, and stabilizers.

* * * * *

SEQUENCE LISTING

<160> NUMBER OF SEQ ID NOS: 4

<210> SEQ ID NO 1
<211> LENGTH: 676
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125

Glu Asp Arg Leu Cys His Lys Thr Tyr Leu Asn Gly Asp His Val Thr
130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
210                 215                 220

Tyr Lys Lys Ala Gly Ser Ala Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270

Pro Thr Gln Leu Pro Tyr Asp His Lys Trp Glu Phe Pro Arg Asn Arg
        275                 280                 285

Leu Ser Phe Gly Lys Thr Leu Gly Ala Gly Ala Phe Gly Lys Val Val
290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
            340                 345                 350
```

```
Ile Val Asn Leu Leu Gly Ala Cys Thr Ile Gly Gly Pro Thr Leu Val
            355                 360                 365

Ile Thr Glu Tyr Cys Cys Tyr Gly Asp Leu Leu Asn Phe Leu Arg Arg
        370                 375                 380

Lys Arg Asp Ser Phe Ile Cys Ser Lys Gln Asp His Ala Glu Ala
385                 390                 395                 400

Ala Leu Tyr Lys Asn Leu Leu His Ser Lys Glu Ser Ser Cys Ser Asp
            405                 410                 415

Ser Thr Asn Glu Tyr Met Asp Met Lys Pro Gly Val Ser Tyr Val Val
        420                 425                 430

Pro Thr Lys Ala Asp Lys Arg Ser Val Arg Ile Gly Ser Tyr Ile
            435                 440                 445

Glu Arg Asp Val Thr Pro Ala Ile Met Glu Asp Glu Leu Ala Leu
            450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
            485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
            515                 520                 525

Ala Arg Leu Pro Val Lys Trp Met Ala Pro Glu Ser Ile Phe Asn Cys
            530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
            565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
            595                 600                 605

Ala Asp Pro Leu Lys Arg Pro Thr Phe Lys Gln Ile Val Gln Leu Ile
            610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
            645                 650                 655

Ile Asn Ser Val Gly Ser Thr Ala Ser Ser Ser Gln Pro Leu Leu Val
            660                 665                 670

His Asp Asp Val
            675

<210> SEQ ID NO 2
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30
```

Pro Trp Ile Pro Phe Thr Met Lys Lys Arg Lys Gln Ile Lys Asp Leu
        35                  40                  45

Gly Ser Glu Leu Val Arg Tyr Asp Ala Arg Val His Thr Pro His Leu
    50                  55                  60

Asp Arg Leu Val Ser Ala Arg Ser Val Ser Pro Thr Thr Glu Met Val
65                  70                  75                  80

Ser Asn Glu Ser Val Asp Tyr Arg Ala Thr Phe Pro Glu Asp Gln Phe
                85                  90                  95

Pro Asn Ser Ser Gln Asn Gly Ser Cys Arg Gln Val Gln Tyr Pro Leu
            100                 105                 110

Thr Asp Met Ser Pro Ile Leu Thr Ser Gly Asp Ser Asp Ile Ser Ser
            115                 120                 125

Pro Leu Leu Gln Asn Thr Val His Ile Asp Leu Ser Ala Leu Asn Pro
        130                 135                 140

Glu Leu Val Gln Ala Val Gln His Val Val Ile Gly Pro Ser Ser Leu
145                 150                 155                 160

Ile Val His Phe Asn Glu Val Ile Gly Arg Gly His Phe Gly Cys Val
                165                 170                 175

Tyr His Gly Thr Leu Leu Asp Asn Asp Gly Lys Lys Ile His Cys Ala
            180                 185                 190

Val Lys Ser Leu Asn Arg Ile Thr Asp Ile Gly Glu Val Ser Gln Phe
        195                 200                 205

Leu Thr Glu Gly Ile Ile Met Lys Asp Phe Ser His Pro Asn Val Leu
    210                 215                 220

Ser Leu Leu Gly Ile Cys Leu Arg Ser Glu Gly Ser Pro Leu Val Val
225                 230                 235                 240

Leu Pro Tyr Met Lys His Gly Asp Leu Arg Asn Phe Ile Arg Asn Glu
                245                 250                 255

Thr His Asn Pro Thr Val Lys Asp Leu Ile Gly Phe Gly Leu Gln Val
            260                 265                 270

Ala Lys Gly Met Lys Tyr Leu Ala Ser Lys Lys Phe Val His Arg Asp
        275                 280                 285

Leu Ala Ala Arg Asn Cys Met Leu Asp Glu Lys Phe Thr Val Lys Val
    290                 295                 300

Ala Asp Phe Gly Leu Ala Arg Asp Met Tyr Asp Lys Glu Tyr Tyr Ser
305                 310                 315                 320

Val His Asn Lys Thr Gly Ala Lys Leu Pro Val Lys Trp Met Ala Leu
                325                 330                 335

Glu Ser Leu Gln Thr Gln Lys Phe Thr Thr Lys Ser Asp Val Trp Ser
            340                 345                 350

Phe Gly Val Leu Leu Trp Glu Leu Met Thr Arg Gly Ala Pro Pro Tyr
        355                 360                 365

Pro Asp Val Asn Thr Phe Asp Ile Thr Val Tyr Leu Leu Gln Gly Arg
    370                 375                 380

Arg Leu Leu Gln Pro Glu Tyr Cys Pro Asp Pro Leu Tyr Glu Val Met
385                 390                 395                 400

Leu Lys Cys Trp His Pro Lys Ala Glu Met Arg Pro Ser Phe Ser Glu
                405                 410                 415

Leu Val Ser Arg Ile Ser Ala Ile Phe Ser Thr Phe Ile Gly Glu His
            420                 425                 430

Tyr Val His Val Asn Ala Thr Tyr Val Asn Val Lys Cys Val Ala Pro
        435                 440                 445

Tyr Pro Ser Leu Leu Ser Ser Glu Asp Asn Ala Asp Asp Glu Val Asp

```
                   450                 455                 460
Thr Arg Pro Ala Ser Phe Trp Glu Thr Ser
465                 470

<210> SEQ ID NO 3
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Pro Asp Glu Leu Pro Leu Asp Glu His Cys Glu Arg Leu Pro Tyr
1               5                   10                  15

Asp Ala Ser Lys Trp Glu Phe Pro Arg Asp Arg Leu Lys Leu Gly Lys
            20                  25                  30

Pro Leu Gly Arg Gly Ala Phe Gly Gln Val Ile Glu Ala Asp Ala Phe
        35                  40                  45

Gly Ile Asp Lys Thr Ala Thr Cys Arg Thr Val Ala Val Lys Met Leu
    50                  55                  60

Lys Glu Gly Ala Thr His Ser Glu His Arg Ala Leu Met Ser Glu Leu
65                  70                  75                  80

Lys Ile Leu Ile His Ile Gly His His Leu Asn Val Val Asn Leu Leu
                85                  90                  95

Gly Ala Cys Thr Lys Pro Gly Gly Pro Leu Met Val Ile Val Glu Phe
            100                 105                 110

Cys Lys Phe Gly Asn Leu Ser Thr Tyr Leu Arg Ser Lys Arg Asn Glu
        115                 120                 125

Phe Val Pro Tyr Lys Val Ala Pro Glu Asp Leu Tyr Lys Asp Phe Leu
    130                 135                 140

Thr Leu Glu His Leu Ile Cys Tyr Ser Phe Gln Val Ala Lys Gly Met
145                 150                 155                 160

Glu Phe Leu Ala Ser Arg Lys Cys Ile His Arg Asp Leu Ala Ala Arg
                165                 170                 175

Asn Ile Leu Leu Ser Glu Lys Asn Val Val Lys Ile Cys Asp Phe Gly
            180                 185                 190

Leu Ala Arg Asp Ile Tyr Lys Asp Pro Asp Tyr Val Arg Lys Gly Asp
        195                 200                 205

Ala Arg Leu Pro Leu Lys Trp Met Ala Pro Glu Thr Ile Phe Asp Arg
    210                 215                 220

Val Tyr Thr Ile Gln Ser Asp Val Trp Ser Phe Gly Val Leu Leu Trp
225                 230                 235                 240

Glu Ile Phe Ser Leu Gly Ala Ser Pro Tyr Pro Gly Val Lys Ile Asp
                245                 250                 255

Glu Glu Phe Cys Arg Arg Leu Lys Glu Gly Thr Arg Met Arg Ala Pro
            260                 265                 270

Asp Tyr Thr Thr Pro Glu Met Tyr Gln Thr Met Leu Asp Cys Trp His
        275                 280                 285

Gly Glu Pro Ser Gln Arg Pro Thr Phe Ser Glu Leu Val Glu His Leu
    290                 295                 300

Gly Asn Leu Leu Gln Ala Asn Ala Gln Gln Asp
305                 310                 315

<210> SEQ ID NO 4
<211> LENGTH: 5
<212> TYPE: PRT
```